United States Patent
Bak et al.

(10) Patent No.: US 12,416,014 B2
(45) Date of Patent: Sep. 16, 2025

(54) LOX3 GENE MODULATION AND ARMYWORM TOLERANCE

(71) Applicant: KWS SAAT SE & Co. KGaA, Einbeck (DE)

(72) Inventors: Aurelie Bak, St. Louis, MO (US); Dietmar Stahl, Einbeck (DE); Daniel Stirnweis, Gottingen (DE); Daniela Scheuermann, Einbeck (DE); Bettina Kessel, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 0 days.

(21) Appl. No.: 18/154,191

(22) Filed: Jan. 13, 2023

(65) Prior Publication Data

US 2023/0313220 A1 Oct. 5, 2023

Related U.S. Application Data

(60) Provisional application No. 63/299,628, filed on Jan. 14, 2022.

(30) Foreign Application Priority Data

Jan. 25, 2022 (EP) .................... 22153142

(51) Int. Cl.
C12N 15/82 (2006.01)
A01H 6/20 (2018.01)
A01H 6/46 (2018.01)
C12N 9/22 (2006.01)

(52) U.S. Cl.
CPC ......... *C12N 15/8279* (2013.01); *A01H 6/204* (2018.05); *A01H 6/4684* (2018.05); *C12N 9/22* (2013.01); *C12N 15/8218* (2013.01); *C12N 2310/20* (2017.05)

(58) Field of Classification Search
CPC ................................................ C12N 15/8279
USPC ....................................................... 800/279
See application file for complete search history.

(56) References Cited

U.S. PATENT DOCUMENTS

2019/0032029 A1* 1/2019 Livore ........... C12Y 202/01006

FOREIGN PATENT DOCUMENTS

| CN | 110684796 A | 1/2020 | |
|---|---|---|---|
| WO | 2021/170785 A1 | 9/2021 | |
| WO | WO-2021207148 A1 * | 10/2021 | ............. C12N 15/11 |

OTHER PUBLICATIONS

Smith et al Nature, 407:319-320 (Year: 2000).*
Wang et al. The Plant Journal 104 1315-1333 (Year: 2020).*
International Search Report and Written Opinion Issued in PCT/EP2023/050685 dated Apr. 20, 2023.
Pathi et al., "Engineering Smut Resistance in Maize by Site-Directed Mutagenesis of Lipoxygenase 3", Frontiers in Plant Science, Oct. 2020, vol. 11, Article 543895, 13 pages.
Bai et al., "Knock-down of OsLOX by RNA interference leads to Improved seed viability in rice", Journal of Plant Biology, Botanical Society of Korea, Seoul, KR, 2015, vol. 58, No. 5, pp. 293-302.
Gao et al., "Inactivation of the Lipoxygenase ZmLOX3 Increases Susceptibility of Maize to *Aspergillus* spp.", Molecular Plant-Microbe Interactions, 2009, vol. 22, No. 2, pp. 222-231.
Gao et al., "Disruption of a Maize 9-Lipoxygenase Results in Increased Resistance to Fungal Pathogens and Reduced Levels of Contamination with Mycotoxin Fumonisin", MPMI, 2007, vol. 20, No. 8, pp. 922-933.
Gao et al., "Maize 9-Lipoxygenase ZmLOX3 Controls Development, Root-Specific Expression of Defense Genes, and Resistance to Root-Knot Nematodes", MPMI, 2008, vol. 21, No. 1, pp. 98-109.
Loutre et al., "Two different CC-NBS-LRR genes are required for Lr10-mediated leaf rust resistance in tetraploid and hexaplold wheat", The Plant Journal, 2009, vol. 60, pp. 1043-1054.
Kim et al., "Increasing the genome-targeting scope and precision of base editing with engineered Cas9-cytidine deaminase fusions", Nature Biotechnology, 2017, vol. 35, No. 4, pp. 371-376.
Gao et al., "Engineered Cpf1 Enzymes with Altered PAM Specificities", BioRxiv, 2016, 17 pages, dx.doi.org/10.1101/091611.
Christensen et al., "Ubiquitin promoter-based vectors for high-level expression of selectable and/or screenable marker genes in monocotyledonous plants", Transgenic Research, 1996, No. 5, pp. 213-218.
Helenius et al., "Gene delivery into intact plants using the HellosTM Gene Gun", Plant Molecular Biology Reporter, 2000, vol. 18, No. 3, pp. 287a-288l.
Diederichsen et al., "Disease response of resynthesized *Brassica napus* L. lines carrying differentresistance to Plasmodiophora brassicae Wor.", Plant Breeding, 1996, vol. 115, pp. 5-10.
Van Eck, "Applying gene editing to tailor precise genetic modifications in plants", J. Biol. Chem., 2020, vol. 295, No. 38, pp. 13267-13276.
Nalam et al., "The green peach aphid, *Myzus persicae*, acquires a Lipoxygenase5-derived oxylipin from *Arabidopsis thaliana*, which promotes colonization of the host plant", Plant Signaling & Behavior, 2013, vol. 8, No. 1, e22735, 10.4161/psb.22735.

(Continued)

*Primary Examiner* — Li Zheng

(74) *Attorney, Agent, or Firm* — Troutman Pepper Locke LLP

(57) ABSTRACT

The present application provides a new technology to confer or enhance insect resistance and, optionally also resistance to fungal pathogens in plants. In particular, the present invention provides a method for conferring or increasing resistance or tolerance to insect and optionally also to fungal pathogens in maize and oil seed rape (OSR) by targeting the endogenous Lox3 gene. By introducing either a gene silencing construct, a genome editing system or a genome modification, which leads to a targeted knock-down or knock-out of the Lox3 gene endogenous to the plant, a new or increased resistance to insect and, optionally fungal pathogens can be created.

16 Claims, 8 Drawing Sheets

Specification includes a Sequence Listing.

(56) References Cited

OTHER PUBLICATIONS

Rayapuram et al., "Using nutritional indices to study LOX3-dependent insect resistance", Plant, Cell and Environment, 2006, vol. 29, pp. 1585-1594. 10.1111/j.1365-3040.2006.01534.x.

Woldemariam et al., "A role for 9-lipoxygenases in maize defense against insect herbivory", Plant Signaling & Behavior, 2018, vol. 13, No. 1, e1422462. https://doi.org/10.1080/15592324.2017.1422462.

* cited by examiner

Figure 7

| Entry Name | FV_G ON | FG_G ON | FV_M UR | FG_M UR | Gene | Plant_2020 | Gene | Plant_2021 | 2020 mean_FV_ GON | mean_FG_ GON | 2021 mean_FV_ MUR | mean_FG_ MUR |
|---|---|---|---|---|---|---|---|---|---|---|---|---|
| PH207 | 12,60 | 41,67 | 45,50 | 38,13 | | | | WVP20-72327/MIX | | | | |
| PH207 | 18,67 | 30,00 | 58,50 | 32,78 | | | | WVP20-72372/MIX | | | | |
| PH207 | 37,50 | 56,00 | 42,22 | 38,89 | | | | WVN19-79936/MIX | 22,92 | 42,56 | 43,92 | 35,36 |
| PH207m034b | | | 16,11 | 8,86 | LOX3-MUT | WVP20-73214/005 | LOX3-MUT | WVP20-73212/007 | | | | |
| PH207m034b | 17,40 | | 35,50 | 12,50 | LOX3-MUT | WVP20-73216/005 | LOX3-MUT | WVP20-73212/007 | | | | |
| PH207m034b | 18,33 | 0,00 | 8,00 | 4,11 | LOX3-MUT | WVP20-73217/003 | LOX3-MUT | WVP20-73212/007 | | | | |
| PH207m034b | 9,60 | 10,00 | 23,00 | 9,33 | LOX3-MUT | WVP20-73217/006 | LOX3-MUT | WVP20-73212/007 | 15,11 | 5,00 | 20,65 | 8,70 |
| PH207w034b | 36,50 | 9,63 | 14,17 | 25,00 | LOX3-WT | WVP20-73214/006 | LOX3-WT | WVP20-73212/007 | | | | |
| PH207w034b | 40,00 | 56,63 | 28,89 | | LOX3-WT | WVP20-73215/005 | LOX3-WT | WVP20-73212/007 | | | | |
| PH207w034b | 19,00 | 30,00 | 24,00 | 1,50 | LOX3-WT | WVP20-73217/004 | LOX3-WT | WVP20-73212/007 | | | | |
| PH207w034b | 9,00 | 36,67 | | 11,50 | LOX3-WT | WVP20-73217/007 | LOX3-WT | WVP20-73212/007 | 26,13 | 33,23 | 20,51 | 16,58 |
| PH207w034b | | | 15,00 | 28,33 | | | | | | | | |
| PH207m034h | 34,44 | 53,50 | n.d. | n.d. | LOX3-MUT | WVP20-73264/004 | | | | | | |
| PH207m034h | 28,50 | 50,00 | n.d. | n.d. | LOX3-MUT | WVP20-73266/004 | | | | | | |
| PH207m034h | 23,00 | 25,00 | n.d. | n.d. | LOX3-MUT | WVP20-73268/001 | | | | | | |

| Sample | | | | | | | LOX3 | ID | | | |
|---|---|---|---|---|---|---|---|---|---|---|---|
| PH207m0 34h | 27,80 | 54,38 | n.d. | | | | LOX3-MUT | WVP20-73270/002 | | 28,44 | 45,72 |
| PH207w0 34h | 57,00 | 46,80 | 28,00 | n.d. | n.d. | n.d. | LOX3-WT | WVP20-73267/002 | | | |
| PH207w0 34h | 28,11 | 28,00 | n.d. | n.d. | n.d. | n.d. | LOX3-WT | WVP20-73267/003 | | | |
| PH207w0 34h | 37,78 | 71,67 | n.d. | n.d. | n.d. | n.d. | LOX3-WT | WVP20-73268/002 | | | |
| PH207w0 34h | 32,40 | 45,50 | n.d. | n.d. | n.d. | n.d. | LOX3-WT | WVP20-73270/004 | | 38,82 | 47,99 |
| PH207m0 34d | n.d. | n.d. | 0,00 | 65,83 | | | LOX3-MUT | WVN18-76855/003 | n.d. | n.d. | |
| PH207m0 34d | n.d. | n.d. | 12,50 | | | | LOX3-MUT | WVN18-76855/008 | n.d. | n.d. | |
| PH207m0 34d | n.d. | n.d. | | 40,00 | | | LOX3-MUT | WVN18-76856/005 | n.d. | n.d. | |
| PH207m0 34d | n.d. | n.d. | 57,50 | 15,00 | | | LOX3-MUT | WVN18-76856/012 | n.d. | n.d. | |
| PH207m0 34d | n.d. | n.d. | 40,56 | 41,43 | | | LOX3-MUT | WVN18-76857/009 | n.d. | n.d. | |
| PH207m0 34d | n.d. | n.d. | 19,38 | 47,50 | | | LOX3-MUT | WVN18-76858/013 | n.d. | n.d. | 25,99 | 41,95 |
| PH207w0 34d | n.d. | n.d. | 100,00 | 53,75 | | | LOX3-WT | WVN18-76854/012 | n.d. | n.d. | |
| PH207w0 34d | n.d. | n.d. | 7,50 | 31,67 | | | LOX3-WT | WVN18-76856/006 | n.d. | n.d. | |
| PH207w0 34d | n.d. | n.d. | 71,67 | 51,67 | | | LOX3-WT | WVN18-76856/009 | n.d. | n.d. | |
| PH207w0 34d | n.d. | n.d. | 57,00 | 45,00 | | | LOX3-WT | WVN18-76857/007 | n.d. | n.d. | |
| PH207w0 34d | n.d. | n.d. | 41,67 | 46,67 | | | LOX3-WT | WVN18-76858/008 | n.d. | n.d. | 55,57 | 45,75 |

Figure 7 cont'd

SEQUENCE LISTING

```
Sequence total quantity: 89
SEQ ID NO: 1           moltype = DNA  length = 201
FEATURE                Location/Qualifiers
misc_feature           1..201
                       note = RNAi target region sense strand before RGA2intronII
source                 1..201
                       mol_type = other DNA
                       organism = synthetic construct
SEQUENCE: 1
```

```
ctgccgcacg ggccgcaagc ccaccaaaac cgaccccaac tcggagagcc gactgtcgct    60
ggtggagcag atctacgtgc cgcgggacga gcgcttcggc cacctcaaga tgtccgactt   120
cctgggctac tccatcaagg ccatcacgca gggcatcatc ccggcggtgc gcacgtacgt   180
ggacaccacc ccgggcgagt t                                             201

SEQ ID NO: 2            moltype = DNA   length = 201
FEATURE                 Location/Qualifiers
misc_feature            1..201
                        note = RNAi target region antisense strand after the
                         RGA2intronII
source                  1..201
                        mol_type = other DNA
                        organism = synthetic construct
SEQUENCE: 2
aactcgcccg gggtggtgtc cacgtacgtg cgcaccgccg ggatgatgcc ctgcgtgatg    60
gccttgatgg agtagcccag gaagtcggac atcttgaggt ggccgaagcg ctcgtcccgc   120
ggcacgtaga tctgctccac cagcgacagt cggctctccg agttggggtc ggttttggtg   180
ggcttgcggc ccgtgcggca g                                             201

SEQ ID NO: 3            moltype = DNA   length = 312
FEATURE                 Location/Qualifiers
misc_feature            1..312
                        note = RGA2intronII sequence from Triticum aestivum
source                  1..312
                        mol_type = other DNA
                        organism = synthetic construct
SEQUENCE: 3
gtatggatag tgtatcttca tactgcattt gtttaatttg aaaatggtta tctagttgcc    60
taacaaaata tagctgggat atcatataac acatgtcag gtgacatgga aaaaatgcc   120
tattttctta tgcactaact attcatcatg tgacatactt ccccaaaaaa ctaaataagc   180
caaattttcc agcttccgag tcctgaaaaa gagtagtgta cctgataca tttatagagt   240
ttttttttcg aaaagaaggg atggccctca tagatagagt actaactaaa agtctacttt   300
taccaatttc ag                                                       312

SEQ ID NO: 4            moltype = DNA   length = 726
FEATURE                 Location/Qualifiers
misc_feature            1..726
                        note = Sequence of RNAi cassette
source                  1..726
                        mol_type = other DNA
                        organism = synthetic construct
SEQUENCE: 4
ctgccgcacg ggccgcaagc ccaccaaaac cgaccccaac tcggagagcc gactgtcgct    60
ggtggagcag atctacgtgc cgcgggacga gcgcttcggc cacctcaaga tgtccgactt   120
cctgggctac tccatcaagg ccatcacgca gggcatcatc ccggcggtgc gcacgtacgt   180
ggacaccacc ccgggcgagt tcgagaggta tggatagtgt atcttcatac tgcatttgtt   240
taatttgaaa atggttatct agttgcctaa caaaatatag ctgggatatc atataacaca   300
tgtgcaggtg acatggaaaa aatgcctat ttttctatgc actaactatt catcatgtga   360
catacttccc caaaaaacta aataagccaa attttcagc ttccgagtcc tgaaaaagag   420
tagtgtacct gatacaattt atagagtttt ttttcgaaaa agaagggatg ccctcatag   480
atagagtact aactaaaagt ctacttttac caatttcag cctcgaactc gcccgggtg   540
gtgtccacgt acgtgcgcac cgccgggatg atgccctgcg tgatggcctt gatggagtag   600
cccaggaagt cggacatctt gaggtggccg aagcgctcgt cccgcggcac gtagatctgc   660
tccaccagcg acagtcggct ctccgagttg ggtcggttt tggtgggctt gcggcccgtg   720
cggcag                                                              726

SEQ ID NO: 5            moltype = DNA   length = 12924
FEATURE                 Location/Qualifiers
misc_feature            1..12924
                        note = Sequence of a complete artificial vector
source                  1..12924
                        mol_type = other DNA
                        organism = synthetic construct
SEQUENCE: 5
aaaaggatct aggtgaagat cctttttgat aatctcatga ccaaaatccc ttaacgtgag    60
ttttcgttcc actgagcgtc agaccccgta gaaaagatca aaggatcttc ttgagatcct   120
tttttttctgc gcgtaatctg ctgcttgcaa acaaaaaaac caccgctacc agcggtggtt   180
tgtttgccgg atcaagagct accaactctt tttccgaagg taactggctt cagcagagcg   240
cagataccaa atactgttct tctagtgtag ccgtagttag gccaccactt caagaactct   300
gtagcaccgc ctacatacct cgctctgcta atcctgttac cagtggctgc tgccagtggc   360
gataagtcgt gtcttaccgg gttggactca agacgatagt taccggataa ggcgcagcgg   420
tcgggctgaa cggggggttc gtgcacacag cccagcttgg agcgaacgac ctacaccgaa   480
ctgagatacc tacagcgtga gctatgagaa agcgccacgc ttcccgaagg gagaaaggcg   540
gacaggtatc cggtaagcgg cagggtcgga acaggagagc gcacgaggga gcttccaggg   600
ggaaacgcct ggtatcttta tagtcctgtc gggtttcgcc acctctgact tgagcgtcga   660
tttttgtgat gctcgtcagg ggggcggagc ctatggaaaa acgccagcaa cgcggccttt   720
ttacggttcc tggccttttg ctggcctttt gctcacatgt tctttcctgc gttatcccct   780
gattctgtgg ataaccgatt accgcctttg agtgagctga taccgctcgc cgcagccgaa   840
cgaccgagcg cagcgagtca gtgagcgagg aagcggaaga gcgcctgatg cggtattttc   900
```

```
tccttacgca tctgtgcggt atttcacacc gcatatggtg cactctcagt acaatctgct   960
ctgatgccgc atagttaagc cagtatacac tccgctatcg ctacgtgact gggtcatggc  1020
tgcgccccga cacccgccaa cacccgctga cgcgccctga cgggcttgtc tgctcccggc  1080
atccgcttac agacaagctg tgaccgtctc cgggagctgc atgtgtcaga ggttttcacc  1140
gtcatcaccg aaacgcgcga ggcaggggta cgtcgaggtc gatccaaccc ctccgctgct  1200
atagtgcagt cggcttctga cgttcagtgc agccgtcttc tgaaaacgac atgtcgcaca  1260
agtcctaagt tacgcgacag gctgccgccc tgcccttttc ctggcgtttt cttgtcgcgt  1320
gttttagtcg cataaagtag aatacttgcg actagaaccg agacattac gccatgaaca  1380
agagcgccgc cgctggcctg ctgggctatg cccgcgtcag caccgacgac caggacttga  1440
ccaaccaacg ggccgaactg cacgcggccg gctgcaccaa gctgttttcc gagaagatca  1500
ccggcaccag gcgcgaccgc ccggagctgg ccaggatgct tgaccaccta cgccctggcg  1560
acgttgtgac agtgaccagg ctagaccgcc tggcccgcag cacccgcgac ctactggaca  1620
ttgccgagcg catccaggag gccggcgcgg gcctgcgtag cctggcagag ccgtgggccg  1680
acaccaccac gccggccggc cgcatggtgt tgaccgtcgt tgaccgggcatt gccgagttcg  1740
agcgttccct aatcatcgac cgcacccgga gcgggcgcga ggccgccaag gcgcgaggcg  1800
tgaagtttgg cccccgccct accctcaccc cggcacagat cgcgcacgcc cgcgagctga  1860
tcgaccagga aggccgcacc gtgaaagagg cggctgcact gcttggcgtg catcgctcga  1920
ccctgtaccg cgcacttgag cgcagcgagg aagtgacgcc caccgaggcc aggcggccgcg  1980
gtgccttccg tgaggacgca ttgaccgagg ccgacgccct ggcggccgcc gagaatgaac  2040
gccaagagga acaagcatga aaccgcacca ggacggccag gacgaaccgt ttttcattac  2100
cgaagagatc gaggcggaga tgatcgcggc cgggtacgtg ttcgagccgc ccgcgcacgt  2160
ctcaaccgtg cggctgcatg aaatcctggc cggttttgtct gatgccaagc tcgcggcctg  2220
gccggcgagc ttggccgctg aagaaaccga gcgccgccgt ctaaaaaggt gatgtgtatt  2280
tgagtaaaac agcttgcgtc atgcggtcgc tgcgtatatg atgcgatgag taaataaaca  2340
aatacgcaag gggaacgcat gaaggttatc gctgtactta accagaaagg cgggtcaggc  2400
aagacgacca tcgcaaccca tctagccgcc tgctgcaac tcgccgggcc cgatgttctg  2460
ttagtcgatt ccgatcccca gggcagtgcc cgcgattggg cggccgtgcg gaagatcaa  2520
ccgctaaccg ttgtcggcat cgaccgcccg acgattgacc gcgacgtgaa ggccatcggc  2580
cggcgcgact tcgtagtgat cgacggagcg ccccaggcgg cggacttggc tgtgtccgcg  2640
atcaaggcag ccgacttcgt gctgattccg gccggcgacggcc gccgttaa catatgggcc  2700
accgccgacc tggtggagct ggttaagcac cgcattgagg tcacggatgg aaggctacaa  2760
gcggcctttg tcgtgtcgcg ggcgatcaaa ggcacgcgca tcggcggtga ggttgccgag  2820
gcgctggccg ggtacgagct gcccattctt gagtccgta tcacgcagcg cgtgagctac  2880
ccaggcactg ccgccgcgg cacaaccgtt cttgaatcga aacccgaggg cgacgctgcc  2940
cgcgaggtcc aggcgctggc cgctgaaatt aaatcaaaac tcattgagt taatgaggta  3000
aagagaaaat gagcaaaagc acaaacacgc taagtgccgg ccgtccgagc gcacgcagca  3060
gcaaggctgc aacgttggcc agcctggcag acacgccagc catgaagcgg gtcaactttc  3120
agttgccggc ggaggatcac accaagctga agatgtacgc ggtacgccaa ggcaagacca  3180
ttaccgagct gctatctgaa tacatccgcg agctaccaga gtaaatgacc aaatgaataa  3240
atgagtagat gaattttagc ggctaaagga ggcggcatgg aaaatcaaga caaccaggc  3300
accgacgccg tggaatgccc catgtgtgga ggaacgggcg gttggccagg cgtaagcggc  3360
tgggttgtct gccggccctg caatggcact ggaaccccca agcccgagga tcggcgtga  3420
gcggtcgcaa accatccggc ccggtacaaa tcggcgcggc gctgggtgat gacctggtgg  3480
agaagttgaa ggccggcgcag gccgccagc ggcaacgcat cgaggcagaa gcacgccccg  3540
gtgaatcgtg gcaagcggcc gctgatcgaa tccgcaaaga atcccggcaa ccgccggcag  3600
ccggtgcgcc gtcgattagg aagccgccca agggcgacga gcaaccagat ttttttcgttc  3660
cgatgctcta tgacgtgggc acccgcgata gtcgcagcat catgacgta gccgttttcc  3720
gtctgtcgaa gcgtgaccga cgagctggcc aggtgatccg ctacgagctt ccagacgggc  3780
acgtagaggt ttccgcaggg ccggccgca tggcgagtgt gtgggattac gacctggtac  3840
tgatggcggt ttcccatcta accgaatcca tgaaccgata ccgggaaggg aagggagaca  3900
agcccggccg cgtgttccgt ccacacgttg cggacgtact caagttctgc cggcgagccg  3960
atggcggaaa gcagaaagac gacctggtag aaacctgcat tcggttaaac accacgcacg  4020
ttgccatgca gcgtacgaag aaggccaaga acggccgcct ggtacggta tccgagggtg  4080
aagccttgat tagccgctac aagatcgtaa agagcgaaac cggcggccg gagtacatcg  4140
agatcgagct agctgattgg atgtaccgcg agatcacaga aggcaagaac cgggacgtgc  4200
tgacggttca ccccgattac ttttgatcg atccggcat cggccgtttt ctctaccgcc  4260
tggcacgccg cgccgcaggc aaggcagaag ccagatggtt gttcaagacg atctacgaac  4320
gcagtggcag cgccggagag ttcaagaagt tctgtttcac cgtgcgcaag ctgatcgggt  4380
caaatgacct gccggagtac gatttgaagg aggagcggg gcaggctggc ccgatcctag  4440
tcatgcgcta ccgcaacctg atcgagggcg aagcatccgc cggttcctaa tgtacggagc  4500
agatgctagg gcaaattgcc ctagcagggg aaaaggtcg aaaaggtctc tttcctgtgg  4560
atagcacgta cattgggaac ccaaagccgt acattgggaa ccggacccg tacattggga  4620
acccaaagcc gtacattggg aaccggtcac acatgtaagt gactgatata aaagagaaaa  4680
aaggcgattt ttccgcctaa aactctttaa aacttattaa aacttcttaaa acccgcctgg  4740
cctgtgcata actgtctggc cagcgcacag ccgaagagct gcaaaaagcg cctacccttc  4800
ggtcgctgcg ctccctacgc cccgccgctt cgcgtcggcc tatcgcggcc gctgccgct  4860
caaaaatggc tggcctacgg ccaggcaatc taccagggcg cggacaagcc gcgccgtcgc  4920
cactcgaccg ccgcgccca catcaaggca ccggtgggta tgcctgacga tgctggaca  4980
ccgaaacctt gcgctctgtt gccagccagg acagaaatgc ctcgacttcg ctgctgtcca  5040
aggttgccgg gtgacgcaca ccgtggaaac ggatgaaggc acgaacccag tggacataag  5100
cctgttcggt tcgtaagctg taatgcaagt agcgtatgcg ctcacgcaac tggtccagaa  5160
ccttgaccga acgcagcggt ggtaacgcg cagtggcggt tttcatggct tgttatgact  5220
gtttttttgg ggtacagtct atgcctcggg catccaagca gcaagcgcgt tacgccgtgg  5280
gtcgatgttt gatgttatgg gcaggcagt cgccctaaaa  5340
caaagttaaa catcatgagg gaagcggtga tcgccgaagt atcgactcaa ctatcagagg  5400
tagttgcgt catcgagcgc catctcgaac cgacgttgct ggccgtacat ttgtacggct  5460
ccgcagtgga tggcggcctg aagccacaca gtgatattga tttgctggtt acggtgaccg  5520
taaggcttga tgaaacaacg cggcgagctt tgatcaacga ccttttggaa acttcggctt  5580
ccctggagag agcgagatt ctccgcgctg tagaagtcac cattgttgtg cacgacgaca  5640
```

-continued

```
tcattccgtg gcgttatcca gctaagcgcg aactgcaatt tggagaatgg cagcgcaatg    5700
acattcttgc aggtatcttc gagccagcca cgatcgacat tgatctggct atccttgctga   5760
caaaagcaag agaacatagc gttgccttgg taggtccagc ggcggaggaa ctctttgatc    5820
cggttcctga acaggatcta tttgaggcgc taaatgaaac cttaacgcta tggaactcgc    5880
cgcccgactg ggctggcgat gagcgaaatg tagtgcttac gttgtcccgc atttggtaca    5940
gcgcagtaac cggcaaaatc gcgccgaagg atgtcgctgc cgactgggca atggagcgcc    6000
tgccggccca gtatcagccc gtcatacttg aagctagaca ggcttatctt ggacaagaag    6060
aagatcgctt ggcctcgcgc gcagatcagt tggaagaatt tgtccactac gtgaaaggcg    6120
agatcaccaa ggtagtcggc aaataatgtc taacaattcg ttcaagccga cgccgcttcg    6180
cggcgcggct taactcaagc gttagatgca ctaagcacat aattgctcac agccaaacta    6240
tcaggtcaag tctgctttta ttattttaa gcgtgcataa taagccctac acaaattggg     6300
agatatatca tgaaaggctg gctttttctt gttatcgcaa tagttggcga agtaatcgca    6360
acatagcttg cttggtcgtt ccgcgtgaac gtcggctcga ttgtacctgc gttcaaatac    6420
tttgcgatcg tgttgcgcgc ctgcccggtg cgtcggctga tctcacggat cgactgcttc    6480
tctcgcaacg ccatccgacg gatgatgttt aaaagtccca tgtggatcac tccgttgccc    6540
cgtcgctcac cgtgttgggg ggaaggtgca catggctcag ttctcaatgg aaattatctg    6600
cctaaccggc tcagttctgc gtagaaacca acatgcaagc tccaccgggt gcaaagcggc    6660
agcggcggca ggatatattc aattgtaaat ggcttcatgt ccgggaaatc tacatggatc    6720
agcaatgagt atgatggtca atatggagaa aaagaaagag taattaccaa ttttttttca    6780
attcaaaaat gtagatgtcc gcagcgttat tataaaatga aagtacattt tgataaaacg    6840
acaaattacg atccgtcgta tttataggcg aaagcaataa acaaattatt ctaattcgga    6900
aatctttatt tcgacgtgtc tacattcacg tccaaatggg agtttagatg agaaacttca    6960
cgatcggctc tagctaggga taacagggta atgcgtgctg cagggctgaa gcggtgcggg    7020
aagagctgca ggctgaggta caccaactac ctgaggccca acctcaagca cgagaacttc    7080
acgtacgcac tggattttgg ttttaggaat tagaaatttt attgatagaa gtattttaca    7140
aatacaaata catactaagg gttttcttata tgctcaacac atgagcgaaa ccctataaga    7200
accctaattc ccttatctgg gaactactca cacattatta tagagagaga tagtttgta     7260
gagagagact ggtgatttca gcttcagatc tttactccgg cagcgttgtg tcgcccgcgt    7320
tgagcggccg ttgcatgagc accgtgtcga tccagcggcc gaacttgaag ccgacggact    7380
tgagcacgcc tgcctgcacg aagccgcagg cggcatggca accgagggac gccgtattgc    7440
cgctgtcgcc gacgttcgca atcagttgcc gccacgggcc gccttcgcaa cgcgcgatga    7500
gcgtgagcaa cagcgtgcgc cctacgcccc gcccgatcgc atcggggggcg atatacaccg   7560
agtcttccag cgtgaaacgg taggcggagc gcggccggta atgcgtggcg tatgcgtagc    7620
cgagcagctt gccgtcgcgt tcggcgacga gatacggcag tccggcgtcg agtaccttgg    7680
cgcaacgcgc gcgcatctcg gtgtcgtcgg gtggcgtcca ttcgaacgat gccgtgccgg    7740
tacgcacgtg atgggcgtag atggccgtga tggcgggcag gtcgtcgtca cgcacgacgc    7800
gcaccgtgca tgcgcaacgc gccagttcga cgccgacgcg ttgcggcgcg tcgggagtgg    7860
aggggtgaga cgaagatgac ggcatggtct gcagctcgag ccgcagctgc acgggtccag    7920
gaaagcaatc gcatagtcaa gctaaatcat caagatgcaa acttttcgcc cttgctaaac    7980
acgtaaaaat tcgaatggac atgtgtggag cagcaaaggc cttacgtccg agaaacaggg    8040
ccactcaacg agttagttaa attcaaagaa agaaacgcct ccttgcaagt tgcaacattc    8100
ctagatcata ctaatgaaaa tgacgtcctt cattaaagaa cagggaagat agattttgc     8160
tccatagatc gtatgatgtg ttcagccaga ctgtcggatg gaccacacgt taatagcagt    8220
gctggacgat gttacatcga gaaagattac tagccttttc atgggagtaa aggatataaa    8280
agaaataagt tcaccacgat tgcaggatag catacaagat cagcgccact gcggcactgt    8340
tcatcgaaaa aaaactgtgg acgaagcttt ccccaaaatt actcaacgaa tcataaacca    8400
agattagtca gatcaagaga cagaggagaa acaaggcgga cctttgcagt cgaggtcctc    8460
tccaaatgaa atgaacttcc ttatatagag gaagggtctt gcgaaggata gtgggattgt    8520
gcgtcatccc ttacgtcagt ggagatatca catcaatcca cttgctttga agacgtggtt    8580
ggaacgtctt ctttttccac gatgttcctc gtgggtgggg gtccatcttt gggaccactg    8640
tcggtagagg catcttgaac gatagccttt ccttatcgcc aatgatggca tttgtagaag    8700
ccatcttcct tttctactgt cctttcgatg aagtgacaga tagctgggca atggaatccg    8760
aggaggtttc ccgatattac ccttttgttga aagtctcaa tagccctctg tcttctgag     8820
actgtatctt tgatattctt ggagtagacg agagtgtcgt gctccaccat gtatcacatc    8880
aatccacttg ctttgaagac gtggttgaa cgtcttcttt ttccacgatg ttcctcgtgg     8940
gtggggtcc atctttggga ccactgtcgg tagaggcatc ttgaacgata gccttccctt     9000
tatcgcaatg atggcatttg tagaagccat cttccttttc tactgtcctt tcgatgaagt    9060
gacagatagc tgggcaatgg aatccgagga ggtttcccga tattaccctt tgttgaaaag    9120
tctcaatagc cctctggtct tctgaacgcg tgctgcaggg ctgaagcggt gcgggaagag    9180
ctgcaggctg aggtacacca actacctgag gcccaacctc aagcacgaga acttcacgta    9240
cgctagggat aacagggtaa tccaatggtc tagaggccat ggcggccgcg tcgagcgatc    9300
tagtaacata tgatgaccg cgcgcgataa tttatcctag tttgcgcgct atattttgtt     9360
ttctatcgcg tattaaatgt ataattgcgg gactctaatc ataaaaccc atctcataaa     9420
taacgtcatg cattacatgt taattattac atgcttaacg taattcaaca gaaattatat    9480
gataatcatc gcaagaccgg caacaggatt caatcttaag aaactttatt gccaaatgtt    9540
tgaacgatcg gggaaattcg agtcgacacg cgtaagcttg aattcctgca gcccggggga    9600
ttgctgccgc acgggccgca agcccaccaa aaccgacccc aactcggaga gccgactgtc    9660
gctggtggga cagatctacg tgccgcggga cgagcgcttc ggccacctca agatgtccga    9720
cttcctgggc tactccatca aggccatcac gcaggcatc atcccgcgcg tgcgcacgta     9780
cgtggacacc accccgggcg agttcgaggc ctgaaattgg taaaagtaga ctttagtta     9840
gtactctatc tatgagggcc atcccttctt ttcgaaaaaa aaactctata aattgtatca    9900
ggtacactac tcttttcag gactcggaag ctggaaaatt tggcttattt agttttttgg     9960
ggaagtatgt cacatgatga atagttagtg catagaaaaa taggcatttt tttccatgtc   10020
acctgcacat gtgttatatg atatcccagc tatattttgt taggcaacta gataaccatt   10080
ttcaaattaa acaaatgcag tatgaagata cactatccat acctctcgaa ctcgcccggg   10140
gtggtgtcca cgtacgtgcg caccgccggg atgatgccct gcgtgatggc cttgatggag   10200
tagcccagga agtcggacat cttgaggtgg ccgaagcgct cgtccgcgg cacgtagatc     10260
tgctccacca gcgacagtcg gctctccgag ttggggtcgg ttttggtggg cttgcggccc   10320
gtgcggcagc aatccccggg tacctctaga cttgtacagc tcgtccatgc cgtacaggaa   10380
```

```
caggtggtgg cggccctcgg agcgacctgc agaagtaaca ccaaacaaca gggtgagcat   10440
cgacaaaaga aacagtacca agcaaataaa tagcgtatga aggcagggct aaaaaaatcc   10500
acatatagct gctgcatatg ccatcatcca agtatatcaa gatcaaaata attataaaac   10560
atacttgttt attataatag ataggtactc aaggttagag catatgaata gatgctgcat   10620
atgccatcat gtatatgcat cagtaaaacc cacatcaaca tgtataccta tcctagatcg   10680
atatttccat ccatcttaaa ctcgtaacta tgaagatgta tgacacacac atacagttcc   10740
aaaattaata aatacaccag gtagtttgaa acagtattct actccgatct agaacgaatg   10800
aacgaccgcc caaccacacc acatcatcac aaccaagcga acaaaaagca tctctgtata   10860
tgcatcagta aaacccgcat caacatgtat acctatccta gatcgatatt tccatccatc   10920
atcttcaatt cgtaactatg aatatgtatg gcacacacat acagatccaa aattaataaa   10980
tccaccaggt agtttgaaac agaattctac tccgatctag aacgaccgcc caaccagacc   11040
acatcatcac aaccaagaca aaaaaagca tgaaagatg acccgacaaa caagtgcacg   11100
gcatatattg aaataaagga aaagggcaaa ccaaacccta tgcaacgaaa caaaaaaaat   11160
catgaaatcg atcccgtctg cggaacggct agagccatcc caggattccc caaagagaaa   11220
cactggcaag ttagcaatca gaacgtgtct gacgtacagg tcgcatccgt gtacgaacgc   11280
tagcagcacg gatctaacac aaacacggat ctaacacaaa catgaacaga agtagaacta   11340
ccgggcccta accatggacc ggaacgccga tctagaaag gtagagaggg ggggggggggg  11400
aggacgaggc gcgtaccttg aagcgagggt gccgacgggt ggatttgggg gagatccact   11460
agttctagag cggccgccac cgcggtgaa ttctcgaggt cctctccaaa tgaaatgaac   11520
ttccttatat agaggaaggg tcttgcgaag gatagtggga ttgtgcgtca tcccttacgt   11580
cagtggagat atcacatcaa tccacttgct ttgaagacgt ggttgaaacg tcttcttttt   11640
ccacgatgtt cctcgtgggt ggggtccat ctttgggacc actgtcggta gaggcatctt   11700
gaacgatagc cttttcctta tcgcaatgat ggcatttgta gaagccatct tcctttttcta  11760
ctgtcctttc gatgaagtga cagatagctg ggcaatggaa tccgaggagg ttccccgata   11820
ttacccttg ttgaaaagtc tcaatagccc tctggtcttc tgagactgta tctttgatat    11880
tcttggagta gacgagagtg tcgtgctcca ccatgtatca catcaatcca cttgcttga   11940
agacgtggtt ggaacgtctt ctttttccac gatgttcctc gtgggtgggg gtccatcttt   12000
gggaccactg tcggtagagg catcttgaac gatagccttt cctttatcgc aatgatggca   12060
tttgtagaag ccatcttcct tttctactgt cctttcgatg aagtgacaga tagctgggca   12120
atggaatccg aggagggtttc ccgatattac cctttgaaa aagtctcaa tagccctct    12180
gtcttctgaa cctgcatagt aaggccttaa gggccagatc ttgggcccctt agtgtatgcc  12240
aagtgtaaag gacgcttgcg tgtatgcgta gttagtgttg ggtcgatggc ctaccttgg   12300
cgattattgg gcccggtacc cgatcagatt gtcgtttccc gccttcggtt taaactatca   12360
gtgtttgaca ggatatattg gcgggtaaac ctaagagaaa agagcgttta ttagaataat   12420
cggatattta aaagggcgtg aaaaggttta tccgttcgtc catttgtatg tgcatgccaa    12480
ccacagggtt cccctcggga gtgcttggca ttccgtgcga taatgacttc tgttcaacca   12540
cccaaacgtc ggaaagcctg acgacggagc agcattccaa aaagatccct tggctcgtct   12600
gggtcggcta gaaggtcgag tgggctgctg tggcttgatc cctcaacgcg gtcgcggacg   12660
tagcgcagcg ccgaaaaatc ctcgatcgca aatccgacgc tgtcgaaaag cgtgatctgc   12720
ttgtcgctct ttcggccgac gtcctggcca gtcatcacgc gccaaagttc cgtcacagga   12780
tgatctggcg cgagttgctg gatctcgcct tcaatccggg tctgtggcgg gaactccacg   12840
aaaatatccg aacgcagcaa gatatcgcgg tgcatctcgg tcttgcctgg gcagtcgccg   12900
ccgacgccgt tgatgtggac gccg                                          12924
SEQ ID NO: 6         moltype = DNA  length = 4801
FEATURE              Location/Qualifiers
source               1..4801
                     mol_type = genomic DNA
                     organism = Zea mays
SEQUENCE: 6
cacagcctca cacagacacc aacgccactg cactgcaaaa gcaagagcag ctagctagta   60
aagatgctga gcgggatcat cgacgggctg acggggcgca acaagcatgc gcggctcaag   120
ggcacggtgg tgctcatgcg caagaacgtg ctggacctca cgacttcgg cgccaccgtc   180
gttgacagca tcagcgagtt cctcggcaag ggggtcacct gccagctcat cagctccacc   240
ctcgtcgacg ccagtgagta ccgcgccgcg ccgccgacgc ctctccgatc tgcgcttccc   300
catgtcgatc gatctcgatc tctctaggct ctagagctat agctctctcg gcccccactt   360
tttacctttg caagcatttt ccctgcatgc gaaacaagcg atagtttact atttgggcgg   420
ccatgctgct gctgcttcgg ctaccttgcc tccgtcatct ttgacgggac atggaaagaa   480
agaaagaata gagagagaga cagagagaga gagagacaaa aagacgagaa aagacgtaa    540
aagctagttg tagcctgggc gcagaacaca gcaccagatg ctggctagct cgtgacaaag   600
taaaaaaaga gaggaacgaa cacagtagta ccaagagatc agggacgaga cctttctact   660
ttgaactgga ttatatattg gattcttat cagtaactta ctgctgctag tatacccta     720
ccctagtctc ggggcgacgt gcctgcgtgc atgcccgacg cgtacgaaac acatcgacgg   780
actcacatgg gccaccgcgc gcgcgcggc ctgctttaac tttcgctgtg cagacaacgg    840
caaccgcggg cgggtcgggg cggaggcgaa cctggagcga tggcctgacga gcctgccgtc   900
gctgacgacc ggcgagtcca agttcggcgt cacgttcgac tgggaggtgg agaagctggg   960
agtgccgggg gccgtcgtcg tcaagaacaa ccacgccgcc gagttcttcc tcaagacaat   1020
caccctcgac gacgtgcccg gccgcggcgc cgtcaccctc gtcgccaact cctgggtcta   1080
ccccggggc aagtaccgct acaaccgcgt cttcttctc aacgatgtga gtcctttctc    1140
gatagatcat tatgtttgtt tgttattttg ttcttggta tcatgtaggc atgtagctag   1200
ccgccatgtc gtcagttgga gtgcagtagg taggaaaaag gacgacatgg gatgggagtg   1260
gttaagaaaa tccatgcaag tgggactagt gtgtaactgg tagtatagct gaagaatcta   1320
gtggtagaat gatcttgtac gtgaataatg tttctgacgc tgagcgctga ggctatccgc   1380
aacctttaac cctaaatttt tccctctata tcattttttc ctctattttc ctctatttt   1440
tttcatctct cgcagcggtt cccctaaat actccccta tatctcacta ccactataaa   1500
atattattttt ctataccaat tatcaatttt ttatctacta acaattactc gtggaccac   1560
agcacagtgt ttagggtgat gaacagtgac acgctagatc tgaagggaga gagagggga    1620
ccgacacgta gggagcctgt agagggcacc gctgcgccg tagggtgctc cctacgcgcc    1680
gcatacaagg ggaggggga gaggcagcgg taaccgctgc gcacagcctg agggcgaggc   1740
```

```
atgtgagttc caccacgtgag tagcagcaaa aggaaacaac ccttcttcac ccggctatca  1800
tctaacgtat cgccccggga gaatcaataa ctctaacgag atgacgaaaa gtcaaaaata  1860
aagtcgtgtg atggccatga aagtcagtca agcaaatcag ctgctaacac gtgtcccta   1920
tctacaggta taagagagta gagtcttgtc aatcaacctg ggttgttttc tatctgcgtt  1980
ttaccgtccg tcagtcagtc ggccaacatg ccacgctgat ctttctgtct tttggtgccg  2040
ccccgattcc gaacggcggc gcagacgtac ctgccaagcc agatgccggc ggcgctgaag  2100
ccgtaccgcg acgacgagct ccgcaacctc cgcggcgacg accagcaggg ccctaccag   2160
gagcacgacc gcgtgtaccg ctacgacgtc tacaacgacc tcggcgagcc cgacggcggc  2220
aacccgcgcc ccatcctcgg cggctccgcc gaccaccgt acccgcgccg ctgccgcacg  2280
ggccgcaagc ccaccaaaac cggtgcgtgc gccgtgcgcg gctcttctat cttctcggac  2340
gcaacatttg ctgcagggca gagaggttgt tgacgctgac ctgtgaccgc atcgcagacc  2400
ccaactcgga gagccgactg tcgctggtgg agcagatcta cgtgccgcgg gacgagcgct  2460
tcggccacct caagatgtcc gacttcctgg gctactccat caaggccatc acgcagggca  2520
tcatcccggc ggtgcgcacg tacgtggaca ccaccccgcg cgagttcgac tccttccagg  2580
acatcatcaa cctgtacgag ggcgggatca agctgcccaa gatccaggcg ctcgaggaca  2640
tgcgcaagct cttcccgctc cagctcgtca aggacctcct ccccgccggc ggggactacc  2700
tgctcaagct ccccatccca cagatcatcc aaggcacgtc acgtataccg atcgatgtca  2760
ggggcggct gttgtctggt ctgcatatat atatgtgctc ctatgtttaa ctgtgactgc  2820
gtacgttcg cggaacagag gacaagaacg cgtggaggac cgacgaggag ttcgcgcggg  2880
aggtgctcgc cggcgtcaac ccgatggtga tcacgcgcct cacggtgagt cactcacttt  2940
gtgcaaaatg cgagacccga cccgagacgg aatgtgcctg acgcgctcga tttacaggag  3000
ttcccgccca agagcacgct ggaccccagc aagtacggcg accacaccag cacgatcacg  3060
gcggagcaca tcgagaagaa cctcgagggc ctcacggtgc agcaggcgct ggacggcaac  3120
aggctctaca tcctggacca ccacgaccgc ttcatgccgt tcctcatcga cgtcaacaac  3180
ctggagggca acttcatcta cgccaccagg acgtcttct tcctgcgcgg cgacggcagg  3240
ctcgcgcccc tcgccatcga gctcagcgag ccgtacatcg acggggacct caccgtggcc  3300
aagagcaagg tctacacgcc ggcgtccagc ggcgtcgagg cctgggtgtg gcagctcgcc  3360
aaggcctatg tcgccgtcaa cgactctggc tggcaccaac tcgtcagcca ctggtacgta  3420
cgaagaacta caactactcc tatatatgtc ctatatgaca atggcatcgc atcgtgtcat  3480
gtctatgaca tcgccaaatg catgcgttga tggtcatgat ctattctctc cgtcgtgcta  3540
ggctgaacac ccacgcgtg atggagccgt tcgtgatcgc gacgaaccgg cagctgagcg  3600
tgacgcaccc ggtgcacaag ctcctgagct cgcacttccg cgacaccatg accatcaacg  3660
cgctggcgcg gcagacgctc atcaacgcgg gcggcatctt cgagatgacc gtcttcccgg  3720
gcaagtacgc gctgggcatg tcctccgtgg tgtacaagag ctggaacttc accgagcagg  3780
gcctcccggc cgacctcgtc aagaggggcg tggcggtggc ggacccgtcc agccgtaca   3840
aggtgcggct gctgatcgag gactaccgt acgcgagcga cgggctgcc atctggcacg   3900
ccatcgagca gtgggtgggc gagtacctgg ccatctacta ccccgacgac ggcgcgctgc  3960
ggggcgacga ggagctgcag gcgtggtgga aggaggtgcg cgaggtcggg cacggcgacc  4020
acaaggacgc gcccggtgg cccaagatgc aggccgtcgc agccgcctgca             4080
ccaccatcat ctggatcgcg tcggcgctcc acgccgccgt caacttcggc cagtaccgt   4140
acgcgggta cctcccgaac aggcccacgg tgagccggcg ccggatgccg gagcccggca   4200
gcaaggagta cgaggagctg gagcgcgacc cggagcgcgg cttcatccac accatcacga  4260
gccagatcca gaccatcatc ggcatctcgc tcatcgagat cctctccaag cactcctccg  4320
acgaggtgta cctcggccag cgcgacacc ccgagtggac ctccgacgcc cgggcgctgg   4380
cggcgttcaa gaggttcagc gacgcgctgg tcaagatcga gggcaaggtg gtgggcgaga  4440
accgcgaccg gcagctgagg aacaggaacg gccccgccga gttcccctac atgctgctct  4500
atcccaacac ctctgaccac agtggccgcg cggcagggct cggccaag ggcatcccca    4560
acagcatctc catctgagcg actggtacca ctaccaccc aggagtgcta cgtacgagct   4620
ggtacatgaa taagctaata taagcaatcg tgtaaacggg aagagagcgg ccggcacgag  4680
acggaccatg tattttgcgt aaacgtgtgg gctggtgaat cgaattacta ccacgtaata  4740
agtgaagtgc ttgttgcaat cattggcctg ccagcttcaa gattcttgca gttactattc  4800
t                                                                  4801

SEQ ID NO: 7        moltype = DNA  length = 2595
FEATURE             Location/Qualifiers
source              1..2595
                    mol_type = genomic DNA
                    organism = Zea mays
SEQUENCE: 7
atgctgagcg ggatcatcga cgggctgacg ggggcgaaca agcatgcgcg gctcaagggc   60
acggtggtgc tcatgcgcaa gaacgtgctg gacctcaacg acttcggcgc caccgtcgtt  120
gacagcatca gcgagttcct cggcaagggg gtcacctgcc agctcatcag ctccaccctc  180
gtcgacgcca acaacggcaa ccgcgggcgg gtcggggcg aggcgaacct ggagcagtgg   240
ctgacgacgc tgccgtcgct gacgaccggc gagtccaagt tcggcgtcac gttcgactgg  300
gaggtggaga agctgggagt gccggggcc gtcgtcgtca agaacaacca cgccgccgag   360
ttcttcctca agacaatcac cctcgacgac gtgcccggcc gcggcgccgt caccttcgtc  420
gccaactcct gggtctaccc cgcgggcaag taccgctaca accgcgtctt cttctccaac  480
gatacgtacc tgccaagcca gatgccggcg cgctgaagc cgtaccgcga cgacgagctc   540
cgcaacctcc gcggcgacga ccagcagggg ccctaccagg agcacgaccg cgtgtaccgc  600
tacgacgtct acaacgacct cggcgagccc gacggcggca acccgcgccc catcctcggc  660
ggctccgccg accaccgta cccgcgccg tgccgcacgg gccgcaagcc caccaaaacc    720
gaccccaact cggagagccg actgtcgctg gtggagcaga tctacgtgcc gcgggacgag  780
cgcttcggcc acctcaagat gtccgacttc ctgggctact ccatcaaggc catcacgcag  840
ggcatcatcc cggcggtgcg cacgtacgtg gacaccaccc cgcgcgagtt cgactccttc  900
caggacatca tcaacctgta cgagggcggg atcaagctgc ccaagatcca ggcgctcgag  960
gacatgcgca agctcttccc gctccagctc gtcaaggacc tcctccccgc cggcggggac  1020
tacctgctca agctccccat cccacagatc atccaagagg acaagaacgc gtggaggacc  1080
gacgaggagt tcgcgcggga ggtgctcgcc ggcgtcaacc cgatggtgat cacgcgcctc  1140
acggagttcc cgcccaagag cacgctggac cccagcaagt acggcgacca caccagcacg  1200
```

```
atcacggcgg agcacatcga agaagaacctc gagggcctca cggtgcagca ggcgctggac 1260
ggcaacaggc tctacatcct ggaccaccac gaccgcttca tgccgttcct catcgacgtc 1320
aacaacctgg agggcaactt catctacgcc accaggacgc tcttcttcct gcgcggcgac 1380
ggcaggctcg cgcccctcgc catcgagctc agcgagccgt acatcgacgg gaccctcacc 1440
gtggccaaga gcaaggtcta cacgccggcg tccagcgcg tcgaggcctg ggtgtggcag 1500
ctcgccaagg cctatgtcgc cgtcaacgac tctggctggc accaactcgt cagccactgg 1560
ctgaacaccc acgcggtgat ggagccgttc gtgatcgcga cgaaccggca gctgagcgtg 1620
acgcacccgt gcacaagct cctgagctcg cacttccgcg acaccatgac catcaacgcg 1680
ctggcgcggc agacgctcat caacggcggc ggcatcttcg agatgaccgt cttcccgggc 1740
aagtacgcgc tgggcatgtc ctccgtggtg tacaagagct ggaacttcac cgagcaggcg 1800
ctccccgccg acctcgtcaa gagggcgtg gcggtggcgg acccgtccag cccgtacaag 1860
gtgcggctgc tgatcgagga ctacccgtac gcgagcgacg gctggccat ctggcacgcc 1920
atcgagcagt gggtgggcga gtacctggcc atctactacc ccgacgacgg cgcgctgcgg 1980
ggcgacgagg agctgcaggc gtggtggaag gaggtgcggg aggtcgggca cggcgaccac 2040
aaggacgcgc cctggtggcc caagatgcag gccgtgtcgg agctcgccag cgcctgcacc 2100
accatcatct ggatcgcgtc ggcgctccac gccgccgtca cttcggcca gtacccgtac 2160
gcggggtacc tcccgaacag gcccacggtg agccggcgcc ggatgccgga gcccggcagc 2220
aaggagtacg aggagctgga gcgcgacccg gagccggtcct tcatccacac catcacgagc 2280
cagatccaga ccatcatcgg catctcgctc atcgagatcc tctccaagca ctcctccgac 2340
gaggtgtacc tcggccagcg cgacacccc gagtggacct ccgacgcccg ggcgctggcg 2400
gcgttcaaga ggttcagcga cgcgctggtc aagatcgagg gcaaggtggt gggcgagaac 2460
cgcgacccgc agctgaggaa caggaaccgg cccgccgagt tcccctacat gctgctctat 2520
cccaacacct ctgaccacag tggcgccgcc gcagggctca ctgccaaggg catccccaac 2580
agcatctcca tctga                                              2595

SEQ ID NO: 8        moltype = AA   length = 864
FEATURE             Location/Qualifiers
source              1..864
                    mol_type = protein
                    organism = Zea mays
SEQUENCE: 8
MLSGIIDGLT GANKHARLKG TVVLMRKNVL DLNDFGATVV DSISEFLGKG VTCQLISSTL  60
VDANNGNRGR VGAEANLEQW LTSLPSLTTG ESKFGVTFDW EVEKLGVPGA VVVKNNHAAE 120
FFLKTITLDD VPGRGAVTFV ANSWVYPAGK YRYNRVFFSN DTYLPSQMPA ALKPYRDDEL 180
RNLRGDDQQG PYQEHDRVYR YDVYNDLGEP DGGNPRPILG GSADHPYPRR CRTGRKPTKT 240
DPNSESRLSL VEQIYVPRDE RFGHLKMSDF LGYSIKAITQ GIIPAVRTYV DTTPGEFDSF 300
QDIINLYEGG IKLPKIQALE DMRKLFPLQL VKDLLPAGGD YLLKLPIPQI IQEDKNAWRT 360
DEEFAREVLA GVNPMVITRL TEFPPKSTLD PSKYGDHTST ITAEHIEKNL EGLTVQQALD 420
GNRLYILDHH DRFMPFLIDV NNLEGNFIYA TRTLFFLRGD GRLAPLAIEL SEPYIDGDLT 480
VAKSKVYTPA SSGVEAWVWQ LAKAYVAVND SGWHQLVSHW LNTHAVMEPF VIATNRQLSV 540
THPVHKLLSS HFRDTMTINA LARQTLINGG GIFEMTVFPG KYALGMSSVV YKSWNFTEQG 600
LPADLVKRGV AVADPSSPYK VRLLIEDYPY ASDGLAIWHA IEQWVGEYLA IYYPDDGALR 660
GDEELQAWWK EVREVGHGDH KDAPWWPKMQ AVSELASACT TIIWIASALH AAVNFGQYPY 720
AGYLPNRPTV SRRRMPEPGS KEYEELERDP ERGFIHTITS QIQTIIGISL IEILSKHSSD 780
EVYLGQRDTP EWTSDARALA AFKRFSDALV KIEGKVVGEN RDPQLRNRNG PAEFPYMLLY 840
PNTSDHSGAA AGLTAKGIPN SISI                                    864

SEQ ID NO: 9        moltype = DNA   length = 4150
FEATURE             Location/Qualifiers
source              1..4150
                    mol_type = genomic DNA
                    organism = Zea mays
SEQUENCE: 9
atgctgagcg ggatcatcga cgggctgacg gggcgaacaa agcatgcgcg gctcaagggc   60
acggtggtgc tcatgcgcaa gaacgtgctg gacctcaacg acttcggcgc caccgtcgtt  120
gacagcatca gcgagttcct cggcaagggg gtcacctgcc agctcatcag ctccaccctc  180
gtcgacgcca gtgagtaccg cgccgcgccg cggcacctc tccgatctgc gcttccccat  240
gtcgatcgat ctcgatctct ctaggctcta gagctatagc tctctcggcc cccactttt  300
acctttgcaa gcatttttcc tgcatgcgaa acaagcgata gtttactatt tgggcggcca  360
tgctgctgct gcttcggcta ccttgcctcc gtcatctttg acgggacatg gaaagaaaga  420
aagaatagag agagagacag agagagagag agagcaaaca ccgagaaaaa gacagcaaag  480
ctagttgtag cctgggcgca gaacacagca ccagatgctg gctagctcgt gacaaagtaa  540
aaaaagagag gaacgaacac agtagtacca agagatcagg gacgagacct ttctactttg  600
aactggatta tatattggat tcttatcag taacttactg ctgctagtat accccctaccc  660
tagtctcggt gcgacgtgcc tgcgtgcatg cccgacgcgt acgaaacaca tcgacggact  720
cacatgggcc accgcgcgcg cgcgtgcctg ctttaacttt cgctgtgcag acaacggcaa  780
ccgcggggcg gtcgggcgg aggcgaacct ggagcagtgg ctgacgagcc tgccgtcgct  840
gacgaccggc gagtccaagt tcggcgtcac gttcgactgg gaggtggaga agctgggagt  900
gccggggcg gtcgtcgtca agaacaacca cgccgccgag ttcttcctca gacaatccat  960
cctcgacgac gtgccggcc gcggcgccgt caccttcgtc gccaactcct gggtctaccc 1020
cgcgggcaag taccgctaca accgcgtctt cttctccaac gatgtgagtc ctttctcgat 1080
agatcattat gtttgtttgt ttattggtat catgtagcta gccgccatgt cgtcagttgg 1140
agtgcagtag gtaggaaaaa ggacgacatg ggatgggagt ggttaagaaa atccatgcaa 1200
gtgggacttg tgtaactg gtagtatagc tgaagaatct agctagtagaa tgatcttgta 1260
cgtgaataat gttctgacg ctgatcgctg agggcgaggc atgtgagttc accacgtgag 1320
tagcagcaaa aggaaacaac cttcttcacc cggctatcat ctaacgtatc gccccgggag 1380
aatcaataac tttattaacg agatgacgaa aagtcaaaaa aaaaagtcg tgtgatggcc 1440
atgatagtca gtcaagcaaa tcagcgtcca acacgtgtcc cttatctaca ggtgtaagag 1500
agtagagtct tgtcaatcaa cctgggttgt tttctatctg cgtttaccg tccgtcagtc 1560
```

-continued

```
agtcggccaa catgccacgc tgatctttct gtcttttggt gccgccccga ttccgaacgg   1620
cggcgcagac gtacctgcca agccagatgc cggcggcgct gaagccgtac cgcgacgacg   1680
agctccgcaa cctccgcggc gacgaccagc agggccccta ccaggagcac gaccgcgtgt   1740
accgctacga cgtctacaac gacctcggcg agcccgacgg cggcaacccg cgccccatcc   1800
tcggcgcgctc cgccgagcgc ccgtacccgc gccgctgccg cacgggccgc aagcccacca   1860
agaccggtgc gtgcgccgtg cgcggctctt ctatcttctc ggacgcaaca tttgctgcag   1920
ggcagagagg ttgttgacgc tgacctgtga ccgcatcgca gacccaaact cggagagccg   1980
gctgtcgctg gtggagcaga tctacgtgcc gcgggacgag cgcttcggcc acctcaagat   2040
gtccgacttc ctgggctact ccatcaaggc catcacgcag ggcatcatcc cggcggtgcg   2100
cacgtacgtg gacaccaccc cgggcgagtt cgactccttc caggacatca tcaacctgta   2160
cgagggcggg atcaagctgc ccaagatcca ggcgctcgag gacatgcgca agctcttccc   2220
gctccagctc gtcaaggacc tcctccccgc aggcggggac tacctgctca agctccccat   2280
cccacagatc atccaaggca cgtcagggg cgggccggct gtctggtctg catatata    2340
tgtgctccta tggttaactg actgctacg tttcgcggaa cagaggacaa gaatgcgtgg   2400
aggaccgacg aggagttcgc gcgggaggtg ctcgccggcg tcaacccgat ggtgatcacg   2460
cgcctcacag taagtcactc actttgtgca aaatgcgaga ccagactccc gagacggaac   2520
gtgcctgacg agctcgattt acaggagttc ccgcccaaga gcacgctgga ccccagcaag   2580
tacggcgacc acaccagcac catcacggcg agcacatcga agaagaacct cgagggcctc   2640
acggtgcagc aggcgctgga cggcaacagg ctctacatcc tggaccacca cgaccgcttc   2700
atgccgttcc tcatcgacgt caacaacctg gagggcaact tcatctacgc caccaggacg   2760
ctcttcttcc tgcgcggcga cggcaggctc gcgcccctcg ccatcgagct cagcgagccg   2820
tacatcgacg gggacctcac cgtggccaag agcaaggtct acacgccggc gtccagcggc   2880
gtcgaggcct gggtgtggca gctcgccaag gcctatgtcg ccgtcaacga ctctggctgg   2940
caccaactcg tcagccactg gtacgtacga aagaactaca accactccta tgtcctatat   3000
gacaatggca tcgcatcgtg tcatgtgtcg tgtctatgtc atcgccaaat gcatgcgttt   3060
cctgctcaac cgccgtccgg tgatatgatc tattctctgc gtgcgtgcat gcaggctgaa   3120
cacgcacgcg gtgatggagc cgttcgtgat cgcgacgaac cggcagctga gcgtgacgca   3180
cccggtgcac aagctcctga gctcgcactt ccgcgacacc atgaccatca acgcgctggc   3240
gcggcagacg ctcatcaacg gcggcggcat cttcgagatg accgtcttcc cgggcaagta   3300
cgcgctgggc atgtcctccg tggtgtacaa gagctggaac ttcaccgagc agggcctccc   3360
cgccgacctc gtcaagaggg gcgtggcggt ggcggacccg tccagcccgt acaaggtgcc   3420
gctgctgatc gaggactacc cgtacgcgag cgacgggctg gccatctggc acgccatcga   3480
gcagtggtg ggcgagtacc tggccatcta ctaccccgac gacggcgcgc tgcggggcga   3540
cgaggagctg caggcgtggt ggaaggaggt gcgcgaggtc gggcacggcg accacaagga   3600
cgccgcctgg tggcccaaga tgcaggccgt gtccgagctc gccacgcct gcaccaccat   3660
catctggatc gcgtcggcgc tccacgccgc cgtcaacttc ggccagtacc cgtacgcggg   3720
gtacctcccg aacaggccca cggtgagccg cgccggatg ccggagcccg gcagcaagga   3780
gtacgaggag ctggagcgcg acccggagcg cgccttcatc cacaccatca cgagccagat   3840
ccagaccatc atcggcatct cgctcatcga gatcctctcc aagcactcct ccgacgagt   3900
gtacctcggc cagcgcgaca cccccgagtg gacctccgac gccgggcgc tggcggcgtt   3960
caagaggttc agcgacgcgc tggtcaagat cgagggcaag gtggtgggcg agaaccgcga   4020
cccgcagctg aggaacagga acggccccgc cgagttcccc tacatgctgc tctacccaa   4080
cacctctgac cacagtggcg ccgccgcagg gctcactgcc aagggcatcc ccaacagcat   4140
ctccatctga                                                         4150

SEQ ID NO: 10           moltype = DNA  length = 2595
FEATURE                 Location/Qualifiers
source                  1..2595
                        mol_type = genomic DNA
                        organism = Zea mays
SEQUENCE: 10
atgctgagcg ggatcatcga cgggctgacg ggggcgaaca agcatgcgcg gctcaagggc    60
acggtggtgc tcatgcgcaa gaacgtgctg gacctcaacg acttcggcgc caccgtcgtt   120
gacagcatca gcgagttcct cggcaagggg gtcacctgcc agctcatcag ctccaccctc   180
gtcgacgcca acaacggcaa ccgcgggcg gtcggggcgg aggcgaacct ggagcagtgg   240
ctgacgagcc tgccgtcgct gacgaccggc gagtccaagt tcggcgtcac gttcgactgg   300
gaggtggaga agctgggagt gccggggcc gtcgtcgtca agaacaacca cgccgccgag   360
ttcttcctca agacaatcac cctcgacgac gtgcccggcc gcggcgccgt caccttcgtc   420
gccaactcct gggtctaccc cgcgggcaag taccgctaca accgcgtctt cttctccaac   480
gatacgtacc tgccaagcca gatgccgcg gcgctgaagc cgtaccgcga cgacgagctc   540
cgcaacctcc gcggcgacga ccagcagggc cctaccagg agcacgaccg cgtgtaccgc   600
tacgacgtct acaacgacct cggcgagccc gacggcggca acccgcgccc catcctcggc   660
ggctccgccg agcacccgta cccgcgccgc tgccgcacgg gccgcaagcc caccaagacc   720
gaccccaact cggagagccg gctgtcgctg gtggagcaga tctacgtgcc gcgggacgag   780
cgcttcggcc acctcaagat gtccgacttc ctgggctact ccatcaaggc catcacgcag   840
ggcatcatcc cggcggtgcg cacgtacgtg gacaccaccc cgggcgagtt cgactccttc   900
caggacatca tcaacctgta cgaggcggg atcaagctgc ccaagatcca ggcgctcgag   960
gacatgcgca agctcttccc gctccagctc gtcaaggacc tcctccccgc aggcggggac  1020
tacctgctca agctccccat cccacagatc atccaaggca caacaaatgc gtggaggacc  1080
gacgaggagt tcgcgcggga ggtgctcgcc ggcgtcaacc cgatggtgat cacgcgcctc  1140
acagagttcc cgcccaagag cacgctggac cccagcaagt acggcgacca ccagcacc   1200
atcacgcgcg agcacatcga agaagaacctc gagggcctca cggtgcagca ggcgctggac  1260
ggcaacaggc tctacatcct ggaccaccac gaccgcttct gccgttcct catcgacgtc   1320
aacaacctgg agggcaactt catctacgcc accaggacgc tcttcttcct gcgcggcga   1380
ggcaggctcg cgcccctcgc catcgagctc agcgagccgt acatcgacgg ggacctcacc   1440
gtggccaaga gcaaggtcta cacgccggcg tccagcggcg tcgaggcctg ggtgtggcag   1500
ctcgccaagg cctatgtcgc cgtcaacgac tctggctggc accaactcgt cagccactgg   1560
ctgaacacgc acgcggtgat ggagccgttc gtgatcgcga cgaaccggca gctgagcgtg   1620
acgcacccgt gcacaagct cctgagctcg cacttccgcg acaccatgac catcaacgcg   1680
```

```
ctggcgcggc agacgctcat caacggcggc ggcatcttcg agatgaccgt cttcccgggc    1740
aagtacgcgc tgggcatgtc ctccgtggtg tacaagagct ggaacttcac cgagcagggc    1800
ctccccgccg acctcgtcaa gaggggcgtg gcggtggcgg acccgtccag cccgtacaag    1860
gtgcggctgc tgatcgagga ctacccgtac gcgagcgacg gctggccat ctggcacgcc     1920
atcgacagt gggtgggcga gtacctggcc atctactacc ccgacgacgg cgcgctgcgg    1980
ggcgacgagg agctgcaggc gtggtggaag gaggtgcgcg aggtcgggca cggcgaccac    2040
aaggacgcgc cctggtggcc caagatgcag gccgtgtcgg agctgccag cgcctgcacc     2100
accatcatct ggatcgcgtc ggcgctccac gccgccgtca acttcggcca gtacccgtac    2160
gcggggtacc tcccgaacag gcccacggtg agccggcgcc ggatgccgga gcccggcagc    2220
aaggagtacg aggagctgga gcgcgacccg gagccgcgcc tcatccacac catcacgagc    2280
cagatccaga ccatcatcgg catctcgctc atcgagatcc tctccaagca ctcctccgac    2340
gaggtgtacc tcgccagcg cgacaccccc gagtggacct ccgacgcccg gcgctggcg     2400
gcgttcaaga ggttcagcga cgcgctggtc aagatcgagg caaggtggt gggcgagaac    2460
cgcgacccgc agctgaggaa caggaacggc cccgccgagt cccctacat gctgctctac    2520
cccaacacct ctgaccacag tggcgccgcc gcagggctca ctgccaaggg catccccaac    2580
agcatctcca tctga                                                     2595

SEQ ID NO: 11          moltype = AA  length = 864
FEATURE                Location/Qualifiers
source                 1..864
                       mol_type = protein
                       organism = Zea mays
SEQUENCE: 11
MLSGIIDGLT GANKHARLKG TVVLMRKNVL DLNDFGATVV DSISEFLGKG VTCQLISSTL    60
VDANNGNRGR VGAEANLEQW LTSLPSLTTG ESKFGVTFDW EVEKLGVPGA VVVKNNHAAE   120
FFLKTITLDD VPGRGAVTFV ANSWVYPAGK YRYNRVFFSN DTYLPSQMPA ALKPYRDDEL   180
RNLRGDDQQG PYQEHDRVYR YDVYNDLGEP DGGNPRPILG GSAEHPYPRR CRTGRKPTKT   240
DPNSESRLSL VEQIYVPRDE RFGHLKMSDF LGYSIKAITQ GIIPAVRTYV DTTPGEFDSF   300
QDIINLYEGG IKLPKIQALE DMRKLFPLQL VKDLLPAGGD YLLKLPIPQI IQEDKNAWRT   360
DEEFAREVLA GVNPMVITRL TEFPPKSTLD PSKYGDHTST ITAEHIEKNL EGLTVQQALD   420
GNRLYILDHH DRFMPFLIDV NNLEGNFIYA TRTLFFLRGD GRLAPLAIEL SEPYIDGDLT   480
VAKSKVYTPA SSGVEAWVWQ LAKAYVAVND SGWHQLVSHW LNTHAVMEPF VIATNRQLSV   540
THPVHKLLSS HFRDTMTINA LARQTLINGG GIFEMTVFPG KYALGMSSVV YKSWNFTEQG   600
LPADVLKRGV AVADPSSPYK VRLLIEDYPY ASDGLAIWHA IYYPDDGALR              660
GDEELQAWWK EVREVGHGDH KDAPWWPKMQ AVSELASACT TIIWIASALH AAVNFGQYPY   720
AGYLPNRPTV SRRRMPEPGS KEYEELERDP ERAFIHTITS QIQTIIGISL IEILSKHSSD   780
EVYLGQRDTP EWTSDARALA AFKRFSDALV KIEGKVVGEN RDPQLRNRNG PAEFPYMLLY   840
PNTSDHSGAA AGLTAKGIPN SISI                                         864

SEQ ID NO: 12          moltype = DNA  length = 4108
FEATURE                Location/Qualifiers
misc_feature           378..388
                       note = n is a, c, g, or t
source                 1..4108
                       mol_type = genomic DNA
                       organism = Zea mays
SEQUENCE: 12
atgctgagcg ggatcatcga cgggctgacg gggcgaaaca agcatgcgcg gctcaagggc     60
acggtggtgc tcatgcgcaa gaacgtgctg gacctcaacg acttcggcgc caccgtcgtt    120
gacagcatca gcgagttcct cggcaagggg gtcacctgcc agctcatcag ctccaccctc    180
gtcgacgcca gtaatggaag ccgccgaccg ccggcacctc tccgatctgc gcttcccgat    240
gtcgatcgat ctcgatctct ctaggctcta gagctatagc tctctcggcc cccactttt    300
accttttgcaa gcattttccc tgcatgcgaa acaagcgata gtttactatt tgggcggcca    360
tgctgctgct gcttcggnnn nnnnnnnnaa tagagagaga gacagagaga gagagagaga    420
gagagagcaa acaccgagaa aaagacagca aagctagttg tagcctgggc gcagaacaca    480
gcaccagatg ctggctagct cgtgacaaag taaaaaaaga gaggaacgaa cacagtagta    540
ccaagagatc agggacgaga cctttctact ttgaactgga ttatatattg gattcttat     600
cagtaactta ctgctgctag tatacccta ccctagtctc ggggcgacgt gcctgcgtgc     660
atgcccgacg cgtacgaaac acatcacgg actcacatgg gccaccgcgc gcgcgcgtgc     720
ctgctttaac tttcgctgtg cagacaacgg caaccgtcgg cgggtcgggg cggaggcgaa    780
cctggagcag tggctgacga gcctgccgtc gctgacgacc ggcgagtcca agttcggcgt    840
cacgttcgac tgggaggtgg agaagctggg agtgccgggg gccgtcgtcg tcaagaacaa    900
ccacgccgcc gagttcttcc tcaagacaat caccctcgac gacgtgcccg gccgcggcgc    960
cgtcaccttc gtcgccaact cctgggtcta cccccgcggc aagtaccgct acaaccgcgt   1020
cttcttctcc aacgatgtga gtccttctc gatagatcat tatgtttgtt tgtttattgg   1080
tatcatgtag ctagccgcca tgtcgtcagt tggagtgcag taggtaggaa aaaggacgac   1140
atgggatggg agtggttaag aaaatccatg caagtggac tagtgtgtaa ctggtagtat   1200
agctgaagaa tctagtggta gaatgatctt gtactgtaat aatgttttct acgctgagcg   1260
ctgagggcga gcatgtgag ttcaccacgt gagtacgac aaaaggaaac gacccttctt    1320
caccccggcta tcatctaacg tatcgccccg ggagaatcaa taactttaac gagatgacga   1380
aaagtcaaaa ataaagtcgt gtgatggcca tgaaagtcag tcaagcaaat cagctgctaa   1440
cacgtgtccc ttatctacag gtgtaagagt agagtcttgt caatcaacct gggttgtttt   1500
ctatctgcgt tttaccgtcc gtcagtcagt cggccaacta gccacgctga tctttctgtc   1560
ttttggtgcc tcccgattc cgaacgcggg cacggcgata cctgccaagc cagatgccgg   1620
cggcgctgaa gccgtaccgc gacgacgagc tccgcaacct ccggcgggac gaccagcagg   1680
gccctacca ggagcacgac cgcgtgtacc gctacgacgt ctacaacgac ctcggcgagc   1740
ccgacgcggc caacccgcgc ccatcctcg gggctccgc cgaccacccg tacccgcgcc   1800
gctgccgcac gggccgcaag cccaccaaaa ccggtgcgtg cgccgtgcgc ggctcttcta   1860
tcttctcgga cgcaacattt gctgcagggc agagaggttg ttgacgctga cctgtgaccg   1920
```

```
catcgcagac cccaactcgg agagccgact gtcgctggtg gagcagatct acgtgccgcg    1980
ggacgagcgc ttcggccacc tcaagatgtc cgacttcctg ggctactcca tcaaggccat    2040
cacgcagggc atcatcccgg cggtgcgcac gtacgtggac accaccccgg gcgagttcga    2100
ctccttccag gacatcatca acctgtacga gggcgggatc aagctgccca agatccaggc    2160
gctcgaggac atgcgcaagc tcttcccgct ccagtcgtc aaggacctcc tccccgccgg    2220
cggggactac ctgctcaagc tcccatccc acagatcatc caaggcacgt cacgtatacc    2280
gatcgatgtc aggggccggc tgttgtctgg tctgcatata tatatgtgct cctatggtta    2340
actgtgactg cgtacgtttc gcggaacaga ggacaagaac gcgtggagga ccgacgagga    2400
gttcgcgcgg gaggtgctcg ccggcgtcaa cccgatggtg atcacgcgcc tcacggtgag    2460
tcactcactt tgtgcaaaat gcgagacccg acccgaccag gaatgtgcct gacgcgtccg    2520
atttacagga gttcccgccc aagagcacgc tggaccccag caagtacggc gaccacacca    2580
gcacgatcac ggcggagcac atcgagaaga acctcgaggg cctcacggtg cagcaggcgc    2640
tggacgccaa caggctctac atcctggacc accacgaccg cttcatgccg ttcctcatcg    2700
acgtcaacaa cctggagggc aacttcatct acgccaccag acgctcttc ttcctgccgg    2760
gcgacggcag gctcgcgccc ctcgccatcg agctcagcga gccgtacatc gacgggacc    2820
tcaccgtggc caagagcaag gtctacacgc cggcgtccag cggcgtcgag gctgggtgt    2880
ggcagctcgc caaggcctat gtcgccgtca acgactctgg ctggcaccaa ctcgtcagcc    2940
actggtacgt acgaagaact acaactactc ctatatatgt cctatatgac aatgccatcg    3000
catcgtgtca tgtctatgac atcgccaaat gcatgcgttg atggtcatga tctattctct    3060
gcgtgcgtgc aggctgaaca cccacgcggt gatggagccg ttcgtgatcg cgacgaaccg    3120
gcagctgagc gtgacgcacc cggtgcacaa gctcctgagc tcgcacttcc gcgacaccat    3180
gaccatcaac gcgctggcgc ggcgagcact catcaacgcg ctcatcaagc tctcgagatgac    3240
cgtcttcccg ggcaagtacg cgctgggcat gtcctccgtg gtgtacaaga gctgaacttt    3300
caccgagcag ggcctccccg ccgacctcgt caagaggggc gtggcggtgg cggacccgtc    3360
cagcccgtac aaggtgcggc tgctgatcga ggactacccg tacgcgagcg acgggctggc    3420
catctggcac gccatcgagc agtgggtggg cgagtacctg gccatctact accccgacga    3480
cggcgcgctg cggggcgacg aggagctgca ggcgtggtgg aaggaggtgc gcgaggtcgg    3540
gcacggcgac cacaaggacg cgccctggtg gcccaagatg caggccgtgt cggagctcgc    3600
cagcgcctgc accaccatca tctggatcgc gtcggcgctc cacgccgccg tcaacttcgg    3660
ccagtacccg tacgcggggt acctcccgaa caggcccacg gtgagccgcc gccgatgcc    3720
ggagcccggc agcaaggagt acgaggagct ggagcgcgac ccggagcgcg ccttcatcca    3780
caccatcacg agccagatcc agaccatcat cggcatctcg ctcatcgaga tcctctccaa    3840
gcactcctcc gacgaggtgt acctcggcca gcgcgacacc cccgagtgga cctccgacgc    3900
ccggggcgctg gcggcgttca agaggttcag cgacgcgctg gtcaagatcg agggcaaggt    3960
ggtgggcgag aaccgcgacc cgcagctgag gaacaggaac ggccccgccg agttccccta    4020
catgctgctc tacccccaaca cctctgacca cagtggcgcc ccgcagggc tcactgccaa    4080
gggcatcccc aacagcatct ccatctga                                      4108
```

```
SEQ ID NO: 13            moltype = DNA   length = 2595
FEATURE                  Location/Qualifiers
source                   1..2595
                         mol_type = genomic DNA
                         organism = Zea mays
SEQUENCE: 13
atgctgagcg ggatcatcga cgggctgacg ggggcgaaca agcatgcgcg gctcaagggc      60
acggtggtgc tcatgcgcaa gaacgtgctg gacctcaacg acttcggcgc caccgtcgtt    120
gacagcatca gcgagttcct cggcaagggg gtcacctgcc agctcatcag ctccaccctc    180
gtcgacgcca acaacggcaa ccgcggggcg gtcgggcgg aggcgaacct ggagcagtgg    240
ctgacgagcc tgccgtcgct gacgaccgga gagtccaagt cggcgtcac gttcgactgg    300
gaggtggaga agctgggagt gccgggggcc gtcgtcgtca agaacaacca cgccgccgag    360
ttcttcctca agacaatcac cctcgacgac gtgcccggcc gcggcgccgt caccttcgtg    420
gccaactcct gggtctaccc cgcgggcaag taccgctaca accgcgtctt cttctccaac    480
gatacgtacc tgccaagcca gatgccgcgc gcgctgaagc cgtaccgcga cgacgagctc    540
cgcaacctcc gcggcgacga ccagcagggc cctaccagg agcacgaccg cgtgtaccgc    600
tacgacgtct acaacgaccc tggcgagccc gacggcgcgca acccgccgtc catcctcggc    660
ggctccgccg accacccgta cccgcgccgc tgccgcacgg gccgcaagcc caccaaaacc    720
gaccccaact cggagagccg actgtcgctg gtggagcaga tctacgtgcc gcgggacgag    780
cgcttcggcc acctcaagat gtccgacttc ctgggctact ccatcaaggc catcacgcag    840
ggcatcatcc cggcggtgcg cacgtacgtg gacaccaccc cgggcgagtt cgactccttc    900
caggacatca tcaacctgta cgaggggcgg atcaagctgc ccaagatcca ggcgctcgag    960
gacatgcgca agctcttccc gctccagtc gtcaaggacc tcctccccgc cggcggggac    1020
tacctgctca agctccccat cccacagatc atccaagagg acaagaacgc gtggaggacc    1080
gacgaggagt tcgcgcggga ggtgctcgcc ggcgtcaagt cgatggtgat cacgcgcctc    1140
acggagttcc cgcccaagag cacgctggac cccagcaagt acggcgacca cacgccgccg    1200
atcacgcgcg ggcacatcga gaagaacctc gagggcctca cggtgcagca ggcgctggac    1260
gccaacaggc tctacatcct ggaccaccac gaccgcttca tgccgttcct catcgacgtc    1320
aacaacctgg agggcaactt catctacgcc accaggacgc tcttcttcct gcgcggcgac    1380
ggcaggctcg cgcccctcgc catcgagctc agcgagccgt acatcgacgg ggaccgtcacc    1440
gtggccaaga gcaaggtcta cacgccggcg tccagcggcg tcgaggctgt ggtgtggcag    1500
ctcgccaagg cctatgtcgc cgtcaacgac tctggcggc accaactcgt cagccactgg    1560
ctgaacaccc acgcggtgat ggagccgttc gtgatcgcga cgaaccggca gctgagcgtg    1620
acgcacccgt gcacaagct cctgagctcg cacttccgcg acaccatgac catcaacgcg    1680
ctggcgcggg agacgctcat caacgcggc ggcatcttcg agatgaccgt cttcccgggc    1740
aagtacgcgc tgggcatgtc ctccgtggtg tacaagagct gaacttcac cgagcagggc    1800
ctcccgccgc acctcgtcaa gaggggcgtg gcggtggcgg accgtccag cccgtacaag    1860
gtgcggctgc tgatcgagga ctacccgtac gcgagcgacg gcctggccat ctggcacgcc    1920
atcgagcagt gggtgggcga gtacctggcc atctactacc ccgacgacgg cgcgctgcgg    1980
ggcgacgagg agctgcaggc gtggtggaag gaggtgcgca ggtcgggca cggcgaccac    2040
aaggacgcgc cctggtggcc caagatgcag gccgtgtcgg agctcgccag cgcctgcacc    2100
```

```
accatcatct ggatcgcgtc ggcgctccac gccgccgtca acttcggcca gtacccgtac   2160
gcggggtacc tcccgaacag gcccacggtg agccggcgcc ggatgccgga gcccggcagc   2220
aaggagtacg aggagctgga gcgcgacccg gagcgcgcct tcatccacac catcacgagc   2280
cagatccaga ccatcatcgg catctcgctc atcgagatcc tctccaagca ctcctccgac   2340
gaggtgtacc tcggccagcg cgacaccccc gagtggacct ccgacgcccg ggcgctggcg   2400
gcgttcaaga ggttcagcga cgcgctggtc aagatcgagg gcaaggtggt ggggcgagaac   2460
cgcgacccgc agctgaggaa caggaacggc cccgccgagt tcccctacat gctgctctac   2520
cccaacacct ctgaccacag tggcgccgcc gcagggctca ctgccaaggg catccccaac   2580
agcatctcca tctga                                                    2595

SEQ ID NO: 14          moltype = AA   length = 864
FEATURE                Location/Qualifiers
source                 1..864
                       mol_type = protein
                       organism = Zea mays
SEQUENCE: 14
MLSGIIDGLT GANKHARLKG TVVLMRKNVL DLNDFGATVV DSISEFLGKG VTCQLISSTL    60
VDANNGNRGR VGAEANLEQW LTSLPSLTTG ESKFGVTFDW EVEKLGVPGA VVVKNNHAAE   120
FFLKTITLDD VPGRGAVTFV ANSWVYPAGK YRYNRVFFSN DTYLPSQMPA ALKPYRDDEL   180
RNLRGDDQQG PYQEHDRVYR YDVYNDLGEP DGGNPRPILG GSADHPYPRR CRTGRKPTKT   240
DPNSESRLSL VEQIYVPRDE RFGHLKMSDF LGYSIKAITQ GIIPAVRTYV DTTPGEFDSF   300
QDIINLYEGG IKLPKIQALE DMRKLFPLQL VKDLLPAGGD YLLKLPIPQI IQEDKNAWRT   360
DEEFAREVLA GVNPMVITRL TEFPPKSTLD PSKYGDHTST ITAEHIEKNL EGLTVQQALD   420
ANRLYILDHH DRFMPFLIDV NNLEGNFIYA TRTLFFLRGD GRLAPLAIEL SEPYIDGDLT   480
VAKSKVYTPA SSGVEAWVWQ LAKAYVAVND SGWHQLVSHW LNTHAVMEPF VIATNRQLSV   540
THPVHKLLSS HFRDTMTINA LARQTLINGG GIFEMTVFPG KYALGMSSVV YKSWNFTEQG   600
LPADLVKRGV AVADPSSPYK VRLLIEDYPY ASDGLAIWHA IEQWVGEYLA IYYPDDGALR   660
GDEELQAWWK EVREVGHGDH KDAPWWPKMQ AVSELASACT TIIWIASALH AAVNFGQYPY   720
AGYLPNRPTV SRRRMPEPGS KEYEELERDP ERAFIHTITS QIQTIIGISL IEILSKHSSD   780
EVYLGQRDTP EWTSDARALA AFKRFSDALV KIEGKVVGEN RDPQLRNRNG PAEFPYMLLY   840
PNTSDHSGAA AGLTAKGIPN SISI                                          864

SEQ ID NO: 15          moltype = DNA   length = 20683
FEATURE                Location/Qualifiers
misc_feature           11321..11676
                       note = n is a, c, g, or t
misc_feature           13711..13986
                       note = n is a, c, g, or t
misc_feature           14689..14733
                       note = n is a, c, g, or t
misc_feature           15101..15387
                       note = n is a, c, g, or t
misc_feature           15987..16486
                       note = n is a, c, g, or t
misc_feature           17031..17530
                       note = n is a, c, g, or t
source                 1..20683
                       mol_type = genomic DNA
                       organism = Zea mays
SEQUENCE: 15
atgctgagcg ggatcatcga cgggctgacg gggcgaaca agcatgcgcg gctcaagggc      60
acggtggtgc tcatgcgcaa gaacgtgctg gacctcaacg acttcggcgc caccgtcgtc   120
gacagcatca gcgagttcct cggcaagggg gtcacctgcc agctcatcag ctccactctc   180
gtcgacgcca gtgagtaccg cgccgccggc acctctccga tctgcgtgcg cttccccatg   240
tcgatcgatc tcgatctctc taggctctag agctatagct ctctcggccg ccactttta    300
cctttgcaag catttccccc ccgcatgcga aacaagcaaa taagcgatag tatactattt   360
gggcggccat gctgctgctt cggctaccctt gcctccgtcg tctttgacgg gacatggaaa   420
gaaagaaaga atagcgagag agagacagag acagcgagag agagagatag agcaaacacc   480
gagaaaaaga cagcaaagct agttgtagcc tgggcgcaga gcacagcacc agatgctggc   540
tagctcgtga caaagtaaaa aaaggaacga acacagtagt gccaagagat caggagcgag   600
accttttctac tttgaactgg attatatatt ggattcttta tcagtaactt actgctgcta   660
gtatacccct accctagtct cggggcgacg tgcctgcgtg catgcccgac gcgtacgaaa   720
cacatcgacg gactcacatg ggccaccgcg cgcgcgcgtg cctgctttaa ctttcgctgt   780
gcagacaacg gcaaccgcgg gcgggtcggg gcggaggcga acctggagca gtggctgacg   840
agcctgccgt cgctgacgac cggcgagtcc aagttcggcg tcacgttcga ctgggaggtg   900
gagaagctgg gagtgccggg ggccgtcgtc gtcaagaaca accacgccgc cgagttcttc   960
ctcaagacaa tcaccctcga cgacgtgccc ggccgcggcg ccgtcacctt cgtcgccaac  1020
tcctgggtct acccccgcggg caagtaccgc tacaaccgcg tcttcttctc caacgatagg  1080
agtcctttct cgatagatca ttatgttgtt ttgttatttt gtttcttggt atcatgtagg  1140
catgtagcta gccgccatgt cgtcagttgg agtgcagtag gtaggaaaaa ggacgacatg  1200
ggatgggagt ggttaagaaa atccatgcaa gtgggactag tgtgtaactg gtagtatagc  1260
tgaagaatct agtggtagaa tgatcttgta cgtgaataat gtttctgacg ctgagcgctg  1320
aggctatccg caaccgttaa ccctaaattt tcccttctat atcattttttt cctctatttt  1380
cctccctatt ttttcatctc ccgcagcggt tccccctaaa tactcccccct atatccactt  1440
accactataa aatattattt tctataccaa ttatcaattt tttatctact aacaattact  1500
cgtggaccca cagcacagtg tttagggtga tgaacagtga cacgctagat ctgaaggggag  1560
agagaagggg accgacacgt agggagcctg tagagggcac cgctgcggcc gtagggtgct  1620
ccctacgcgc gcgcatacaag gggagggggg agaggcagcg gtaaccgctg cgcacagcct  1680
gagggcgagg catgtgagtt caccacgtga gtagcagcaa aaggaaacaa cccttcttca  1740
```

```
cccggctatc atctaacgta tcgccccggg agaatcaata actctaacga gatgacgaaa   1800
agtcaaaaat aaagtcgtgt gatgccatg  aaagtcagtc aagcaaatca gctgctaaca   1860
cgtgtccctt atctacaggt gtaagagagt agagtcttgt caatcaacct gggttgtttt   1920
ctatctgcgt tttaccgtcc gtcagtcagt cggccaacat gccacgctga tctttctgtc   1980
ttttggtgcc gccccgattc cgaacggcgg cgcagacgta cctgccaagc cagatgccgg   2040
cggcgctgaa gccgtaccgc gacgacgagc tccgcaacct ccgcggcgac gaccagcagg   2100
gcccctacca ggagcacgac cgcgtgtacc gctacgacgt ctacaacgac ctcggcgagc   2160
ccgacgcgg  caacccgcgc cccatcctcg gcggctccgc cgaccacccg tacccgcgcc   2220
gctgccgcac gggccgcaag cccaccaaaa ccggtgcgtg cgccgtgcgc ggctcttcta   2280
tcttctcgga cgcaacattt gctgcagggc agagaggttg ttgacgctga cctgtgaccg   2340
catcgcagac cccaactcgg agagccgact gtcgctggtg gagcagatct acgtgccgcg   2400
ggacgagcgc ttcggccacc tcaagatgtc cgacttcctg ggctactcca tcaaggccat   2460
cacgcagggc atcatcccgg cggtgcgcac gtacgtggac accaccccgg gcgagttcga   2520
ctccttccag gacatcatca acctgtacga gggcgggatc aagctgccca agatccgagc   2580
gctcgaggac atgcgcaagc tcttcccgct ccagctcgtc aaggacctcc tcccgccgg    2640
cggggactac ctgctcaagc tccccatccc acagatcatc caaggcacgt cacgtatacc   2700
gatcgatgtc aggggccggc tgttgtctgg tctgcatata tatatgtgct cctatggtta   2760
actgtgactg cgtacgtttc gcggaacaga ggacaagaac gcgtggagga ccgacgagga   2820
gttcgcgcgg gaggtgctcg ccggcgtcaa cccgatggtg atcacgcgcc tcacggtgag   2880
tcactcactt tgtgcaaaat gcgagacccg acccgagacg gaatgtgcct gacgcgctcg   2940
atttacagga gttcccgccc aagagcacgc tggaccccag caagtacggc gaccacacca   3000
gcacgactac ggcggagcac atcgagaaga acctcgacgt gcctcacggt gcagcaggcg   3060
tggacggcaa caggctctac atcctggacc accacgaccg cttcatgccg ttcctcatcg   3120
acgtcaacaa cctggagggc aacttcatct acgccaccag gacgctcttc ttcctgcgcg   3180
gcgacggcag gctcgcgccc ctcgccatcg agctcagcga gccgtacatc gacggggacc   3240
tcaccgtggc caagagcaag gtctacacgc cggcgtccag ggcgtcgagg gctgggtgt    3300
ggcagctcgc caaggccatt gtcgccgtca acgactctgg ctggcaccaa tcgtcagcc    3360
actggtacgt acgaagaact acaactactc ctatatatgt cctatatgac aatggcatcg   3420
catcgtgtca tgtctatgac atcgccaaat gcatgcgttg atggtcatga tctattctct   3480
gcgtcgctgc aggctgaaca cccacgcggt gatggagccg ttcgtgatcg cgacgaaccg   3540
gcagctgagc gtgacgcacc cggtgcacaa gctcctgagc tcgcacttcc gcgacaccat   3600
gaccatcaac gcgctggcgc ggcagacgct catcaacggc ggcggcatct tcgagatgac   3660
cgtcttcccg ggcaagtacg cgctgggcat gtcctccgtg gtgtacaaga gctggaactt   3720
caccgagcag ggcctccccg ccgacctcgt caagaggggc gtggcggtgg cggacccgtc   3780
cagcccgtac aaggtgcggc tgctgatcga ggactacccg tacgcgagcg acgggctggc   3840
catctggcac gccatcgagc agtgggtggg cgagtacctg gccatctact accccgacga   3900
cggcgcgctg cggggcgacg aggagctgca ggcgtggtgg aaggaggtgc gcgaggtcgg   3960
gcacggcgac cacaaggacg cgccctggtg gcccaagatg caggccgtgt cggagctcgc   4020
cagcgcctgc accaccatca tctgggatcgc gtcggccgtc cacgccgccg tcaacttcgg   4080
ccagtacccg tacgcggggt acctcccgaa caggcccacg gtgagccggc gccggatgcc   4140
ggagcccggc agcaagggag tacgaggagct ggagcgcgac ccgagcgcg  gcttcatcca   4200
caccatcacg agccagatcc agaccatcat cggcatctcg ctcatcgaga tcctctccaa   4260
gcactcctcc gacgaggtgt acctcggcca cgcgcgacacc ccgagtgga cctccgacgc   4320
ccggcgctg  gcggcgttca agaggttcag cgacgcgctg gtcaagatcg agggcaaggt   4380
ggtgggcgag aaccgcgacc gcagctgag  gaacaggaac ggccccgccg agttcccccta  4440
catgctgctc tatcccaaca cctctgacca cagtggcgcc gccgcagggc tcactgccaa   4500
gggcatcccc aacagcatct ccatctgagc gactggtacc actaccaccc caggagtgct   4560
acgtacgagc tggtacatga ataagctaat ataagcaatc gtgtaaacgg aagagagcc    4620
gccggcacga gacggaccat gtattttgcg taaacgtgtg ggctggtgaa tcgaattact   4680
accacgtaat aagtgaagtg cttgttcaa  tcattggcct gccagcttca agattcttgc   4740
agttactatt ctagtcgttt cgcagtgctc ctcgatcaca catttcacg aggtgtttta    4800
ttacaataat ttggagctat tcaatttcaa agcctatgta gaatactata tgttgtaggg   4860
acattagtcc cacatagcta accaaaaata aaatttaatc gatttaaata tcaacggtcc   4920
agtggtcatc tattaagatt atgctcaaca gaccatgcat gcatatgttg tgtaagatta   4980
tgacaacatt atttagaggt gtcttgataa gtgtccttgc cgaaaacata gtggattctt   5040
atatgcttt  gttcactgcc aaagagttgt ggaatacgac aatcattgcg aaaaagggtg   5100
gcatcaaagt ttgccactgg acacagcgga aaccaccaag gaacgataac tggttttcca   5160
aagcagtgga ctcgccccca aaataatcag agaactcagg gcagtggaaa ctgctgacct   5220
caaggtggta ctagcagacg cctttataaa gaaccgtag  atgcaatctt ctggagagag   5280
agagagagaa aaaaaaaaga agaagttgct agatgaatc  gtgcaaatct tcacctaatg   5340
gcgactgcta ccaccgaata aaaagaagt gcaaatcttc acctagacgt tctcagaaac    5400
ggcaccatgc tgcagctgcg atacgaacca ggctggggcg gcaggtgaag ctgacacggt   5460
gccgctgctg caccgggcga ataaataata gtactgacaa taatgctaaa ttagaatgga   5520
acagacgaca tgattagaat gatatgtctc cctttgttcc acgtgtttg                5580
gtgaagccgt gccctagtata aactatata  tactacgttg gtacagcact aaattccctt   5640
ttccccattt tcagtggttg gcctttccca ttctgatcgg cccaaagcag cgcttttagca  5700
attgactaat ccgtcgacct ttggcgccta gcctttccta tgggcatgtt tcctatggtt   5760
gcaaattcca tctaaggcgc atccaaatcg tacaaagaca gtagatgagc tgtccgtcct   5820
tcctcctctc tagctgctgg cgggcgggt  gcacttggtg atgtcgatta gttttagttt   5880
tatggcctat ttggttcagt ctgccaggca aagaatccta accctaggca ctcaaaataa   5940
gataatcata gtatcttaag cttgattaaa tctataaaat gaaaaaaaaa acaataactt   6000
ttgtaccatt agatcctttt attagttatg tctttatagt ataccatttt gatgtcataa   6060
atctctataa atatttttta taactctaat caaaattgag atatttgggc tctaaaaaa    6120
ctaggataat ttataattca gtttgaaaag tacaagaaga taactaaact agaagagaaa   6180
gacaattttcc aaaaacgtac cgtggacgta cgtttcgatg ctcgttacga tgtggacgct   6240
ttatttgcaa atgtttcacg tgcggtacg  cgttcacgta ccataagctc tatggatata   6300
atagtataat caggcccgtt taccatgtct cctgccgcct tcgactcctt tttatttttag  6360
cgtactgtac tttgaacgga ttaggagcta agcgaagcta caatttagct tgtataaacc   6420
tgcagccgtg tcaaactgta ctagtcaaaa gtcaaaagaa cagttccagc gcgagcaata   6480
```

```
tggccgctgc cctcctctca acgttctgct tttggacttg tgtgatgttt ggttcgtata      6540
tttaggggat aagtaactga taatgttaaa ctatatttgt ttaaattaac tgtaattaga      6600
tacacactat aaagtgatgc tgatctattc aagcttatta ctgttgatac ttaagcgtga      6660
atcattatca ttactattta tgttataata tatgaaccaa acggcagtac cgtacagcag      6720
caaagaagct agaacaaaat tcttttctaa tttttccata tagtcgagcc tacgaggtat      6780
gttttctgag agaatataga ttatgataga tctaagagtg tttctataat aatctagcca      6840
actgccaaat acattcgtag ttaatctttc tagtccgcct gacattccta gtatacgtac      6900
tacagtgcag ggcatcttaa attcggatca ggttgccaat catcgaaaat tgtgatccac      6960
ttgcgcatat gatatggtca agacgtcaag ttggataggg ggggagtagt agtagttgaa      7020
tgggcaagag cgcgtatttt atatagacgt atagcgtcac aagccgccag gaagggaaaa      7080
aaaaatatag tgtgtgagta gcgaagaaaa ctctccccct ctgaaaattc ttgcattttg      7140
acgacatccg attcaatcat tcagtagtac gtagtgtatt tattttattg ggatttagaa      7200
aaccagaccc tgatatgatc ctacgacggc tggatgcag tttagtgtta ttcgactgtt       7260
tcacgcgatt actccctccg tttcttttta tttgtcgcta gatagtgtta cactatccaa      7320
cgacaaataa aaagaaacgg aggaagtatt taggaagtga cgagtctagc taacccgatt      7380
ggttcaaatc ctttcttcat caatcaaccg ttaaacggcc gtgtcaatcg gtgttggcga      7440
accgttaaaa ccgtagcagc cccagtggag tggggccttc ttgtcgagtt acacggtgtt      7500
ttatcctatc ccgtggtcgc taacacgcac atgcctgga tgacagatga cactaacacg        7560
cacatgctca attactacta acgcagaagt caggtgcaat taaagagcag taaatgccca      7620
agtccctgtt ctgcttccag gacaggacag gaacactgtg atgaaacaac attcatcagg      7680
acggcacgcg accgccgatg ttcggcgacg acagctccgt aacatttcac cgctgaagcc      7740
tgaaggggaga gggacctggc gtgcgctagc agctgctgat agcgccagcc agacatggca      7800
ccacacgaga cacggccgcc cggttgaccg gcgaagcagc ccgggggttt ccaagtcatc      7860
gccggtttcc gcgggttcgc cgtcgccagt cgccaacttt ggacagacag agacagtcag      7920
ctcgggctct cgtctcgtcc gtgctcgctc tcgtctcgca tcgcacctgc gcgttgctgg      7980
ctcggcgtgg acctggcgcg gcgccggagc cccgttagaa accgcgcgtg tgcccgtgct      8040
atccatggtc tcctgtaaat ggtgtaatct tatcttattt accgcatcac cattaacaat      8100
ttaacacgag acgcacgaca cccaagcctg tgatgccgac gtataccaca ccatctaatc      8160
caaatccctg cattttttag tctctcagtc atcatcgact catcgttttt ttaatccatt      8220
cacttttttt tccacctttt cgtatacacg tcgctgtgcc ctccatcgct gggctggcaa      8280
gagaacgcga ggcgaagcag ccgcggccgc ccgccattat atcgcgggct cgcggcacag      8340
ggcagcggca gttccataca tacatacacc aaccgtgcgt gaaggaaggc ctttgctcgc      8400
cgccacatca cattggcagg cgaggcgagg gagcgagcag cagggcaagg catccacacc      8460
cacacccacc ggacactccc tgagaagcga gaagcgagaa gcgaagagcg gccggccacc      8520
atgttctggc acggggtcgc ggaccggctg acggggaaga acaagaggc gtgaacgag         8580
ggaaagatcc gcgcacggt gaggctggtc aagaaggagg tgctgacgt cggcgacttc        8640
aacgcctcgc tcctcgacgg cgtacacagg atcctcggct gggacgacgg cgtcgccttc      8700
cagctcgtca gcgccaccgc ggccgacccc agtaagcgcg accctgcatc acgcccccct      8760
cccctaccc ccctatggaa gattggaagt cgaccgaacg cccccgctcc cggtggccgt        8820
gggccgtgaa cgccggcggc cgcgctcgct ggacgtgggg cggaacctac gccatgcgtc      8880
ggacgtgcgt ttcgccgtcc atttcggtt tccccctttc cttactttc tctatacgaa        8940
ggatacgaag aaacatttta tcaaacaatt ccaatggatg ctgatgaaaa acctgtagaa      9000
tccgtgcccg tctgataaaa aaaaaaaact gcgactttgt ttttctgacg aaccgtcaat      9060
cttgacgcaa gcagacaggc atgggacagg atcctcgggc gcgtaataac cgcctgcagt      9120
gtgttggtct ctggtacgtg ggacccgtag cgcctgggtc cgtgtctcag cgacccaggc      9180
gctttttggc gttttgtgtg gtagggcttg cgttttcaag tctgaactgg gaactgggaa      9240
cctgtagcc ccggacatgg aatgaacag ttgtttgggg gcattcaatg cgattgagat        9300
ggcgtccgtg aaaactttac tgtaatttc actgcaaacg attgattgac tgattgattg      9360
aacgagtctt caggcaacgg gagccgcggc aaggtcggga aggcggcgca cctgcaggag      9420
gcggtggtgt cgctcaagtc gacgacggac ggggagaccg tgtaccgggt gagcttcgag      9480
tgggacgggt cgcagggcgt cccgggcgcc gtcctggtca ggaacctgca gcacgccgag      9540
ttcttcctca gtcgctcac cctcgagggc gtccccggca ggggcaccgt cgtcttcgtc       9600
gccaactcgt ggatctaccc gcacaatctc tactcccagg aacgcgtctt cttcgccaac      9660
gacgtgagta ttcttcccct tcggtttctt ttttgggttc gctggcgacg tgagtattct      9720
tactcaggat acgaaatctt gagcaatgtg acacacttgc gtgtgataaa cacatccaga      9780
gcttatttgc tacgaaatgt ggctacagag cacggatcgg gtgctagtca actattcatc      9840
atttttttta aaaactctcc taaccgtttt aggttcgttc tagatcaaac tatttaaact      9900
ttaaccaaca atacatatat aaaattaaat tatttgaac taaagaatt atatattatt        9960
gtagttcaac ttacgataaa tctagtaact ttttatgtt gtaaaatctt ataaaaatc       10020
tgatataatc agttaaagtt gacactgatt gacttagcat aaatctaaaa cgactaattt     10080
catgtggacg aaaagagtat gtgtgtatca tgttagatat atctagatcc ttacgtgata     10140
agaatacgtg ctctactgtt agctcctttt tattaatgta aaaacctaga ttgggtatag     10200
atccagttta gtggacattt ggttacctat gaattctggg aatgagataa actttatctg     10260
ctattcaacc atacgtttga ttttctata ttgggtaatg tactgtagga agaatctca      10320
aatactaact ccattgttaa atatatgacg tcattgattt tttttaaaa aaaactttaa     10380
ccactcagct tattcaataa aaaatatata ttattattta ctttgttata attttttta     10440
ttatttaagg taatttaagc atgaatttag atttttaaat aaatatttg aataaaataa     10500
gtgttcaaag ttttttaaaa ttcaactgta tcatatatta aaaaacggat gtactatcaa     10560
ctttgtgctg cattttttag gtagcgtgca gacttcatgt tataaaaatt caactttgtg     10620
ctgcattttt tgggtagtgt gcagacttca tgttataaaa attcaccgtt tgagccttag     10680
ctcccaaact ggccagcctg gtcttcgggt caagtccaca ggcggccgta cagcatcgac     10740
aaccattatt gctatatact attattgtcc gtactgcact atcgatcgaa cacacgcacc     10800
cacagacgca tcactcatgt tacgatagc cggcagcaat caaagtgttc gtctggctac      10860
agtaaattct tgcgtgatt tgtgtataggg ccttcaccat catttgctga tcgatccaga     10920
actggttgat aggagtcaga agaaatgaa caagtcttgt atagttctct cttggtagtc     10980
caaagaaaag gagaaatcaa tacaaaggtt aagtctggta catcacagta tcatactatc     11040
acagaccgag catcctgaag tccaaattat ctcatgttgc atcatatttt ctttatcgga     11100
cacgtaggag agctacatat cattattatc gagaaaagaa tgtttttta acatgcagaa     11160
gagccatgtg gctcatgttg caccgcaatc cataacaagg acgcatagat agattaaccc     11220
```

```
agtgttggaa gtcaaattga gcagcgcgga cagtccagcg ctgaggccgg acggtccgcg    11280
gtccggacag tccgcggtgg tggcgcggac ggtccgcgcg nnnnnnnnnn nnnnnnnnnn    11340
nnnnnnnnnn nnnnnnnnnn nnnnnnnnnn nnnnnnnnnn nnnnnnnnnn nnnnnnnnnn    11400
nnnnnnnnnn nnnnnnnnnn nnnnnnnnnn nnnnnnnnnn nnnnnnnnnn nnnnnnnnnn    11460
nnnnnnnnnn nnnnnnnnnn nnnnnnnnnn nnnnnnnnnn nnnnnnnnnn nnnnnnnnnn    11520
nnnnnnnnnn nnnnnnnnnn nnnnnnnnnn nnnnnnnnnn nnnnnnnnnn nnnnnnnnnn    11580
nnnnnnnnnn nnnnnnnnnn nnnnnnnnnn nnnnnnnnnn nnnnnnnnnn nnnnnnnnnn    11640
nnnnnnnnnn nnnnnnnnnn nnnnnnnnnn nnnnnngccg gcgactttcg ccggcccctg    11700
cgcacgcgcg gaccgtccgg cctgtaggtg cggaccgtcc ggccgtcagg cagggaacct    11760
ttgcccctgc tccaggtcgc ggaccgtccg gtccctggtc gcggaccgtc cgcgcctgtg    11820
cagagagcac caccgccggt tcttgttgag tgtttggcgc ccgaaaaagg tgtcaacata    11880
cttttggcga ctccgctggg gaaggtgttt agatctacta aaaatcaggc cctcaaatgg    11940
ccggttctaa agatcacacc gatatctccc cggacaatat cctgaagccg ctgttgaaa     12000
gtctgacgac cgatgagcaa cagcaatacg aggactacat gcgtcaagcg agggagaaat    12060
tcttatcaca atacacggtg gatcgccacc aaaaagttgt caaacatgga gagactgacg    12120
tcgcatctct tctatcttcg cttcaagtcc ccaacgtaag taaacccgac gacatccaat    12180
ttattaaaca gtatgtagat cagcagcagg atcaaatgaa acaacagatt gtagggttag    12240
aaaagtcaat tagaaaatta acgcgtacgt tggagaagtc tcttgctcct agttttccat    12300
catatgagac tagtaacagg atatctatgt ctaatacatc ggcaacaaat ggggatttgc    12360
agccccagcc attatatggt atgccgatga actcatatac aggacaagta ccaccaccgc    12420
catccctgct tggtagatcg gcacccatga acacggtcgg accgtccgag cttctgcccg    12480
gaccgtccgg cccatatgca gaccgtccgg cttgctctgc gcgtcaactat ggggccgccc   12540
taggaccacc gtcgtccctg cttggtagac cggtgacctt ggacgcggtc ggaccgtccg    12600
agcttctgcc tggaccgtcc ggcccttacg cggaccgtcc ggctttccct gccggacagt    12660
ctgggcccga ccaggactaa ccacatgcg tcccgataat ggcaaacgca accggtcagt     12720
tcggatttac caccggacaa gctgatacg catacgcaga acctgttgtt gcacaccatg     12780
caccaaatta ttacacacca cagcagcagt atgtttcgcc ctctacatat ttaaaccata    12840
acgcaccata caatcacaga ccgatcaaca ctatcgatcg gtcacggcaa gaaggtcggt    12900
atactaatgc ccgaccaaat gatccccaca gcccaggatc cggtggtctg ccaccgggtg    12960
caatggagaa aattagggaa gagatgactg aactatttcg agataagtcc ggagttagtg    13020
tagccagagt agggcaatca taccaaaagc cgtataatca ccggtttgac actgtcccat    13080
atccacaagg ggcaaggata ccagaatttt ctaagttttc tggtgagaat gggagaagca    13140
cacacgaaca cataggccag ttcctagcac acctaggcga attggccgat ggagaagcat    13200
ttcgtgttcg gttattttct ttatccctta ctggtactgc ttttgcatgg tacgccgccc    13260
tgcctcctaa ttccattaat tcctggaatg agttagaaag taaatttcat gaacatttat    13320
ttaccgggga atatgaatta gggttagctg acttagcttc agttcgacaa ggacgcgaag    13380
aatcggttaa tgattatatc cggaggttcc gggacactag aaaccgatgc tttcggatcc    13440
atgtcgcaga caaagagcta gcagggttag cttttaatgg gttgctatcc tacttaagag    13500
acaaattaga tgggaccccag ttcttttcga tagcccagct acatcagcgg gcttagcct    13560
gtgaaagccg atttaaagag acatcaaaat cggccgcccg tactatacat ctaatagagc    13620
gtgatagttc agatgatgaa tccgcatatg tatataccgc tgagtttatt tggccaacaa    13680
aggccaaatc ttcagcatgt tcttccttac nnnnnnnnnn nnnnnnnnnn nnnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnncctg ttaatacaat agatatcgca tgcaaaaaga tcttagttcg acccgaaatg    14040
gccgataaaa gcaaaagcaa agacatcatc attgacgatc ctcgcacgtc aaatatatcg    14100
caaaaggaga ttgctcgaaa ggctccggac gataaggcta aaaagtccgg aggcaccggg    14160
gggcaggcac aattaatgag ccaagcacga cagcctggcc tgagcatcac aaacggtgtg    14220
acacctacgt gcggacagtc cggtgctcag acagacggtt cggctaactc tgccggacaa    14280
tccgcttatg gccaaaggcg tcagcctcca cacaaagcct taaaagggaa agagacgcaa    14340
cgacaaagca catatggtcg gttgatcaaa actgactcta cctttgatca gttactcccc    14400
aagaatacta gcaagaagac cgttctacgt gatcggtcaa cgaagaaaca tcggtcacct    14460
gctaaaacaa aacgggtaaa caaaacggct cgaaaggcga cacaacaagc atcgcctatt    14520
catcctatga gaccaaggta ctttccaccc gtttactcat cctcggtata ttatcctgtt    14580
caaacatgga atggtacgat gatgaatcca tggtatatgt atagtctgtc atgtgggcc    14640
gcacctacac gcgggcccgc gacgccagga gggctgaggc tagggcgtnn nnnnnnnnnn    14700
nnnnnnnnnn nnnnnnnnnn nnnnnnnnnn nnnggctgct acacgccttc gccgatgtct    14760
tcaccgagcc gagcggacta cctccagcac gcggccacga gcaccacatc gtcctcaagc    14820
caggctcctc cccggtggcg gtgcgaccgt acaggtaccc ggcggcgcac aaggacgaac    14880
ttgagcggca gtgcgccgcc atgatcgacc agggcatcgt ccgccgcagt gactcggcgt    14940
tctcttcccc ggtcatcctt gtcaagaagc tggacgggtc gtggcgcttc tgcgtcgact    15000
accgccgtt gaacgcgctc actgtcaaag acgcgtatcc gattccggtc gtcgacgagc    15060
tcctcgacga gctccatggt gcacgcctct tcaccaagct nnnnnnnnnn nnnnnnnnnn    15120
nnnnnnnnnn nnnnnnnnnn nnnnnnnnnn nnnnnnnnnn nnnnnnnnnn nnnnnnnnnn    15180
nnnnnnnnnn nnnnnnnnnn nnnnnnnnnn nnnnnnnnnn nnnnnnnnnn nnnnnnnnnn    15240
nnnnnnnnnn nnnnnnnnnn nnnnnnnnnn nnnnnnnnnn nnnnnnnnnn nnnnnnnnnn    15300
nnnnnnnnnn nnnnnnnnnn nnnnnnnnnn nnnnnnnnnn nnnnnnnnnn nnnnnnnnnn    15360
nnnnnnnnnn nnnnnnnnnn nnnnnnnnacg tcatttcagc ggctggtgtc gctatggatc    15420
ccgcgaaggt ccaggccatc cacgactggc gccaacctcg ttcggcgcgc gccgtgcggg    15480
gcttcctcgg tctggcaggc tactatcgca agttcgtcca caactacggc gccattgcag    15540
cacccctcac agcactcctg aagaaagagg ggttcgtgtg gtccgacgag gcaagcgccg    15600
cttttcgtgc cctcaaaagg gcagtgacga cagcaccagt gttgacatta ccggacttca    15660
ccaagccctt catcgtggag tgcgacgcgt ccacctatgg cttcggggcg gtgctcatac    15720
aggaggctca tccgctcgcc ttcttcagtc gaccggtggc gccccgccat cgctccctag    15780
cggcctatga gcgcgaactc atcgggctcg tgcttgccgt acggcattgg aggccgtacc    15840
tatggggcg acgcttcgtc gtcaagacag accactacag cctcaagtac ctcctcgatc     15900
agcgcctggc gaccattcca caacatcatt gggtgggtaa gctcctcggg ttcgacttct    15960
```

```
ccgtcgagta caagtcagga gcaacgnnnn nnnnnnnnnn nnnnnnnnnn nnnnnnnnnn  16020
nnnnnnnnnn nnnnnnnnnn nnnnnnnnnn nnnnnnnnnn nnnnnnnnnn nnnnnnnnnn  16080
nnnnnnnnnn nnnnnnnnnn nnnnnnnnnn nnnnnnnnnn nnnnnnnnnn nnnnnnnnnn  16140
nnnnnnnnnn nnnnnnnnnn nnnnnnnnnn nnnnnnnnnn nnnnnnnnnn nnnnnnnnnn  16200
nnnnnnnnnn nnnnnnnnnn nnnnnnnnnn nnnnnnnnnn nnnnnnnnnn nnnnnnnnnn  16260
nnnnnnnnnn nnnnnnnnnn nnnnnnnnnn nnnnnnnnnn nnnnnnnnnn nnnnnnnnnn  16320
nnnnnnnnnn nnnnnnnnnn nnnnnnnnnn nnnnnnnnnn nnnnnnnnnn nnnnnnnnnn  16380
nnnnnnnnnn nnnnnnnnnn nnnnnnnnnn nnnnnnnnnn nnnnnnnnnn nnnnnnnnnn  16440
nnnnnnnnnn nnnnnnnnnn nnnnnnnnnn nnnnnnnnnn nnnnnngctc atgggcacta  16500
agctgcacat gtcgtccgcc ttccacccac agtccgacgg ccagacggaa gcggccaacc  16560
gcgtcatcat tatgtacctc cgctgtttca caggcgaccg tcctcgacaa tggcttcgct  16620
ggctgccgtg ggccgaatac gtgtacaaca cggcatacca gtcctcgctc cgggagacgc  16680
cattccgggt ggtgtatggt cgtgacccgc cctccatccg ctcttatgag cctggtgaaa  16740
cgagggtgga tgcggtcgca cgcaacatgg aggaacgcga gcattcctg gccgatgtgc  16800
gctatcgcct cgagcaggcc caagcggtgc agaaacgtca ctacgacaag caacaccggc  16860
cagtgacata tgcagtcggc gactgggcac tccttcgact cgccagcga gctccgtcct  16920
cactgccaca acagacatcg ggcaaactaa agccccgctt cctcggaccc taccgcgtca  16980
tcgagctcat caacaatgtc gccgttcgcc tggagctacc accacaggcc nnnnnnnnnn  17040
nnnnnnnnnn nnnnnnnnnn nnnnnnnnnn nnnnnnnnnn nnnnnnnnnn nnnnnnnnnn  17100
nnnnnnnnnn nnnnnnnnnn nnnnnnnnnn nnnnnnnnnn nnnnnnnnnn nnnnnnnnnn  17160
nnnnnnnnnn nnnnnnnnnn nnnnnnnnnn nnnnnnnnnn nnnnnnnnnn nnnnnnnnnn  17220
nnnnnnnnnn nnnnnnnnnn nnnnnnnnnn nnnnnnnnnn nnnnnnnnnn nnnnnnnnnn  17280
nnnnnnnnnn nnnnnnnnnn nnnnnnnnnn nnnnnnnnnn nnnnnnnnnn nnnnnnnnnn  17340
nnnnnnnnnn nnnnnnnnnn nnnnnnnnnn nnnnnnnnnn nnnnnnnnnn nnnnnnnnnn  17400
nnnnnnnnnn nnnnnnnnnn nnnnnnnnnn nnnnnnnnnn nnnnnnnnnn nnnnnnnnnn  17460
nnnnnnnnnn nnnnnnnnnn nnnnnnnnnn nnnnnnnnnn nnnnnnnnnn nnnnnnnnnn  17520
nnnnnnnnnn gccggcgact ttcgccggcc cctgcgcacg cgcggaccgt ccggcctgta  17580
ggtgcggacc gtctggccgt caggcaggga acctttgccc ctgctccagg tcgcggaccg  17640
tccggtccct ggtcgcggac cgtccgcgcc tgtgcagaga gcaccgccgc cggttcttgt  17700
tgagtgtttg gcgcccgaaa aaggtgtcaa cacccagtcg tgcattgacg gttgatatgg  17760
cttgattatt tactgaccga aaaaatcact ttactcaccg tgatttttat ggttgtagaa  17820
tttcttcttg ggtatatcgg caatagatca gatccacgca atagaaaaca ctagaacaca  17880
agtcaacaca gagctaatca aaattcctgt gctgcagact tatctgccaa gcaaaatgcc  17940
tgcggcattg gtgccttacc ggcaggacga gctcaagatt ctccgcggcg acgataatcc  18000
tggaccatac aaggagcacg accgcgtcta ccgttacgac tactacaacg acctcggtga  18060
gccagacaag ggtgaagacc atgcccggcc tgtcctcggg ggcagccaag aacacccgta  18120
tccccgtcgc tgcaggaccg gccggcgtcc aacagagaca ggtaggttca aggaagcaag  18180
ctacattctg gtccatacaa caagatgcca gaaatttgtc ctgaaaccct tgttggctaa  18240
ccttttttacg cagaccccaa ctcggagagc aggctgtttc tgctgaacct gaacatctac  18300
gtcccgcgcg acgagcggtt tgggcatctc aagatgtcgg acttcctcgg gtactcactg  18360
aaggcgatca tcgaggctgt cctttccacg ctggggacgt tcgtcgacga tacgcccaag  18420
gagttcgatt cgttcgaaga catccttggg ctctacgagc cgggtccaga ggcgcccaac  18480
aacccactgg tagcagaggt caggaagaga aatccccagc agttcctcag aagcattctg  18540
cccaatggta gccatgacca ccccctgaag atgccccttc caaatatcat cagatcaggt  18600
aactggactt catggaatgc cttttttcta catgttaata gtcctaaaaa ggttttaggt  18660
ttgccatgac tgaggctaaa tcttggtact caccagatgt gttgaaaaag gctccagagt  18720
ttaagtttgg ctggagggacc gacgaagagt ttgcggggga gacgcttgca ggcgtgaacc  18780
cagtgctcat caaacgtctg acggttagca tctatcttcc atcatatgga ctggccaatt  18840
caatatacct gccccgcaac taagtaaaag ggccttaaaa aattctttt ttttcatggt  18900
ctcaggagtt cccagctaaa agtaccctgg acccaagtca atacgagac catacgagca  18960
agatcaccga agctcacatc cagcataaca tggaaggcct gtcagtgcag aatgtatgct  19020
tggactgaac gcgcatacta taacaaccga aagattcaat acagataatt gattaaaacc  19080
atcgactgat tgccaaaacg aaccctgtgc aggcactgaa gaagaacagg ctcttcatcc  19140
tagaccacca tgaccatttc atgccgtacc tcaacaagat caacgagttg gaggggaact  19200
tcatctacgc cagcaggacc ctactgttcc tgaaggacga tggcacgctg aagccctcg  19260
ccgtcgagct gagcctgccc cacccctgatg gccagcagca cggcgcggtc agcaaggtgt  19320
acaccccagc tcactccggc gctgagggcc acgtctggca acttgccaag gcttatgcct  19380
gcgtgaacga ctccgcctgg catcagctga tcagccactg gtacagagag ctcttcctta  19440
atttgttttt ctccttgata ccaaaatgca aaaattgct ttttcatgtt cagagacaac  19500
taaaaacact aatcttgtgt gtgtttgcag gctgaacacg cacgcggtga tcgagccgtt  19560
cgtcatcgca acgaaccggc agctgagcgt ggtgcatcca gtgcacaagc tgctgagccc  19620
acactaccgt gacacgctga acatcaacgc cctggcacgc cagacgctca tcaacgccga  19680
cggcatcttc gagcgcaccg tgttccctgc aaagtacgcg ctgggatgt cctccgacgt  19740
gtacaagagc tggaatttca acgagcaggc tctcccagca gacctcgtca agagtacgt  19800
acatgtatag tactaactac attgagcagt aaacgccat agcagtgacg agatggttct  19860
gacgggttta tttgctcctc tggttgtgcg tttcagaggt gtggctgtgc cggaccagtc  19920
gagccctac ggtgtccggt tgctgatcaa ggactaccct tacgccgtgg acgggctggt  19980
catctggtgg gcgatcgagc ggtgggtcaa ggagtacctg gacgtctact accccaacga  20040
cggcgagctc cagcgcgcacg tggagctgca gcgtggtgg aaggaggtgc gcgaggaggc  20100
gcacggcgac ctcaaggacc gagactggtg gccaggatg gacgccgtcc agcggctggc  20160
cagggcgtgc acgaccgtca tctgggtagc gtccgcgctg cacgcggccg tcaacttcgg  20220
gcagtacccg tacgccgggt acctgccgaa ccggccgacc gtgagccggc ggccgatgcc  20280
ggagccgggc agcgacgact acaagaagct ggaggcgggg cagaaggagg cggacgcggt  20340
gttcatcgag accatcacca gccagttcga gaccatctcgc tcatcgagat  20400
cctctccaag cactcctccg acgaggtgta cctcggccag cgcgacgagc ctgagcgctg  20460
gacgtcggac gccagggcgc tggacgcgtt cagaaggttc ggaagccggc tggtggagat  20520
cgagaagcgg atcaggacga tgaacgcacg cccgacgttg aagaaccgga aggggccggt  20580
ggagatgccg tacatgctgc tgtaccccaa cacgtcggat gtcaccggcg agaagggcga  20640
gggggctcact gccatgggca ttcccaacag catctcccata tga           20683
```

```
SEQ ID NO: 16           moltype = DNA   length = 5376
FEATURE                 Location/Qualifiers
source                  1..5376
                        mol_type = genomic DNA
                        organism = Zea mays
SEQUENCE: 16
atgctgagcg ggatcatcga cgggctgacg ggggcgaaca agcatgcgcg gctcaagggc    60
acggtggtgc tcatgcgcaa gaacgtgctg gacctcaacg acttcggcgc caccgtcgtc   120
gacagcatca gcgagttcct cggcaagggg gtcacctgcc agctcatcag ctccactctc   180
gtcgacgcca caacggcaa ccgcgggcgg tcggggcgg aggcgaacct ggagcagtgg    240
ctgacgagcg tgccgtcgct gacgaccggc gagtccaagt tcggcgtcac gttcgactgg   300
gaggtggaga agctgggagt gccggggggcc gtcgtcgtca agaacaacca cgccgccgag   360
ttcttcctca agacaatcac cctcgacgac gtgcccgacc gcgggcgcgt caccttcgtc   420
gccaactcct gggtctaccc cgcgggcaag taccgctaca accgcgtctt cttctccaac   480
gatacgtacc tgccaagcca gatgccgcg gcgctgaagc cgtaccgcga cgacgagctc   540
cgcaacctcc gcggcgacga ccagcagggc ccctaccagg agcacgaccg cgtgtaccgc   600
tacgacgtct acaacgacct cggcgagccc gacggcgggca acccgcgccc catcctcggc   660
ggctccgccg accacccgta cccgcgccgc tgccgcacgg gccgcaagcc caccaaaacc   720
gaccccaact cggagagccg actgtcgctg tggagcaga tctacgtgcc gcgggacgag    780
cgcttcggcc acctcaagat gtccgacttc ctgggctact ccatcaaggc catcacgcag   840
ggcatcatcc cggcggtgcg cacgtacgtg gacaccgagt cgactcctca                900
caggacatca tcaacctgta cgagggcggg atcaagctgc ccaagatcca ggcgctcgag    960
gacatgcgca agctcttccc gctccagctc gtcaaggacc tcctcccgc cggcggggac   1020
tacctgctca agctccccat cccacagatc atccaaggca cgtcacgtat accgatcgat   1080
gtcagggcg ggctgttgtc tggtctgcat atatatatgt gctcctatga ggacaagaac   1140
gcgtggagga ccgacgagga gttcgcgcgg gaggtgctcg ccggcgtcaa cccgatggtg   1200
atcacgcgcc tcacggagtt cccgcccaag agcacgctgg accccagcaa gtacggcgac   1260
cacaccagca cgatcacggc ggagcacatc gagaagaacc tcgagggcct cacggtgcag   1320
caggcgctgg acggcaacag gctctacatc ctggaccacc acgaccgctt catgccgttc   1380
ctcatcgacg tcaacaacct tggagggcaac ttcatcctacg ccaccaggac gctcttcttc   1440
ctgcgcggcg acggcaggct cgcgcccctc gccatcgagc tcagcgagcc gtacatcgac   1500
ggggacctca ccgtggccaa gagcaaggtc tacacgccgg cgtccagcgg cgtcgaggcc   1560
tgggtgtggc agctcgccaa ggcctatgtc gccgtcaacg actctggctg gcaccaactc   1620
gtcagcgagc ggctgaacac ccacgcggtg atggagccgt tcgtgatcgc gacgaaccgg   1680
cagctgagcg tgacgcaccc ggtgcacaag ctcctgagct cgcacttccg cgacaccatg   1740
accatcaacg cgctggcgcg gcagacgctc atcaacggcg gcggcatctt cgagatgacc   1800
gtcttcccgg gcaagtacgc gctgggcatg tcctccgtgt tgtacaagag ctggaacttc   1860
accgagcagg gcctcccgc cgacctcgtc aagaggggcg tggcggtggc ggacccgtcc   1920
agcccgtaca aggtgcggct gctgatcgag gactaccgt acgcgagcga cgggctggcc   1980
atctggcacg ccatcgagca gtgggtgggc gagtacctgg ccatctacta ccccgacgac   2040
ggcgcgctgc ggggcgacga ggagctgcag gcgtggtgga aggaggtgcg cgaggtcggg   2100
cacggcgacc acaaggacgc gccctggtgg cccaagtgc aggccgtgtc ggagctcgcc   2160
agcgcctgca ccaccatcat ctggatcgcg tcgcgctcc acgccgccgt caacttcggc   2220
cagtaccccgt acgcggggta cctcccgaac aggcccacgg tgagccggcg ccggatgccg   2280
gagcccggca gcaaggagta cgaggagctg agcgcgacc cggagcgcgg cttcatccac   2340
accatcacga gccagatcca gaccatcatc ggcatctcgc tcatcgagat cctctccaag   2400
cactcctccg acgaggtgta cctcggccag cgcgacaccc ccgagtggac ctccgacgcg   2460
cgggcgctgg cggcgttcaa gaggttcagc gacgcgctgg tcaagatcga gggcaaggtg   2520
gtgggcgaga accgcgaccc gcagctgagg aacaggaacg gccccgccga gttcccctac   2580
atgctgctct atcccaacac ctctgaccac agcgaggcgg ggagcgagc agcagggcaa   2640
ggcatccaca cccacaccca ccggacactc cctgagaagc gagaagcgag aagcgaagag   2700
cggccggcca ccatgttctg gcacggggtc gcggaccggc tgacggggaa gaacaaggag   2760
gcgtggaacg agggaaagat ccgcggcacg gtgaggctgg tcaagaagga ggtgctggac   2820
gtcggcgact tcaacgcctc gtcctcgac ggcgtacaca ggatcctcgg ctgggacgag   2880
ggcgtcgcct tccagctcgt cagcgccacc gcgaccgacc ccagcaacgg gagccgcggc   2940
aaggtcggga aggcggcgca cctggaggag gcggtggtgt cgctcaagtc gacgacggac   3000
ggggagaccg tgtaccgggt gagcttcgag tgggacgggt cgcagggcgt cccgggcgcc   3060
gtcctggtca ggaacctgca gcacgccgag ttcttcctca agtcgctcac cctcgagggc   3120
gtccccggca ggggcaccgt cgtcttcgtc gccaactcgt ggatctaccc gcacaatcga   3180
tactcccagg aacgcgtctt cttcgccaac gacacttatc tgccaagcaa aatgcctgcg   3240
gcattggtgc cttaccggca ggacgagctc aagattctcc gcggcgacga taatcctgga   3300
ccatacaagg agcacgaccg cgtctaccgt tacgactact caacgacct cggtgagcca   3360
gacaagggtg aagaccatgc ccggcctgtc ctcggggcga gccaagaaca cccgtatccc   3420
cgtcgctgca ggaccggccg gcgtccaaca gagacagaca ccaactcgga gagcaggctg   3480
tttctgctga acctgaacat ctacgtcccg cgcgacgagc ggtttgggca tctcaagatg   3540
tcggacttcc tcgggtactc actgaaggcg atcatcgagg ctgtccttcc gacgctgggg   3600
acgttcgtcg acgatacgcc caaggagttc gattcgttcg aagacatcct tgggctctac   3660
gagccgggtc cagaggcgc caacaaccca ctggtagcag aggtcaggaa ggaatcctac   3720
agcgagttcc tcagaagcat tctgcccaat ggtagccatg accacccct gaagatgccc   3780
cttccaaata tcatcagatc agatgtgttg aaaaaggctc cagagtttaa gtttggctgg   3840
aggaccgacg aagagtttgc gagggagacg cttgcaggcg tgaacccagt gctcatcaaa   3900
cgtctgacgg agttcccagc taaaagtacc ctggacccaa gtcaatacgg agaccatacg   3960
agcaagatca gcgaagctca catccagcat aacatggaag gctgtcagt gcagaatgca   4020
ctgaagaaga acaggctctt catcctagac caccatgacc atttcatgcc gtacctcaac   4080
aagatcaacg agttggaggg gaacttcatc tacgccagca ggaccctact gttcctgaag   4140
gacgatggca cgctgaagcc cctggccgtc gagctgagcc tgcccacccc tgatgggccag   4200
cagcacggcg cggtcagcaa ggtgtacacc ccagctcact ccggcgctga gggccacgtc   4260
tggcaacttg ccaaggctta tgcctgcgtg aacgactccg cctggcatca gctgatcagc   4320
```

-continued

```
cactggctga acacgcacgc ggtgatcgag ccgttcgtca tcgcaacgaa ccggcagctg    4380
agcgtggtgc atccagtgca caagctgctg agcccacact accgtgacac gctgaacatc    4440
aacgccctgg cacgccagac gctcatcaac gccgacggca tcttcgagcg caccgtgttc    4500
cctgcaaagt acgcgctggg gatgtcctcc gacgtgtaca agagctggaa tttcaacgag    4560
caggctctcc cagcagacct cgtcaagaga ggtgtggctg tgccgaccca gtcgagcccc    4620
tacggtgtcc ggttgctgat caaggactac ccttacgccg tggacgggct ggtcatctgg    4680
tgggcgatcg agcggtgggt caaggagtac ctggacgtct actacccaa cgacggcgag    4740
ctccagcgcg acgtggagct gcaggcgtgg tggaaggagg tgcgcgagga ggcgcacggc    4800
gacctcaagg accgagactg gtggcccagg atggacgccg tccagcggct ggcagggcg    4860
tgcacgaccg tcatctggt agcgtccgcc ctgcacgccg tcgtcaactt cgggcagtac    4920
ccgtacgccg ggtacctgcc gaaccggccc accgtgagcc ggcggccgat gccggagccg    4980
ggcagcgacg actacaagaa gctggagcg gggcagaagg aggcggacgc ggtgttcatc    5040
cgcaccatca ccagccagtt ccagaccatc ctgggcatct cgctcatcga gatcctctcc    5100
aagcactcct ccgacgaggt gtacctcggc cagcgcgacg agcctgagcg ctggacgtcg    5160
gacgccaggg cgctgacgc gttcagaagg ttcggaagcc ggctggtgga gatcgagaag    5220
cggatcagga cgatgaacga cagcccgacg ttgaagaacc ggaaggggcc ggtggagatg    5280
ccgtacatgc tgctgtaccc caacacgtcg gatgtcaccg cgagaagg cgaggggctc    5340
actgccatgg gcattcccaa cagcatctcc atatga                             5376
```

```
SEQ ID NO: 17           moltype = AA   length = 1791
FEATURE                 Location/Qualifiers
source                  1..1791
                        mol_type = protein
                        organism = Zea mays
SEQUENCE: 17
MLSGIIDGLT GANKHARLKG TVVLMRKNVL DLNDFGATVV DSISEFLGKG VTCQLISSTL     60
VDANNGNRGR VGAEANLEQW LTSLPSLTTG ESKFGVTFDW EVEKLGVPGA VVVKNNHAAE    120
FFLKTITLDD VPGRGAVTFV ANSWVYPAGK YRYNRVFFSN DTYLPSQMPA ALKPYRDDEL    180
RNLRGDDQQG PYQEHDRVYR YDVYNDLGEP DGGNPRPILG GSADHPYPRR CRTGRKPTKT    240
DPNSESRLSL VEQIYVPRDE RFGHLKMSDF LGYSIKAITQ GIIPAVRTYV DTTPGEFDSF    300
QDIINLYEGG IKLPKIQALE DMRKLFPLQL VKDLLPAGGD YLLKLPIPQI IQGTSRIPID    360
VRGRLLSGLH IYMCSYEDKN AWRTDEEFAR EVLAGVNPMV ITRLTEFPPK STLDPSKYGD    420
HTSTITAEHI EKNLEGLTVQ QALDGNRLYI LDHHDRFMPF LIDVNNLEGN FIYATRTLFF    480
LRGDGRLAPL AIELSEPYID GDLTVAKSKV YTPASSGVEA WVWQLAKAYV AVNDSGWHQL    540
VSHWLNTHAV MEPFVIATNR QLSVTHPVHK LLSSHFRDTM TINALARQTL INGGGIFEMT    600
VPPGKYALGM SSVVYKSWNF TEQGLPADLV KRGVAVADPS SPYKVRLLIE DYPYASDGLA    660
IWHAIEQWVG EYLAIYYPDD GALRGDEELQ AWWKEVREVG HGDHKDAPWW PKMQAVSELA    720
SACTTIIWIA SALHAAVNFG QYPYAGYLPN RPTVSRRRMP EPGSKEYEEL ERDPERGFIH    780
TITSQIQTII GISLIEILSK HSSDEVYLGQ RDTPEWTSDA RALAAFKRFS DALVKIEGKV    840
VGENRDPQLR NRNGPAEFPY MLLYPNTSDH SEARERAAGQ GIHTHTHRTL PEKREARSEE    900
RPATMFWHGV ADRLTGKNKE AWNEGKIRGT VRLVKKEVLD VGDFNASLLD GVHRILGWDD    960
GVAFQLVSAT AADPSNGSRG KVGKAAHLEE AVVSLKSTTD GETVYRVSFE WDGSQGVPGA   1020
VLVRNLQHAE FFLKSLTLEG VPGRGTVVFV ANSWIYPHNL YSQERVFFAN DTYLPSKMPA   1080
ALVPYRQDEL KILRGDDNPG PYKEHDRVYR YDYYNDLGEP DKGEDHARPV LGGSQEHPYP   1140
RRCRTGRRPT ETDPNSESRL FLLNLNIYVP RDERFGHLKM SDFLGYSLKA IIEAVLPTLG   1200
TFVDDTPKEF DSFEDILGLY EPGPEAPNNP LVAEVRKRIP SEFLRSILPN GSHDHPLKMP   1260
LPNIIRSDVL KKAPEFKFGW RTDEEFARET LAGVNPVLIK RLTEFPAKST LDPSQYGDHT   1320
SKITEAHIQH NMEGLSVQNA LKKNRLFILD HHDHFMPYLN KINELEGNFI YASRTLLFLK   1380
DDGTLKPLAV ELSLPHPDGQ QHGAVSKVYT PAHSGAEGHV WQLAKAYACV NDSAWHQLIS   1440
HWLNTHAVIE PFVIATNRQL SVVHPVHKLL SPHYRDTLNI NALARQTLIN ADGIFERTVF   1500
PAKYALGMSS DVYKSWNFNE QALPADLVKR GVAVPDQSSP YGVRLLIKDY PYAVDGLVIW   1560
WAIERWVKEY LDVYYPNDGE LQRDVELQAW WKEVREEAHG DLKDRDWWPR MDAVQRLARA   1620
CTTVIWVASA LHAAVNFGQY PYAGYLPNRP TVSRRPMPEP GSDDYKKLEA GQKEADAVFI   1680
RTITSQFQTI LGISLIEILS KHSSDEVYLG QRDEPERWTS DARALDAFRR FGSRLVEIEK   1740
RIRTMNDSPT LKNRKGPVEM PYMLLYPNTS DVTGEKGEGL TAMGIPNSIS I            1791
```

```
SEQ ID NO: 18           moltype = DNA   length = 18
FEATURE                 Location/Qualifiers
misc_feature            1..18
                        note = Primer S3460 for Lox3 of Zea mays
source                  1..18
                        mol_type = other DNA
                        organism = synthetic construct
SEQUENCE: 18
cctcgtcgac gccaacaa                                                   18
```

```
SEQ ID NO: 19           moltype = DNA   length = 19
FEATURE                 Location/Qualifiers
misc_feature            1..19
                        note = Primer S3461 for Lox3 of Zey mays
source                  1..19
                        mol_type = other DNA
                        organism = synthetic construct
SEQUENCE: 19
acgtgacgcc gaacttgga                                                  19
```

```
SEQ ID NO: 20           moltype = DNA   length = 25
FEATURE                 Location/Qualifiers
misc_feature            1..25
```

```
                        note = Primer S3428 for Elongation factor 1-alpha
source                  1..25
                        mol_type = other DNA
                        organism = synthetic construct
SEQUENCE: 20
ggtaaagaga agtcccacat caaca                                          25

SEQ ID NO: 21           moltype = DNA  length = 23
FEATURE                 Location/Qualifiers
misc_feature            1..23
                        note = Primer S3429 for Elongation factor 1-alpha
source                  1..23
                        mol_type = other DNA
                        organism = synthetic construct
SEQUENCE: 21
ctccttctca aacctctcga tca                                            23

SEQ ID NO: 22           moltype = DNA  length = 1913
FEATURE                 Location/Qualifiers
source                  1..1913
                        mol_type = genomic DNA
                        organism = Zea mays
SEQUENCE: 22
ttgtagttca tgcgcagtaa gagttgtaac ctcataatat gaccaaattc ctgatctgct    60
ttatagagtt gttgtgccta attttgaatt cgtcttactg gctcaaaatt atgtgcgcac   120
acttattagt ttgctctttta ttttctatgc ctgcttatt ttttatatt acattgattg   180
ctctgtttaa tatttgcttc tttattttta cactgcttat gtgtatcaag ctttttttcaa  240
gctcataact ccggttacaa cgttagatct agtttctgat cccatctgat aaatttgttt   300
ctaatcgttg attcgtcttg ttaacagttc aatctcacct ccaaccatgg gtaaagaaa    360
gtcccacatc aacattgtgg ttattggcca cgttgactct ggcaagtcga ccaccacagg   420
acacctgatc tacaagcttg gaggcattga caagcgtgtg atcgagaggt ttgagaagga   480
ggctgctgaa atgaacaagc ggtccttcaa gtacgcatgg gtgctcgaca agctcaaggc   540
tgagcgtgag agaggtatca ccattgatat cgctctgtgg aagtttgaga ccaccaagta   600
ctactgcacg gtcattgatg cccctggaca ccgtgacttc atcaagaaca tgatcactgg   660
tacctcccag gctgactgtg ctgtccttat cattgactcc accactggtg gttttgaggc   720
tggtatctcc aaggatggcc agacccgtga acatgctctc cttgcgttca cccttggagt   780
gaagcagatg atttgctgct gcaacaagat ggatgcaacc actccaaaat actccaaggc   840
acgttatgat gagattgtga aggaagtctc atcctacctc aagaaagttg ggtacaaccc   900
tgataagatt gccttcgttc ccatttctgg ttttgagggc gacaacatga ttgagaggtc   960
caccaacctt gactggtaca aaggcccaac cctgcttgag gctcttgacc agatcaccga  1020
gcccaagagg ccttcggaca gcccctgcg tctgccctc caggatgtgt acaagattgg  1080
tggtattgga actgtaccgg ttggtcgtgt ggagactgg gtcatcaagc ctggtatggt   1140
agtcaccttt ggtccaactg gcctgactac tgaggtgaag tctgttgaga tgcaccatga  1200
ggcgcttcag gaggctcttc cgggcgacaa tgttggcttc aacgtgaaga acgttgctgt  1260
caaggatctc aagcgtgggt tcgtggcctc caactccaag gatgaccctg ccaaggaggc  1320
tgccagcttc acctcccagg tcatcatcat gaaccacccc tgggcagattg gcaacggcta  1380
tgcccagtg ctggactgcc acacctccca catcgccgtc aagtttgcg agctcattac  1440
caagatcgac aggcgatctg gcaaggagct cgaaaggag cccaagttcc tgaagaacgg   1500
tgatgctggt atggtgaaga tgattccac caagcctatg gtggtggaga cattctccgc  1560
gtatcctccc ctgggtaggt ttgccgtccg cgacatgagg cagacggttg ctgttggagt  1620
catcaagagt gtgagaaga aggacccaac cggcgccaag gtgaccaagg cggccgcaa   1680
gaagaaatga tgcgatcccg tgtctgcttt tgcagtgcct ggataacttg ccactaaagt  1740
tgtgtatgcg gttgttgctg ttattgcgtg gactgtttgc tgcggtgtct cctgtttgtt  1800
tgggtagcgc agcgtcggcc tcttcaggtg tctgttgtct gttgtcttta ctatcagtaa  1860
tgctcctgag acttgtattt ctccttttgg cgccgctaaa tggaattttc gaa        1913

SEQ ID NO: 23           moltype = AA  length = 447
FEATURE                 Location/Qualifiers
source                  1..447
                        mol_type = protein
                        organism = Zea mays
SEQUENCE: 23
MGKEKSHINI VVIGHVDSGK STTTGHLIYK LGGIDKRVIE RFEKEAAEMN KRSFKYAWVL    60
DKLKAERERG ITIDIALWKF ETTKYYCTVI DAPGHRDFIK NMITGTSQAD CAVLIIDSTT   120
GGFEAGISKD GQTREHALLA FTLGVKQMIC CCNKMDATTP KYSKARYDEI VKEVSSYLKK   180
VGYNPDKIAF VPISGFEGDN MIERSTNLDW YKGPTLLEAL DQITEPKRPS DKPLRLPLQD   240
VYKIGGIGTV PVGRVETGVI KPGMVVTFGP TGLTTEVKSV EMHHEALQEA LPGDNVGFNV   300
KNVAVKDLKR GFVASNSKDD PAKEAASFTS QVIIMNHPGQ IGNGYAPVLD CHTSHIAVKF   360
AELITKIDRR SGKELEKEPK FLKNGDAGMV KMIPTKPMVV ETFSAYPPLG RFAVRDMRQT   420
VAVGVIKSVE KKDPTGAKVT KAAAKKK                                      447

SEQ ID NO: 24           moltype = AA  length = 494
FEATURE                 Location/Qualifiers
source                  1..494
                        mol_type = protein
                        organism = Zea mays
SEQUENCE: 24
MDTSHHYHPW LNFSLAHHCD LEEEERGAAA ELAAIAGAAP PPKLEDFLGG GVATGGPEAV    60
APAEMYDSDL KFIAAAGFLG GSAAAAATSP LSSLDQAGSK LALPAAAAAP APEQRKAVDS   120
```

```
FGQRTSIYRG VTRHRWTGRY EAHLWDNSCR REGQSRKGRQ VYLGGYDKEE KAARAYDLAA    180
LKYWGSSTTT NFPVAEYEKE VEEMKNMTRQ EFVASLRRKS SGFSRGASIY RGVTRHHQHG    240
RWQARIGRVA GNKDLYLGTF STEEEAAEAY DIAAIKFRGL NAVTNFEISR YNVETIMSSN    300
LPVASMSSSS AAAAGGRSSK ALESPPSGSL DGGGGMPVVE GSTAPPLFIP VKYDQQQQEY    360
LSMLALQHHH QQQQAGNLLQ GPLVGFGGLY SSGVNLDFAN SHGTAAPSSM AHHCYANGTA    420
SASHEHQHQH QMQQGGENET QPQPQQSSSS CSSLPFATPV AFNGSYESSI TAAGPFGYSY    480
PNVAAFQTPI YGME                                                     494

SEQ ID NO: 25           moltype = DNA  length = 1485
FEATURE                 Location/Qualifiers
source                  1..1485
                        mol_type = genomic DNA
                        organism = Zea mays
SEQUENCE: 25
atggacacct cgcaccacta tcatccatgg ctcaacttct ccctcgccca ccactgtgac     60
ctcgaggagg aggagagggg cgcggccgcc gagctggccg cgatagccgg cgccgcgccg    120
ccgccgaagc tggaggactt cctcggcgga ggcgtcgcca ccggtggtcc ggaggcggtg    180
gcgccgcgcg agatgtacga ctcggacctc aagttcatag ccgccgccgg gttccttggc    240
ggctcggcgg cggcggcggc gacgtcgccg ctgtcctccc tcgaccaggc cggttccaag    300
ctggccttgc ctgcggcggc ggctgctccg gcgccggagc agaggaaggc cgtcgactcc    360
tttgggcagc gcacgtccat ctaccgcggc gtcacgggc accggtggac tggcaggtac     420
gaggcacatc tgtgggacaa cagctgccga cgcgaaggcc agcgcaa ggccgccaa        480
gtatatttgg gtggctatga taggaggag aaggctgcca gggcgatga tcttgcagct     540
ttgaagtact ggggttctag caccaccacc aactttccgg ttgctgagta tgagaaggag    600
gtcgaggaga tgaagaacat gacgcgacaa gagtttgttg cttcccttcg aaggaagagc    660
agtggattct ctcgggttgc ttccatctac agaggtggaa ccagacatca ccagcatgga    720
cggtggcagg cgaggatcgg aagggtggcc ggtaacaagg acctctacct tgggacgttc    780
agcaccgagg aggaagctgc agaggcctac gacatagcgg ccatcaagtt cagaggcctg    840
aacgccgtca caacttcga gatcagccgg tacaacgtgg agaccataat gagcagcaac    900
cttccagtcg cgagcatgtc gtcgtcgtcg gcggcgggcg ggggtggccg gagcagcaag    960
gcgctggagt cccctccgtc cggctcgctt gacggcggcg gcggcatgcc agtcgtcgaa   1020
ggcagcacgg caccgccgct gttcattccg gtgaagtacg accagcagca gcaggagtac   1080
ctgtcgatgc tcgcgttgca gcaccaccac cagcagcaac aagcagggaa cctgttgcag   1140
gggccgctag taggggtcgg cggcctctac tcctccgggg tgaacctgga tttcgccaac   1200
tcccacggca cggcggctcc gtcgtcgatg cccaccact gctacgccaa tggcaccgcg   1260
tccgcctcgc atgagcacca gcaccagcac cagatgcagc agggcggcga gaacgagacg   1320
cagccgcagc gcagcagag ctccagcagc tgctcctccc tgccattcgc caccccggtc   1380
gctttcaatg gtcctatga aagctccatc acggcggcag gccccttttgg atactcctac   1440
ccaaatgtgg cagcctttca gacgccgatc tatggaatgg aatga                  1485

SEQ ID NO: 26           moltype = AA  length = 164
FEATURE                 Location/Qualifiers
REGION                  1..164
                        note = Regeneration booster P8
source                  1..164
                        mol_type = protein
                        organism = synthetic construct
SEQUENCE: 26
MVSKGEEVIK EFSGSTRWNP TAEQVKVLRE IYYRAGLRTP SADQIRQISS QLKRYGKVEG     60
KNVFYWFQNH KARERQKKRL STVGSAGSAA GSGEFRHVKT LPLFPLHNNE DSGSGLDLDL    120
NLELRLSATA AATSGSQRAS ALDLDLELRL GFALGNESCG LHDN                    164

SEQ ID NO: 27           moltype = DNA  length = 498
FEATURE                 Location/Qualifiers
misc_feature            1..498
                        note = Regeneratio booster P8 CDS
source                  1..498
                        mol_type = other DNA
                        organism = synthetic construct
SEQUENCE: 27
atggtttcga aggggaaga agtcattaaa gagttttcag gtctacgcg ctggaaccct       60
accgctgaac aagtcaaggt tttgagggaa atatattacc gcgcgggtct taggacgcca   120
tccgcggatc agatccgcca aatatcctca cagctgaaac ggtatggaaa ggtggaagga   180
aaaaacgtgt tttattggtt ccagaaccat aaagcgcggg aaagacaaaa aaagcggctc   240
agcaccgttg ggagcgctgg ctcagcagcg ggttcaggtg agttcaggca cgttaaaaca   300
ctgcccttgt tccctttgca caataatgaa gactcaggga gcggtttgga cttggatctg   360
aaccttgagt tgcgcctgtc ggcgactgct gctgccactt cgggctcaca gcgggcgtct   420
gccctcgatc tggacttgga gctcagactc ggtttcgcgc ttggtaatga gtcgtgtgga   480
ctgcacgaca actagtga                                                 498

SEQ ID NO: 28           moltype = AA  length = 1252
FEATURE                 Location/Qualifiers
REGION                  1..1252
                        note = LbCpf1-RR
source                  1..1252
                        mol_type = protein
                        organism = synthetic construct
SEQUENCE: 28
MAPKKKRKVS KLEKFTNCYS LSKTLRFKAI PVGKTQENID NKRLLVEDEK RAEDYKGVKK     60
```

```
LLDRYYLSFI NDVLHSIKLK NLNNYISLFR KKTRTEKENK ELENLEINLR KEIAKAFKGN  120
EGYKSLFKKD IIETILPEFL DDKDEIALVN SFNGFTTAFT GFFDNRENMF SEEAKSTSIA  180
FRCINENLTR YISNMDIFEK VDAIFDKHEV QEIKEKILNS DYDVEDFFEG EFFNFVLTQE  240
GIDVYNAIIG GFVTESGEKI KGLNEYINLY NQKTKQKLPK FKPLYKQVLS DRESLSFYGE  300
GYTSDEEVLE VFRNTLNKNS EIFSSIKKLE KLFKNFDEYS SAGIFVKNGP AISTISKDIF  360
GEWNVIRDKW NAEYDDIHLK KKAVVTEKYE DDRRKSFKKI GSFSLEQLQE YADADLSVVE  420
KLKEIIIQKV DEIYKVYGSS EKLFDADFVL EKSLKKNDAV VAIMKDLLDS VKSFENYIKA  480
FFGEGKETNR DESFYGDFVL AYDILLKVDH IYDAIRNYVT QKPYSKDKFK LYFQNPQFMR  540
GWDKDKETDY RATILRYGSK YYLAIMDKKY AKCLQKIDKD DVNGNYEKIN YKLLPGPNKM  600
LPRVFFSKKW MAYYNPSEDI QKIYKNGTFK KGDMFNLNDC HKLIDFFKDS ISRYPKWSNA  660
YDFNFSETEK YKDIAGFYRE VEEQGYKVSF ESASKKEVDK LVEEGKLYMF QIYNKDFSDK  720
SHGTPNLHTM YFKLLFDENN HGQIRLSGGA ELFMRRASLK KEELVVHPAN SPIANKNPDN  780
PKKTTTLSYD VYKDKRFSED QYELHIPIAI NKCPKNIFKI NTEVRVLLKH DDNPYVIGID  840
RGERNLLYIV VVDGKGNIVE QYSLNEIINN FNGIRIKTDY HSLLDKKEKE RFEARQNWTS  900
IENIKELKAG YISQVVHKIC ELVEKYDAVI ALEDLNSGFK NSRVKVEKQV YQKFEKMLID  960
KLNYMVDKKS NPCATGGALK GYQITNKFES FKSMSTQNGF IFYIPAWLTS KIDPSTGFVN 1020
LLKTKYTSIA DSKKFISSFD RIMYVPEEDL FEFALDYKNF SRTDADYIKK WKLYSYGNRI 1080
RIFRNPKKNN VFDWEEVCLT SAYKELFNKY GINYQQGDIR ALLCEQSDKA FYSSFMALMS 1140
LMLQMRNSIT GRTDVDFLIS PVKNSDGIFY DSRNYEAQEN AILPKNADAN GAYNIARKVL 1200
WAIGQFKKAE DEKLDKVKIA ISNKEWLEYA QTSVKHKRPA ATKKAGQAKK KK         1252

SEQ ID NO: 29           moltype = DNA   length = 3759
FEATURE                 Location/Qualifiers
misc_feature            1..3759
                        note = LbCpf1-RR CDS
source                  1..3759
                        mol_type = other DNA
                        organism = synthetic construct
SEQUENCE: 29
atggcgccga agaagaagcg caaggtgtcc aagctcgaga agttcacgaa ctgctactcc   60
ctctccaaga ccctccgctt caaggccatc cccgtgggca agacccagga gaacatcgac  120
aacaagcgcc tcctggtcga ggacgagaag agggcggagg actacaaggg cgtgaagaag  180
ctcctggacc gctactacct ctccttcatc aacgacgtcc tgcacagcat caagctcaag  240
aacctgaaca actacatctc cctgttccgc aagaagacga ggaccgagaa ggagaagaac  300
gagctcgaga acctggagat caacctccgc aaggagatcg ccaaggcgtt caagggcaac  360
gagggctaca agagcctgtt caagaaggac atcatcgaga cgatcctccc ggagttcctg  420
gacgacaagg acgagatcgc cctcgtgaac tccttcaacg gcttcaccac ggcgttcacc  480
ggcttcttcg acaaccgcga gaacatgttc agcgaggagg ccagtccac gagcatcgcg  540
ttccgctgca tcaacgagaa cctgaccagg tacatctcca acatggacat cttcgagaag  600
gtcgacgcca tcttcgacaa gcacgaggtg caggagatca aggagaagat cctcaacagc  660
gactacgacg tcgaggactt cttcgagggc gagttcttca acttcgtcct gacgcaggag  720
ggcatcgacg tgtacaacgc catcatcggt ggcttcgtga ccgagtccgg cgagaagatc  780
aagggcctca acgagtacat caacctgtac aaccagaaga caaagcaaga gctcccgaag  840
ttcaagcccc tctacaagca ggtcctgtcc gaccgcgagt ccctgagctt ctacggcgag  900
ggctacacga gcgacgagga ggtcctcgag gtgttcagga caccctgaa caagaacagc  960
gagatcttct ccagcatcaa gaagctcgag aagctgttca gaacttcga cgagtactcc 1020
agcgccggca tcttcgtcaa gaacggcccc gcgatctcca cgatcagcaa ggatatcttc 1080
ggcgagtgga acgtgatcag ggacaagtgg aacgccgagt acgacgacat ccacctcaag 1140
aagaaggcgg tggtcaccga agtacgag acgaccgca ggagtccttt caagaagatc 1200
ggctccttca gcctcgagca gctgcaggag tacgccgacg cggacctctc cgtggtcgag 1260
aagctgaagg agatcatcat ccagaaggtc gacgagatca caaggtgta cggctccgac 1320
gagaagctgt tcgacgccga cttcgtcctc gagaagtccc tgaagaagaa cgacgccgtg 1380
gtcgcgatca tgaaggacct cctggactcc gtgaagagct tcgagaacta catcaaggcg 1440
ttcttcggcg agggcaagga gacgaaccgc gacgagtcct tctacggcga cttcgtcctc 1500
gcctacgaca tcctcctgaa ggtggaccac atctacgacg cgatcaggaa ctacgtgacc 1560
cagaagccgt acagcaagga caagttcaag ctgtacttcc agaacccca gttcatgcgc 1620
ggctgggaca aggacaagga cggactac cgcgccacca tcctccgcta cggcagcaag 1680
tactacctgg ccatcatgga caagaagtac gcgaagtgcc tccagaagat cgacaaggac 1740
gacgtcaacg gcaactacga gaagatcaac tacaagctgc tgcccgggcc caacaagatg 1800
ctgccgaggg tgttcttctc caagaagtgg atggcctact acaaccccag cgaggacatc 1860
cagaagatct acaagaacgg cacgttcaag aagggcgaca tgttcaacct caacgactgc 1920
cacaagctga tcgacttctt caaggactcc atcagccgct accgaagtg gtccaacgcc 1980
tacgacttca acttcagcga gacagagaag tacaaggaca tcgcgggctt ctacagggag 2040
gtcgaggagc agggctacaa ggtgtccttc gagtccgcca agaagggagg ggtcgacaag 2100
ctcgtggagg agggcaagct gtacatgttc cagatctaca acaaggactt ctccgacaag 2160
agccacggca cgcccaacct ccacaccatg tacttcaagc tcctgttcga cgagaacaac 2220
cacggccaga tccgcctctc cggcggcgcc gagctgttca tgaggagggc gagcctcaag 2280
aaggaggagc tggtggtcca ccccgctaac agcccaatcg cgaacaagaa cccgacaac 2340
cccaagaaga ccacgaccct ctcctacgac gtgtacaagg acaagcgctt cagcgaggac 2400
cagtacgagc tgcacatccc gatcgccatc aacaagtgcc ccaagaacat cttcaagatc 2460
aacaccgagg tcagggtgct cctgaagcac gacgacaacc cctacgtgat cggcatcgac 2520
cgcggcgaga ggaacctcct gtacatcgtg gtcgtggacg gcaagggcaa catcgtggag 2580
cagtactccc tgaacgagat catcaacaac ttcaacggca tccgcatcaa gacggactac 2640
cacagcctcc tggacaagaa ggagaaggag cgcttcgagg cgcagaactg gacctcc    2700
atcgagaaca tcaaggagct caaggcgggc tacatcagcc aggtcgtgca caagatctgc 2760
gagctggtcg agaagtacga cgccgtgatc gcgctcgagg acctgaactc cggcttcaag 2820
aacagcaggg tcaaggtgga gaagcaggtc taccagaagt tcgagaagat gctcatcgac 2880
aagctgaact acatggtgga caagaagtcc aacccgtgcg ctacgggcgg cgcgctcaag 2940
ggctaccaga tcaccaacaa gttcgagagc ttcaagtcca tgagcaccca gaacggcttc 3000
```

-continued

```
atcttctaca tcccggcctg gctgacgtcc aagatcgacc ccagcaccgg cttcgtcaac   3060
ctcctgaaga cgaagtacac ctccatcgcg gacagcaaga agttcatctc cagcttcgac   3120
cgcatcatgt atgtgccgga ggaggacctc ttcgagttcg ccctggacta caagaacttc   3180
tccaggacgg acgcggatta catcaagaag tggaagctct acagctacgg caaccgcatc   3240
aggatcttcc gcaacccaa gaagaacaac gtcttcgact gggaggaggt gtgcctcacc   3300
tccgcctaca aggagctgtt caacaagtac ggcatcaact accagcaggg cgacatcagg   3360
gcgctcctgt gcgagcagag cgacaaggcc ttctactcca gcttcatggc gctcatgtcc   3420
ctcatgctgc agatgcgcaa cagcatcacg ggcaggaccg acgtcgactt cctgatctcc   3480
ccggtgaaga acagcgacgg catcttctac gacacgcgca actacgagg ccaggagaac   3540
gcgatcctgc caaagaacgc ggacgccaac ggcgcctaca acatcgcgag gaaggtgctg   3600
tgggccatcg gccagttcaa gaaggcgag gacgagaagc tcgacaaggt caagatcgcc   3660
atctccaaca aggagtggct ggagtacgcg cagacctcgg tgaagcacaa gaggcccgct   3720
gccaccaaga aggcgggcca ggccaagaag aagaagtga                          3759
```

| SEQ ID NO: 30 | moltype = AA length = 238 |
|---|---|
| FEATURE | Location/Qualifiers |
| REGION | 1..238 |
| | note = tdTomato |
| source | 1..238 |
| | mol_type = protein |
| | organism = synthetic construct |

SEQUENCE: 30
```
MVSKGEEVIK EFMRFKVRME GSMNGHEFEI EGEGEGRPYE GTQTAKLKVT KGGPLPFAWD    60
ILSPQFMYGS KAYVKHPADI PDYKKLSFPE GFKWERVMNF EDGGLVTVTQ DSSLQDGTLI   120
YKVKMRGTNF PPDGPVMQKK TMGWEASTER LYPRDGVLKG EIHQALKLKD GGHYLVEFKT   180
IYMAKKPVQL PGYYYVDTKL DITSHNEDYT IVEQYERSEG RHHLFLYGMD ELYKSRGT     238
```

| SEQ ID NO: 31 | moltype = DNA length = 717 |
|---|---|
| FEATURE | Location/Qualifiers |
| misc_feature | 1..717 |
| | note = tdTomato |
| source | 1..717 |
| | mol_type = other DNA |
| | organism = synthetic construct |

SEQUENCE: 31
```
atggtgagca agggcgagga ggtcatcaaa gagttcatgc gcttcaaggt cgcatggag    60
ggctccatga acggccacga gttcgagatc gagggcgagg gcgagggccg cccctacgag   120
ggcacccaga ccgccaagct gaaggtgacc aaggggcggcc cctgcccctt cgcctgggac   180
atcctgtccc cccagttcat gtacggctcc aaggcgtacg tgaagcaccc cgccgacatc   240
cccgattaca agaagctgtc cttccccgag ggcttcaagt gggagcgcgt gatgaacttc   300
gaggacggcg gtctggtgac cgtgacccag gactcctccc tgcaggacgg cacgctgatc   360
tacaaggtga agatgcgcgg caccaacttc cccccgacg gccccgtaat gcagaagaag   420
accatgggct gggaggcctc caccgagcgc ctgtacccc gacggcgtg aagggc        480
gagatccacc aggccctgaa gctgaaggac ggcggccact acctggtgga gttcaagacc   540
atctacatgg ccaagaagcc cgtgcaactg cccggctact actacgtgga caccaagctg   600
gacatcacct cccacaacga ggactacacc atcgtggaac agtacgagcg ctccgaggc   660
cgccaccacc tgttcctgta cggcatggac gagctgtaca agtctagagg tacctga      717
```

| SEQ ID NO: 32 | moltype = DNA length = 21 |
|---|---|
| FEATURE | Location/Qualifiers |
| misc_feature | 1..21 |
| | note = Protospacer m7GEP336 |
| source | 1..21 |
| | mol_type = other DNA |
| | organism = synthetic construct |

SEQUENCE: 32
gcacgttctt gcgcatgagc a                                              21

| SEQ ID NO: 33 | moltype = DNA length = 21 |
|---|---|
| FEATURE | Location/Qualifiers |
| misc_feature | 1..21 |
| | note = Protospacer m7GEP337 |
| source | 1..21 |
| | mol_type = other DNA |
| | organism = synthetic construct |

SEQUENCE: 33
gcgccaccgt cgttgacagc a                                              21

| SEQ ID NO: 34 | moltype = DNA length = 21 |
|---|---|
| FEATURE | Location/Qualifiers |
| misc_feature | 1..21 |
| | note = Protospacer m7GEP338 |
| source | 1..21 |
| | mol_type = other DNA |
| | organism = synthetic construct |

SEQUENCE: 34
ctgtgcagac aacggcaacc g                                              21

| SEQ ID NO: 35 | moltype = DNA length = 21 |
|---|---|

```
FEATURE                 Location/Qualifiers
misc_feature            1..21
                        note = Protospacer m7GEP339
source                  1..21
                        mol_type = other DNA
                        organism = synthetic construct
SEQUENCE: 35
agcttctcca cctcccagtc g                                              21

SEQ ID NO: 36           moltype = AA  length = 1791
FEATURE                 Location/Qualifiers
REGION                  1..1791
                        note = Zm00008a004913
source                  1..1791
                        mol_type = protein
                        organism = synthetic construct
SEQUENCE: 36
MLSGIIDGLT GANKHARLKG TVVLMRKNVL DLNDFGATVV DSISEFLGKG VTCQLISSTL    60
VDANNGNRGR VGAEANLEQW LTSLPSLTTG ESKFGVTFDW EVEKLGVPGA VVVKNNHAAE   120
FFLKTITLDD VPGRGAVTFV ANSWVYPAGK YRYNRVFFSN DTYLPSQMPA ALKPYRDDEL   180
RNLRGDDQQP PYQEHDRVYR YDVYNDLGEP DGGNPRPILG GSADHPYPRR CRTGRKPTKT   240
DPNSESRLSL VEQIYVPRDE RFGHLKMSDF LGYSIKAITQ GIIPAVRTYV DTTPGEFDSF   300
QDIINLYEGG IKLPKIQALE DMRKLFPLQL VKDLLPAGGD YLLKLPIPQI IQGTSRIPID   360
VRGRLLSGLH IYMCSYEDKN AWRTDEEFAR EVLAGVNPMV ITRLTEFPPK STLDPSKYGD   420
HTSTITAEHI EKNLEGLTVQ QALDGNRLYI LDHHDRFMPF LIDVNNLEGN FIYATRTLFF   480
LRGDGRLAPL AIELSEPYID GDLTVAKSKV YTPASSGVEA WVWQLAKAYV AVNDSGWHQL   540
VSHWLNTHAV MEPFVIATNR QLSVTHPVHK LLSSHFRDTM TINALARQTL INGGGIFEMT   600
VFPGKYALGM SSVVYKSWNF TEQGLPADLV KRGVAVADPS SPYKVRLLIE DYPYASDGLA   660
IWHAIEQWVG EYLAIYYPDD GALRGDEELQ AWWKEVREVG HGDHKDAPWW PKMQAVSELA   720
SACTTIIWIA SALHAAVNFG QYPYAGYLPN RPTVSRRRMP EPGSKEYEEL ERDPERGFIH   780
TITSQIQTII GISLIEILSK HSSDEVYLGQ RDTPEWTSDA RALAAFKRFS DALVKIEGKV   840
VGENRDPQLR NRNGPAEFPY MLLYPNTSDH SEARERAAGQ GIHTHTHRTL PEKREARSEE   900
RPATMFWHGV ADRLTGKNKE AWNEGKIRGT VRLVKKEVLD VGDFNASLLD GVHRILGWDD   960
GVAFQLVSAT AADPSNGSRG KVGKAAHLEE AVVSLKSTTD GETVYRVSFE WDGSQGVPGA  1020
VLVRNLQHAE FFLKSLTLEG VPGRGTVVFV ANSWIYPHNL YSQERVFFAN DTYLPSKMPA  1080
ALVPYRQDEL KILRGDDNPG PYKEHDRVYR YDYYNDLGEP DKGEDHARPV LGGSQEHPYP  1140
RRCRTGRRPT ETDPNSESRL FLLNLNIYVP RDERFGHLKM SDFLGYSLKA IIEAVLPTLG  1200
TFVDDTPKEF DSFEDILGLY EPGPEAPNNP LVAEVRKRIP SEFLRSILPN GSHDHPLKMP  1260
LPNIIRSDVL KKAPEFKFGW RTDEEFARET LAGVNPVLIK RLTEFPAKST LDPSQYGDHT  1320
SKITEAHIQH NMEGLSVQNA LKKNRLFILD HHDHFMPYLN KINELEGNFI YASRTLLFLK  1380
DDGTLKPLAV ELSLPHPDGQ QHGAVSKVYT PAHSGAEGHV WQLAKAYACV NDSAWHQLIS  1440
HWLNTHAVIE PFVIATNRQL SVVHPVHKLL SPHYRDLNTI NALARQTLIN ADGIFERTVF  1500
PAKYALGMSS DVYKSWNFNE QALPADLVKR GVAVPDQSSP YGVRLLIKDY PYAVDGLVIW  1560
WAIERWVKEY LDVYYPNDGE LQRDVELQAW WKEVREEAHG DLKDRDWWPR MDAVQRLARA  1620
CTTVIWVASA LHAAVNFGQY PYAGYLPNRP TVSRRPMPEP GSDDYKKLEA GQKEADAVFI  1680
RTITSQFQTI LGISLIEILS KHSSDEVYLG QRDEPERWTS DARALDAFRR FGSRLVEIEK  1740
RIRTMNDSPT LKNRKGPVEM PYMLLYPNTS DVTGEKGEGL TAMGIPNSIS I           1791

SEQ ID NO: 37           moltype = AA  length = 1790
FEATURE                 Location/Qualifiers
REGION                  1..1790
                        note = WVP18-09358-016
source                  1..1790
                        mol_type = protein
                        organism = synthetic construct
SEQUENCE: 37
MLSGIIDGLT GANKHARLKG TVVLMRKNVL DLNDFGATVV DSISEFLGKG VTCQLISSTL    60
VDANNGNRGR VGAEANLEQW LTSLPSLTTG ESKFGVTFDW EVEKLGVPGA VVVKNNHAAE   120
FFLKTITLDD VPGRGAVTFV ANSWVYPAGK YRYNRVFFSN DTYLPSQMPA ALKPYRDDEL   180
RNLRGDDQQG PYQEHDRVYR YDVYNDLGEP DGGNPRPILG GSADHPYPRR CRTGRKPTKT   240
DPNSESRLSL VEQIYVPRDE RFGHLKMSDF LGYSIKAITQ GIIPAVRTYV DTTPGEFDSF   300
QDIINLYEGG IKLPKIQALE DMRKLFPLQL VKDLLPAGGD YLLKLPIPQI IQGTSRIPID   360
VRGRLLSGLH IYMCSYEDKN AWRTDEEFAR EVLAGVNPMV ITRLTEFPPK STLDPSKYGD   420
HTSTITAEHI EKNLEGLTVQ QALDGNRLYI LDHHDRFMPF LIDVNNLEGN FIYATRTLFF   480
LRGDGRLAPL AIELSEPYID GDLTVAKSKV YTPASSGVEA WVWQLAKAYV AVNDSGWHQL   540
VSHWLNTHAV MEPFVIATNR QLSVTHPVHK LLSSHFRDTM TINALARQTL INGGGIFEMT   600
VFPGKYALGM SSVVYKSWNF TEQGLPADLV KRGVAVADPS SPYKVRLLIE DYPYASDGLA   660
IWHAIEQWVG EYLAIYYPDD GALRGDEELQ AWKEVREVGH GDHKDAPWWP KMQAVSELAS   720
ACTTIIWIAS ALHAAVNFGQ YPYAGYLPNR PTVSRRRMPE PGSKEYEELE RDPERGFIHT   780
ITSQIQTIIG ISLIEILSKH SSDEVYLGQR DTPEWTSDAR ALAAFKRFSD ALVKIEGKVV   840
GENRDPQLRN RNGPAEFPYM LLYPNTSDHS EARERAAGQG IHTHTHRTLP EKREARSEER   900
PATMFWHGVA DRLTGKNKEA WNEGKIRGTV RLVKKEVLDV GDFNASLLDG VHRILGWDDG   960
VAFQLVSATA ADPSNGSRGK VGKAAHLEEA VVSLKSTTDG ETVYRVSFEW DGSQGVPGAV  1020
LVRNLQHAEF FLKSLTLEGV PGRGTVVFVA NSWIYPHNLY SQERVFFAND TYLPSKMPAA  1080
LVPYRQDELK ILRGDDNPGP YKEHDRVYRY DYYNDLGEPD KGEDHARPVL GGSQEHPYPR  1140
RCRTGRRPTE TDPNSESRLF LLNLNIYVPR DERFGHLKMS DFLGYSLKAI IEAVLPTLGT  1200
FVDDTPKEFD SFEDILGLYE PGPEAPNNPL VAEVRKRIPS EFLRSILPNG SHDHPLKMPL  1260
PNIIRSDVLK KAPEFKFGWR TDEEFARETL AGVNPVLIKR LTEFPAKSTL DPSQYGDHTS  1320
KITEAHIQHN MEGLSVQNAL KKNRLFILDH HDHFMPYLNK INELEGNFIY ASRTLLFLKD  1380
```

```
DGTLKPLAVE LSLPHPDGQQ HGAVSKVYTP AHSGAEGHVW QLAKAYACVN DSAWHQLISH    1440
WLNTHAVIEP FVIATNRQLS VVHPVHKLLS PHYRDTLNIN ALARQTLINA DGIFERTVFP    1500
AKYALGMSSD VYKSWNFNEQ ALPADLVKRG VAVPDQSSPY GVRLLIKDYP YAVDGLVIWW    1560
AIERWVKEYL DVYYPNDGEL QRDVELQAWW KEVREEAHGD LKDRDWWPRM DAVQRLARAC    1620
TTVIWVASAL HAAVNFGQYP YAGYLPNRPT VSRRPMPEPG SDDYKKLEAG QKEADAVFIR    1680
TITSQFQTIL GISLIEILSK HSSDEVYLGQ RDEPERWTSD ARALDAFRRF GSRLVEIEKR    1740
IRTMNDSPTL KNRKGPVEMP YMLLYPNTSD VTGEKGEGLT AMGIPNSISI               1790

SEQ ID NO: 38           moltype = AA  length = 1791
FEATURE                 Location/Qualifiers
REGION                  1..1791
                        note = WVP18-09344-014
source                  1..1791
                        mol_type = protein
                        organism = synthetic construct
SEQUENCE: 38
MLSGIIDGLT GANKHARLKG TVVLMRKNVL DLNDFGATVV DSISEFLGKG VTCQLISSTL     60
VDANNGNRGR VGAEANLEQW LTSLPSLTTG ESKFGVTFDW EVEKLGVPGA VVVKNNHAAE    120
FFLKTITLDD VPGRGAVTFV ANSWVYPAGK YRYNRVFFSN DTYLPSQMPA ALKPYRDDEL    180
RNLRGDDQQG PYQEHDRVYR YDVYNDLGEP DGGNPRPILG GSADHPYPRR CRTGRKPTKT    240
DPNSESRLSL VEQIYVPRDE RFGHLKMSDF LGYSIKAITQ GIIPAVRTYV DTTPGEFDSF    300
QDIINLYEGG IKLPKIQALE DMRKLFPLQL VKDLLPAGGD YLLKLPIPQI IQGTSRIPID    360
VRGRLLSGLH IYMCSYEDKN AWRTDEEFAR EVLAGVNPMV ITRLTEFPPK STLDPSKYGD    420
HTSTITAEHI EKNLEGLTVQ QALDGNRLYI LDHHDRFMPF LIDVNNLEGN FIYATRTLFF    480
LRGDGRLAPL AIELSEPYID GDLTVAKSKV YTPASSGVEA WVWQLAKAYV AVNDSGWHQL    540
VSHWLNTHAV MEPFVIATNR QLSVTHPVHK LLSSHFRDTM TINALARQTL INGGGIFEMT    600
VFPGKYALGM SSVVYKSWNF TEQGLSADLV KRGVAVADPS SPYKVRLLIE DYPYASDGLA    660
IWHAIEQWVG EYLAIYYPDD GALRGDEELQ AWWKEVREVG HGDHKDAPWW PKMQAVSELA    720
SACTTIIWIA SALHAAVNFG QYPYAGYLPN RPTVSRRRMP EPGSKEYEEL ERDPERGFIH    780
TITSQIQTII GISLIEILSK HSSDEVYLGQ RDTPEWTSDA RALAAFKRFS DALVKIEGKV    840
VGENRDPQLR NRNGPAEFPY MLLYPNTSDH SEARERAAGQ GIHTHTHRTL PEKREARSEE    900
RPATMFWHGV ADRLTGKNKE AWNEGKIRGT VRLVKKEVLD VGDFNASLLD GVHRILGWDD    960
GVAFQLVSAT AADPSNGSRG KVGKAAHLEE AVVSLKSTTD GETVYRVSFE WDGSQGVPGA   1020
VLVRNLQHAE FFLKSLTLEG VPGRGTVVFV ANSWIYPHRNL YSQERVFFAN DTYLPSKMPA   1080
ALVPYRQDEL KILRGDDNPG PYKEHDRVYR YDYYNDLGEP DKGEDHARPV LGGSQEHPYP   1140
RRCRTGRRPT ETDPNSESRL FLLNLNIYVP RDERFGHLKM SDFLGYSLKA IIEAVLPTLG   1200
TFVDDTPKEF DSFEDILGLY EPGPEAPNNP LVAEVRKRIP SEFLRSILPN GSHDHPLKMP   1260
LPNIIRSDVL KKAPEFKFGW RTDEEFARET LDAGVNPVLIK RTEFPAKST LDPSQYGDHT   1320
SKITEAHIQH NMEGLSVQNA LKKNRLFILD HHDHFMPYLN KINELEGNFI YASRTLLFLK   1380
DDGTLKPLAV ELSLPHPDGQ QHGAVSKVYT PAHSGAEGHV WQLAKAYACV NDSAWHQLIS   1440
HWLNTHAVIE PFVIATNRQL SVVHPVHKLL SPHYRDTLNI NALARQTLIN ADGIFERTVF   1500
PAKYALGMSS DVYKSWNFNE QALPADLVKR GVAVPDQSSP YGVRLLIKDY PYAVDGLVIW   1560
WAIERWVKEY LDVYYPNDGE LQRDVELQAW WKEVREEAHG DLKDRDWWPR MDAVQRLARA   1620
CTTVIWVASA LHAAVNFGQY PYAGYLPNRP TVSRRPMPEP GSDDYKKLEA GQKEADAVFI   1680
RTITSQFQTI LGISLIEILS KHSSDEVYLG QRDEPERWTS DARALDAFRR FGSRLVEIEK   1740
RIRTMNDSPT LKNRKGPVEM PYMLLYPNTS DVTGEKGEGL TAMGIPNSIS I            1791

SEQ ID NO: 39           moltype = AA  length = 1790
FEATURE                 Location/Qualifiers
REGION                  1..1790
                        note = WVP18-09309-014_339-009
source                  1..1790
                        mol_type = protein
                        organism = synthetic construct
SEQUENCE: 39
MLSGIIDGLT GANKHARLKG TVVLMRKNVL DLNDFGATVV DSISEFLGKG VTCQLISSTL     60
VDANNGNRGR VGAEANLEQW LTSLPSLTTG ESKFGVTFDW EVEKLGVPGA VVVKNNHAAE    120
FFLKTITLDD VPGRGAVTFV ANSWVYPAGK YRYNRVFFSN DTYLPSQMPA ALKPYRDDEL    180
RNLRGDDQQG PYQEHDRVYR YDVYNDLGEP DGGNPRPILG GSADHPYPRR CRTGRKPTKT    240
DPNSESRLSL VEQIYVPRDE RFGHLKMSDF LGYSIKAITQ GIIPAVRTYV DTTPGEFDSF    300
QDIINLYEGG IKLPKIQALE DMRKLFPLQL VKDLLPAGGD YLLKLPIPQI IQGTSRIPID    360
VRGRLLSGLH IYMCSYEDKN AWRTDEEFAR EVLAGVNPMV ITRLTEFPPK STLDPSKYGD    420
HTSTITAEHI EKNLEGLTVQ QALDGNRLYI LDHHDRFMPF LIDVNNLEGN FIYATRTLFF    480
LRGDGRLAPL AIELSEPYID GDLTVAKSKV YTPASSGVEA WVWQLAKAYV AVNDSGWHQL    540
VSHWLNTHAV MEPFVIATNR QLSVTHPVHK LLSSHFRDTM TINALARQTL INGGGIFEMT    600
VFPGKYALGM SSVVYKSWNF TEQGLPADLV KRGVAVADPS SPYKVRLLIE DYPYASDGLA    660
IWHAIEQVGE YLAIYYPDDG ALRGDEELQA WWKEVREVGH GDHKDAPWWP KMQAVSELAS    720
ACTTIIWIAS ALHAAVNFGQ YPYAGYLPNR PTVSRRRMPE PGSKEYEELE RDPERGFIHT    780
ITSQIQTIIG ISLIEILSKH SSDEVYLGQR DTPEWTSDAR ALAAFKRFSD ALVKIEGKVV    840
GENRDPQLRN RNGPAEFPYM LLYPNTSDHS EARERAAGQG IHTHTHRTLP EKREARSEER    900
PATMFWHGVA DRLTGKNKEA WNEGKIRGTV RLVKKEVLDV GDFNASLLDG VHRILGWDDG    960
VAFQLVSATA ADPSNGSRGK VGKAAHLEEA VVSLKSTTDG ETVYRVSFEW DGSQGVPGAV   1020
LVRNLQHAEF FLKSLTLEGV PGRGTVVFVA NSWIYPHNLY SQERVFFAND TYLPSKMPAA   1080
LVPYRQDELK ILRGDDNPGP YKEHDRVYRY DYYNDLGEPD KGEDHARPVL GGSQEHPYPR   1140
RCRTGRRPTE TDPNSESRLF LLNLNIYVPR DERFGHLKMS DFLGYSLKAI IEAVLPTLGT   1200
FVDDTPKEFD SFEDILGLYE PGPEAPNNPL VAEVRKRIPS EFLRSILPNG SHDHPLKMPL   1260
PNIIRSDVLK KAPEFKFGWR TDEEFARETL AGVNPVLIKR LTEFPAKSTL DPSQYGDHTS   1320
KITEAHIQHN MEGLSVQNAL KKNRLFILDH HDHFMPYLNK INELEGNFIY ASRTLLFLKD   1380
DGTLKPLAVE LSLPHPDGQQ HGAVSKVYTP AHSGAEGHVW QLAKAYACVN DSAWHQLISH   1440
```

```
WLNTHAVIEP FVIATNRQLS VVHPVHKLLS PHYRDTLNIN ALARQTLINA DGIFERTVFP  1500
AKYALGMSSD VYKSWNFNEQ ALPADLVKRG VAVPDQSSPY GVRLLIKDYP YAVDGLVIWW  1560
AIERWVKEYL DVYYPNDGEL QRDVELQAWW KEVREEAHGD LKDRDWWPRM DAVQRLARAC  1620
TTVIWVASAL HAAVNFGQYP YAGYLPNRPT VSRRPMPEPG SDDYKKLEAG QKEADAVFIR  1680
TITSQFQTIL GISLIEILSK HSSDEVYLGQ RDEPERWTSD ARALDAFRRF GSRLVEIEKR  1740
IRTMNDSPTL KNRKGPVEMP YMLLYPNTSD VTGEKGEGLT AMGIPNSISI            1790

SEQ ID NO: 40           moltype = AA   length = 1791
FEATURE                 Location/Qualifiers
REGION                  1..1791
                        note = WVP18-09307-014
source                  1..1791
                        mol_type = protein
                        organism = synthetic construct
SEQUENCE: 40
MLSGIIDGLT GANKHARLKG TVVLMRKNVL DLNDFGATVV DSISEFLGKG VTCQLISSTL  60
VDANNGNRGR VGAEANLEQW LTSLPSLTTG ESKFGVTFDW EVEKLGVPGA VVVKNNHAAE  120
FFLKTITLDD VPGRGAVTFV ANSWVYPAGK YRYNRVFFSN DTYLPSQMPA ALKPYRDDEL  180
RNLRGDDQQG PYQEHDRVYR YDVYNDLGEP DGGNPRPILG GSADHPYPRR CRTGRKPTKT  240
DPNSESRLSL VEQIYVPRDE RFGHLKMSDF LGYSIKAITQ GIIPAVRTYV DTTPGEFDSF  300
QDIINLYEGG IKLPKIQALE DMRKLFPLQL VKDLLPAGGD YLLKLPIPQI IQGTSRIPID  360
VRGRLLSGLH IYMCSYEDKN AWRTDEEFAR EVLAGVNPMV ITRLTEFPPK STLDPSKYGD  420
HTSTITAEHI EKNLEGLTVQ QALDGNRLYI LDHHDRFMPF LIDVNNLEGN FIYATRTLFF  480
LRGDGRLAPL AIELSEPYID GDLTVAKSKV YTPASSGVEA WVWQLAKAYV AVNDSGWHQL  540
VSHWLNTHAV MEPFVIATNR QLSVTHPVHK LLSSHFRDTM TINALARQTL INGGGIFEMT  600
VPPGKYALGM SSVVYKSWNF TEQGLPADLV KRGVAVADPS SPYKVRLLIE DYPYASDGLA  660
IWHAIEQWVG EYLAIYYPDD GALRGDEELQ AWWKEVREVG HGDHKDAPWW PKMQAVSELA  720
SACTTIIWIA SALHAAVNFG QYPYAGYLPN RPTVSRRRMP EPSSKEYEEL ERDPERGFIH  780
TITSQIQTII GISLIEILSK HSSDEVYLGQ RDTPEWTSDA RALAAFKRFS DALVKIEGKV  840
VGENRDPQLR NRNGPAEFPY MLLYPNTSDH SEARERAAGQ GIHTHTHRTL PEKREARSEE  900
RPATMFWHGV ADRLTGKNKE AWNEGKIRGT VRLVKKEVLD VGDFNASLLD GVHRILGWDD  960
GVAFQLVSAT AADPSNGSRG KVGKAAHLEE AVVSLKSTTD GETVYRVSFE WDGSQGVPGA  1020
VLVRNLQHAE FFLKSLTLEG VPGRGTVVFV ANSWIYPHNL YSQERVFFAN DTYLPSKMPA  1080
ALVPYRQDEL KILRGDDNPG PYKEHDRVYR YDYYNDLGEP DGGSQEHPYP LGGSQEHPYP  1140
RRCRTGRRPT ETDPNSESRL FLLNLNIYVP RDERFGHLKM SDFLGYSLKA IIEAVLPTLG  1200
TFVDDTPKEF DSFEDILGLY EPGPEAPNNP LVAEVRKRIP SEFLRSILPN GSHDHPLKMP  1260
LPNIIRSDVL KKAPEFKFGW RTDEEFARET LAGVNPVLIK RLTEFPAKST LDPSQYGDHT  1320
SKITEAHIQH NMEGLSVQNA LKKNRLFILD HHDHFMPYLN KINELEGNFI YASRTLLFLK  1380
DDGTLKPLAV ELSLPHPDGQ QHGAVSKVYT PAHSGAEGHV WQLAKAYACV NDSAWHQLIS  1440
HWLNTHAVIE PFVIATNPQL SVVHPVHKLL SPHYRDTLNI NALARQTLIN ADGIFERTVF  1500
PAKYALGMSS DVYKSWNFNE QALPADLVKR GVAVPDQSSP YGVRLLIKDY PYAVDGLVIW  1560
WAIERWVKEY LDVYYPNDGE LQRDVELQAW WKEVREEAHG DLKDRDWWPR MDAVQRLARA  1620
CTTVIWVASA LHAAVNFGQY PYAGYLPNRP TVSRRPMPEP GSDDYKKLEA GQKEADAVFI  1680
RTITSQFQTI LGISLIEILS KHSSDEVYLG QRDEPERWTS DARALDAFRR FGSRLVEIEK  1740
RIRTMNDSPT LKNRKGPVEM PYMLLYPNTS DVTGEKGEGL TAMGIPNSIS I          1791

SEQ ID NO: 41           moltype = DNA   length = 5376
FEATURE                 Location/Qualifiers
misc_feature            1..5376
                        note = Zm00008a004913
source                  1..5376
                        mol_type = other DNA
                        organism = synthetic construct
SEQUENCE: 41
atgctgagcg ggatcatcga cgggctgacg ggggcgaaca agcatgcgcg gctcaagggc  60
acggtggtgc tcatgcgcaa gaacgtgctg gacctcaacg acttcggcgc caccgtcgtc  120
gacagcatca gcgagttcct cggcaagggg gtcacctgcc agctcatcag ctccactctc  180
gtcgacgcca acaacggcaa ccgcgggcgg gtcggggcgg aggcgaacct ggagcagtgg  240
ctgacgagcc tgccgtcgct gacgaccggc gagtccaagt tcggcgtcac gttcgactgg  300
gaggtggaga agctgggagt gccggggcc gtcgtcgtca gaacaaccac gccgccgag  360
ttcttcctca agacaatcac cctcgacgac gtgccggcc gcggcgccgt caccttcgtc  420
gccaactcct gggtctaccc cgcggggaag taccgctaca accgcgtctt cttctccaac  480
gatacgtacc tgccaagcca gatgccggcg gcgctgaagc cgtaccgcga cgacgagctc  540
cgcaacctcc gcggcgacga ccagcagggc ccctaccagg agcacgaccg cgtgtaccgc  600
tacgacgtct acaacgacct cggcgagccc gacggcggca acccgcgccc catcctcggc  660
ggctccgccg accaccgta cccgcgccgc tgccgcacgg gccgcaagcc caccaaaacc  720
gaccccaact cggagagccg actgtcgctg gtggagcaga tctacgtgcc gcgggacgag  780
cgcttcggcc acctcaagat gtccgacttc ctgggctact ccatcaagc catcacgcag  840
ggcatcatcc cggccgtgcg cacgtacgtg gacaccaccc cgggcgagtt cgactcctcc  900
caggacatca tcaacctgta cgagggcggg atcaagctgc ccaagatcca ggcgctcgag  960
gacatgcgca agctcttccc gctccagctc gtcaaggacc tcctccccgc cggcggggac  1020
tacctgctca agctccccat cccacagatc atccaaggca gtcacgtat ccgatcgat  1080
gtcaggggc ggctgttgtc tggtctgcat atatatatgt gctcctatga ggacaagaac  1140
gaggagga ccgacgagga gttcgcgcgg gaggtgctcg ccggcgtcaa cccgatggtg  1200
atcacgcgc tcacggagtt cccgcccaag agcacgctgg accccagcaa gtacggcgac  1260
cacaccagca cgatcacggc ggagcacatc gagaagaacc tcgagggcct cacggtgcag  1320
caggcgctgg acggcaacag gctctacatc ctggaccacc acgaccgctt catgccgttc  1380
ctcatcgacg tcaacaacct ggagggcaac ttcatctacg ccaccaggac gctcttcttc  1440
ctgcgcggcg acggcaggct cgcgccctc gccatcgagc tcagcgagcc gtacatcgac  1500
```

-continued

```
gggggacctca  ccgtggccaa  gagcaaggtc  tacacgccgg  cgtccagcgg  cgtcgaggcc  1560
tgggtgtggc  agctcgccaa  ggcctatgtc  gccgtcaacg  actctggctg  gcaccaactc  1620
gtcagccact  ggctgaacac  ccacgcggtg  atggagccgt  tcgtgatcgc  gacgaaccgg  1680
cagctgagcg  tgacgcaccc  ggtgcacaag  ctcctgagct  cgcacttccg  cgacaccatg  1740
accatcaacg  cgctggcgcg  gcagacgctc  atcaacgcgc  gcggcatctt  cgagatgacc  1800
gtcttcccgg  gcaagtacgc  gctgggcatg  tcctccgtgg  tgtacaagag  ctggaacttc  1860
accgagcagg  gcctccccgc  cgacctcgtc  aagaggggcg  tggcggtggc  ggacccgtcc  1920
agcccgtaca  aggtgcggct  gctgatcgag  gactacccgt  acgcgagcga  cgggctggcc  1980
atctggccag  ccatcgagca  gtgggtgggc  gagtacctgg  ccatctacta  ccccgacgac  2040
ggcgcgctgc  ggggcgacga  ggagctgcag  cgtggtgga   aggaggtgcg  cgaggtcgga  2100
cacggcgacc  acaaggacgc  gccctggtgg  cccaagatgc  aggccgtgtc  ggagctcgcc  2160
agcgcctgca  ccaccatcat  ctggatcgcg  tcggcgctcc  acgccgccgt  caacttcggc  2220
cagtaccccgt acgcggggta  cctcccgaac  aggcccacgt  gagccggcg   ccggatgccg  2280
gagcccggca  gcaaggagta  cgaggagctg  cgaggagctg  cttcatccac  2340
accatcacga  gccagatcca  gaccatcatc  ggcatctcgc  tcatcgagat  cctctccaag  2400
cactcctccg  acgaggtgta  cctcggccag  cgcgacaccc  ccgagtggac  ctccgacgcc  2460
cgggcgctgc  cggcgttcaa  gaggttcagc  gacgcgctgg  tcaagatcga  gggcaaggtg  2520
gtgggcgaga  accgcgaccc  cagctgagg   aacaggaacg  gccccgccga  gttcccctac  2580
atgctgctct  atcccaacac  ctctgaccac  agcgaggcga  gggagcgagc  agcagggcaa  2640
ggcatccaca  cccacaccca  ccggacactc  cctgagaagc  gagaagcgag  aagcgaagag  2700
cggccggcca  ccatgttctg  gcacgggtc   gcggaccgg   tgacggggaa  gaacaaggag  2760
gcgtggaacg  agggaaagat  ccgcggcacg  gtgaggctgg  tcaagaagga  tgctggac    2820
gtcggcgact  tcaacgcctc  gctcctcgac  ggcgtacaca  ggatcctcgg  ctggacgaa   2880
ggcgtcgcct  tccagctcgt  cagcgccacc  gcggccgacc  ccagcaacgg  gagccgcggc  2940
aaggtcggga  aggcggcgca  cctggaggag  gcggtggtgt  cgctcaagtc  gacgacggac  3000
ggggagaccg  tgtaccgggt  gagcttcgag  tgggacggga  cgcagggcgt  cccggcgccc  3060
gtcctggtca  ggaacctgca  gcacgccgag  ttcttcctca  agtcgctcac  cctcgagggc  3120
gtccccggca  ggggcaccgt  cgtcttcgtc  gccaactcgt  ggatctaccc  gcacaatctc  3180
tactcccagg  aacgcgtctt  cttcgccaac  gacacttatc  tgccaagcaa  aatgcctgcg  3240
gcattggtgc  cttaccggca  ggacgagctc  aagattctcc  gcggcgacga  taatcctgcc  3300
ccatacaagg  agcacgaccg  cgtctaccgt  tacgactact  acaacgacct  cggtgagcca  3360
gacaagggtg  aagaccatgc  ccggcctgtc  ctcgggggca  gccaagaaca  cccgtatccc  3420
cgtcgctgca  ggaccggccg  gcgtccaaca  gagacagacc  ccaactcgga  gagcaggctg  3480
tttctgctga  acctgaacat  ctacgtcccg  cgcgagcgagc  ggtttgggca  tctcaagatg  3540
tcggacttcc  tcgggtactc  actgaaggcg  atcatcgagc  ctgtccttcc  gacgctgggg  3600
acgttcgtcg  acgatacgcc  caaggagttc  gattcgttcg  aagacatcct  tgggctctac  3660
gagccgggtc  cagaggcgcc  caacaaccca  ctggtagcag  aggtcaggaa  gagaatcccc  3720
agcgagttcc  tcagaagcat  tctgcccaat  ggtagccatg  accaccccct  gaagatgccc  3780
cttccaaata  tcatcagatc  agatgtgttg  aaaaaggctc  cagagtttaa  gtttggctgg  3840
aggaccgacg  aagagtttgc  gagggagacg  cttgcaggcg  tgaacccagt  gctcatcaaa  3900
cgtctgacgg  agttcccagc  taaaagtacc  ctggacccaa  gtcaatacgg  agaccatacg  3960
agcaagatca  ccgaagctca  catccagcat  aacatggaag  gcctgtcagt  gcagaatgca  4020
ctgaagaaga  acaggctctt  catcctagac  caccatgacc  atttcatgcc  gtacctcaac  4080
aagatcaacg  agttggaggg  gaacttcatc  tacgccagca  ggaccctact  gttcctgaag  4140
gacgatggca  cgctgaagcc  cctggccgtc  gagctgagcc  tgcccacccc  tgatggccag  4200
cagcacgcg   cggtcagcaa  ggtgtacacc  ccagctcact  ccggcgctga  gggccacgtc  4260
tggcaacttg  ccaaggctta  tgcctgcgtg  aacgactccg  tctggcatca  gctgatcagc  4320
cactggctga  acacgcacgc  ggtgatcgag  ccgttcgtca  tcgcaacgaa  ccggcagctg  4380
agcgtggtgc  atccagtgca  caagctgctg  agcccacact  accgtgacac  gctgaacatc  4440
aacgccctgc  cacgccagac  gctcatcaac  gccgacggca  tcttcgagcg  caccgtgttc  4500
cctgcaaagt  acgcgctggg  gatgtcctcc  gacgtgtaca  agagctggaa  tttcaacgag  4560
caggctctcc  cagcagacct  cgtcaagaga  ggtgtggctg  tgccggacca  gtcgagcccc  4620
tacggtgtcc  ggttgctgat  caaggactac  ccttacgccg  tggacgggct  ggtcatctgg  4680
tgggcgatca  gcggtgggt   caaggagtac  ctggacgtct  actacccaa   cgacggcgag  4740
ctccagcgcg  acgtggagct  gcagcgtgg   tggaaggagg  tgcgcgagga  ggcgcacggc  4800
gacctcaagg  accgactg    gtggcccagg  atgacgccg   tccagcggct  ggcagggcg   4860
tgcacgaccg  tcatctgggt  agcgtccgcg  ctgcacgcgg  ccgtcaactt  cggcagtac   4920
ccgtacgccg  ggtacctgcc  gaaccggccg  accgtgagcc  ggcggccgat  gccggagccg  4980
ggcagccgacg  actacaagaa  gctggaggcg  gggcaaggag  aggcggacgc  ggtgttcatc  5040
cgcaccatca  ccagccagtt  ccagaccatc  ctgggcatct  cgctcatcga  gatcctctcc  5100
aagcactcct  ccgacgaggt  gtacctcggc  cagcgcgacg  agcctgagcg  ctggacgtcg  5160
gacgccaggg  cgctggacgc  gttcagaagg  ttcggaagcc  ggctggtgga  gatcgagaag  5220
cggatcagga  cgatgaacga  cagcccgacg  ttgaagaacc  ggaagggcc   ggtggagatg  5280
ccgtacatgc  tgctgtaccc  caacacgtcg  gatgtcaccg  gcgagaaggg  cgaggggctc  5340
actgccatgg  gcattcccaa  cagcatctcc  atatga                              5376

SEQ ID NO: 42         moltype = DNA   length = 5376
FEATURE               Location/Qualifiers
misc_feature         1..5376
                      note = WVP18-09358-016
source                1..5376
                      mol_type = other DNA
                      organism = synthetic construct
SEQUENCE: 42
atgctgagcg  ggatcatcga  cgggctgacg  gggcgaacaa  agcatgcgcg  gctcaagggc   60
acggtggtgc  tcatgcgcaa  gaacgtgctg  gacctcaacg  acttcggcgc  caccgtcgtc  120
gacagcatca  gcgagttcct  cggcaagggg  gtcacctgcc  agctcatcag  ctccactctc  180
gtcgacgcca  acaacggcaa  ccgcgggcgg  gtcgggcgg   aggcgaacct  ggagcagtgg  240
ctgacgagcc  tgccgtcgct  gacgaccggc  gagtccaagt  tcggcgtcac  gttcgactgg  300
```

```
gaggtggaga agctgggagt gccggggcc gtcgtcgtca agaacaacca cgccgccgag   360
ttcttcctca agacaatcac cctcgacgac gtgcccggcc gcggcgccgt caccttcgtc   420
gccaactcct gggtctaccc cgcgggcaag taccgctaca accgcgtctt cttctccaac   480
gatacgtacc tgccaagcca gatgccgcg gcgctgaagc cgtaccgcga cgacgagctc   540
cgcaacctcc gcggcgacga ccagcgggc ccctaccagg agcacgaccg cgtgtaccgc   600
tacgacgtct acaacgacct cggcgagccc gacggcggca acccgcgccc catcctcggc   660
ggctccgccg accacccgta cccgcgccgc tgccgcacgg gccgcaagcc caccaaaacc   720
gaccccaact cggagagccg actgtcgctg gtggagcaga tctacgtgcc gcgggacgag   780
cgcttcggcc acctcaagat gtccgacttc ctgggctact ccatcaaggc catcacgcag   840
ggcatcatcc cggcggtgcg cacgtacgtg gacaccaccc cgggcgagtt cgactccttc   900
caggacatca tcaacctgta cgagggcggg atcaagctgc ccaagatcca ggcgctcgag   960
gacatgcgca agctcttccc gctccagctc gtcaaggacc tcctcccgc cggcggggac  1020
tacctgctca agctcccat cccacagatc atccaaggca cgtcacgtat accgatcgat  1080
gtcagggcc ggctgttgtc tggtctgcat atatatatgt gctcctatga ggacaagaac  1140
gcgtggagga ccgacgagga gttcgcgcgg gaggtgctcg ccggcgtcaa cccgatggtg  1200
atcacgcgcc tcacggagtt cccgcccaag agcacgctgg accccagcaa gtacggcgac  1260
cacaccagca cgatcacggc ggagcacatc gagaagaacc tcgagggcct cacggtgcag  1320
caggcgctgg acggcaacag gctctacatc ctggaccacc acgaccgctt catgccgttc  1380
ctcatcgacg tcaacaacct ggagggcaac ttcatctacg ccaccaggac gctcttcttc  1440
ctgcgcggcg acggcaggct cgcgcccctc gccatcgagc tcagcgagcc gtacatcgac  1500
ggggacctca ccgtggccaa gagcaaggtc tacacgccgg cgtccagcgg cgtcgaggcc  1560
tgggtgtggc agctcgccaa ggcctatgtc gccgtcaacg actctggctg gcaccaactc  1620
gtcagccact ggctgaacac ccacgcggtg atggagccgt tcgtgatcgc gacgaaccgc  1680
cagctgagcg tgacgcaccc ggtgcacaag ctcctgagct cgcacttccg cgacaccatg  1740
accatcaacg cgctggcgcg gcagacgctc atcaacggcg gcggcatctt cgagatgacc  1800
gtcttcccgg gcaagtacgc ggcggcatg tcctccgtgg tgtacaagag ctggaacttc  1860
accgagcagg gcctccccgc cgacctcgtc aagagggagg tggccggtgg cgaccccgtc  1920
agcccgtaca aggtcggct gctgatcgag gactaccccgt acgcgagcga cgggctggcc  1980
atctggcacg ccatcgagca gtgggtgggc gagtacctgg ccatctacta ccccgacgac  2040
gccgcgctgc ggggcgaca ggagctgcag gcgtggtgaa aggaggtgcg cgaggtcgg  2100
cacggcgacc acaaggacgc gccctggtgg cccaagatgc aggccgtgtc ggagctcgg  2160
agcgcctgca ccaccatcat ctggatcgcg tcggcgctcc acgccgccgt caacttcggc  2220
cagtacccgt acgcggggta cctcccgaac aggcccacgg tgagccggcg ccggatgccg  2280
gagcccggca gcaaggagta cgaggagctg gagcgcgaac cggacgcgcg cttcatccac  2340
accatcacga gccagatcca gaccatcatc ggcatctcgc tcatcgagat cctctccaag  2400
cactcctccg acgaggtgta cctcggccag cgcgacaccc ccgagtggac ctccgacgcc  2460
cgggcgctgg cggcgttcaa gaggttcagc gacgcgctgg tcaagatcga gggcaaggtg  2520
gtgggcgaga accgcgaccc gcagctgagg aacaggaacg gccccgccga gttcccctac  2580
atgctgctct atcccaacac ctctgaccac agcgaggcga ggggagcgagc agcagggcaa  2640
ggcatccaca cccacaccca ccggacactc cctgagaagc gagaagcgag aagcgaagag  2700
cggccggcca ccatgttctg gcacgggtc gcggaccggc tgacgggaa gaacaaggag  2760
gcgtggaacg agggaaagat ccgcggcacg gtgaggctgg tcaagaagga ggtgctggac  2820
gtcggcgact tcaacgcctc gctcctcgac ggcgtacaca ggatcctgg ctgggacgag  2880
ggcgtcgcct tccagctcgt cagcgccacc gcggccgacc ccagcaacgg gagccgcggc  2940
aaggtcggga aggcggcgca cctggaggag gcggtggtgt cgctcaagtc gacgacggac  3000
ggggagaccg tgtaccgggt gagcttcgag tgggacgggt cgcagggcgt cccgggcgcc  3060
gtcctggtca ggaacctgca gcacgccgaa ttcttcctca agtcgctcac cctcgagggc  3120
gtccccggca ggggcaccgt cgtcttcgtc gccaactcgt ggatctaccc gcacaatctc  3180
tactcccagg aacgcgtctt cttcgccaac gacacttatc tgccaagcaa aatgcctgcg  3240
gcattggtgc cttaccggca ggacgagctc aagattctcc gcggcgacga taatcctgga  3300
ccatacaagg agcacgaccg cgtctaccgt tacgactact caaacgacct cggtgagcca  3360
gacaagggtg aagaccatgc ccggcctgtc ctcggggggca gccaagaaca cccgtatccc  3420
cgtcgctgca ggaccggccg gcgtccaaca gagacagacc ccaactcgga gagcaggctg  3480
tttctgctga acctgaacat ctacgtcccg cgcgacgagc ggtttgggca tctcaagatg  3540
tcggacttcc tcgggtactc actgaaggcg atcatcgagg ctgtccttcc gacgctgggg  3600
acgttcgtcg acgatacgcc caaggagttc gattcgttcg aagacatcct tgggctctac  3660
gagccgggtc cagaggcgcc caacaaccca ctggtagcag aggtcaggaa gagaatcccc  3720
agcgagttcc tcagaagcat tctgcccaat ggtagccatg accaccccct gaagatgccc  3780
cttccaaata tcatcagatc agatgtgttg aaaaaggctc aagatttaa gtttggctgg  3840
aggaccgacg aagagtttgc gagggagacg cttgcaggcg tgaacccagt gctcatcaaa  3900
cgtctgacgg agttcccagc taaaagtacc ctggacccaa gtcaatacgg agaccatacg  3960
agcaagatca ccgaagctca catccagcat aacatggaag gcctgtcagt gcagaatgca  4020
ctgaagaaga acaggctctt catcctagac caccatgacc atttcatgcc gtacctcaac  4080
aagatcaacg agttggaggg gaacttcatc tacgccaaga gaccctact gttcctgaag  4140
gacgatggca cgctgaagcc cctgccgtc gagctgagcc tgcccacccc tgatggccag  4200
cagcacggcc cggtcagcaa ggtgtacacc ccagctcact ccggcgctga ggccacgtc  4260
tggcaacttg ccaaggctta tgcctgcgtg aacgactccg cctggcatca gctgatcagc  4320
cactggctga acacgcacgc ggtgatcgag ccgttcgtca tcgcaacgaa ccggcagctg  4380
agcgtggtgc atccagtgca caagctgctg agccacact accgtgacac gctgaacatc  4440
aacgccctgg cacgcagac gctcatcaac gccgacgtgca tcttcgagcg caccgtgttc  4500
cctgcaaagt acgcgctggg gatgtcctcc gacgtgtaca agagctgaa tttcaacgag  4560
caggctctcc cagcagacct cgtcaagaga ggtgtggctg tgccgacca gtcgagcccc  4620
tacggtgtcc ggttgctgat caaggactac ccttacgccc tggacgggct ggtcatctgg  4680
tgggcgtaca gcggtgggt caaggagtac ctggacgtct actacccaa caccggcagg  4740
ctccagcgcg acgtcaaggct gcaggcgtgg tggaaggagg tgcgcaggag gcgcacggc  4800
gacctcaagg accgagactg gtgcccagg atgacgccc tccagcggct ggccagggcg  4860
tgcacgaccg tcatctgggt agcgtccgcg ctgcacgcgg ccgtcaactt cgggcagtac  4920
ccgtacgccg ggtacctgcc gaaccggccg accgtgagcc ggcggccgat gcggagccgg  4980
ggcagcgacg actacaagaa gctggaggcg gggcagaagg aggcggacgc ggtgttcatc  5040
```

```
cgcaccatca ccagccagtt ccagaccatc ctgggcatct cgctcatcga gatcctctcc   5100
aagcactcct ccgacgaggt gtacctcggc cagcgcgacg agcctgagcg ctggacgtcg   5160
gacgccaggg cgctggacgc gttcagaagg ttcggaagcc ggctggtgga gatcgagaag   5220
cggatcagga cgatgaacga cagcccgacg ttgaagaacc ggaaggggcc ggtggagatg   5280
ccgtacatgc tgctgtaccc caacacgtcg gatgtcaccg gcgagaaggg cgaggggctc   5340
actgccatgg gcattcccaa cagcatctcc atatga                             5376
```

| SEQ ID NO: 43 | moltype = DNA length = 5376 |
|---|---|
| FEATURE | Location/Qualifiers |
| misc_feature | 1..5376 |
| | note = WVP18-09344-014 |
| source | 1..5376 |
| | mol_type = other DNA |
| | organism = synthetic construct |

SEQUENCE: 43

```
atgctgagcg ggatcatcga cgggctgacg ggggcgaaca agcatgcgcg gctcaagggc     60
acggtggtgc tcatgcgcaa gaacgtgctg gacctcaacg acttcggcgc caccgtcgtc    120
gacagcatca gcgagttcct cggcaagggg gtcacctgcc agtcatcag ctccactctc     180
gtcgacgcca acaacggcaa ccgcgggcgg gtcggggcgg aggcgaacct ggagcagtgg    240
ctgacgagcc tgccgtcgct gacgaccggc gagtccaagt tcggcgtcac gttcgactgg    300
gaggtggaga agctgggagt gccgggggcc gtcgtcgtca gaacaaccg cgccgccgag     360
ttcttcctca agacaatcac cctcgacgac gtgcccggcc gcggcgccgt caccttcgtc    420
gccaactcct gggtctaccc cgcgggcaag taccgctaca accgcgtctt cttctccaac    480
gatacgtacc tgccaagcca gatgccgcg cgctgaagc cgtaccgcga cgacgagctc      540
cgcaacctcc gcggcgacga ccagcagggc cctaccagg agcacgaccg cgtgtaccgc     600
tacgacgtct acaacgacct cggcgagccc gacggcggca acccgccgtt catcctcgtc    660
ggctccgccg accacccgta cccgcgccgc tgccgcacgg accgcaagcc caccaaaacc    720
gaccccaact cggagagccg actgtcgctg tggagcaga tctacgtgcc gcgggacgag     780
cgcttcggcc acctcaagat gtccgacttc ctgggctact ccatcaaggc catcacgcag    840
ggcatcatcc cggcggtgcg cacgtacgtc gacaccaccc cgggcgagtt cgactcctc    900
caggacatca tcaacctgta cgagggcggg atcaagctgc ccaagatcca ggcgctcgag    960
gacatgcgca agctcttccc gctccagctc gtcaaggacc tcctccccgc cggcggggac   1020
tacctgctca agctccccat cccacagatc atccaaggca cgtcacgtat accgatcgat   1080
gtcagggcgc ggctgtttgc tggtctgcat atatatatgt gctcctatga ggacaagaac   1140
gcgtggagga ccgacgagga gttcgcgcgg gaggtgctcg ccggcgtcaa cccgatggtg   1200
atcacgcgcc tcacggagtt cccgcccaag agcacgctgg accccagcaa gtacggcgac   1260
cacaccagca cgatcacggc ggagcacatc gagaagaacc tcgagggcct cacggtgcag   1320
caggcgctgg acggcaacag gctctacatc ctggaccacc acgaccgctt catgccgttc   1380
ctcatcgacg tcaacaacct ggagggcaac ttcatctacg caccaggac gctcttcttc   1440
ctgcgcggcg acggcaggct cgcgcccctc gccatcgagc tcagcgagcc gtacatcgac   1500
ggggacctca ccgtggccaa gagcaaggtc tacacgccgg cgtccagcgg cgtcgaggcc   1560
tgggtgtggc agctcgccaa ggcctatgtc gccgtcaacg actctggctg caccaactc   1620
gtcagcgact ggctgaacac ccacgcggtg atggagccgt tcgtgatcgc gacgaaccgg   1680
cagctgagcg tgacgcaccc ggtgcacaag ctcctgagct cgcacttccg cgacaccatg   1740
accatcaacg cgctggcgcg gcagacgctc atcaacggcg gcgcatctt cgagatgacc   1800
gtcttccggg gcaagtacgc gctgggcatg tcctccgtgg tgtacaagag ctggaacttc   1860
accgagcagg gcctctccgc cgacctcgtc aagaggggcg tggcggtggc ggacccgtc    1920
agcccgtaca aggtgcggct gctgatcgag gactacccgt acgcgagcga cgggctggcc   1980
atctggcacg ccatcgagca gtgggtgggc gagtacctgg ccatctacta ccccgacgac   2040
ggcgcgctgc ggggcgacga ggagctgcag gcgtggtgga aggaggtgcg cgaggtcggg   2100
cacggcgacc acaaggacgc gccctggtgg cccaagatgc aggccgtgtc ggagctcgcc   2160
agcgcctgca ccaccatcat ctggatcgcg tcgcgctcc acgccgccgt caacttcggc    2220
cagtaccccgt acgcggggta cctcccgaac aggcccacgg tgagccggcg ccggatgccg   2280
gagcccggca gcaaggagta cgaggagctg gagcgcgacc cggagcgcgg cttcatccac   2340
accatcacga gccagatcca gaccatcatc ggcatctcgc tcatcgagat cctctccaag   2400
cactcctccg acgaggtgta cctcggccag cgcgacaccc ccgagtggac ctccgacgcc   2460
cgggcgctgg cggcgttcaa gaggttcagc gacgcgctgg tcaagatcga gggcaaggtg   2520
gtgggcgaga accgcgaccc gcagctgagg aacaggaacg ccccgccgga ttcccctac    2580
atgctgctct atcccaacac ctctgaccac agcgaggcga gggagcgagc agcagggcaa   2640
ggcatccaca cccacacccc cgggacactc cctgaagagc gagaagcgaa aagcgaaagg   2700
cggccggcca ccatgttctg gcacgggtc gcggaccggc tgacggggaa gaacaaggag   2760
gcgtggaacg agggaaagat ccgcggcacg gtgaggctgg tcaagaagga ggtgctggac   2820
gtcggcgact tcaacgcctc gctcctcgac ggcgtacaca ggatcctcgg ctgggacgac   2880
ggcgtcgcct tccagtcgt cagcgccacc gcggccgacc ccagcaacgg aggccgaggc   2940
aaggtcggga aggcggcgca cctggaggag gcgtggtgt cgctcaagtc gacgacggac   3000
ggggagaccg tgtaccgggt gagcttcgag tgggacgggt cgcagggcgt cccgggcgcc   3060
gtcctggtca ggaacctgca gcacgccgag ttcttcctca gtcgctcac cctcgagggc   3120
gtccccggca ggggcaccgt cgtcttcgtc gccaactcgt ggatctaccc gcacaatctc   3180
tactcccagg aacgcgtctt cttcgccaac gacacttgt tgccaagcaa aatgcctgcg   3240
gcattggtgc cttaccggca ggacgagctc aagattctcc gcggcgacga taatcctgga   3300
ccatacaagg agcacgaccg cgtctaccgt tacgactact caacgacct cggtgagcca   3360
gacaaggggtg aagaccatgc ccggcctgtc ctcggggca gccaagaaca cccgtatccc   3420
cgtcgctgca ggaccggccg gcgtccaaca gagacagacc ccaactcgga gagcaggctg   3480
ttttctgctga acctgaacat ctacgtcccg cgcagcggca ggtttgggca tctcaagatg   3540
tcggacttcg tcgggtactc actgaaggcg atcatcgagg ctgtcctcc gacgctgggg   3600
acgttcgtcg acgatacgcc caaggagttc gattcgttcg aagacatcct tgggctctac   3660
gagccgggtc cagaggcgcc caacaaccca ctggtagcag aggtcaggaa gagaatcccc   3720
agcgagttcc tcagaagcat tctgcccaat ggtagccatg accaccccct gaagatgccc   3780
cttccaaata tcatcagatc agatgtgttg aaaaaggctc cagagtttaa gtttggctgg   3840
```

```
aggaccgacg aagagtttgc gagggagacg cttgcaggcg tgaacccagt gctcatcaaa 3900
cgtctgacgg agttcccagc taaaagtacc ctggacccaa gtcaatacgg agaccatacg 3960
agcaagatca ccgaagctca catccagcat aacatggaag gcctgtcagt gcagaatgca 4020
ctgaagaaga acaggctctt catcctagac caccatgacc atttcatgcc gtacctcaac 4080
aagatcaacg agttggaggg gaacttcatc tacgccagca ggaccctact gttcctgaag 4140
gacgatggca cgctgaagcc cctgccgtc gagctgagcc tgccccaccc tgatggccaa 4200
cagcacggcg cggtcagcaa ggtgtacacc ccagctcact ccggcgctga gggcacgtc 4260
tggcaacttg ccaaggctta tgcctgcgtg aacgactccg cctggcatca gctgatcagc 4320
cactggctga acacgcacgc ggtgatcgag ccgttcgtca tcgcaacgaa ccggcagctg 4380
agcgtggtgc atccagtgca caagctgctg agcccacact accgtgacac gctgaacatc 4440
aacgccctgg cacgccagac gctcatcaac gccgacggca tcttcgagcg caccgtgttc 4500
cctgcaaagt acgcgctggg gatgtcctcc gacgtgtaca agagctggaa tttcaacgag 4560
caggctctcc cagcagacct cgtcaagaga ggtgtggctg tgccggacca gtcgagcccc 4620
tacggtgtcc ggttgctgat caaggactac ccttacgccg tggacgggct ggtcatctgg 4680
tgggcgatcg agcggtgggt caaggagtac ctggacgtct actacccaa cgacggcgag 4740
ctccagcgcg acgtggagct gcaggcgtgg tggaaggagg tgcgcgagga ggcgcacggc 4800
gacctcaagg accgagactg gtgggcccagg atggacgccg tccagcggct ggccagggcg 4860
tgcacgaccg tcatctgggt agcgtccgcg ctgcacggcc ccgtcaactt cgggcagtac 4920
ccgtacgccg ggtacctgcc gaaccggcca accgtgagcc ggcggccgat ccggagccg 4980
ggcagcgacg actacaagaa gctggaggcg gggcagaagg aggcggacgc ggtgttcatc 5040
cgcaccatca ccagccagtt ccagaccatc ctgggcatct cgctcatcga gatcctctcc 5100
aagcactcct ccgacgaggt gtacctcggc cagccgacg agcctgagcg ctggacgtcg 5160
gacgccaggg cgctgacgc gttcagaagg ttcggaagcc ggctggtgga gatcgagaag 5220
cggatcagga cgatgaacga cagcccgacg ttgaagaacc ggaaggggcc ggtggagatg 5280
ccgtacatgc tgctgtaccc caacacgtcg gatgtcaccg gcgagaaggg cgaggggctc 5340
actgccatgg gcattcccaa cagcatctcc atatga                            5376

SEQ ID NO: 44          moltype = DNA   length = 5376
FEATURE                Location/Qualifiers
misc_feature           1..5376
                       note = WVP18-09309-014_339-009
source                 1..5376
                       mol_type = other DNA
                       organism = synthetic construct
SEQUENCE: 44
atgctgagcg ggatcatcga cgggctgacg ggggcgaaca agcatgcgcg gctcaagggc 60
acggtggtgc tcatgcgcaa gaacgtgctg gacctcaacg acttcggcgc caccgtcgtc 120
gacagcatca gcgagttcct cggcaagggg gtcacctgcc agctcatcag ctccactctc 180
gtcgacgcca acaacggcaa ccgcggggcgg gtcggggcgg aggcgaacct ggagcagtga 240
ctgacgagcc tgccgtcgct gacgaccggc gagtccaagt tcggcgtcac gttcgactgg 300
gaggtggaga agctgggagt gccggggcc gtcgtcgtca agaacaacca cgccgccgag 360
ttcttcctca agacaatcac cctcgacgac gtgcccggcc gcgcgccgt caccttcgtc 420
gccaactcct gggtctaccc cgcgggcaag taccgctaca gccgtcttc cttctccaac 480
gatacgtacc tgccaagcca gatgccggcg gcgctgaagc cgtaccgcga cgacgagctc 540
cgcaacctcc gcggcgacga ccagcagggc cctaccagg agcacgaccg cgtgtaccgc 600
tacgacgtct acaacgacct cggcgagccc gacgcggca accgcgcc catcctcggc 660
ggctccgccg accaccgta accggccgc tgccgcaagcc accaaaaacc 720
gacccccaac tcggagagccg actgtcgctg gtggagcaga tctacgtgcc gcgggacgag 780
cgcttcggcc acctcaagat gtccgacttc ctgggctact ccatcaaggc catcacgcag 840
ggcatcatcc cggcggtgcg cacgtacgtg acaccaccc cgggcgagtt cgactccttc 900
caggacataa tcaacctgta cgagggcggg atcaagctgc ccaagatcca ggcgctcgaa 960
gacatgcgca agctcttccc gctccagctc gtcaaggacc tcctccccgc cggcggggac 1020
tacctgctca agctccccat cccacagatc atccaaggca cgtcacgtat accgatcgat 1080
gtcagggcgc ggctgttgtc tggtctgcat atatatatgt gctccatga ggacaagaac 1140
gcgtggagga ccgacgagga gttcgcgcgg gaggtgctcg ccggcgtcaa cccgatggtg 1200
atcacgcgcc tcacggagtt ccgcccaag agcacgctg accccagcaa gtacggcgac 1260
cacaccagca cgatcacggc ggagcacatc gagaagaacc tcgagggcct cacggtgcag 1320
caggcgctag acggcaacag gctctacatc ctggaccacc acgaccgctt catgccgttc 1380
ctcatcgacg tcaacaacct ggagggcaac ttcatctacg ccaccaggac gctcttcttc 1440
ctgcgcggca acggcaggct cgcgccctc gccatgagc tcagcgagc gtacatcgac 1500
ggggacctca ccgtggccaa gagcaaggtc tacacgccgg cgtccagcgg cgtcgaggcc 1560
tgggtgtggc agctcgccaa ggcctatgtc gccgtcaacg actctggctg gcaccaactc 1620
gtcagccact ggctgaacac ccacgcgtg atggagccgt tcgtgatcgc gacgaaccgg 1680
cagctgagcg tgacgcaccc ggtgcacaag ctcctgagcc gcacttccg cgacaccatg 1740
accatcaacg cgctggcgcg gcagacgctc atcaacggcc gcggcatctt cgagatgacc 1800
gtcttcccgg gcaagtacgc gctgggcatg tcctccgtgg tgtacaagag ctggaacttc 1860
accgagcagg gcctccccgc cgacctcgtc aagaggggcg tggcggtggc ggacccgtcc 1920
agcccgtaca aggtgcggct gctgatcgag gactaccgt acgcgagcga cggctggcc 1980
atctcgcaca ccatcgagca gtgagtgggc gagtactgga ccatctacta ccccgacgac 2040
ggcgcgctgc ggggcgacga ggagctgcag gcgtggtgga aggaggtcg caggtcggg 2100
cacggcgacc acaaggacgc gccctggtgg cccaagatgc aggccgtgtc ggagctcgcc 2160
agcgcctgca ccaccatcat ctggatcgcg tcggcgctcc acgccgccgt caacttcggc 2220
cagtaccccgt acgcggggta cctcccgaac aggcccacgg tgagcggcg ccggatgccg 2280
gagcccgcca gcaaggagta cgaggagctg gagcgcgacg aggggcggg cttcatccac 2340
accatcacga gccagatcca gaccatcatc ggcatctcgc tcatcgagat cctctccaag 2400
cactcctccg acgaggtgta cctcggccag cgcgacaccc ccgagtggac ctccgacgcc 2460
cgggcgctgg cggcgttcaa gaggttcagc gacgcgctgg tcaagatcga gggcaaggtg 2520
gtgggcgaga accgcgaccc gcagctgagg aacaggaacg gccccgccga gttccctac 2580
atgctgctct atcccaacac ctctgaccac agcgaggcga gggagcgagc agcagggcaa 2640
```

```
ggcatccaca cccacaccca ccggacactc cctgagaagc gagaagcgag aagcgaagag   2700
cggccggcca ccatgttctg cacggggtc gcggaccggc tgacggggaa gaacaaggag    2760
gcgtggaacg agggaaagat ccgcggcacg gtgaggctgg tcaagaagga ggtgctggac   2820
gtcggcgact tcaacgcctc gctcctcgac ggcgtacaca ggatcctcgg ctgggacgac   2880
ggcgtcgcct tccagctcgt cagcgccacc gcggccgacc ccagcaacgg gagccgcgac   2940
aaggtcggga aggcggcgca cctggaggag gcggtggtgt cgctcaagtc gacgacggac   3000
ggggagaccg tgtaccgggt gagcttcgag tgggacgggt cgcagggcgt cccgggcgcc   3060
gtcctggtca ggaacctgca gcacgccgag ttcttcctca agtcgctcac cctcgagggc   3120
gtccccggca ggggcaccgt cgtcttcgtc gccaactcgt ggatctaccc gcacaatctc   3180
tactcccagg aacgcgtctt cttcgccaac gacacttatc tgccaagcaa aatgcctgcg   3240
gcattggtgc cttaccggca ggacgagctc aagattctcc gcggcgacga taatcctgga   3300
ccatacaagg agcacgaccg cgtctaccgt tacgactact acaacgacct cggtgagcca   3360
gacaagggtg aagaccatgc ccggcctgtc ctcgggggca gccaagaaca cccgtatccc   3420
cgtcgctgca ggaccggccg gcgtccaaca gagacagacc ccaactcgga gagcaggctg   3480
tttctgctga acctgaacat ctacgtcccg cgcgacgagc ggtttgggca tctcaagatg   3540
tcggacttcc tcgggtactc actgaaggcg atcatcgagg ctgtccttcc gacgctgggg   3600
acgttcgtcg acgatacgcc caaggagttc gattcgttcg aagacatcct tgggctctac   3660
gagccgggtc cagaggcgcc caacaaccca ctggtagcag aggtcaggaa gagaatcccc   3720
agcgagttcc tcagaagcat tctgcccaat ggtagccatg accaccccct gaagatgccc   3780
cttccaaata tcatcagatc agatgtgttg aaaaaggctc cagagtttaa gtttggctgg   3840
aggaccgacg aagagtttgc gagggagacg cttgcaggcg tgaacccagt gctcatcaaa   3900
cgtctgacgg agttcccagc taaaagtacc ctggacccaa gtcaatacgg agaccatacg   3960
agcaagatca ccgaagctca catccagcat aacatggaag gcctgtcagt gcagaatgca   4020
ctgaagaaga acaggctctt catcctagac caccatgacc atttcatgcc gtacctcaac   4080
aagatcaacg agttggaggg gaacttcatc tacgccagca ggaccctact gttcctgaag   4140
gacgatgcca cgctgaagcc cctggccgtc gagctgaccc tgccccaccc tgatggccag   4200
cagcacggcg cggtcagcaa ggtgtacacc ccagctcact ccggcgctga gggccacgtc   4260
tggcaacttg ccaaggctta tgcctgcgtg aacgactccg cctggcatca gctgatcagc   4320
cactggctga acacgcacgc ggtgatcgag ccgttcgtca tcgcaacgaa ccggcagctg   4380
agcgtggtgc atccagtgca caagctgctg agcccacact accgtgacac gctgaactc   4440
aacgccctgg cacgccagac gctcatcaac gccgacgtca tcttcgagcg caccgtgttc   4500
cctgcaaagt acgcgctggg gatgtcctcc gactgtacag agagctggaa tttcaacgag   4560
caggctctcc cagcagacct cgtcaagaga ggtgtggctg tgccggacca gtcgagcccc   4620
tacggtgtcc ggttgctgat caaggactac ccttacgccg tggacgggct ggtcatctgg   4680
tgggcgatcg agcggtgggt caaggagtac ctggacgtct actaccccaa cgacggcgag   4740
ctccagcgcg acgtggagct gcaggcgtgg tggaaggagg tgccgagga ggcgcacggc   4800
gacctcaagg accgagactg gtgcccagg atggacgccg tccagcggct ggccagggcg   4860
tgcacgaccg tcatctgggt agcgtccgcg ctgcacgcgg ccgtcaactt cgggcagtac   4920
ccgtacgccg ggtacctgcc gaaccggccg accgtgacgc ccggcgat gccggagccg   4980
ggcagcgacg actacaagaa gctggaggcg gggcagaagg aggcggacgc ggtgttcatc   5040
cgcaccatca ccagccagtt ccagaccatc ctgggcatct cgctcatcga gatcctctcc   5100
aagcactcct ccgacgaggt gtacctcggc cagcgcgacg agcctgagcg ctggacgtcg   5160
gacgccaggg cgctggacgc gttcagaagg ttcggaaagc ggtggtgga gatcgagaag   5220
cggatcagga cgatgaacga cagcccgacg ttgaagaacc ggaagggcc ggtggagatg   5280
ccgtacatgc tgctgtaccc caacacgtcg gatgtcaccg gcgagaaggg cgaggggctc   5340
actgccatgg gcattcccaa cagcatctcc atatga                            5376
```

SEQ ID NO: 45              moltype = DNA   length = 5376
FEATURE                    Location/Qualifiers
misc_feature               1..5376
                           note = WVP18-09307-014
source                     1..5376
                           mol_type = other DNA
                           organism = synthetic construct SEQUENCE: 45
```
atgctgagcg ggatcatcga cgggctgacg ggggcgaaca agcatgcgcg gctcaagggc     60
acgtggtgc tcatgcgcaa gaacgtgctg gacctcaacg acttcggcgc caccgtcgtc    120
gacagcatca gcgagttcct cggcaagggg gtcacctgcc agctcatcag ctccactctc   180
gtcgacgcca acaacggcaa ccgcgggcgg gtcgggcgg aggcgaacct ggagcagtgg    240
ctgacgagcc tgccgtcgct gacgaccggc gagtccaagt tcggcgtcac gttcgactgg   300
gaggtggaga agctgggagt gccggggcc gtcgtcgtca agaacaacca cgccgccgag    360
ttcttcctca agacaatcac cctcgacgac gtgcccggcc gcggcgccgt caccttcgtc   420
gccaactcct gggtctaccc cgcgggcaag taccgctaca accgcgtctt cttctccaac   480
gatacgtacc tgccaagcca gatgccgcg gcgctgaagc cgtactgca cgacgactcg    540
cgcaacctcc gcggcgacga ccagcagggc ccctaccagg agcacgaccg cgtgtaccgc   600
tacgacgtct acaacgacct cggcgagccc gacgcggca acccgcgccc catcctcggc   660
ggctccgcca ccaccgta ccccgcgcgc tgccgcacgg gccgcaagcc caccaaaaccc     720
gaccccaact cggagagccg actgtcgctg gtggagcaga tctcgtgcc gcgggacgag   780
gcttcggcc acctcaagat gtccgacttc ctgggctact catcaaggc catcacgcag    840
ggcatcatcc cggcggtgcg cacgtacgtg gacaccaccc cgggcgagtt cgactccttc   900
caggacatca tcaacctgta cgagggcggg atcaagctgc caagatcca ggcgctcgag   960
gacatgcgca agctcttccc gctccagctc gtcaaggacc tctcccgcc cggcggggac   1020
tacctgctca agctccccat cccacagatc atccaaggca cgtcacgtat accgatcgat   1080
gtcagggcg tgcgtgttgtc tggtctgcat atatatatgt gctcctatga ggacaagaac   1140
gcgtggagga ccgacgagga gttcgcgcgg gaggtgctcg ccgcgtcaa cccgatggtg    1200
atcacgcgcc tcacggagtt cccgcccaag agcacgctgg accccagcaa gtacggcgac   1260
cacaccagca cgatcacggc ggagcacatc gagaagaacc tcgagggcct cacggtgcag   1320
caggcgctgg acgcaacag gctctacatc ctggaccacc acgaccgctt catgccgttc    1380
ctcatcgacg tcaacaacct ggagggcaac ttcatctacg ccaccaggac gctcttcttc   1440
```

```
ctgcgcggcg acggcaggct cgcgccccte gccatcgagc tcagcgagcc gtacatcgac  1500
ggggacctca ccgtgccaa  gagcaaggtc tacacgccgg cgtccagcgg cgtcgaggcc  1560
tgggtgtggc agctcgccaa ggcctatgtc gccgtcaacg actctggctg caccaactc   1620
gtcagccact ggctgaacac ccacgcggtg atggagccgt tcgtgatcgc gacgaaccgg  1680
cagctgagcg tgacgcaccc ggtgcacaag ctcctgagct cgcacttccg cgacaccatg  1740
accatcaacg cgctggcgcg gcagacgctc atcaacggcg gcggcatctt cgagatgacc  1800
gtcttcccgg gcaagtacgc gctgggcatg tcctccgtgg tgtacaagag ctggaacttc  1860
accgagcagg gcctccccgc cgacctcgtc aagaggggcg tggcggtggc ggacccgtcc  1920
agcccgtaca aggtgcggct gctgatcgag gactaccgat acgcgagcga cgggctggcc  1980
atctggcacg ccatcgagca gtgggtgggc gagtacctgg ccatctacta ccccgacgac  2040
ggcgcgctgc ggggcgacga ggagctgcag gcgtggtgga aggaggtgcg cgaggtcggg  2100
cacggcgacc acaaggacgc gccctggtgg cccaagatgc aggccgtgtc ggagctcgcc  2160
agcgcctgca ccaccatcat ctggatcgcg tcggcgctcc acgccgccgt caacttcggc  2220
cagtacccgt acgcgggggta cctcccgaac aggcccaacg tgagccggcg ccggatgccg  2280
gagcccagca gcaaggagta cgaggagctg gagcgcgacc cggacgcgcg gcttcatccac  2340
accatcacga gccagatcca gaccatcatc ggcatctcgc tcatcgagat cctctccaag  2400
cactcctccg acgaggtgta cctcggccag cgcgacaccc ccgagtggac ctccgacgcc  2460
cgggcgctgg cggcgttcaa gaggttcagc gacgcgctgg tcaagatcga gggcaaggtg  2520
gtgggcgaga accgcgaccc gcagctgagg aacaggaacg gccccgccga gttccctac   2580
atgctgctct atcccaacac ctctgaccac agcgaggcga gggagcgagc agcagggcaa  2640
ggcatccaca cccacaccca ccggacactc cctgagaagc gagaagcgag aagcgaagag  2700
cggccgcca  ccatgttctg gcacggggtc gcggaccggc tgacgggaa  gaacaaggag  2760
gcgtggaacg agggaaagat ccgcggcacg gtgaggctgg tcaagaagga ggtgctggac  2820
gtcggcgact tcaacgcctc gctcctcgac ggcgtacaca ggatcctcgg ctgggacgac  2880
ggcgtcgcct tccagctcgt cagcgccacc gcggccgacc ccagcaacgg gagccgcggc  2940
aaggtcggga aggcggcgca cctggaggag gcggtggtgt cgctcaagtc gacgacggac  3000
ggggagaccg tgtaccgggt gagcttcgag tgggacgggt cgcagggcgt cccgggcgcg  3060
gtcctggtca ggaacctgca gcacgccgag ttcttcctca gtcgctcac  cctcgagggc  3120
gtccccggca ggggcaccgt cgtcttcgtc gccaactcgt ggatctaccc gcacaatctc  3180
tactcccagg aacgctcttc cttcgccaag gacacttatc tgccaagcaa aatgcctgcg  3240
gcattggtgc cttaccggca ggacgagctc aagattctcc gcggcgacga taatcctgga  3300
ccatacaagg agcacgaccg cgtctaccgt tacgactact acaacgacct cggtgagcca  3360
gacaagggtg aagaccatgc ccggcctgtc ctcgggggca gccaagaaca cccgtatccc  3420
cgtcgctgca ggaccggccg cgtccaaca  gagacagaac ccaactcgga gagcaggctg  3480
tttctgctga acctgaacat ctacgtcccg cgcgacgagc ggtttgggca tctcaagatg  3540
tcggacttcc tcgggtactc actgaagcg  atcatcgagg ctgtccttcc gacgctgggg  3600
acgttcgtcg acgatacgcc caaggagttc gattcgttcg aagacatcct tgggctctac  3660
gagccgggtc cagaggcgcc caacaaccca ctggtagcag aggtcaggaa gagaatcccc  3720
agcgagttcc tcagaagcat tctgcccaat ggtagccatg accacccct  gaagatgccc  3780
cttccaaata tcatcagatc agatgtgttg aaaaaggctc cagagtttaa gtttggctgg  3840
aggaccgacg aagagtttgc gagggagacg cttgcaggcg tgaacccagt gctcatcaaa  3900
cgtctgacgg agttcccagc taaaagtacc ctggacccaa gtcaatacgg agaccatacg  3960
agcaagatca ccgaagctca catccagcat aacatggaag gcctgtcagt gcagaatgca  4020
ctgaagaaga acaggctctt catcctagac caccatgacc atttcatgcc gtacctcaac  4080
aagatcaacg agttggaggg gaacttcatc tacgccagca ggaccctact gttcctgaag  4140
gacgatggca cgctgaagcc cctggccgtc gagctgagcc tgcccaccc  tgatggccag  4200
cagcacggcc cggtcagcaa ggtgtacacc ccagctcact ccggcgctga gggccacgtc  4260
tgcaacttg  ccaaggctta tgcctgcgtg aacgactccg cctggcatca gctgatcagc  4320
cactggctga acacgcacgc ggtgatcgag ccgttcgtca tcgcaacgaa ccggcagctg  4380
agcgtggtgc atccagtgca caagctgctg agcccacact accgtgacac gctgaacatc  4440
aacgccctgg cacgccagac gctcatcaac gccgacgtca tcttcgagcg caccgtgttg  4500
cctgcaaagt acgcgctggg gatgtcctcc gactgtaca  agagctggaa tttcaacgag  4560
caggctctcc cagcagacct cgtcaagaga ggtgtgggctg tgccggacca gtcgagcccc  4620
tacggtgtcc ggttgctgat caaggactac ccttacgccg tggacgggct ggtcatctgg  4680
tgggcgatcg agcggtgggt caaggagtac ctggacgtct actaccccaa cacggcgag   4740
ctccagcgcg acgtggagct gcaggcgtgg tggaaggagg tgcgcgagga ggcgcacggc  4800
gacctcaagg accgagactg gtgcccagg  atgacgccg  tccagcggct ggccagggcg  4860
tgcacgaccg tcatctgggt agcgtccgcg ctgcacgcgg ccgtcaactt cgggcagtac  4920
ccgtacgccg ggtacctgcc gaaccggccg accgtgagcc ggcggccgat gccggagccg  4980
ggcagcgcga actacaagaa gctggagacg gggcagaagg aggcggacgc ggtgttcatc  5040
cgcaccatca ccagccagtt ccagaccatc ctgggcatct cgctcatcga gatcctctcc  5100
aagcactcct ccgacgaggt gtacctcggc cagcgcgacg agcctgagcg ctggacgtcg  5160
gacgccaggg cgctggacgc gttcagaagg ttcgaagcc  ggctgtggga gatcgagaag  5220
cggatcagga cgatgaacga cagcccgacg ttgaagaacc ggaaggggcc ggtggagatg  5280
ccgtacatgc tgctgtaccc caacacgtcg gatgtcaccg gcgagaaggg cgaggggctc  5340
actgccatgg gcattcccaa cagcatctcc atatga                            5376

SEQ ID NO: 46           moltype = DNA   length = 24
FEATURE                 Location/Qualifiers
misc_feature            1..24
                        note = crRNA1
source                  1..24
                        mol_type = other DNA
                        organism = synthetic construct
SEQUENCE: 46
accgccgctt tctcctcctc ctcg                                          24

SEQ ID NO: 47           moltype = DNA   length = 24
FEATURE                 Location/Qualifiers
```

```
misc_feature           1..24
                       note = crRNA2.1
source                 1..24
                       mol_type = other DNA
                       organism = synthetic construct
SEQUENCE: 47
aggagactct tgttaagcat ttag                                             24

SEQ ID NO: 48          moltype = DNA  length = 24
FEATURE                Location/Qualifiers
misc_feature           1..24
                       note = crRNA2.2
source                 1..24
                       mol_type = other DNA
                       organism = synthetic construct
SEQUENCE: 48
aggagactct ttttaagcat ttgg                                             24

SEQ ID NO: 49          moltype = DNA  length = 24
FEATURE                Location/Qualifiers
misc_feature           1..24
                       note = GGAGTGTCGTATTTGAGGAGTCCT
source                 1..24
                       mol_type = other DNA
                       organism = synthetic construct
SEQUENCE: 49
ggagtgtcgt atttgaggag tcct                                             24

SEQ ID NO: 50          moltype = DNA  length = 17090
FEATURE                Location/Qualifiers
misc_feature           1..17090
                       note = pZFNnptII-LbCpf1-tDT-lox3_TTTV
source                 1..17090
                       mol_type = other DNA
                       organism = synthetic construct
SEQUENCE: 50
ggagacggtc acagcttgtc tgtaagcgga tgccggagc agacaagccc gtcagggcgc        60
gtcagcgggt gttggcggt gtcggggcgc agccatgacc cagtcacgta gcgatagcgg       120
agtgtatact ggcttaacta tgcggcatca gagcagattg tactgagagt gcaccatatg      180
cggtgtgaaa taccgcacag atgcgtaagg agaaaatacc gcatcaggcg ctcttccgct      240
tcctcgctca ctgactcgct gcgctcggtc gttcggctgc ggcgagcggt atcagctcac      300
tcaaaggcgg taatcggtta tccacagaat caggggataa cgcaggaaag aacatgtgag      360
caaaaggcca gcaaaaggcc aggaaccgta aaaaggccgc gttgctggcg ttttttccata     420
ggctccgccc ccctgacgag catcacaaaa atcgacgctc aagtcagagg tggcgaaacc      480
cgacaggact ataaagatac caggcgtttc cccctggaag ctccctcgtg cgctctcctg      540
ttccgaccct gccgcttacc ggatacctgt ccgcctttct cccttcggga agcgtggcgc      600
tttctcatag ctcacgctgt aggtatctca gttcggtgta ggtcgttcgc tccaagctgg      660
gctgtgtgca cgaaccccc gttcagcccg accgctgcgc cttatccggt aactatcgtc       720
ttgagtccaa cccggtaaga cacgacttat cgccactggc agcagccact ggtaacagga      780
ttagcagagc gaggtatgta ggcggtgcta cagagttctt gaagtggtgg cctaactacg      840
gctacactag aagaacagta tttggtatct gcgctctgct gaagccagtt accttcggaa      900
aaagagttgg tagctcttga tccggcaaac aaaccaccgc tggtagcggt ggtttttttg      960
tttgcaagca gcagattacg cgcagaaaaa aaggatctca agaagatcct ttgatctttt     1020
ctacgggtc tgacgctcag tggaacgaaa actcacgtta agggattttg gtcatgagat      1080
tatcaaaaag gatcttcacc tagatccttt tcggcgtcca catcaacggc gtcgagtgcg     1140
actgccagg caagaccgag atgaccgcg atatcttgct gcgttcggat attttcgtgg      1200
agttcccgcc acagacccgg attgaaggcg agatccagca actcgcgcca gatcatcctg     1260
tgacggaact ttggcgcgtg atgactggcc aggacgtcgg ccgaaagagc gacaagcaga     1320
tcacgctttt cgacagcgtc ggatttgcga tcgaggattt ttcggcgctg cgctacgtcc     1380
gcgaccgcgt tgagggatca agccacacga gccactccga cccttctagcc gacccagacg     1440
agccaaggga tctttttgga atgctgctcc gtcgtcaggc tttccgacgt ttgggtggtt     1500
gaacagaagt cattatcgca cggaatgcca agcactcccg aggggaaccc tgtgttggc     1560
atgcacatac aaatggacga acggataaac ctttttcacgc cctttaaat atccgattat     1620
tctaataaac gctcttttct cttaggttta cccgccaata tcctgtca aacactgata     1680
gtttaaaccg aaggcgggaa acgacaatct gatcgggtac cggcccccc ctcgaggtcg     1740
acggtatcga taagcttgat cctagggagc tcaagcctat actgtactta acttgattgc     1800
ataattactt gatcatagac tcatagtaaa cttgattaca cagataagtg aagaaacaaa     1860
ccaattcaag acataaccaa agagaggtga aagactgttt tatatgtcta acattgcacc     1920
ttaatatcac actgttagtt ccttttcttac ttaaattcaa cccattaaag taaaaacaat     1980
agataataat aatttgagaa tgaacaaaag gaccatatca tttattaact cttatccatc     2040
catttgcatt ttgatgtccg aaaacaaaaa ctgaaagaac acagtaaatt acaagcagaa     2100
caaatgatag aagaaaacag cttttccaat gccataaatc tcaaacttag taggattctg     2160
gtgtgtgggc aatgaaactg atgcattgaa cttgacgaac gttgtcgaaa ccgatgatac     2220
ggacgaaagc tgggaggcct ggagctcggc gcgcctcact tctcttttt ggcctgtgcc     2280
gctttcttag tagcagcagg cctcttgtgc ttaacggagg tctgagcgta ctcaagccac     2340
tctttgttgg agatgcgat cttcaccttg tcgagcttct catcttccgc tttcttaaac     2400
tgcccgatag cccagagaac ctttctcgca atgttgtaag cccgtttgc atcagcattc      2460
ttcggcagga tagcgttctc ttgagcctca tagttacggc tgtcgtagaa gatcccgtca    2520
gagttcttga ccggagagat aaggaagtcc acatcggtc ttccggtgat agagttcctc     2580
```

```
atctggagca tgagagacat gagggccatg aatgagctgt agaatgcctt gtcgctctgc  2640
tcgcacaaaa gagccctgat atcaccctgc tggtagttga tgccgtactt gttgaacagt  2700
tcttgtagg cagaggtgag gcacacttct tcccagtcga acacgttgtt tttcttcgga   2760
tttcggaaga tcctgatacg gttcccgtag gagtagagct tccacttctt aatgtagtcg  2820
gcgtcggtcc tgctgaagtt cttatagtcg agagcgaact cgaaaagatc ctcttccggc  2880
acgtacatga tcctgtcgaa agacgagatg aacttcttgc tgtcggcgat cgaggtgtac  2940
ttggtcttga gcaggttcac gaaaccagta gaaggatcga tcttgctggt gagccaagca  3000
gggatataga agatgaagcc gttctgggtg ctcatgctct tgaaggactc gaacttgttc  3060
gtgatctggt atcccttaag agcaccaccg gtagcgcaag ggttgctctt tttgtccatc  3120
atgtagttga gcttgtcgat gagcatcttc tcgaacttt ggtagacctg cttctcaacc   3180
ttcactctac tgttcttgaa cccagagttg aggtcctcaa gagcgatcac agcatcgtac  3240
ttttccacca gctcgcagat cttatgcacc acctgagaga tgtagccggc cttcaactct  3300
ttgatgtttt cgatagaagt ccagttctgc ctggcctcga aacgctcttt ttcttctta   3360
tcgaggagtg agtggtagtc ggtcttgatc ctgatgccgt tgaaattgtt gataatctcg  3420
ttcaggctgt actgctcgac gatgtttccc tttccgtcca ccacaacgat gtagaggagg  3480
tttctctcac cacgatcgat tccgatacg taagggttat catcgtgctt gagcagcacc   3540
ctcacctcgg tattgatctt gaagatgttc ttcgggcact tgttgatagc gatcgggata  3600
tgaagctcgt actggtcctc gctgaacctt ttgtccttgc agacgtcgta agacagcgtg  3660
gtggtctttt tcgggttgtc aggattcttg ttagcgattg gagagttggc cgggtgaaca  3720
accaactctt ctttcttgag tgaggcccta cgcatgaaga gttcagcacc accagaaagt  3780
ctgatctgcc cgtggttgtt ctcgtcgaaa agcagcttga agtacatcgt atggaggtta  3840
ggagttccgt ggctcttgtc ggagaagtcc ttgttataga tcgaacat atagagcttg    3900
ccctcttcga ccaacttgtc aacctctttc ttggaggcgc tctcgaagct aaccttgtaa  3960
ccctgttcct caacctcacg gtagaacccg gcgatatcct tgtacttttc tgtctcgctg  4020
aagttaaagt cgtaagcgtt agaccacttc gggtaacgcg agatgctgtc cttgaagaaa  4080
tcgatgagct tgtggcagtc gttgaggttg aacatgtcgc ctttcttgaa gtcccgttc   4140
ttgtagattt tctggatgtc ctcagacggg ttgtagtagg ccatccattt cttgctgaag  4200
aacaccttag gaagcatctt gttcggtccc ggaaggagct tgtagttgat cttctcatag  4260
ttcccgttca cgtcatcctt gtcgatcttt tggaggcact tggcgtattt cttgtccatg  4320
atggccaggt agtacttaga cccgtacctg aggatggtga ccctgtaatc tgtctctttg  4380
tctttgtccc atccgcccat gaactgcggg ttctgaaagt acaacttgaa cttgtccttg  4440
ctgtaaggct tctgggtcac gtagtttctg atggcgtcgt agatatggtc caccttgagg  4500
aggatatcgt aagcgagcac gaaatcccg tagaaagact cgtccctatt agtctctttg   4560
ccctctccga agaaggcctt gatatagttc tcgaaagact tcacgctgtc gagcaaatcc  4620
ttcatgatcg cgacgacagc gtcgttcttc ttcagactct tctcgaggac gaaatcagca  4680
tcgaacaact tctcagagga cccgtacacc ttgtagatct cgtcgacctt ctggatgatg  4740
atctctttga gcttctcgac cacgctgaga tcagcatcag cgtattcttg aagctgctcg  4800
aggctgaaag agccgatctt cttgaacgac ttacgcctgt catcctcgta cttctcagtg  4860
acgacagcct tcttcttgag gtggatgtca tcgtactcag cattccactt gtccctcagt  4920
acgttccact cgccgaaaat atccttgctg atggtgctga tagcaggtcc gttcttaacg  4980
aagatcccag cgctgctgta ctcgtcgaag ttcttgaaaa gttctccaa cttcttgatg   5040
gacgagaaga tctcgctgtt cttgttgagg gtgttacgga aaacctcaag cacttcctcg  5100
tcagaggtgt aaccctcacc gtaaaatgag aggctcteae gatcagagag aacetgettg   5160
tagagcggct tgaacttcgg gagcttctgc ttcgttttct ggttgtacag gttgatgtac  5220
tcgttgagtc cctaatctt ctccccagac tcggtcacga atcctccgat aatagcgttg    5280
tacacgtcga tgccctcttg ggtgagaacg aagttgaaga actccccttc aaaaaagtcc  5340
tcgacgtcgc agtcgctgtt gaggatcttc tcttgatt cttgcacctc gtgcttatcg    5400
aagatggcgt ccaccttctc gaagatgtcc atgttgctga tgtaacgcgt gaggttctcg  5460
ttgatgcatc tgaaagcgat agaggtgctc ttggcctctt cgctgaacat gttttccctg  5520
ttgtcgaaga atccggtgaa ggcagtagtg aatccgttga agctgttcac gagagcgatc  5580
tcatccttat cgtccaggaa ctcaggcagg attgtctcga taatatcctt cttgaagagg  5640
ctcttgtatc cctcgtttcc cttgaaagcc ttggcgatct cttacgag gttgatctcg    5700
aggttctcaa gctctttgtt ctctttctcg gtcctggttt tcttacgaa gaggctgatg    5760
tagttgttga ggttcttgag cttgatgctg tggagcacat cgttgatgaa gctgaggtag  5820
tacctgtcga ggagcttctt cacgcccttg taatcttcag ctctcttctc atcctcgacg  5880
aggagcctct tgttgtcgat attctcttgg gtctttccca cagggatagc cttgaacctg  5940
agggtcttag agaggctgta gcagttggta aactttctcga gcttgctaac cttcctcttc  6000
ttcttaggag ccatggagga agccattgtt tggcgcgccg aattcgctgc acatacataa  6060
catatcaaga tcagaacaca catatacaca cacaaataca atcaagtcaa caactccaaa  6120
aagtccagat ctacatatat acatacgtaa ataacaaat catgtaaata atcacaatca   6180
tgtaatccag atctatgcac atatatatat acacaattaa taaaaaaaat gatataacag  6240
atctatatct atgtatgtaa caacacaatc agatgagaga agtgatgttt tcagatctgt  6300
atacataca acacaaacag atgaacaatt gatacgtaga tccatatgta tacgtacaat   6360
tagctacacg attaaatgaa aaaaatcaac gattcggat tggtacacac aaacgcaaca   6420
atatgaagaa attcatatct gattagatat aaacataacc acgtgtagat acacagtcaa  6480
atcaacaaat ttatagcttc taaacgatg agatgaacaa gataaagata ttcacataag    6540
gcatacataa gataagcaga ttaacaaact agcaataata catacctaat taaaacaagg  6600
aataacagag agagagagag agagagagat ttaccttgaa aatgaagagg agaagagagg  6660
atttcttaaa attggggta gagaaagaaa gatgatgaat tgtgagaaag gagagagataa   6720
agggggggtt gtatatatag gctgtagaag attatttttg tgtttgaggc ggtgaaggaa  6780
gaggggatct gactatgaca cgtttgcggt tacgtatttc gataggagtc tttcaacgct  6840
taacgccgtt actctatatg accgtttggg ccgtaacggg gccgtttgtt aacgctgatg  6900
ttgattcttt tctttctttc tttcttcctt ttttaaagaa gcaattgtac aatcgttgct  6960
agctgtcaaa cggataattc ggataacgat atgcctatat tcatatcgt aatttttgaa    7020
ttcgtaatca tgtcatagct gtttcctgtg tgaaattgtt atccgctcac aattccacac  7080
aacatacgag ccgaagcat aaagtgtaaa gcctggggtg cctaatgagt gagctaactc     7140
acattaattg cgttgcgctc actgcccgct ttccagtcgg gaaacctgtc gtgccagatc  7200
gaattcctgc agcccgggtt cagaagacca gagggctatt gagactttc aacaaagggt    7260
aatatcggga aacctcctcg gattccattg cccagctatc tgtcacttca tcgaaaggac  7320
```

```
agtagaaaag gaagatggct tctacaaatg ccatcattgc gataaaggaa aggctatcgt   7380
tcaagatgcc tctaccgaca gtggtcccaa agatggaccc ccaccacga ggaacatcgt    7440
ggaaaaagaa gacgttccaa ccacgtcttc aaagcaagtg gattgatgtg atacatggtg   7500
gagcacgaca ctctcgtcta ctccaagaat atcaaagata cagtctcaga agaccagagg   7560
gctattgaga cttttcaaca aagggtaata tcgggaaacc tcctcggatt ccattgccca   7620
gctatctgtc acttcatcga aaggacagta gaaaaggaag atggcttcta caaatgccat   7680
cattgcgata aaggaaaggc tatcgttcaa gatgcctcta ccgacagtgg tcccaaagat   7740
ggaccccac ccacgaggaa catcgtgaaa aagaagacg ttccaaccac gtcttcaaag     7800
caagtggatt gatgtgatat ctccactgac gtaagggatg acgcacaatc ccactatcct   7860
tcgcaagacc cttcctctat ataaggaagt tcatttcatt tggagagggg ttccatggtg   7920
agcaagggcg aggaggtcat caaagagttc atgcgcttca aggtgcgcat ggagggctcc   7980
atgaacggcc acgagttcga gatcgagggc gagggcgagg ccgcccta cgagggcacc     8040
cagaccgcca agctgaaggt gaccaagggc ggccccctgc ccttcgcctg gacatcctg    8100
tccccccagt tcatgtacgg ctccaaggcg tacgtgaagc acccgccga catccccgat    8160
tacaagaagc tgtccttccc cgagggcttc aagtgggagc gcgtgatgaa cttcgaggac   8220
ggcggtctgg tgaccgtgac ccaggactcc tccctgcagg acggcacgct gatctacaag   8280
gtgaagatgc gcggcaccaa cttccccccc gacggccccg taatgcagaa gaagaccatg   8340
ggctggagg cctccaccga gcgcctgtac ccccgcgacg gcgtgctgaa gggcgagatc     8400
caccaggccc tgaagctgaa ggacggcggc cactacctgg tggagttcaa gaccatctac   8460
atggccaaga agcccgtgca actgcccggc tactactacg tggacaccaa gctggacatc   8520
acctcccaca acgaggacta caccatcgtg aacagtacg agcgctccga gggccgccac    8580
cacctgttcc tgtacggcat ggacgagctg tacaagtcta gagttacctg ataatttcta   8640
ctaagtgtag ataccgccgc tttctcctcc tcctcgtaat ttctactaag tgtagatagg   8700
agactcttgt taagcattta gtaatttcta ctaagtgtag ataggagact cttttaagc    8760
atttggtaat ttctactaag tgtagatgga gtgtcgtatt tgaggagtcc ttaatttcta   8820
ctaagtgtag atcgaatttc cccgatcgtt caaacatttg gcaataaagt tcttaaagat   8880
tgaatcctgt tgccggtctt gcgatgatta tcatataatt tctgttgaat tacgttaagc   8940
atgtaataat taacatgtaa tgcatgacgt tatttatgag atgggtttt atgattagag    9000
tcccgcaatt atacatttaa tacgcgatag aaaacaaaat atagcgcgca aactaggata   9060
aattatcgcg cgcggtgtca tctatgttac tagatccgct gagcggccgc catgccact    9120
agtgcggccg ccatgccctc tagagccgat cgtgaagttt ctcatctaag cccccatttg   9180
gacgtgaatg tagacacgtc gaaataaaga tttccgaatt agaataattt gtttattgct   9240
ttcgcctata aatacgacgg atcgtaattt gtcgttttat caaatgtac tttcattta     9300
taataacgct gcggacatct acattttga attgaaaaaa aattggccat acccaccat     9360
cgacatgatt ggcaccaagg tgttggaccg actcaaccag ttctgggata tggccccaca   9420
gtccggaatg acccccgccg atgacgcggg acaagccgtt ttacgtttgg aactgacaga   9480
accgcaacgt tgaaggagcc actcagccgc gggtttctgg agtttaatga gctaagcaca   9540
tacgtcagaa accattattg cgcgttcaaa agtcgcctaa ggtcactatc agctagcaaa   9600
tatttcttgt caaaaatgct ccactgacgt tccataaatt ccctcggta tccaattaga    9660
gtctcatatt cactctcaat ccatacaaaa acacatccaa aatcacgaaa aatgggagct   9720
tggattgaac aagatggatt gcacgcaggt tctccggccg cttgggtgga gaggctattc   9780
ggctatgact gggcacaaca gacaatcggc tgctctgatg ccgccgtgtt ccggctgtca   9840
gcgcagggc gcccggttct ttttgtcaag accgacctgt ccggtgccct gaatgaactt    9900
caggacgagg cagcgcggct atcgtggctg gccacgacgg cgttccttg cgcagctgtg    9960
ctcgacgttg tcactgaagc gggaagggac tggctgctat tgggcgaagt gccggggcag  10020
gatctcctgt catctcacct tgctcctgcc gagaaagtat ccatcatggc tgatgcaatg  10080
cggcggctgc atacgcttga tccggctacc tgcccattg accaccaagc gaaacatgcc  10140
atcgagcgag cacgtactcg gatggaagcc ggtcttgtcg atcaggatga tctggacgaa  10200
gagcatcagg ggctcgcgcc agccgaactg ttcgccaggc tcaaggcgcg catgcccgac  10260
ggcgaggatc tcgtcgtgac tcatggcgat gcctgcttgc cgaatatcat ggtggaaaat  10320
ggccgctttt ctggattcat cgactgtggc cggctgggtg tggcggaccg ctatcaggac  10380
atagcgttgg ctacccgtga tattgctgaa gagcttggcg gcgaatgggc tgaccgcttc  10440
ctcgtgcttt acggtatcgc cgctcccgat tcgcagcgca tcgccttcta tcgccttctt  10500
gacgagttct tctgacccga tgagctaagc tagctatatc atcaatttat gtattacaca  10560
taatatcgca ctcagtcttt catctacggc aatgtaccag ctgatataat cagttattga  10620
aatatttctg aatttaaact tgcatcaata aatttatgtt tttgcttgga ctataatacc  10680
tgacttgtta ttttatcaat aaatatttaa actatattc tttcaatccg gaccataccc   10740
caccatcgac atgattggca cccaggtgtt ggaccgactc aaccagtct gggatatggc   10800
cccacagata acatagagaa acccaacgga taatataagc aaacacaaat tacaatggtt  10860
cactacccag cagaaaaatt accaacattt caaatgttgt gccttctaaa agttaagact  10920
agaagaacat ctatagagca gaattgaagc atagaaacga atttccccga tcgttcaaac  10980
atttggcaat aaagtttctt aagattgaat cctgttgccg tcttgcgat gattatcata   11040
taatttctgt tgaattacgt taagcatgta ataattaaca tgtaatgcat gacgttattt  11100
atgagatgtt tttttatgat tagagtcccg caattataca tttaatacgc gatagaaaac  11160
aaaatatagc gcgcaaacta ggataaatta tcgcgcgcgg tgtcatctat gttactagat  11220
cgctcgaact agagccgatc gtgaagtttc tcatctaagc ccccatttgg acgtgaatgt  11280
agacacgtcg aaataaagat ttccgaatta gaataatttg tttattgctt cgcctataa   11340
atacgacgga tcgtaatttg tcgttttatc aaaatgtac ttcatttat aataacgctg     11400
cggacatcta cattttgaa ttgaaaaaaa attggtaatt actctttctt ttctccata     11460
ttgaccatca tactcattgc tgatccatgt agatttcccg gacatgaagc catttacaat  11520
tgaatatatc ctgccgccgc tgccgctttg cacccggtgg agcttgcatg ttggtttcta  11580
cgcagaactg agccggttag gcagataatt ccattgaga actgagccat gtgcaccttc   11640
cccccaacac ggtgagcgac ggggcaacgg agtgatccac atgggacttt taaacatcat  11700
ccgtcggatg gcgttgcgag agaagccgac atcaccgccg acgaccgggca             11760
ggcgcgcaac acgatcgcaa agtatttgaa cgcaggtaca atcgagccga cgttcacgcg  11820
gaacgaccaa gcaagctatg ttgcgattac ttcgccaact attgcgataa caagaaaaag  11880
ccagcctttc atgatatatc tcccaatttg tgtagggctt attatgcacg cttaaaaata  11940
ataaaagcag acttgacctg atagtttggc tgtgagcaat tatgtgctta gtgcatctaa  12000
cgcttgagtt aagccgcgcc gcgaagcggg gtcggcttga acgaattgtt agacattatt  12060
```

```
tgccgactac cttggtgatc tcgcctttca cgtagtggac aaattcttcc aactgatctg   12120
cgcgcgaggc caagcgatct tcttcttgtc caagataagc ctgtctagct tcaagtatga   12180
cgggctgata ctgggccggc aggcgctcca ttgcccagtc ggcagcgaca tccttcggcg   12240
cgattttgcc ggttactgcg ctgtaccaaa tgcgggacaa cgtaagcact acatttcgct   12300
catcgccagc ccagtcgggc ggcgagttcc atagcgttaa ggtttcattt agcgcctcaa   12360
atagatcctg ttcaggaacc ggatcaaaga gttcctccgc cgctggacct accaaggcaa   12420
cgctatgttc tcttgctttt gtcagcaaga tagccagatc aatgtcgatc gtggctggct   12480
cgaagatacc tgcaagaatg tcattgcgct gccattctcc aaattgcagt tcgcgcttag   12540
ctggataacg ccacggaatg atgtcgtcgt gcacaacaat ggtgacttct acagcgcgga   12600
gaatctcgct ctctccaggg gaagccgaag tttccaaaag gtcgttgatc aaagctcgcc   12660
gcgttgtttc atcaagcctt acggtcaccg taaccagcaa atcaatatca ctgtgtggct   12720
tcaggccgcc atccactgcg gagccgtaca aatgtacggc cagcaacgtc ggttcgagat   12780
ggcgctcgat gacgccaact acctctgata gttgagtcga tacttcggcg atcaccgctt   12840
ccctcatgat gtttaacttt gttttagggc gactgccctg ctgcgtaaca tcgttgctgc   12900
tccataacat caaacatcga cccacgcgcgt aacgcgcttg ctgcttggat gcccgaggca   12960
tagactgtac cccaaaaaaa cagtcataac aagccatgaa aaccgccact cgcgccgttac   13020
caccgctgcg ttcggtcaag gttctggacc agttgcgtga gcgcatacgc tacttgcatt   13080
acagcttacg aaccgaacag gcttatgtcc actgggttcg tgccttcatc cgtttccacg   13140
gtgtgcgtca cccggcaacc ttgggcagca gcgaagtcga ggcatttctg tcctggctgg   13200
cgaacgagcg caaggtttcg gtctccacgc atcgtcaggc ataccaccg gtgccttgat   13260
gtgggcgccg gcggtcgagt ggcgacggcg cggcttgtcc gcgccctggt agattgcctg   13320
gccgtaggcc agccatttt gagcggccag cggccgacgc gaagcggcgg   13380
ggcgtaggga gcgcagcgac cgaagggtag gcgcttttg cagctcttcg gctgtgcgct   13440
ggccagacag ttatgcacag gccaggcggg ttttaagagt tttaataagt tttaaagagt   13500
tttaggcgga aaaatcgcct ttttctctt ttatatcagt cacttacatg tgtgaccggt   13560
tccaatgta cggctttggg ttcccaatgt acgggttccg gttcccaatg tacggcttg   13620
ggttccaat gtacgtgcta tccacaggaa agagaccttt tcgaccttt tcccctgcta   13680
gggcaatttg ccctagcatc tgctccgtac attaggaacc ggcggatgct tcgccctcga   13740
tcaggttgcg gtagcgcatg actaggatcg ggccagcctg ccccgcctcc tccttcaaat   13800
cgtactccgg caggtcattt gacccgatca gcttgcgaca ggtgaaacag aacttcttga   13860
actctccggc gctgccactg cgttcgtaga tcgtccttgaa caaccatctg gcttctgcct   13920
tgcctgcggc gcggcgtgcc aggcggtaga gaaaacggcc gatgccggga tcgatcaaaa   13980
agtaatcggt gtgaaccgtc agcacgtccg ggttcttgcc ttctgtgatc tcgcggtaca   14040
tccaatcagc tagctcgatc tcgatgtact ccggccgcgc ggttcgctc tttacgatct   14100
tgtagcggct aatcaaggct tcaccctcgg ataccgtcac caggcggccg ttcttggcct   14160
tcttcgtacg ctgcatggca acgtcgcgtgg tgtttaaccg aatgcaggtt tctaccaggt   14220
cgtctttctg ctttccgcca tcggctcgcc ggcagaactt gagtacgtcc gcaacgtgtg   14280
gacggaacac gcggccgggc ttgtctccct tccttcccg gtatcggttc atggattcgg   14340
ttagatggga aaccgccatc agtaccaggt cgtaatccca cacactcgcc atgccggcgg   14400
gcccgtgcgga aacctctacg tgcccgtctg gaagctcgta gcggatcacc tcgccagctc   14460
gtcggtcacg cttcgacaga cggaaaaacgg ccacgtccat gatgctgcga ctatcgcggg   14520
tgcccacgtc atagagcatc ggaacgaaaa aatctggttg ctcgtcgccc ttgggcggct   14580
tcctaatcga cggcgcaccg gctgccggcg gttgccggga ttcttggga attcgatcag   14640
cggccgcttg ccacgattca ccggggcgtg cttctgcctc gatgcgttgc cgctgggcgg   14700
cctgcgccgc cttcaacttc tccaccaggt catcacccag cgccgcgccg atttgtaccg   14760
ggccggatgg tttgcgaccg ctcacgccga ttcctcgggc ttggggggttc cagtgccatt   14820
gcagggccgg cagacaaccc agccgcttac gcctggccaa ccgcccgttc ctccacacat   14880
ggggcattcc acggcgtcgg tgcctggttg ttcttgattt tccatgccgc ctcctttagc   14940
cgctaaaatt catctactca tttattcatt tgctcattta ctctggtagc tgcgcgatgt   15000
attcagatag cagctcggta atggtcttgc cttggcgtac cgcgtacatc ttcagcttgg   15060
tgtgatcctc cgccggcaac tgaaagttga cccgcttcat ggctggcgtg tctgccaagg   15120
tggccaacgt tgcagccttg ctgctgcgtg cgctcggacg gccggcactt agcgtgtttg   15180
tgcttttgct catttctct ttacctcatt aactcaaatg agttttgatt taatttcagc   15240
ggccagcgcc tggacctcgc gggcagcgtc gccctcgggt tctgattcaa gaacggttgt   15300
gccggcgggcg gcagtgcctg ggtagctcac gcgctgcgtg atacgggact caagaatggg   15360
cagctcgtac ccggccagcg cctcggcaac ctcaccgccg atgcgcgtgc ctttgatcgc   15420
ccgcgacacg acaaaggccg cttgtagcct tccatccgtg acctcaatgc gctgcttaac   15480
cagctccacc aggtcggcgg tggcccatat gtcgtaaggg cttggctgca ccggaatcag   15540
cacgaagtcg gctgccttga tcgcggacac agccaagtcc gccgcctggg gcgctcgtca   15600
gatcactacg aagtcgcgcc ggcgatggc cttcacgtcg cggtcaatcg tcgggcggtc   15660
gatgccgaca acggttagcg gttgatcttc ccgcacggcc gcccaatcgc gggcactgcc   15720
ctggggatcg gaatcgacta acagaacatc ggccccggcg agttgcaggg cgcgggctag   15780
atgggttgcg atggtcgtct tgcctgaccc gcctttctgg ttaagtacag cgataacctt   15840
catgcgttcc ccttgcgtat ttgttatt actcatcgca tcatatacgc agcgaccgca   15900
tgacgcaagc tgttttactc aaatacacat caccttttta gacggcgcg ctcgctttct   15960
tcagcggcca agctcgccgg ccaggccgcg agcttggcat cagacaaacc ggccaggatt   16020
tcatgcagcc gcacgttga gacgtgcgcg ggcggctcga acacgtaccc ggccgcgatc   16080
atctccgcct cgatctcttc ggtaatgaaa aacgcgttcgt cctggccgtc ctggtgcggt   16140
ttcatgcttg ttcctcttgg cgttcattct cggcgcgcg cggccggtca   16200
atgcgtcctc acggaaggca ccgcgccgcc tggcctcggt gggcgtcact tcctcgctgc   16260
gctcaagtgc gcggtacagg gtcgagcgat gcacgccaag cagtgcagcc gctcttttca   16320
cggtgcggcc ttcctggtcg atcagctcgc gggcgtcgcg gatctgtgcc ggggtgaggg   16380
tagggcgggg gccaaacttc acgcctcgcg ccttggcgg ctcgcgcccg ctcgggtgc   16440
tgatgat tagggaacgc tgaactcgg caatgccgg gaacatgc aacaccatgc   16500
ggccggccgc cgtggtggtg tcggcccacg gctctgccag gctacgcagg cccgcgccgg   16560
cctcctggat gcgctcggca atgtccagta ggtcgcgggt gctgcgggcc aggcggtcta   16620
gcctggtcac tgtcacaacg tcgccagggc gtaggtggtc aagcatcctg ccagctccgg   16680
gcggtcgcgc cctggtgccg gtgatcttct cggaaaacag cttggtgcag ccggccgcgt   16740
gcagttcggc ccgttggttg gtcaagtcct ggtcgtcgg gctgacgcgg gcatagccca   16800
```

-continued

```
gcaggccagc ggcggcgctc ttgttcatgg cgtaatgtct ccggttctag tcgcaagtat    16860
tctactttat gcgactaaaa cacgcgacaa gaaaacgcca ggaaaagggc agggcggcag    16920
cctgtcgcgt aacttaggac ttgtgcgaca tgtcgttttc agaagacggc tgcactgaac    16980
gtcagaagcc gactgcacta tagcagcgga ggggttggat cgacctcgac gtacccctgc    17040
ctcgcgcgtt tcggtgatga cggtgaaaac ctctgacaca tgcagctccc                17090

SEQ ID NO: 51          moltype = DNA   length = 18
FEATURE                Location/Qualifiers
misc_feature           1..18
                       note = cruaxxxxxxf02x
source                 1..18
                       mol_type = other DNA
                       organism = synthetic construct
SEQUENCE: 51
ggccagggct tccgtgat                                                    18

SEQ ID NO: 52          moltype = DNA   length = 21
FEATURE                Location/Qualifiers
misc_feature           1..21
                       note = cruaxxxxxxr01x
source                 1..21
                       mol_type = other DNA
                       organism = synthetic construct
SEQUENCE: 52
ccgtcgttgt agaaccattg g                                                21

SEQ ID NO: 53          moltype = DNA   length = 19
FEATURE                Location/Qualifiers
misc_feature           1..19
                       note = nptIIxxxf01
source                 1..19
                       mol_type = other DNA
                       organism = synthetic construct
SEQUENCE: 53
gctgtgctcg acgttgtca                                                   19

SEQ ID NO: 54          moltype = DNA   length = 18
FEATURE                Location/Qualifiers
misc_feature           1..18
                       note = nptIIxxxr01
source                 1..18
                       mol_type = other DNA
                       organism = synthetic construct
SEQUENCE: 54
cggcacttcg cccaatag                                                    18

SEQ ID NO: 55          moltype = DNA   length = 20
FEATURE                Location/Qualifiers
misc_feature           1..20
                       note = tDTxxxf04
source                 1..20
                       mol_type = other DNA
                       organism = synthetic construct
SEQUENCE: 55
tcctcgttgt gggaggtgat                                                  20

SEQ ID NO: 56          moltype = DNA   length = 19
FEATURE                Location/Qualifiers
misc_feature           1..19
                       note = tDTxxxr01
source                 1..19
                       mol_type = other DNA
                       organism = synthetic construct
SEQUENCE: 56
gtgcaactgc ccggctact                                                   19

SEQ ID NO: 57          moltype = DNA   length = 29
FEATURE                Location/Qualifiers
misc_feature           1..29
                       note = CruaxxxMGB
source                 1..29
                       mol_type = other DNA
                       organism = synthetic construct
SEQUENCE: 57
agtccttatg tgctccactt tctggtgca                                        29

SEQ ID NO: 58          moltype = DNA   length = 15
FEATURE                Location/Qualifiers
misc_feature           1..15
```

```
                        note = nptIIxxxMGB
source                  1..15
                        mol_type = other DNA
                        organism = synthetic construct
SEQUENCE: 58
aagcgggaag ggact                                                        15

SEQ ID NO: 59           moltype = DNA   length = 18
FEATURE                 Location/Qualifiers
misc_feature            1..18
                        note = tDTxxxMGB
source                  1..18
                        mol_type = other DNA
                        organism = synthetic construct
SEQUENCE: 59
agcttggtgt ccacgtag                                                     18

SEQ ID NO: 60           moltype = DNA   length = 19
FEATURE                 Location/Qualifiers
misc_feature            1..19
                        note = LbCpf1- Fw
source                  1..19
                        mol_type = other DNA
                        organism = synthetic construct
SEQUENCE: 60
tgccggaaga ggatctttt                                                    19

SEQ ID NO: 61           moltype = DNA   length = 23
FEATURE                 Location/Qualifiers
misc_feature            1..23
                        note = LbCpf1- Rv
source                  1..23
                        mol_type = other DNA
                        organism = synthetic construct
SEQUENCE: 61
agtcggcgtc ggtcctgctg aag                                               23

SEQ ID NO: 62           moltype = DNA   length = 18
FEATURE                 Location/Qualifiers
misc_feature            1..18
                        note = Probe for nuclease test
source                  1..18
                        mol_type = other DNA
                        organism = synthetic construct
SEQUENCE: 62
agttcgctct cgactata                                                     18

SEQ ID NO: 63           moltype = DNA   length = 24
FEATURE                 Location/Qualifiers
misc_feature            1..24
                        note = IR106_lox3_F1
source                  1..24
                        mol_type = other DNA
                        organism = synthetic construct
SEQUENCE: 63
cctctgacct ccaaaagacc ctta                                              24

SEQ ID NO: 64           moltype = DNA   length = 22
FEATURE                 Location/Qualifiers
misc_feature            1..22
                        note = IR106_lox3_F2
source                  1..22
                        mol_type = other DNA
                        organism = synthetic construct
SEQUENCE: 64
ccattacttg tttggtcggc gt                                                22

SEQ ID NO: 65           moltype = DNA   length = 21
FEATURE                 Location/Qualifiers
misc_feature            1..21
                        note = IR106_lox3_F3
source                  1..21
                        mol_type = other DNA
                        organism = synthetic construct
SEQUENCE: 65
gccatcactt gttttctcgg c                                                 21

SEQ ID NO: 66           moltype = DNA   length = 20
FEATURE                 Location/Qualifiers
```

```
misc_feature          1..20
                      note = IR106_lox3_F4
source                1..20
                      mol_type = other DNA
                      organism = synthetic construct
SEQUENCE: 66
ccgtcacttg ttttctcggc                                               20

SEQ ID NO: 67         moltype = DNA  length = 25
FEATURE               Location/Qualifiers
misc_feature          1..25
                      note = IR106_lox3_R1
source                1..25
                      mol_type = other DNA
                      organism = synthetic construct
SEQUENCE: 67
tcaaaggcta atataactga cacgt                                         25

SEQ ID NO: 68         moltype = DNA  length = 23
FEATURE               Location/Qualifiers
misc_feature          1..23
                      note = IR106_lox3_R2
source                1..23
                      mol_type = other DNA
                      organism = synthetic construct
SEQUENCE: 68
ggcaaacgcg tttccttaat tca                                           23

SEQ ID NO: 69         moltype = DNA  length = 20
FEATURE               Location/Qualifiers
misc_feature          1..20
                      note = IR106_lox3_R3
source                1..20
                      mol_type = other DNA
                      organism = synthetic construct
SEQUENCE: 69
ataacgctga tgtgctaagc                                               20

SEQ ID NO: 70         moltype = DNA  length = 24
FEATURE               Location/Qualifiers
misc_feature          1..24
                      note = IR106_lox3_R4
source                1..24
                      mol_type = other DNA
                      organism = synthetic construct
SEQUENCE: 70
gttaataacg ctgatgtact aagc                                          24

SEQ ID NO: 71         moltype = DNA  length = 22
FEATURE               Location/Qualifiers
misc_feature          1..22
                      note = 946R
source                1..22
                      mol_type = other DNA
                      organism = synthetic construct
SEQUENCE: 71
gctctctcgg ccccacttt tt                                             22

SEQ ID NO: 72         moltype = DNA  length = 20
FEATURE               Location/Qualifiers
misc_feature          1..20
                      note = 1145F
source                1..20
                      mol_type = other DNA
                      organism = synthetic construct
SEQUENCE: 72
tgttctgcgc ccaggctaca                                               20

SEQ ID NO: 73         moltype = DNA  length = 20
FEATURE               Location/Qualifiers
misc_feature          1..20
                      note = 346F
source                1..20
                      mol_type = other DNA
                      organism = synthetic construct
SEQUENCE: 73
tcgcgaacac accggtcgta                                               20

SEQ ID NO: 74         moltype = DNA  length = 20
```

```
FEATURE              Location/Qualifiers
misc_feature         1..20
                     note = 1948R
source               1..20
                     mol_type = other DNA
                     organism = synthetic construct
SEQUENCE: 74
actcacatgc ctcgccctca                                              20

SEQ ID NO: 75        moltype = DNA   length = 5145
FEATURE              Location/Qualifiers
source               1..5145
                     mol_type = genomic DNA
                     organism = Brassica napus
SEQUENCE: 75
gtgaatccat atcggtcaaa aacagcggta caaacacctc tgaatatacc attttcaata    60
ccactactta tgactatttt tgtgtcaagt aattagctct tcaccggaac agaagtgtac   120
tataagctag gtaaatacaa cgtattgttc attcagaata attgtgtgta ctcttttatc   180
tcataacata agtattttct aatatttaaa agaaatacat ttattcatga gaagtatatc   240
atacgaattt tctcaaaaaa gtatatcata agaaagagac ttaacatcac aaagactaat   300
tactttgaaa actagcatgt tgacaaaaag aaagaagagt gaacataatt aagaattcac   360
attttgtaaa aggaaaagga aaaaacatgg ctactgcgta gacggtagtc caatcaacaa   420
aaaaacgtgt ggacggcaat gagatccttc tatctctata tatctctctc acttgccgat   480
tattagtaac cagaacgtac accaactaat aaactctcaa cttcttcttg tttgccaaca   540
ttatattaca aaacaactca agattcattc catttaatac taactgatta catcatcgtt   600
atggcctag ctaaagagtt aatgggttat cctctgacct ccaaaagacc cttacttgtt   660
tggtcggcgt cgcatttcaa gaagaggaca cagccaacac aattctcgat caagcctttt   720
gataggagac caagaacgtc caaatccggg gtcgttgcgg ccatcagtga agatttggtc   780
aaaacgctac gtttcaacac aaccaccggt gacagaaaga gcgaggagga ggagaaagcg   840
gcggtgaaat tcaaggtgag agctgtggtt acggtgagga acaagaacaa ggaggatttt   900
aaggagactc ttgttaagca tttagatgct tttggtgata agatcggtcg aaacgttgtc   960
ttggagcttg ttagcaccga acttgatcca agtaagtcgc tttagtaaac tcggttgaaa  1020
aacagaacta gataaaatat ttttaaaaat ggaaactttc tatttgggca tttctaaaat  1080
cgtgtaatat aaaatgggtt atctcaaaat ctctttattt gagatgggtt ttcgaatact  1140
aagataaata tcaaatcttt taactcgaac agaaacgaat atgccgaaga aaagcaatgc  1200
ggcagtttta aaggactggt caaagaagtc gaaaaccaag gcggagaggg ttcattacac  1260
ggcggagttc acgtggacg cagcatttgg ctcaccggga gccatcaccg tcatgaataa  1320
acaccagaaa gagttctttc tggagagcat ccatcgaa ggtttcgcac ttggccctgt  1380
tcactttcca tgcaactctt gggttcagtc ccaaaaggat cacccaggga aacgaatctt  1440
tttcactaat aaggtaatta attttaaata tctgaatgat acagttatt acttaaatag  1500
ttaaattact catggtccca agccattagc tcacgtcatt ttcgatctcc cgcaaaatct  1560
tattcaatat tcatgtccgg tgggtccata taataattat ataccccttg tccaagttct  1620
aactatatgt aattaatgtt gttacaaatg acgttatgta aatttgtgtg  1680
cagccgcttt tgccgagtga gacacctgat ggattgaaaa aattgaggga gagagagttg  1740
aagaatctaa gaggagatgg gagtggacgc aggaagttat cagacagaat ctatgacttt  1800
gatgtgtaca acgatcttgg aaatcccgac aagtcatcag aactctctcg gcccaagctc  1860
ggcggcaaag agattcctta ccctagacga tgtcgtaccg gtcgccatcc aactgatacc  1920
ggtacaattc ataacaaaac attttataca tattttgagt acaatatgta attaatgaat  1980
ctctaatagt atgtgatttt tatatgcatt gttgacagat aaagaagcgg agagccgagt  2040
agagaagcca ttacctatgt acgtaccacg agatgagcaa ttcaagagca ctaagcgaaa  2100
aactttcgca gcagggaggc taaaagcggt cttacaccac ctagttccct cgctgaaagc  2160
cagcattta gctgaggact ttgctgactt tggcgagata gatggtctat ataaagaagg  2220
attgctactc aagttagggt ttcaagatga aatctttgac aagttccctt tgcccaaggc  2280
catcgttaat acactccaag aatcttctaa aggactcctc aaatacgaca ctcccaaaat  2340
actatcaagt aagcacactt aattaatatg atccttttgac atcaacttttt gttttttctta  2400
tagaaaattg aacttctacc atttacaacc acatatattt caaagagttt ttaatttatt  2460
atatttgatc tttgataact gagacccatc atgaatttttt catccccacc aaaagaaaac  2520
actttagttg gaaagcaaac agaacccact aaaaagaata cagaaacgat cgacatatga  2580
ttcacgttgt tttcttaatt cgttacaacg tgtcagttat attagccttt gaataaaaaa  2640
gcccgtttgc ctttatttaa ttcatcaccg taacatggtt agtagttagt acaagttatt  2700
agttaattga ttacaaaaaa tttaaaataa tgcagaggat aaaaatgcat ggctacgtga  2760
tgatgagttt gcacgtcaag ccatagctgg aatcaatcca gtcaacattg agagggtaag  2820
gactttccca ccggtcagta atcttgaccc cgaaatctac ggtccacaac actccgctct  2880
cacttccgac cacatcattg gacatctcga cggactactg gtacaacaag tacgtataac  2940
aaatccacat tgcttgattt agtatgtaac taaacgtaat tatttattaa ctaagtttta  3000
ttttacatat tattttccag gcgttggaag agaacagatt gtatatgttg aattaccacg  3060
acatatttt accgttccta gaccgaatca atgcgctaga cggacgcaaa gcttatgcta  3120
ctcgaaccat attctttttg actcgtcttg tacacttaga gcccgtagcc attgagctaa  3180
gtctccctcc acatggcccc aaccaccggt ccaaacgcgt ggttacacct cccgtcgatg  3240
caacctctaa ttgggtgtgg cagctcgcta agcccacgt tagctctaac gacgctgggg  3300
tccaccagct tgtcaatcac tggttagtac ttaaaaacat tcaagttatt aaacatatac  3360
gtttcatgta gtgactctag agttattgat ccttttgttg gtgtgcaggt tacgaaccca  3420
tgcgtgcttg gaaccgttta tattagctgc acatagacaa ctgagcgcta tgcatccgat  3480
attcaagcta ttagacccgc acatgaggta cacgttggaa tggctagaca  3540
atcgttgatc agtgcagacg gtgtgattga agaaggcttc actgccggct catacggcat  3600
ggaaatgagc ccgccgcat acaagagcag ctggcggttc gacatggaag gctccctgc  3660
cgatctcatt cgcaggtact ttagctgac aaaataatac tcttagatta tttcaaacac  3720
aacattaaac attttcattg tatattatat agtatttgat tattttaaac tgtgtttgt  3780
tttttcagag gaatagcagt tcctgacccg acacaaccac atggagttaa actcctaatc  3840
```

```
gaagactatc catacgccaa cgacggtctt ctactctggt cggctatcca aacctgggtc   3900
cgaacctacg tggaacgcta ctacccaaac ccgaacctaa tcaaaacaga ctcggagctc   3960
caatcctggt actccgaatc aatcaacgtc ggccacgccg atctccgcga cgccgagtgg   4020
tggccagagc taaacaccgt cgacgatctc gtctccatcc tcaccacact gatctggctc   4080
gcctcagctc agcacgcggc tctcaacttc ggacagtacc cgtacggcgg ctacgtcccg   4140
aaccgtcctc cgctgatgcg gcggttgatc cccgacgagt cggatccgtt gtacgcgagt   4200
ttcatctccg atccggagaa gttttacttc tcggcgatgc cgagtttgtt gcagacgtcg   4260
aagtttatgg cggtggttga tactctgtca acgcattcgc cagatgagga gtatatcggg   4320
gagagacagc agccgtcgat ttggacggga gatggggaga tcgttgatgc gttttatgga   4380
ttcgcggcgg agatcggacg gatagagaag gagattgaga aaaggaactc tgatcctgac   4440
cgtagaaata ggtgcgggc tggtgttttg ccgtatgagc tgttggttcc gagttccgag    4500
cctggtgtta cgtgcagagg tgtacctaat agtgtgtcga tatagaagga aattaaatat   4560
agggaaacat gtagaaattg ctataaataa ttttttggaag aaattaaaat atattaaatt   4620
tatagttaca ttacttcatc gtaaatttgt attttataga tgttttttt ccgaagatag     4680
cttgaaattt atgtaactcg aatattttta aaagtacttg gacgatgctt cttggattct   4740
gacctaactt gagtcgcagg ctatcttcgc acacgtataa acctagcaat tttaagttgc   4800
tgagaggaag atggatagat ttgtaccttt ttaatatggc aagtcaaaga gccatgacaa   4860
agtttattcg tgggatttta ttcacctaac ctggatggtt ggatcataga agatcatttc   4920
attggtagga acacaggaac ttaagttgga atgaaggatt caaagaggca gagtcatcaa   4980
cttagattta tcagaccaga gccaacgacc tgaccgatcg agttgcgctt agaagctgac   5040
gtagagagga ccgcaaagac aagataaata ggagacatgc attctttga aaagctgtaa    5100
taataagatc aacttaaaaa atctaactat ttgcctataa gacca                   5145

SEQ ID NO: 76          moltype = DNA   length = 5366
FEATURE                Location/Qualifiers
source                 1..5366
                       mol_type = genomic DNA
                       organism = Brassica napus SEQUENCE: 76
gtacaaaaac ttgaatatac cactttcgtt actacttatt gttactattt gtgattaaca    60
atgtgtacct gaacactacg tgattatcag tcaaacgatc tgtcctgtaa ataatactat   120
tactatacgc tacgtaaata cagcgtattg ttccctgtca cgctaataca tggtaatatc   180
ttttatctca tgtcgcataa catacgtttt ctaacattta aaagagagac atttattatg   240
atatcattaa aaatgtaaac atcgcaacaa tatgatagt caattaatca ctttgaaaac    300
tatattgttg acaaaaaaaa tctagcttaa gtgatatgtt ttgagagttc acattttcag   360
aaaaataata aaactaaaac atgacttgc gtagacaata gtccaatgaa ccaaaaaacg    420
tgtggacggc aaagagttcc ttctctatat atacatctct ttcacttgcc gattattagt   480
aagcagaacg tacaaacaac taataaactc tcaacaattt cttcttcttc gccaacacta   540
tacaacaaaa cagctcaaga ttcaatattc aattcaatac taattgatta caccatcgtg   600
atggccttag ttaaagagat aatgggtcat cctctgatat caggaaggcc atcacttgtt   660
ttctcggctt ctcatttcaa gaagaagaca cagacaacgc aattctcgat caagcctttc   720
gatcggagac caaaaacgtc caaatccggc gtcgtttcgg ccattagtga agatttagta   780
aaaacgctgc gttttagcac aacaaccgga gacagaaaga gcgaggagga ggagaaagcg   840
gcggtgaaat tcaaagtgag agctgtggtt acagtgagga acaagaacaa ggaggatttt   900
aaggagactc ttttttaagca tttggatgct tttggtgaca agatcggtcg gaacatcgtc   960
ttggagctta ttagcaccga acttgatcca agtaagtcac tttcttcttt gcttttatca  1020
caaaacagag cactcaggaa aactttctaa aaatagaaat ttttaaaaat cgtgtattaa   1080
aaatggatca tctcaaatat ccaatcttg attcaaacag aaacgaattt gccgaagaaa   1140
agcaatgctg cggtgttaaa ggattggtca gagaaatcga aaaccaaggc ggagagggtt   1200
cattacacgg cggagttcac ggtggacgca gcgtttggca cgccgggagc catcaccatc   1260
atgaataaac accagaaaga gttttttcta gagtgcataa ccatcgaagg tttcgcactt   1320
ggccctgttc actttccatg caactcttgg gttcagtccc aaaatgatca ccctgagaaa   1380
cgaatcttct tcactaatca ggtaactgat aaaatatct gactgataca taattaatta    1440
cggtcccaga ccatttaagt cacgtcattt tcgatctcca acgaattaat cacatatact   1500
aatcagtttc aaaatcttct ccaatattca tgtctggtgg gtccatataa taatacttat   1560
tagccagctt tcaactatat tcccataaat aaatatgttgt ggttataaat tattaaagat   1620
caagttatgt taatttgtgt gcagccgttt ttgccgagtg agacacctga aggattaaga   1680
aaattaaggg ggaaagagtt gaagaatcta cgaggagatg ggactggagt caggaagtta   1740
tcagacagaa tctatgactt tgatgtctac aacgatcttg gaaatcccga caagtcatct   1800
gaactctctc gtccgaaact cggtggcaga gagaggcctt acccctagacg tgtcgcact    1860
ggtcgccagc caactgatac cggtacaatt cataacaaca ttcttaaaaa caatatctct   1920
aatagtatat gtgttttggg tgttatgaaa tcaagcggat catgaaattt tgagacgata   1980
aacaagtcag taattaacga ttttttttaa aaaaaattaa aaaattggag agatacattt   2040
ttataaattg actctaattt tttgaagtt ctacagccaa tgtttcattt ggtcatgtcc     2100
aattgtccat gactggtact gtgaaaaaaa tgtatctgat gttttatctg cattgttggc   2160
agataatgaa gcgagagcc gagtggaaaa gccattacct atgtacgtgc cacgagacga    2220
gcaatttgaa gagactaagc aggacacttt cgccgcaggg aggttaaaag cggtgttaca   2280
ccaccttgtt ccgtcgctta aagctagtat tttagctgat gacttttctg acttcggaga   2340
gattgatgat ctctacaaaa aggcttgct actgaagtta ggattcaag atgagatatt     2400
caacaagttc cctttgccta agggcatcgt taatacccct caagaatctt cgaaaggact   2460
cctcaaatac gacactccca aaatattatc gagtaagctc acttaattca taaaaatttt   2520
taacatcaaa ttttgatttt aataaaaagg gtgttttaat agaaaatgaa ctttgatttt   2580
gtggcgattg ttggtctttg ataattggga ccattatgaa gtgttatcgt cctaccaaaa   2640
agtaagaaat atcattttta gttgaaaagc aggaataaaa gcaaacatat                2700
gcatgtttca cgtgcttttc ttgactcgtt ataacgctcg tgctagttat agtagtatta   2760
gtttgtgaat aaacaaaagc gcgtttgcct tcattaatt caaaatcata acatgcttag     2820
cacatcagcg ttattaacta attgactttt tttttaaaat gaatgcagag gataaaaacg   2880
catggctacg agatgacgag ttcgcacgtc aagccatagc tggaatcaat ccagtcaaca   2940
ttgagagagt caagactttc ccaccgtca gtaatcttga ccccgaaatc tacggtccac     3000
```

```
aacactccgc tctcacttcc gaccacatca tcggacatct tgacggcttg tccgttcaac 3060
aagtacgttt tatactataa acaaatccaa attactcgaa taattactaa aagtgaaatt 3120
tgatcaacta atttttgttt aattattttt caggcgttgg aagagaacag attgtatatg 3180
ttggattacc atgacatatt cttaccgttc ctagaccaaa tcaatgcgct cgatggacgt 3240
aaagcatatg ctactcgaac cattttcttc ttgactcgtc ttggaacact taagcccgta 3300
gccatcgagc taagcctccc ttcccatggc ccgaaccacc gatccaaacg agttgttaca 3360
cctcctgtcg atgcaacctc taactgggtg tggcagctcg ctaaagcaca tgttagctcc 3420
aacgatgctg gagtccacca acttgttaac cactggttag tactcaaaac gttaacttac 3480
taatcattta tgtaacaagt tgttaataat gaatatagag ttattgatat atttatcaat 3540
ttttgttcta aaggttacga acccatgcat gcttggaacc gtttataata gctgcacata 3600
ggcaattaag cgctatgcat ccgatattca aactattgga tccacacatg aggtatacgt 3660
tggagatcaa tgcactggct agacaatcat tgatcagtgc agacggtgtg attgaaggag 3720
gcttcactgc tggccaatac ggtttggaaa tgagctccgc agcctacaaa agtagttggc 3780
ggttcgacat ggaaggcctc cctgccgatc tcattcgcag gtattgtagc taaactttgt 3840
tagacatata ctattcttga ttatgtcaaa cacaatttta tacgtatgat atctaatatt 3900
gatcgtttta ttttgttttt tagaggaatg gcagttccag acccaacaca accacatgga 3960
cttaaactcc tgatcgaaga ctatccatat gcgaacgacg gtcttctaat atggtccgca 4020
atccaaacat gggtccgaac ttacgtggaa cgttactatc caaactcgaa ctcaattcaa 4080
acagactcgg aactccaatc gtggtactcg gagtcaatca acgtaggcca tgcagatctc 4140
cgcgaagccg agtggtggcc aaagttagac accgtggacg acctagtctc catcctcacc 4200
acactagtct ggctcgcctc cgctcaacac gccgctctca acttcggaca gtatccgtat 4260
ggaggttacg tcccaaaccg acctccgctg atgcgacggt taatccctga cgagtcggat 4320
ccggagtacg caagttttat ctcggatcct gagaaatttt attttcttc gatgccgagt 4380
ttgttgcaaa cgtcgaagtt tatggcgtg gttgatacgt tgtcaacgca ttctccggat 4440
gaggagtata tcgggagag acaacaaccg tccacttgga ccgagatgc ggagattgtt 4500
gatgcgtttt atggatttgc ggcggagatt ggacgatgg aaaaagagat tgagaaaaga 4560
aacagtgatc ctaaccgtag aaacaggtgt ggagctggga ttttgcctta cgagttgttg 4620
gttccgagtt ctgagccagg tgttacgtgc agaggtgtac ctaatagtgt atcgatatag 4680
aatgagatta aatataggag aaaatgtaga aatctgttat atatgatttt tgaaaatgaa 4740
ataaaatata taaattggta catttgaatt ttgcagatat gttctcgaag ctagatttaa 4800
attcatattc ataatatttt gaaatatatt cagacaatgg atttgttcat ctccggttaa 4860
ttatggccca aaagaccata aaatttatga aatttgaaaa tttaaaatac catatgctta 4920
ttgttgcgac gatggattat gatttgggct cattttatag ataacttcaa agtgactccc 4980
tttcgaattg gatcatggag atctcgattg ctcaacttaa attttcaaa agaaaacttc 5040
aaagtggctc tgtttcaact ttaaattgga cctaaaacca aggcttctg ggttctgacc 5100
taacttgggt cacacactat ctcctcagac gtataaaata tatatttgta cctttcatc 5160
agggaaatta aggcagatcg agatatacac taaagagtca agacaaggtt tgttcttatg 5220
gttttaacct aatctgacat acatacgaac cttaagttgg gtagaaaaat cgaacgtaca 5280
aaaagctatt tgtgtctggt tgattctgat ccaatgatgc agagtaatca acttaattag 5340
atttatcaga caaaaagcca acaacc                                  5366

SEQ ID NO: 77         moltype = DNA  length = 5154
FEATURE               Location/Qualifiers
source                1..5154
                      mol_type = genomic DNA
                      organism = Brassica napus
SEQUENCE: 77
aaatttgaat taacatgttg taaattggag aagtggtgaa tccatatcgg ttaaaaacag   60
cggtacaaaa ggtatttacc tattttgtgt caagtaatta gctcttcacc ggaacagaag  120
tgtactataa gctaggtaaa tacaacgtat tgttcattca gaataatagt gtgtactctc  180
ttatctcata acgtaactat tttctaacat ttaaaagaaa tcatttatt catgagaagt  240
atatcataag aattttctca aaagtgtata tcatagaaag agacttaaca tcacaaagac  300
taattacttt gaaaactagc atgttgacaa aaagaaagaa gagtgaacat gagaattcac  360
attttgtaaa aggaaaaaat aaaagcatgg ctattgcgta gacggtagtt caattaacaa  420
aaaaacgtgt ggacggcaat gagatccttc tatctctata tatctctctc acttgccgat  480
tattagtaac cagaacgtac accaactaat aaactctcag cttcttcttg tttgccaaca  540
ctaatctaca aaaaaactca agattcattc catttaatac taactgatta catcatcgtg  600
atggccttag ctaaagagtt aatgggttat ccactgaccct ccaaaaggcc attacttgtt  660
tggtcggcgt cgcatttcaa gaagaggaca cagccaacac aattatcgat caagccttt   720
gatcggagac caagaacgtc caaatccggg gtcgttgcgg ccatcagtga agatttggtc  780
aaaacgctac gtttcaacac aaccaccggt gacagaaaga gcgaggagga ggagaaagcg  840
gcggtgaaat tcaaggtgag agctgtgtt acggtgagga acaagaacaa ggaggatttt  900
aaggagactc ttgttaagca tttagatgct tttggtgata agatcggtcg aaacattgtc  960
ttggagcttg ttagcaccga acttgatcca agtaagtcgc tttagtaact cggttgaaaa 1020
acagaacatg ataaaatatt tctaaaaatg gaaactttat atttgggcat ttctataatc 1080
gtgtaatata aatgggttta tctcaaaatc tcttgatctg agatgggttt tcgaatacta 1140
agataaaatat taaatctttt aactcgaaca gaaacgaata tgccgaagaa aagcaatgcg 1200
gcagttttaa aggactggtc aaagaagtcg aaaaccaagg cggaaagggt tcattacacg 1260
gcggagttca cggttggacgc agcatttggc tcaccggagc ccatccaccgt catgaataaa 1320
caccagaaag aattctttct agagagcatc accatcgaag gtttcgcagt tggtcctgtt 1380
cactttccat gcaattcttg ggttcagtcc caaaaggatc acccagagaa acgaatctttt 1440
ttcactaatc aggtaattaa tttaaaatat ctgagtgata cagttattta cttaaatagt 1500
tcatttactc atggtcccaa gccattaact cacgtcattt tcgatttccc gcaaaatctt 1560
attcaatatt catgtccggt gggtccatat aaattaata taccccttgt ccaagttcta 1620
actatatgta attatgttgt tacaaatgat taaaccttac gttatataaa tttatgtgca 1680
gccgttttg ccgagtggga cacctgatgg attgaaaaaa ttgagggaga gagagttgaa 1740
gaatctaaga ggagatggga gtggagtgag gaagttatca gacagaatct atgacttga 1800
tgtgtacaac gatcttggaa atcccgacaa gtcatcagaa ctctctcgcc ccaagcttgg 1860
cggcaaagag attccttacc ctagacgatg tcgtaccggt cgccatccaa ctgataccgg 1920
```

```
tacaattcat aaaaaaacat tttatacata ttttgagtac aatatgtaat taatgaatct  1980
ctaatagtat gtgattttta tatgcattgt tgacagataa agaagcggag agccgagtgg  2040
agaagccatt acctatgtac gtaccacgag atgagcaatt tgaagagact aagcagaaaa  2100
ctttcgctgc agggaggtta aaagcggtct tacaccacct agttccgtct ctcaaagcca  2160
gcattttagc tgaggacttt gctgactttg gcgagataga tggtctctat aaagaaggat  2220
tgctactcaa gttagggttt caagatgaaa tttttaacaa gttcccttg cccaaggcca   2280
tcgttaatac actccaagaa tcttctaaag gactcctcaa atacgacact cccaaaatat  2340
tatcgagtaa gcataattaa cttataagat cctttaacat caacttttgt tttttttaat  2400
agaaaattga acttctacca tttacagcca catattattt ccaagagttt tatctgattt  2460
tattagctcc tatatttgat ctttgataac tgagacccat catgaaattt tcatcccacc   2520
aaaaagaaaa caacatcact ttagttgaaa agcaaaaagg acccactaaa agaatacaga  2580
aaccacatat gattcacgtg gttttcttaa ttcgttacaa cgtgtcaatt atactattag  2640
cttttgaatt aaggaaacgc gtttgccttt aacatggttt agtacatgca agttattaat  2700
tagttaatta atttcaaaaa attaaaatta tgcagaggat aaaaatgcat ggctacgaga  2760
tgacgagttt gcacgtcaag ccatagctgg aatcaatcca gtcaacattg agagggtcag  2820
gactttccca cccgtcagta atcttgaccc cgaaatctac ggtccacaac actccgctct  2880
cacttccgac cacatcattg gacatctcga cggactatcc gtacaacaag tacgtttata  2940
ttacaacaaa tccacattgc ttgattaagt acgtaactaa atgtgaatac tgattaacta  3000
aatgttattt tacttgttgt tttttttcagg cgttggaaga gaacaggttg tataagttgga 3060
attaccatga catattctta ccgttcctag accggatcaa tgcactagac ggacgcaaag   3120
cttatgctac tcgaaccata ttcttcttga ctcgtctagg aacactaaa cccgtagcca   3180
ttgagctaag cctccctccc catggtccca accatcggtc caaacgcgtg gttacacctc  3240
ctgtcgacgc aacctctaat tgggtgtggc agctcgctaa agcccacgtt agctctaacg  3300
acgctggtgt ccaccagctt gtcaatcact ggttagtact taaaaatatt aaagttatta  3360
aacatctatg tttcaaatag tgactctaga gttattgatc ttttgttggt gtgcaggtta  3420
cgaacccatg cgtgcttgga accgtttata ttagctgaac atagacaaat gagcgctatg  3480
catccgatat tcaagctatt ggatccgcac atgaggtaca cgttggaaat caatgcattg  3540
gctagacaat cgttgatcag tgcagacggt gtgattgaag aaggcttcac tgccggctca  3600
tacggcatgg agatgagcgc cgccgcatac aagagcagtt ggcggtttga catggaaggc  3660
ctccctgctg atctcattcg gaggtaattt aattagacaa agatactagt ctttattatt  3720
tcaaacacaa cattatacat tttcattgaa tattatatag tattttgatta tttttaaactg  3780
tgttttattc ttttcagagg aatggcagtt cctgactcga cacaaccaca tggacttaaa  3840
ctcctaatcg aagactatcc atacgctaac gacggtcttc tactctggtc ggctatccaa  3900
acctgggtcc gaacctacgt ggaacgctac tatcccaacc cgaacctaat caaaacagac  3960
tcggagctcc agtcctggta ctccgaatca atcaacgtcg gccacgctga tctccgcgac  4020
gccgagtggt ggccaaagct aaacaccgtc gacgacctcg cctccatcct caccacacta  4080
atctggctcg cctcagctca acacgcgct ctcaacttcg gacagtaccc gtacggcggc  4140
tacgtcccca accgtcctcc gctgatgcgg cggttgatcc ccgacgagtc tgatccggag  4200
tacgcggagt tcatctccga tccggagaag ttttacttct cggcgatgcc gagtttgctg  4260
cagacgtcga agtttatggc ggtggttgat actctgtcaa cgcattcgcc ggatgaggag  4320
tatatcgggg agagacagca accgtcgatt tggacgggag atgcggagat cgttgatgcg  4380
ttttatggat tcgcggcgga gatcggacgg atagagaagg agattgagga aaggaactct  4440
gatcctgacc gtagaaatag gtgcgggggct ggtgttttgc cttatgagct gttggttccg  4500
agttccgagc ctggtgttac ttgcagaggt gtacctaata gtgtatcgat atagaaggaa  4560
atttaatata gggaaaatgt agaaattgct ataataatt tttggaaaaa attaaaatat    4620
attaaattat agttacatca tcgtaaattt gtaattata gatgtttttt ttacgaagat    4680
agcttcaaat ttatgtaact cgaatatttt taaaagtaact tggacgatgc ttcttggatt 4740
ttgacctaac ttgactcgca ggctatcttc gcacacgtat aaacctagca attttaagtt  4800
gctgtgagag aagatgtat agattcgtac cttttaata tggcaaatca aggcactcaa   4860
gagccatgac agtttattcg tgggatttta ttaacctatc atttcattgg taggaacaca  4920
tgaaccttaa gttggcacga aagattcaac ggcgcagagt tatcaactta gtttttatcg  4980
accagagcca acgacctgac cgatcgagtt gcgttcagaa gctgacgtag agaggaccac  5040
acaaagagac gataaataga agacatgcat tctttttgaaa agctgtaata ataagatcaa  5100
cttagaaaat ctaatcaatt tgcctataag actaaattat atgagaatat atac         5154

SEQ ID NO: 78           moltype = DNA   length = 5330
FEATURE                 Location/Qualifiers
source                  1..5330
                        mol_type = genomic DNA
                        organism = Brassica napus
SEQUENCE: 78
cgtacaaaaa ctttaatata ccactttcgt tactactaat tgttactatt cgtggttaac   60
aatgtgtacc tgaacactac gtggttatca gtcaaacgat ccgtcctgta aataatactg  120
ccactatacg ctacgtaaat acaacgtatt gttccttgtc acgctgatac atgatgtat   180
cttttatctc atgtcataac atacgttttc taacatttaa aagagagaca tttattatga  240
tatcattaaa aatgtaaaca tcgcaacaat acgagtagtc aaactaatca ctttgaaaac  300
tatattgttg acaaaaaaaa aatctagctt aagtgaatat gttttgagag ttcacatttt  360
cagaaaaata ataaaactaa aacatgactt tgcgtagaaa atagtccaat gaaccaaaaa  420
acgtgtggac ggcaaagagt tccttctcta tatatacatc tctttcactt gccgattatt  480
agtaagcaga acgtacaaac aactaataaa ctctcaacaa cttcttcttc ttcgccaaca  540
ctatacaaca aaacagctca aggttcattc aattcgatac taattgatta caccatcgtg  600
atggccttag ttaaagagat aatgggtcat cctctgatat caggaaggcc gtcacttgtt  660
ttctcggctt ctcatttcaa gaagaagaca cagacaacgc aattctcgat caagcctttt  720
gatcggagac caaaacgtc caaatccggc gtcgtttccg ccattagtga agatttagta  780
aaaacgctgc gttttagcac aacaaccgga gacagaaaga gcgaggagga ggagaaagcg  840
gcggtgaaat tcaaagtgag agctgttgtt acagtgagga acaagaacaa ggaggatttt  900
aaggagactc ttttttaagca tttggatgct tttggtgaca agatcggtcg gaacatcgtc  960
ttggagctta ttagcaccga acttgatcca agtaagtcac ttactttttt attttttat   1020
aactcggtta cagaacagag cactcaggaa aactttctaa aaatagaaaa atttaaaaat  1080
```

```
cgtgtaatta aaaatggatc atctcaaata tccaatcttt gctccaaaca gaaacgaatt      1140
tgccgaagaa gagcaatgca gcggtgttaa aggattggtc agagaaatcg aaaaccaagg      1200
cggagagggt tcattacacg gcggagttca cagtcgacgc agcgtttggc acgccgggag      1260
ccatcaccat catgaataaa caccagaaag agttttttct agagtgcata accatcgaag      1320
gtttcgcact tggccctgtt cacttttccat gcaactcttg ggtcagtcc caaaatgatc      1380
accctgagaa acgaatcttc ttcactaatc aggtaattga ttaaaatatc tgactgatac      1440
ataattaatt acggtcccag acaatttaag tcacgtcatt ttcgatctcc aacgaattaa      1500
ttacatatac taatcagttt caaaatcttc tacaatattc atgtctggtg ggtccatata      1560
ataatactta ttagccagct ttcaactata ttcccataaa taatatgtgg ttataaatta      1620
ttaaaaatca agttatgtta atttgtgtgc agccgttttt gccgagtgag acacctgaag      1680
gattaagaaa actaagggg aaagagttga agaatctaag aggagatggg actggagtca       1740
ggaagttatc agacagaatc tatgactttg atgtctacaa cgatcttgga aatcccgaca      1800
agtcatatga actctctcgt ccgaagctcg gtggcagaga gaggccttac cctagacggt      1860
gtcgcactgg tcgccagcca actgataccg gtacaattca taacaacatt cttaaaaaca      1920
atatctctaa tagtatatgt ttttgggtgt tatgaaatca agcggatcct gaaattttga      1980
gacgataaac aagtcagtaa ggatttttat ttttttaaaa ttaaaaaatc ggagagattc      2040
atttttataa attgactcca attttttttga agttttagaa ccaatgtttc atttggtttg     2100
catgtccatg attggttttg tgaaaatatg tatctgatgt tttatctgca tcgttggcag      2160
ataatgaagc ggagagccga gtggaaaagc cattacctat gtacgtgcca cgagacgagc      2220
aatttgaaga gactaagcag gatactttcg ccgcagggag gttaaaagcg gtgttacacc     2280
accttgttcc gtcgcttaaa gctagtattt tagctgatga ctttcttgac tttgagaga      2340
ttgatgatct ctacaaagaa ggcttgctac tcaagttagg gtttcaagat gagatcttta     2400
acaagttccc tttgcctaag ggcatcgtta atacccttca agaatcttcg aaaggactcc     2460
tcaaatacga cactccgaaa atattatcga gtaagctcac ttaattcata aaattcttta     2520
acatcaaatt ttgattttaa taaaaaggtt gtttttaata gaaaatgaac tttaatattt     2580
tgtggcgatt gttggtcttt gataattggg accattatga agtgttatcg tcctaccaaa     2640
aagtaagaaa taatcatttt agttgaaaag gaggaataaa aagagtacg tacataagca     2700
aacatatgtt tcacgtgctt ttcttaactc gttataacgc tcgtgctagt aatagtatta    2760
gtttgtgaat aaacaaaagc gcgtttgcct ttcattaatt caaaatcata aaacatgctt   2820
agtacatcag cgttattaac taattgactt ttttgtaaaa tgaacgcaga ggataaaaac     2880
gcatggctac gagatgacga gttcgcacgt caagccatag ctggaatcaa tccagtcaac     2940
attgagagag tcaagacttt cccaccgtc agtaatcttg accccgaaat ctacggtcca      3000
caacactccg ctctcacttc cgaccacatc atcggacatc ttgacggctt gtccgttcaa    3060
caagtacgtt ttatactata aacaaatcca aattaagccc tttctcaaaa aaaaaaaaa     3120
aaaacaaatc caaattactc gaataattac taaatgtgaa atttgatcaa ctaatttttt    3180
attcttcagg cgctggaaga gaacagattg tttatgttgg attaccacga catattctta    3240
ccgttcctgg accggatcaa tgcgctcgac ggacgcaaag catatgctac tcgaaccata   3300
ttcttcttga ctcgtctcgg aacacttaag cccgtagcca tcgagctgag cctcccttcc   3360
catggcccga accaccgatc caaacgagtt gttcacctcc ctgtcgatgc aacctctaac   3420
tgggtgtggc agctcgctaa agcacatgtt agctctaacg atgctggagt ccaccaactt   3480
gtcaaccact ggtagtact caaaacacat tgagttatta aacatttatt taacaagttg    3540
ttaataataa atataggact gacatgtttt tatccttctt ttgatgttgt aaaggttacg   3600
aacacatgca tgcttggaac cgtttataat agctgcacat aggcaattaa gcgctatgca   3660
tccgatattt aaactattgg atccacacat gaggtacacg ttggagatca atgcactggc   3720
tagacaatca ttgatcagtg cagacggtgt gattgaagga ggtttcactg ctggccaata   3780
cggtttggaa atgagctccg cagcatacaa agtagttgg cggttcgata tggaaggcct     3840
ccctgccgat ctcattcgca ggtattgtat aaacttttt agacatatac tagtcttgat    3900
tatgtcagac acaaatatac gttttttattg tatgatatct aatatcgatc gttttattt   3960
gtttttttt cagaggaatg gcagttccag acccaacaca accacatgga cttaaactcc     4020
tgatcgaaga ctatccatat gcgaacgacg gtcttttaat atggtccgca atccaaacat   4080
gggtccgaac ttacgtggaa cgttactatc caaactcgaa ctcaatccag acagactgg    4140
aactccaatc atggtactcc gagtcaatca acgtaggcca tgcagatcta cgcgaagcca   4200
agtggtggcc aaagttagac accgtggacg acctagtctc catcctcacc acactagtct  4260
ggctcgcctc cgctcaacac gccgctctca acttcggaca gtatccgtat ggaggttacg   4320
tcccaaaccg acctccgctg atgcgacggt taatccctca cgagtcggat ccggagtacg  4380
caagtttat ctcggatcca gagaaattt atttttcgtc catgccgagt ttgttgcaaa     4440
cgtcgaagtt tatgcggtg gttgatactt tgtcaacgca ttcgcctgat gaggagtata    4500
taggggagag acaacaaccg tccacttgga ccggagatgc ggagattgtt gatgcgtttt  4560
atggatttgc ggcggagatt ggacggattg aaaaagagat tgagaaaaga aacagtgatc   4620
ctagccgtag aaacaggtgt ggagctggag ttttgcctta cgagttgttg gttcctagtt   4680
ctgagccagg tgttacgtgc agaggtgtac ctaatagtgt atcgatatag aatgagatta  4740
aatataggta aaaacgtaga aatctgttat tatatgattt ttgaaaatga aataaaatat  4800
ataattggta catttgaatt ttgcagatat gttttcgaag ctagatttaa attcatgttc   4860
ataatatttt gaaatatatt cagacaatgg attgtgcat gtcaggttaa ttatagccaa     4920
agaagaccat aaaatatatg aaaactgaaa attaaaaata ccatatgctt atcgttgcga   4980
cgatggatca tgatttgggc tcattttata gataacttca aagtgactcc tcccttcaa    5040
attggatcat ggagatctcg attgctcaac ttaaattttt caaaaaaac tacttcaaag   5100
tggctctgtt tcaactttaa gttggacctg aaatttggca tggcttcttg ggttctaacc   5160
taacttgggt cacaaactat ctcctcatac gtataaaaaa tatatttgta ccttttcatc   5220
agggaaatta aggcagatcg agatatacac taaagggcca agacaaggtt tgttcttatg   5280
gtttttaacct aatctgatat caggagaaca tttcattggt atacatacga                5330

SEQ ID NO: 79     moltype = AA  length = 919
FEATURE           Location/Qualifiers
source            1..919
                  mol_type = protein
                  organism = Brassica napus
SEQUENCE: 79
MALAKELMGY PLTSKRPLLV WSASHFKKRT QPTQFSIKPF DRRPRTSKSG VVAAISEDLV    60
```

```
KTLRFNTTTG DRKSEEEEKA AVKFKVRAVV TVRNKNKEDF KETLVKHLDA FGDKIGRNVV    120
LELVSTELDP KTNMPKKSNA AVLKDWSKKS KTKAERVHYT AEFTVDAAFG SPGAITVMNK    180
HQKEFFLESI TIEGFALGPV HFPCNSWVQS QKDHPGKRIF FTNKPLLPSE TPDGLKKLRE    240
RELKNLRGDG SGARKLSDRI YDFDVYNDLG NPDKSSELSR PKLGGKEIPY PRRCRTGRHP    300
TDTDKEAESR VEKPLPMYVP RDEQFEETKQ KTFAAGRLKA VLHHLVPSLK ASILAEDFAD    360
FGEIDGLYKE GLLLKLGFQD EIFDKFPLPK AIVNTLQESS KGLLKYDTPK ILSKDKNAWL    420
RDDEFARQAI AGINPVNIER VRTFPPVSNL DPEIYGPQHS ALTSDHIIGH LDGLSVQQAL    480
EENRLYMLNY HDIFLPFLDR INALDGRKAY ATRTIFFLTR LGTLKPVAIE LSLPPHGPNH    540
RSKRVVTPPV DATSNWVWQL AKAHVSSNDA GVHQLVNHWL RTHACLEPFI LAAHRQLSAM    600
HPIFKLLDPH MRYTLEINAL ARQSLISADG VIEEGFTAGS YGMEMSAAAY KSSWRFDMEG    660
LPADLIRRGI AVPDPTQPHG VKLLIEDYPY ANDGLLLWSA IQTWVRTYVE RYYPNPNLIK    720
TDSELQSWYS ESINVGHADL RDAEWWPELN TVDDLVSILT TLIWLASAQH AALNFGQYPY    780
GGYVPNRPPL MRRLIPDESD PLYASFISDP EKFYFSAMPS LLQTSKFMAV VDTLSTHSPD    840
EEYIGERQQP SIWTGDAEIV DAFYGFAAEI GRIEKEIEKR NSDPDRRNRC GAGVLPYELL    900
VPSSEPGVTC RGVPNSVSI                                                 919

SEQ ID NO: 80          moltype = AA   length = 919
FEATURE                Location/Qualifiers
source                 1..919
                       mol_type = protein
                       organism = Brassica napus
SEQUENCE: 80
MALVKEIMGH PLISGRPSLV FSASHFKKKT QTTQFSIKPF DRRPKTSKSG VVSAISEDLV     60
KTLRFSTTTG DRKSEEEEKA AVKFKVRAVV TVRNKNKEDF KETLFKHLDA FGDKIGRNIV    120
LELISTELDP KTNLPKKSNA AVLKDWSEKS KTKAERVHYT AEFTVDAAFG TPGAITIMNK    180
HQKEFFLECI TIEGFALGPV HFPCNSWVQS QNDHPEKRIF FTNQPFLPSE TPEGLRKLRG    240
KELKNLRGDG TGVRKLSDRI YDFDVYNDLG NPDKSSELSR PKLGGRERPY PRRCRTGRQP    300
TDTDNEAESR VEKPLPMYVP RDEQFEETKQ DTFAAGRLKA VLHHLVPSLK ASILADDFSD    360
FGEIDDLYKK GLLLKLGFQD EIFNKFPLPK GIVNTLQESS KGLLKYDTPK ILSKDKNAWL    420
RDDEFARQAI AGINPVNIER VKTFPPVSNL DPEIYGPQHS ALTSDHIIGH LDGLSVQQAL    480
EENRLYMLDY HDIFLPFLDQ INALDGRKAY ATRTIFFLTR LGTLKPVAIE LSLPSHGPNH    540
RSKRVVTPPV DATSNWVWQL AKAHVSSNDA GVHQLVNHWL RTHACLEPFI IAAHRQLSAM    600
HPIFKLLDPH MRYTLEINAL ARQSLISADG VIEGGFTAGQ YGLEMSSAAY KSSWRFDMEG    660
LPADLIRRGM AVPDPTQPHG LKLLIEDYPY ANDGLLIWSA IQTWVRTYVE RYYPNSNSIQ    720
TDSELQSWYS ESINVGHADL REAEWWPKLD TVDDLVSILT TLVWLASAQH AALNFGQYPY    780
GGYVPNRPPL MRRLIPDESD PEYASFISDP EKFYFSSMPS LLQTSKFMAV VDTLSTHSPD    840
EEYIGERQQP STWTGDAEIV DAFYGFAAEI GRIEKEIEKR NSDPNRRNRC GAGVLPYELL    900
VPSSEPGVTC RGVPNSVSI                                                 919

SEQ ID NO: 81          moltype = AA   length = 919
FEATURE                Location/Qualifiers
source                 1..919
                       mol_type = protein
                       organism = Brassica napus
SEQUENCE: 81
MALAKELMGY PLTSKRPLLV WSASHFKKRT QPTQLSIKPF DRRPRTSKSG VVAAISEDLV     60
KTLRFNTTTG DRKSEEEEKA AVKFKVRAVV TVRNKNKEDF KETLVKHLDA FGDKIGRNIV    120
LELVSTELDP KTNMPKKSNA AVLKDWSKKS KTKAERVHYT AEFTVDAAFG SPGAITVMNK    180
HQKEFFLESI TIEGFAVGPV HFPCNSWVQS QKDHPEKRIF FTNQPFLPSG TPDGLKKLRE    240
RELKNLRGDG SGVRKLSDRI YDFDVYNDLG NPDKSSELSR PKLGGKEIPY PRRCRTGRHP    300
TDTDKEAESR VEKPLPMYVP RDEQFEETKQ KTFAAGRLKA VLHHLVPSLK ASILAEDFAD    360
FGEIDGLYKE GLLLKLGFQD EIFNKFPLPK AIVNTLQESS KGLLKYDTPK ILSKDKNAWL    420
RDDEFARQAI AGINPVNIER VRTFPPVSNL DPEIYGPQHS ALTSDHIIGH LDGLSVQQAL    480
EENRLYKLDY HDIFLPFLDR INALDGRKAY ATRTIFFLTR LGTLKPVAIE LSLPPHGPNH    540
RSKRVVTPPV DATSNWVWQL AKAHVSSNDA GVHQLVNHWL RTHACLEPFI LAAHRQMSAM    600
HPIFKLLDPH MRYTLEINAL ARQSLISADG VIEEGFTAGS YGMEMSAAAY KSSWRFDMEG    660
LPADLIRRGM AVPDSTQPHG LKLLIEDYPY ANDGLLLWSA IQTWVRTYVE RYYPNPNLIK    720
TDSELQSWYS ESINVGHADL RDAEWWPKLN TVDDLASILT TLIWLASAQH AALNFGQYPY    780
GGYVPNRPPL MRRLIPDESD PEYASFISDP EKFYFSAMPS LLQTSKFMAV VDTLSTHSPD    840
EEYIGERQQP SIWTGDAEIV DAFYGFAAEI GRIEKEIEER NSDPDRRNRC GAGVLPYELL    900
VPSSEPGVTC RGVPNSVSI                                                 919

SEQ ID NO: 82          moltype = AA   length = 919
FEATURE                Location/Qualifiers
source                 1..919
                       mol_type = protein
                       organism = Brassica napus
SEQUENCE: 82
MALVKEIMGH PLISGRPSLV FSASHFKKKT QTTQFSIKPF DRRPNTSKSG VVSAISEDLV     60
KTLRFSTTTG DRKSEEEEKA AVKFKVRAVV TVRNKNKEDF KETLFKHLDA FGDKIGRNIV    120
LELISTELDP KTNLPKKSNA AVLKDWSEKS KTKAERVHYT AEFTVDAAFG TPGAITIMNK    180
HQKEFFLECI TIEGFALGPV HFPCNSWVQS QNDHPEKRIF FTNQPFLPSE TPEGLRKLRG    240
KELKNLRGDG TGVRKLSDRI YDFDVYNDLG NPDKSYELSR PKLGGRERPY PRRCRTGRQP    300
TDTDNEAESR VEKPLPMYVP RDEQFEETKQ DTFAAGRLKA VLHHLVPSLK ASILADDFSD    360
FGEIDDLYKE GLLLKLGFQD EIFNKFPLPK GIVNTLQESS KGLLKYDTPK ILSKDKNAWL    420
RDDEFARQAI AGINPVNIER VKTFPPVSNL DPEIYGPQHS ALTSDHIIGH LDGLSVQQAL    480
EENRLFMLDY HDIFLPFLDR INALDGRKAY ATRTIFFLTR LGTLKPVAIE LSLPSHGPNH    540
RSKRVVTPPV DATSNWVWQL AKAHVSSNDA GVHQLVNHWL RTHACLEPFI IAAHRQLSAM    600
HPIFKLLDPH MRYTLEINAL ARQSLISADG VIEGGFTAGQ YGLEMSSAAY KSSWRFDMEG    660
```

```
LPADLIRRGM AVPDPTQPHG LKLLIEDYPY ANDGLLIWSA IQTWVRTYVE RYYPNSNSIQ   720
TDSELQSWYS ESINVGHADL REAEWWPKLD TVDDLVSILT TLVWLASAQH AALNFGQYPY   780
GGYVPNRPPL MRRLIPDESD PEYASFISDP EKFYFSSMPS LLQTSKFMAV VDTLSTHSPD   840
EEYIGERQQP STWTGDAEIV DAFYGFAAEI GRIEKEIEKR NSDPSRRNRC GAGVLPYELL   900
VPSSEPGVTC RGVPNSVSI                                                919

SEQ ID NO: 83           moltype = DNA  length = 2760
FEATURE                 Location/Qualifiers
source                  1..2760
                        mol_type = genomic DNA
                        organism = Brassica napus
SEQUENCE: 83
atggccttag ctaaagagtt aatgggttat cctctgacct ccaaaagacc cttacttgtt    60
tggtcggcgt cgcatttcaa gaagaggaca cagccaacac aattctcgat caagcctttt   120
gataggagac caagaacgtc caaatccggg tcgttgcgg ccatcagtga agatttggtc    180
aaaacgctac gtttcaacac aaccaccggt gacagaaaga gcgaggagga ggagaaagcg   240
gcggtgaaat tcaaggtgag agctgtggtt acggtgagga caagaacaa ggaggatttt    300
aaggagactc ttgttaagca tttagatgct tttggtgata agatcggtcg aaacgttgtc   360
ttggagcttg ttagcaccga acttgatcca aaaacgaata tgccgaagaa agcaatgcg    420
gcagttttaa aggactggtc aaagaagtcg aaaaccaagg cggagagggt tcattacacg   480
gcggagttca cggtggacgc agcatttggc tcaccgggag ccatcaccgt catgaataaa   540
caccagaaag agttctttct ggagagcatc accatcgaag ttcgcact tggccctgtt    600
cactttccat gcaactcttg ggttcagtcc caaaaggatc acccagggaa acgaatcttt   660
ttcactaata agccgttttt gccgagtgag acacctgatg gattgaaaaa attgagggag   720
agagagttga agaatctaag aggagatggg agtggacgga ggaagttatc agacagaatc   780
tatgactttg atgtgtacaa cgatcttgga aatcccgaca agtcatcaga actctctcgg   840
cccaagctcg gcggcaaaga gattcctac cctagacgat gtcgtaccgg tcgccatcca   900
actgataccg ataaagaagc gggagagccga gtagagaagc cattacctat gtacgtacca   960
cgagatgagc aattcgaaga gactaagcag aaaactttcg cagcagggag gctaaaagcg  1020
gtcttacacc acctagttcc ctcgctgaaa gccagcattt tagctgagga ctttgctgac  1080
tttggcgaga tagatggtct atataagaa ggattgctac tcaagttagg gtttcaagat   1140
gaaatctttg acaagttccc tttgccaag gccatcgtta atacactcca agaatcttct   1200
aaaggactcc tcaaatacga cactcccaaa atactatcaa aggataaaaa tgcatggcta   1260
cgtgatgatg agtttgcacg tcaagccata gctggaatca atccagtcaa cattgagagg   1320
gtaaggactt tcccaccggt cagtaatctt gaccccgaaa tctacggtcc acaacactcg   1380
gctctcactt ccgaccacat cattggacat ctcgacggac tatccgtaca caagcgttg    1440
gaagagaaca gattgtatat gttgaattac cacgacatat ttttaccgtt cctagaccga   1500
atcaatgcgc tagacggacg caaagcattat gctactcgaa ccatattctt tttgactcgt   1560
cttggtacac ttaagcccgt agccattgag ctaagtctcc ctccacatgg ccccaaccac  1620
cggtccaaac gcgtggttac acctcccgtc gatgcaacct ctaattgggt gtggcagctc   1680
gctaaagccc acgttagctc taacgacgct ggggtccacc agcttgtcaa tcactggtta   1740
cgaacccatg cgtgcttgga accgtttata ttagctgcac atagacaact gagcgctatg   1800
catccgatat tcaagctatt agacccgcac atgaggtaca cgttgaaat caatgcattg   1860
gctagacaat cgttgatcag tgcagacggt gtgattgaag aaggcttcac tgccggctca   1920
tacggcatgg aaatgagcgc cgccgcatac aagagcagct ggcggttcga catggaaggc   1980
ctccctgccg atctcattcg cagaggaata gcagttcctg acccgacaca accacatgga   2040
gttaaactcc taatcgaaga ctatccatac gccaacgacg gtcttctact ctggtcggct   2100
atccaaacct gggtccgaac ctacgtgaaa cgctactacc aaacccgaa cctaatcaaa    2160
acagactcgg agctccaatc ctggtactcc gaatcaatca cgtcggcca cgccgatctc   2220
cgcgacgccg agtggtggcc agagctaaac ccgtcgacg atctcgtctc catcctcacc   2280
acactgatct ggctcgcctc agctcagcac gcggctctca cttcggaca gtacccgtac    2340
ggcggctacg tcccgaaccg tcctccgctg atgcggcggt tgatcccga cgagtcggat   2400
ccgttgtacg cgagtttcat ctccgatccg gagaagtttt acttctcggc gatgccgagt  2460
ttgttgcaga cgtcgaagtt tatggcggtg gttgatactc tgtcaacgca ttcgccagat  2520
gaggagtata tcgggagag acagcagccg tcgatttgga cggagatgg ggagatcgtt   2580
gatgcgtttt atggattcgc ggcggagatc ggacggatag agaaggagat tgagaaaagg   2640
aactctgatc ctgaccgtag aaataggtgt ggggctggtg ttttgccgta tgagctgttg   2700
gttccgagtt ccgagcctgg tgttacgtgc agaggtgtac ctaatagtgt gtcgatatag  2760

SEQ ID NO: 84           moltype = DNA  length = 2760
FEATURE                 Location/Qualifiers
source                  1..2760
                        mol_type = genomic DNA
                        organism = Brassica napus
SEQUENCE: 84
atggccttag ttaaagagat aatgggtcat cctctgatat caggaaggcc atcacttgtt    60
ttctcggctt ctcatttcaa gaagaagaca cagacaacgc aattctcgat caagcctttc   120
gatcggagac caaaaacgtc caaatccggc gtcgtttcgg ccattagtga agatttagta   180
aaaacgctgc gttttagcac aaccaccgga gacagaaaga gcgaggagga ggagaaagcg   240
gcggtgaaat tcaaagtgag agctgtggtt acagtgagga caagaacaa ggaggatttt    300
aaggagactc tttttaagca tttgatgct tttggtgaca agatcggtcg gaacatcgtc    360
ttggagctta ttagcaccga acttgatcca aaaacgaatt tgccgaagaa agcaatgct   420
gcggtgttaa aggattggtc agagaaatcg aaaaccaagg cggagagggt tcattacacg   480
gcggagttca cggtggacgc agcgtttggc tcgccgggag ccatcaccat catgaataaa   540
caccagaaag agttttttct agagtgcata accatcgaag ttcgcact tggccctgtt    600
cactttccat gcaactcttg ggttcagtcc caaaatgatc accctgagaa acgaatcttc   660
ttcactaata agccgttttt gccgagtgag acacctgaag gattaagaaa attaggggg   720
aaagagttga agaatctacg aggagatggg actggagtca ggaagttatc agacagaatc   780
tatgactttg atgtctacaa cgatcttgga aatcccgaca agtcatctga actctctcgt   840
```

```
ccgaaactcg gtggcagaga gaggccttac cctagacggt gtcgcactgg tcgccagcca  900
actgataccg ataatgaagc ggagagccga gtggaaaagc cattacctat gtacgtgcca  960
cgagacgagc aatttgaaga gactaagcag gacactttcg ccgcagggag gttaaaagcg 1020
gtgttacacc accttgttcc gtcgcttaaa gctagtattt tagctgatga cttttctgac 1080
ttcggagaga ttgatgatct ctacaaaaaa ggcttgctac tgaagttagg atttcaagat 1140
gagatattca acaagttccc tttgcctaag ggcatcgtta atacccctcca agaatcttcg 1200
aaaggactcc tcaaatacga cactcccaaa atattatcga aggataaaaa cgcatggcta 1260
cgagatgacg agttcgcacg tcaagccata gctggaatca atccagtcaa cattgagaga 1320
gtcaagactt tcccacccgt cagtaatctt gaccccgaaa tctacggtcc acaacactcc 1380
gctctcactt ccgaccacat catcggacat cttgacggct tgtccgttca acaagcgttg 1440
gaagagaaca gattgtatat gttggattac catgacatat tcttaccgtt cctagaccaa 1500
atcaatgcgc tcgatggacg caaagcatat gctactcgaa ccattttctt cttgactcgt 1560
cttggaacac ttaagcccgt agccatcgag ctaagcctcc cttcccatgg cccgaaccac 1620
cgatccaaac gagttgttac acctcctgtc gatgcaacct ctaactgggt gtggcagctc 1680
gctaaagcac atgttagctc caacgatgct ggagtccacc aacttgttaa ccactggtta 1740
cgaacccatg catgcttgga accgtttata atagctgcac ataggcaatt aagcgctatg 1800
catccgatat tcaaactatt ggatccacac atgaggtata cgttggagat caatgcactg 1860
gctagacaat cattgatcag tgcagacggt gtgattgaag gaggcttcac tgctggccaa 1920
tacggtttgg aaatgagctc cgcagcctac aaaagtagtt ggcggttcga catggaaggc 1980
ctccctgccg atctcattcg cagaggaatg gcagttccag acccaacaca accacatgga 2040
cttaaactcc tgatcgaaga ctatccatat gcgaacgacg gtcttctaat atggtccgca 2100
atccaaacat gggtccgaac ttacgtggaa cgttactatc caaactcgaa ctcaattcaa 2160
acagactcgg aactccaatc gtggtactcg gagtcaatca acgtaggcca tgcagatctc 2220
cgcgaagccg agtggtggcc aaagttagac accgtggacg acctagtctc catcctcacc 2280
acactagtct ggctcgcctc cgctcaacac gccgctctca acttcggaca gtatccgtat 2340
ggaggttacg tcccaaaccg aacctccgct atgcgacggt taatccctga cgagtcgaat 2400
ccggagtacg caagttttat ctcggatcct gagaaatttt attttcttc gatgccgagt 2460
ttgttgcaaa cgtcgaagtt tatggcggtg gttgatacgt tgtcaacgca ttctccggat 2520
gaggagtata tcggggagag acaacaaccg tccacttgga ccgagatgc ggagattgtt 2580
gatgcgtttt atggatttgc ggcggagatt ggacggatga aaaagagat tgagaaaaga 2640
aacagtgatc ctaaccgtag aaacaggtgt ggagctggga ttttgcctta cgagttgttg 2700
gttccgagtt ctgagccagg tgttacgtgc agaggtgtac ctaatagtgt atcgatatag 2760

SEQ ID NO: 85            moltype = DNA   length = 2760
FEATURE                  Location/Qualifiers
source                   1..2760
                         mol_type = genomic DNA
                         organism = Brassica napus
SEQUENCE: 85
atggccttag ctaaagagtt aatgggttat ccactgacct ccaaaaggcc attacttgtt   60
tggtcggcgt cgcatttcaa gaagaggaca cagccaacac aattatcgat caagcctttt  120
gatcggagac caagaacgtc caaatccggg gtcgttgcgg ccatcagtga agatttggtc  180
aaaacgctac gtttcaacac aaccaccggt gacagaagga gcgaggagga gagaaaagcg  240
gcggtgaaat tcaaggtgag agctgtggtt acggtgagga acaagaacaa ggaggatttt  300
aaggagactc ttgttaagca tttagatgct tttggtgata gatcggtcg aaacattgtc  360
ttggagcttg ttagcaccga acttgatcca aaaacgaata tgccgaagaa aagcaatgcg  420
gcagttttaa aggactggtc aaagaagtcg aaaaccaagg cggaaaggt tcattacacg  480
gcggagttca cggtggacgc agcatttggc tcaccgggag ccatcaccgt catgaataaa  540
caccagaaag aattctttct agagagcatc accatcgaag gtttcgcagt tggtcctgtt  600
cactttccat gcaattcttg ggttcagtcc caaaaggatc acccagagaa acgaatcttt  660
ttcactaatc agccgttttt gccgactggg acacctggtg gattgaaaaa attgagggag  720
agagagttga gaatctaag aggagatggg agtggagtga ggaagttatc agacagaatc  780
tatgactttg atgtgtacaa cgatcttgga aatcccgaca gtcatcaga actctctcgc  840
cccaagcttg cggcaaaga gattcctac cctagacgat gtcgtaccgg tcgccatcca  900
actgataccg ataaagaagc ggagagccga gtggagaagc cattacctat gtacgtacca  960
cgagatgagc aatttgaaga gactaagcag gacactttcg ctgcagggag gttaaaagcg 1020
gtcttacacc acctagttcc gtctctcaaa gccagcattt tagctgagga cttttgctgac 1080
tttggcgaga tagatggtct ctataaagaa ggattgctac tcaagttagg gtttcaagat 1140
gaaatttta acaagttccc tttgcccaag gccatcgtta atacactcca agaatcttct 1200
aaaggactcc tcaaatacga cactcccaaa atattatcga aggataaaaa tgcatggcta 1260
cgagatgacg agtttgcacg tcaagccata gctggaatca atccagtcaa cattgagagg 1320
gtcaggactt tcccacccgt cagtaatctt gaccccgaaa tctacggtcc acaacactcc 1380
gctctcactt ccgaccacat cattggacat ctcgacggac tatccgtaca acaagcgttg 1440
gaagagaaca ggttgtataa gttggattac catgacaccgg tcttaccgtt cctagaccgg 1500
atcaatgcac tagacggacg caaagcttat gctactcgaa ccatattctt cttgactcgt 1560
ctaggaacac ttaaacccgt agccattgag ctaagcctcc ctcccatgg tccaaccat 1620
cggtccaaac gcgtggttac acctcctgtc gacgcaacct ctaattgggt gtggcagctc 1680
gctaaagccc acgttagctc taacgacgct ggtgtccacc agcttgtcaa tcactggtta 1740
cgaacccatg cgtgcttgga accgtttata ttagctgcac atagacaaat gagcgctatg 1800
catccgatat tcaagctatt ggatccgcac atgaggtaca cgttggaaat caatgcattg 1860
gctagacaat cgttgatcag tgcagacggt gtgattgaag aaggcttcac tgccggctca 1920
tacggcatga gatgagcgc cgccgcatac aagagcagtt ggcggtttga catggaaggc 1980
ctccctgctg atctcattcg gagaggaatg gcagttcctg actcgacaca accacatgga 2040
cttaaactcc taatcgaaga ctatccatac gctaacgacg tcttctact ctggtcggca 2100
atccaaacct gggtccgaac ctacgtgaaa cgctactatc caacccgaa cctaatcaaa 2160
acagactcgg agctccagtc ctggtactcc gaatcaatca acgtcggcca cgctgatctc 2220
cgcgacgccg agtggtggcc aaagctaaac accgtcgacg acctcgcctc catcctcacc 2280
acactaatct ggctcgcctc agctcaacac gcggctctca acttcggaca gtacccgtac 2340
ggcggctacg tccccaaccg tcctccgctg atgcggcggt tgatccccga cgagtctgat 2400
```

```
ccggagtacg cgagtttcat ctccgatccg gagaagtttt acttctcggc gatgccgagt   2460
ttgctgcaga cgtcgaagtt tatgcggtg gttgatactc tgtcaacgca ttcgccggat    2520
gaggagtata tcggggagag acagcaaccg tcgatttgga cgggagatgc ggagatcgtt   2580
gatgcgtttt atggattcgc ggcggagatc ggacggatag agaaggagat tgaggaaagg   2640
aactctgatc ctgaccgtag aaataggtgc ggggctggtg ttttgcctta tgagctgttg   2700
gttccgagtt ccgagcctgg tgttacttgc agaggtgtac ctaatagtgt atcgatatag   2760

SEQ ID NO: 86          moltype = DNA   length = 2760
FEATURE                Location/Qualifiers
source                 1..2760
                       mol_type = genomic DNA
                       organism = Brassica napus
SEQUENCE: 86
atggccttag ttaaagagat aatgggtcat cctctgatat caggaaggcc gtcacttgtt   60
ttctcggctt ctcatttcaa gaagaagaca cagacaacgc aattctcgat caagcctttt   120
gatcggagac caaacacgtc caaatccggc gtcgtttccg ccattagtga agatttagta   180
aaaacgctgc gttttagcac aacaaccgga gacagaaaga gcgaggagga ggagaaagcg   240
gcggtgaaat tcaaagtgag agctgttgtt acagtgggga acaagaacaa gaaggatttt   300
aaggagactc tttttaagca tttgatgct tttggtgaca agatcggtcg gaacatcgtc   360
ttggagctta ttagcaccga acttgatcca aaaacgaatt tgccgaagaa gagcaatgca   420
gcggtgttaa aggattggtc agagaaatcg aaaccaagg cggagagggt tcattacacg    480
gcggagttca cagtcgacgc agcgtttggc acgccgggag ccatcaccat catgaataaa   540
caccagaaag agttttttct agagtgcata accatcgaag gtttcgcact ggccctgtt    600
cactttccat gcaactcttg ggttcagtcc caaaatgatc ccctgagaa cgaatcttc     660
ttcactaatc agccgttttt gccgagtgag acacctgaag gattaagaaa actaagggga   720
aaagagttga agaatctaag ggagatgtgg actggagtca ggaagttatc agacagaatc   780
tatgactttg atgtctacaa cgatcttgga aatcccgaca agtcatatga actctctcgt   840
ccgaagctcg gtggcagaga gaggccttac cctagacggt gtcgcactgg tcgccagcca   900
actgataccg ataatgaagc ggagagccga gtggaaaagc cattacctat gtacgtgcca   960
cgagacgagc aatttgaaga gactaagcag gatactttcg ccgcagggag gttaaaagcg   1020
gtgttacacc accttgttcc gtcgcttaaa gctagtattt tagctgatga cttttctgac   1080
tttggagaga ttgatgatct ctacaaagaa ggcttgctac tcaagttagg gtttcaagat   1140
gagatcttta acaagttccc tttgcctaag ggcatcgtta taccctcca agaatcttcg    1200
aaaggactcc tcaaatacga cactccgaaa atattatcga aggataaaaa cgcatggcta   1260
cgagatgacg agttcgcacg tcaagccata gctggaatca atccagtcaa cattgagaga   1320
gtcaagactt tccacccgt cagtaatctt gaccccgaaa tctacggtcc acaacactcc    1380
gctctcactt ccgaccacat catcggacat cttgacggct tgtccgttca acaagcgctg   1440
gaagagaaca gattgtttat gttggattac acgactacat tcttaccgtt cctggaccgg   1500
atcaatgcgc tcgacggacg caaagcatat gctactcgaa ccatattctt cttgactcgt   1560
ctcggaacac ttaagcccgt agccatcgag ctgagcctcc cttcccatgg cccgaaccac   1620
cgatccaaac gagttgttac acctcctgtc gatgcaacct ctaactgggt gtggcagctc   1680
gctaaagcac atgttagctc taacgatgct ggagtccacc aacttgtcaa ccactggtta   1740
cgaacacatg catgcttgga accgtttata atagctgcaat aaggcaatt aagcgctatg   1800
catccgatat ttaaactatt ggatccacac atgaggtaca cgttggagat caatgcactg   1860
gctagacaat cattgatcag tgcagacggt gtgattgaag aggtttcac tgctggccaa   1920
tacggtttgg aaatgagctc cgcagcatac aaaagtagtt ggcggttcga tatggaaggc   1980
ctcctgccg atctccattcg cagaggaatg gcagttccac acccaacaca accacatgga   2040
cttaaactcc tgatcgaaga ctatccatat gcgaacgacg tcttttaat atggtccgca    2100
atccaaacat gggtccgaac ttacgtgaaa cgttactatc caaactgaa ctcaatccag    2160
acagactcgg aactccaatc atggtactcc gagtcaatca acgtaggcca tgcagatcta   2220
cgcgaagccg agtggtggcc aaagttagac accgtggacg acctagtctc catcctcacg   2280
acactagtct ggctcgcctc cgctcaacac gccgctctca acttcggaca gtatccgtat   2340
ggaggttacg tcccaaaccg acctccgctg atgcgacggt taatccctga cgagtcggat   2400
ccggagtacg caagttttat ctcggatcca gagaaatttt attttccgtc catgccgagt   2460
ttgttcaaa cgtcgaagtt tatgcggtg gtttgatact tgtcaacgca ttcgcctgat     2520
gaggagtata taggggagag acaacaaccg tccacttgga ccggagatgc ggagattgtt   2580
gatgcgtttt atggatttgc ggcggagatt ggacggattg aaaaagagat tgagaaaaga   2640
aacagtgatc ctagccgtag aaacaggtgt ggagctggag ttttgcctta cgagttgttg   2700
gttcctagtt ctgagccagg tgttacgtgc agaggtgtac ctaatagtgt atcgatatag   2760

SEQ ID NO: 87          moltype = DNA   length = 2094
FEATURE                Location/Qualifiers
source                 1..2094
                       mol_type = genomic DNA
                       organism = Zea mays
SEQUENCE: 87
atgccggcgg cgctgaagcc gtaccgcgac gacgagctcc gcaacctccg cggcgacgac   60
cagcagggcc cctaccagga gcacgaccgc gtgtaccgct acgacgtcta caacgacctc   120
ggcgagcgga acgcgcggaa cccgcgcccc atcctccgg gctccgcgca ccacccgtac     180
ccgcgccgct gccgcacggg ccgcaagccc accaaaaccg accccaactc ggagagccga   240
ctgtcgctgg tggagcagat ctacgtgccg cggacgagc gcttcggcca cctcaagatg   300
tccgacttcc tgggctactc catcaaggcc atcacgcagg catcatccc ggcggtcgcg    360
acgtacgtgg acaccacccc gggcgagttc gactccttcc aggacatcat caacctgtac   420
gagggcggga tcaagctgcc caagatccag cgctcgcaag acatcgcaa gctcttccgg   480
ctccagctcg tcaaggacct cctccccgcc ggcggggact acctgctcaa gctcccatc    540
ccacagatca tccaagagga caagaacgcg tggaggaccg acgaggagtt cgcgcgggag   600
gtgctcgccg gcgtcaaccc gatggtgatc acgcgcctca cggagttccc gcccaagagc   660
acgctggacc ccagcaagta cggcgaccac accagcacga tcacgcggga gcacatcgag   720
aagaacctcg agggcctcac ggtgcagcag gcgctggacg gcaacaggct ctacatcctg   780
```

```
gaccaccacg accgcttcat gccgttcctc atcgacgtca acaacctgga gggcaacttc   840
atctacgcca ccaggacgct cttcttcctg cgcggcgacg gcaggctcgc gcccctcgcc   900
atcgagctca gcgagccgta catcgacggg gacctcaccg tggccaagag caaggtctac   960
acgccggcgt ccagcggcgt cgaggcctgg gtgtggcagc tcgccaaggc ctatgtcgcc  1020
gtcaacgact ctggctggca ccaactcgtc agccactggc tgaacaccca cgcggtgatg  1080
gagccgttcg tgatcgcgac gaaccggcag ctgagcgtga cgcacccggt gcacaagctc  1140
ctgagctcgc acttccgcga caccatgacc atcaacgcgc tggcgcggca gacgctcatc  1200
aacggcggcg gcatcttcga gatgaccgtc ttccccggga gtacgcgct gggcatgtcc   1260
tccgtggtgt acaagagctg gaacttcacc gagcagggcc tccccgccga cctcgtcaag  1320
aggggcgtgg cggtggcgga cccgtccagc ccgtacaagg tgcggctgct gatcgaggac  1380
tacccgtacg cgagcgacgg gctggccatc tggcacgcca tcgagcagtg ggtgggcgag  1440
tacctggcca tctactaccc cgacgacggc gcgctgcggg cgacgaggac gctgcaggcg  1500
tggtggaagg aggtgcgcga ggtcgggcac ggcgaccaca aggacgcgcc ctggtggccc  1560
aagatgcaag ccgtgtcgga gctcgccagc gcctgcacca ccatcatctg gatcgcgtcg  1620
gcgctccacg ccgccgtcaa cttcggccag taccgtacg cggggtacct cccgaacagg    1680
cccacggtga gccggcgccg gatgccgag cccggcagca aggagtacga ggagctggag    1740
cgcgacccgg agcgcggctt catccacacc atcacgagcc agatccagac catcatcggc  1800
atctcgctca tcgagatcct ctccaagcac tcctccgacg aggtgtacct cggccagcgc  1860
gacacccccg agtggacctc cgacgcccgg gcgctggcgg cgttcaagag gttcagcgac  1920
gcgctggtca agatcgaggg caaggtggtg ggcgagaacc gcgacccgca gctgaggaac  1980
aggaacggcc ccgccgagtt ccctacatg ctgctctatc ccaacacctc tgaccacagt    2040
ggcgccgccg cagggctcac tgccaagggc atccccaaca gcatctccat ctga          2094

SEQ ID NO: 88        moltype = DNA   length = 2795
FEATURE              Location/Qualifiers
source               1..2795
                     mol_type = genomic DNA
                     organism = Zea mays
SEQUENCE: 88
catgccacgc tgatctttct gtcttttggt gccgcccga ttccgaacgg cggcgcagac     60
gtacctgcca agccagatgc cggcggcgct gaagccgtac cgcgacgacg agctccgcaa   120
cctccgcggc gacgaccagc agggccccta ccaggagcac gaccgcgtgt accgctacga   180
cgtctacaac gacctcggcg agcccacgg cggcaacccg cgcccatcc tcggcggctc     240
cgccgaccac ccgtacccgc gccgctgccg cacgggccgc aagcccacca aaccggtgc    300
gtgccgcgtg cgcggctctt ctatcttctc ggacgcaaca tttgctgcag ggcagagagg   360
ttgttgacgc tgacctgtga ccgcatcgca gaccccaact cggagagccg actgtcgctg   420
gtggagcaga tctacgtgcc gcgggacgag cgcttcggcc acctcaagat gtccgacttc   480
ctgggctact ccatcaaggc catcacgcag gcatcatcc cggcggtgcg cacgtacgtg    540
gacaccaccc cgggcgagtt cgactccttc caggacatca tcaaccctgta cgagggcgtg   600
atcaagctgc ccaagatcca ggcgctcgag gacatgcgca agctcttccc gctccagctc   660
gtcaaggacc tcctccccgc cggcggggac tacctgctca agctcccat cccacagatc    720
atccaaggca cgtcacgtat accgatcgat gtcaggggc ggctgttgtc tggtctgcat    780
atatatatgt gctcctatgg ttaactgtga ctgcgtacgt ttgcggaac agaggacaag    840
aacgcgtgga ggaccgacga ggagttcgcg cgggaggtgc tcgccggcgt caacccgatg   900
gtgatcacgc gcctcacggt gagtcactca ctttgtgcaa aatgcgagac ccgacccgag   960
acggaatgtg cctgacgcgc tcgatttaca ggagttcccg cccaagagca cgctggaccc  1020
cagcaagtac ggcgaccaca ccagcacgat cacggcgaca cacatcgaga agaacctcga  1080
gggcctcacg gtgcagcagg cgctggacgg caacaggctc tacatcctgg accaccacga  1140
ccgcttcatg ccgttcctca tcgacgtcaa caacctggag ggcaacttca tctacgccac  1200
caggacgctc ttcttcctgc gcggcgacgg caggctcgcg cccctcgcca tcgagctcag  1260
cgagccgtac atcgacgggg acctcaccgt ggccaagagc aaggtctaca cgccggcgtc  1320
cagcggcgtc gaggcctggg tgtggcagct cgccaaggcc tatgtcgccg tcaacgactc  1380
tggctggcac caactcgtca gccactggta cgtacgaaga actacaacta ctcctatata  1440
tgtcctatat gacaatggca tcgcatcgtg tcatgtctat gacatcgcca aatgcatgcg  1500
ttgatggtca tgatctattc tctgcgtgcg tacaggctga acaccacgc ggtgatggag    1560
ccgttcgtga tcgcgacgaa ccggcagctg agcgtgacgc acccggtgca caagctcctg  1620
agctcgcact tccgcgacac catgaccatc aacgcgctgg cgcggcagac gctcatcaac  1680
ggcggcggca tcttcgagat gaccgtcttc ccgggcaagt acgcgctggg catgtcctcc  1740
gtggtgtaca agagctggaa cttcaccgag cagggcctcc ccgccgacct cgtcaagagg  1800
ggcgtggcgg tggcggaccc gtccagcccg tacaaggtgc ggctgctgat cgaggactac  1860
ccgtacgcga gcgacgggct ggccatctgg cacgccatcg agcagtgggt gggcgagtac  1920
ctggccatct actaccccga cgacggcgcg ctgcggggcg acgaggagct gcaggcgtgg  1980
tggaaggagg tgcgcgaggt cgggcacggc gaccacaagg acgcgcctg gtggcccaag    2040
atgcaggccg tgtcggagct cgccagcgcc tgcaccacca tcatctggat cgcgtcggcg  2100
ctccacgccg ccgtcaactt cggccagtac ccgtacgcgg ggtacctccc gaacaggccc  2160
acggtgagcc ggcgccggat gccggagccc ggcagcaagg agtacgagga gctggagcgc  2220
gacccggagc gcggcttcat ccacaccatc acgagccaga tccagaccat catcggcatc  2280
tcgctcatcg agatcctctc caagcactcc tccgacgagg tgtacctcgg ccagcgcgac  2340
acccccgagt ggacctccga cgcccgggcg ctggcggcgt tcaagaggtt cagcgacgcg  2400
ctggtcaaga tcgagggcaa ggtggtgggc gagaaccgcg acccgcagct gaggaacagg  2460
aacggccccg ccgagttccc ctacatgctg ctctatccca acacctctga ccacagtggc  2520
gccgccgcag ggctcactgc caagggcatc cccaacagca tctccatctg agcgactggt  2580
accactacca ccccaggagt gctacgtacg agctggtaca tgaataagct aatataagca  2640
atcgtgtaaa cgggaagaga gcggccggca cgagacggca catgtatttt gcgtaaacgt  2700
gtgggctggt gaatcgaatt actaccacgt aataagtgaa gtgcttgttg caatcattgg  2760
cctgccagct tcaagattct tgcagttact attct                              2795

SEQ ID NO: 89        moltype = AA   length = 697
FEATURE              Location/Qualifiers
```

```
source              1..697
                    mol_type = protein
                    organism = Zea mays
SEQUENCE: 89
MPAALKPYRD DELRNLRGDD QQGPYQEHDR VYRYDVYNDL GEPDGGNPRP ILGGSADHPY   60
PRRCRTGRKP TKTDPNSESR LSLVEQIYVP RDERFGHLKM SDFLGYSIKA ITQGIIPAVR  120
TYVDTTPGEF DSFQDIINLY EGGIKLPKIQ ALEDMRKLFP LQLVKDLLPA GGDYLLKLPI  180
PQIIQEDKNA WRTDEEFARE VLAGVNPMVI TRLTEFPPKS TLDPSKYGDH TSTITAEHIE  240
KNLEGLTVQQ ALDGNRLYIL DHHDRFMPFL IDVNNLEGNF IYATRTLFFL RGDGRLAPLA  300
IELSEPYIDG DLTVAKSKVY TPASSGVEAW VWQLAKAYVA VNDSGWHQLV SHWLNTHAVM  360
EPFVIATNRQ LSVTHPVHKL LSSHFRDTMT INALARQTLI NGGGIFEMTV FPGKYALGMS  420
SVVYKSWNFT EQGLPADLVK RGVAVADPSS PYKVRLLIED YPYASDGLAI WHAIEQWVGE  480
YLAIYYPDDG ALRGDEELQA WWKEVREVGH GDHKDAPWWP KMQAVSELAS ACTTIIWIAS  540
ALHAAVNFGQ YPYAGYLPNR PTVSRRRMPE PGSKEYEELE RDPERGFIHT ITSQIQTIIG  600
ISLIEILSKH SSDEVYLGQR DTPEWTSDAR ALAAFKRFSD ALVKIEGKVV GENRDPQLRN  660
RNGPAEFPYM LLYPNTSDHS GAAAGLTAKG IPNSISI                           697
```

LOX3 GENE MODULATION AND ARMYWORM TOLERANCE

CROSS-REFERENCE TO RELATED APPLICATIONS

This application claims the benefit of, and priority to, European Patent Application No. 22153142.9, filed Jan. 25, 2022 and U.S. Provisional Application No. 63/299,628, filed on Jan. 14, 2022. These applications are herein incorporated by reference in their entirety.

SEQUENCE LISTING

The instant application contains a Sequence Listing which has been submitted in XML format via Patent Center and is hereby incorporated by reference in its entirety. Said XML copy, created on Dec. 21, 2022, is named 245761000200.xml, and is 274,027 bytes in size.

TECHNICAL FIELD

The present application provides a new technology to confer or enhance insect resistance and, optionally also resistance to fungal pathogens in plants. In particular, the present invention provides a method for conferring or increasing resistance or tolerance to insect and optionally also to fungal pathogens in maize and oil seed rape (OSR) by targeting the endogenous Lox3 gene. By introducing either a gene silencing construct, a genome editing system or a genome modification, which leads to a targeted knock-down or knock-out of the Lox3 gene endogenous to the plant, a new or increased resistance to insect and, optionally fungal pathogens can be created. Further provided are resistant or tolerant maize or oil seed rape plants, cells, tissues, organs, or seeds, which are obtained or obtainable by the method according to the present invention. Expression constructs and vectors for the different approaches described herein are also provided as well as the use of such constructs and methods to confer or increase insect and optionally fungal resistance in plants.

BACKGROUND

In nature, there is a large variety of organisms causing disease in plants and/or negatively affecting plant health otherwise. These pathogens can be subdivided into (i) infectious organisms, which include fungi, oomycetes, bacteria, viruses, viroids, virus-like organisms, phytoplasmas, protozoa, nematodes, and parasitic plants and (ii) ectoparasites, such as insects, mites, vertebrates, and other pests negatively affecting plant health by eating plant tissue.

Monitoring and securing plant health in both natural and cultivated plant populations are paramount tasks for a reliable supply of food products and a large number of commodities on a global scale. Taken together, pests and diseases in plants cause up to 40% yield losses every year. Accordingly, there are numerous examples throughout history demonstrating the severe effects of plant disease on society.

For instance, the Great Famine of Ireland from 1845 to 1852 with a total number of deaths of approximately 1 million and the Highland potato famine from 1846 to 1856. The proximate cause of these famines was potato blight, a serious potato and tomato disease caused by the oomycete *Phytophthora infestans*.

From 2010 to 2011, 750,000 hectares of trees in the western Unites States were lost to an infestation by the mountain pine beetle. This infestation was (at least in part) driven by droughts as insects generally thrive in a warmer climate. Droughts also make plant tissue even more nutritious for insects since the lack of water concentrates the contained amino acids. Accordingly, the threat of insects on agricultural crops increases as global warming proceeds.

Insects are among the most relevant organisms attacking and causing damage to agricultural and horticultural crops. The damage they cause is two-fold, namely (i) the direct injuries they cause to a plant for instance by eating plant tissue, and (ii) the indirect injuries caused by fungal, bacterial, or viral infections they transmit. Currently, a global average of 15% of crops is exclusively lost to insects. At the same time, crop yields need to be increased by at least 40% in order to be able to reliably feed a population of approximately 9 billion people projected to inhabit the Earth in 2050.

Within the class of insects, a particularly relevant species causing harm to plants is the fall armyworm (*Spodoptera frugiperda*) within in the order Lepidoptera, which is the larval life stage of a fall armyworm moth. It shows large-scale invasive behaviour and it is regarded as a pest that can damage and even destroy a wide variety of crops causing large economic damage. It is one of the most damaging pests in corn (*Zea mays*). Geographically, the fall armyworm is distributed in eastern and central North America and in South America. Due to its susceptibility to colder temperatures, it can only survive the winter in the southern-most regions of the United States, namely Texas and Florida. However, seasonally it will spread across the eastern United States and up to southern Canada. A CLIMEX model of its potential global distribution indicated much of the potential distribution range in Europe, South Africa, China, and Australia. In recent years, the fall armyworm has already been found in at least 28 African countries (e.g., in Ghana, Togo, Benin, Nigeria, and Sao Tome), in Asia (e.g., in the Chinese province of Yunnan and at least 25 other Chinese provinces, in India, in Sri Lanka, and in Bangladesh), and across the Australian continent (e.g., in Western Australia, Queensland, the Northern Territory, New South Wales, North Queensland, and the Torres Strait Islands).

The fall armyworm's global distribution bears the potential for further severe economic damage. For example, it caused significant damage to maize crops in Africa in 2016. Moreover, heavy infestation of fall armyworm was reported for plantations in Sri Lanka and has reached China's north-eastern corn belt in 2020 and China's Ministry of Agriculture and Rural Affairs has rated the situation as 'very grave'. The fall armyworm is also expected to severely impact Australia's wool industry as it feeds on all major grazing plants.

Another extremely relevant species causing major damage to plants is the corn leafhopper (*Dalbulus maidis*) within the order Hemiptera. This species is widely spread through most tropical and subtropical regions on earth including Southeast Asia and China, Australia, Africa, and both North and South America. The corn leafhopper is predominantly a pest of maize and its relatives with high economic importance. In addition to the direct damage caused by its herbivorous lifestyle, it also functions as a vector for several species-specific maize viruses, such as maize stripe virus (MSV), maize mosaic virus (MMV), and maize tenuivirus (MStV). The latter two are pathogenic viruses, which might reduce crop yields by 9 to 90%. It has even been suggested that the spreading of *Dalbulus maidis* together with MMV and MStV to the New.

World contributed to the collapse of the Mayan civilization. Infestation with *Dalbulus maidis* will lead to physical damage the plant as the insect breaks through the vascular tissue of the plant in order to feed on the exuding sap. Eventually, this damage will cause yellowing of leaves, wilting, stem weakness, and finally death. The feeding behaviour alone of *Dalbulus maidis* might cause 10 to 15% crop loss.

Another exemplary insect species of major importance for plant damage is the globally distributed green peach aphid (*Myzus persicae*), which is the most significant aphid pest of peach trees and is known to attack more than 240 plant species from 64 different families. As a result of an infestation by the green peach aphid, peach trees exhibit decreased growth, shriveling of the leaves and death of various tissues. Prolonged infestation can lead to a drastic decrease in yield of various root and foliage crops. Furthermore, the green peach aphid can be a serious pest problem for oil seed rape crop. For example, a drastic infestation of oil seed rape by the green peach aphid in the southeast of Romania was reported in autumn 2018. In this instance, a high pest density of 243 aphids per oil seed rape leaf was reported. Moreover, the green peach aphid acts as a vector for plant viruses, such as pepper potyviruses, potato virus Y (PVY), tobacco etch virus (TEV), and cucumber mosaic virus (CMV), which can be passed on to many different food crops.

The green belly stink bug (*Dichelops melacanthus*) is a key pest in corn and wheat, two of the most important crop plants on a global scale. It is distributed in nearly all of South America and attacks at least 29 plant species. Besides corn and wheat, other affected crops of major economic importance include soybean, oats, and triticale. In the early life stages of plants, the damage caused by *Dichelops melacanthus* can be particularly severe as the insect physically damages the vascular tissue in order to feed on sap and thereby possibly introduces salivary toxic enzymes into the stem base of the plants. Eventually, this leads to withering of leaves, wilting, and finally to death of the plant.

Fungi and fungi-like organisms constitute the largest number of plant pathogens and are responsible for a wide range of plant diseases, which have been reported to lead up to 100% crop loss. For instance, most vegetable diseases are due to fungal infections. Causes for fungal infections include spreading through water and wind and through contaminated soils, animals, seedlings, and other plant materials. Fungi enter plants through naturally occurring openings, such as stomata and wounds caused by e.g., pruning, harvesting, insects, hail, and other causes for mechanical damage.

*Leptosphaeria maculans* (anamorph: *Phoma lingam*) is a globally distributed fungal pathogen of the phylum Ascomycota, which is the causal agent of *phoma* stem canker or blackleg disease in *Brassica* crops. The fungus can directly penetrate plant roots. Symptoms of blackleg disease include basal stem cankers, small grey lesions on leaves, and root rot. Basal stem cankers are the main cause for drastic crop yield losses. *Leptosphaeria maculans* infects a variety of different *Brassica* species including oilseed rape (*Brassica napus*) and cabbage (*Brassica oleracea*). It is especially virulent in oilseed rape. Infections can lead to decrease in crop yields by about 10 to 20%. The release of ascospores by *Leptosphaeria maculans* typically occurs from September to November at moderate temperatures between 8° C. and 15° C. and a relatively high humidity. During this time, agricultural oilseed rape is the most vulnerable.

Another economically relevant fungal plant pathogen is the soil-borne Plasmodiophora *brassicae*, which belongs to the group Phytomyxea and causes clubroot in a large number of plants from the family Brassicaceae. Symptoms of clubroot include gall formation and distortion on latent roots giving rise to the shape of a club or spindle. In cabbages, these effects on the roots lead to underdeveloped heads or even an overall failure to head at all, which is often followed by decline in vigor and death of the plant. Other symptoms include wilting, yellowing and stunted growth. In the late 19th century, severe epidemics of clubroot lead to the loss of major parts of cabbage crops in St. Petersburg. Presently, clubroot is still a disease of great economic relevance affecting approximately 10% of cultured areas. Clubroot infections can affect entire fields and thus significantly reduce crop yields and even result in no crop yield at all. On the field, the pathogen can survive for years as resting spores.

Hence, there is an urgent and rapidly growing demand for efficient strategies to minimize and confine the economic damage caused by plant pathogens.

The most commonly used form of protection against insects is different insecticides. In southern regions, insecticides have to be applied every day to corn in order to be able to manage fall armyworm infestation. In 2020, a biopesticide—namely a caterpillar-specific virus—was approved under emergency regulations in Australia in order to control the fall armyworm. Different Parasitoids (e.g., the wasp *Trichogramma pretiosum*) are also used. The use of insecticides has many disadvantages. For instance, many insecticides non-selectively harm or even kill other species in addition to the targeted ones. A prominent example of this phenomenon is the observed decline of pollinators, such as bees due to colony collapse disorder (CCD). Even sub-lethal amounts of insecticides can affect bee foraging behaviour. The loss of pollinators results in a reduction of crop yields. Besides that, birds may be killed when consuming plants or insects that were in contact with insecticides. Populations of insectivorous birds also decline due to the collapse of their prey populations. Especially the spraying of insecticides on corn and wheat in Europe is believed to have caused a decline in flying insects of about 80%, which in turn has reduced the European bird population by one to two thirds. Runoff and percolation of (improperly applied) insecticides can negatively affect the quality of water sources and harm the natural ecology, which has an indirect effect on human populations through biomagnification and bioaccumulation.

Alternatively, in order to manage insect infestation different agricultural techniques, such as e.g., planting early, avoiding staggered planting, and inter-cropping are applied. These strategies are extremely cost- and time-intensive, cannot universally be applied due to ecological limitations and thus bear several risks. For example, inter-cropping has successfully been applied against fall army worm infestations in small-scale greenhouse, garden and field experiments. However, at larger commercial scales the pest damage to only a very small portion of crop plants could be reduced using this method.

Fungal plant diseases may be controlled employing fungicides and various other agricultural techniques. Typically applied fungicides include EBI and MBC fungicides, which can decrease instances of disease in crop populations. However, the use of fungicides bears similar disadvantages as described above for insecticides. Additionally, some fungicides also negatively affect the overall growth of the crop plants. Cultural methods include stubble and crop rotation. Removing stubble has been shown to decrease the risk of *Leptosphaeria maculans* infection in *Brassica* species. In canola crops, crop rotation has been shown to reduce blackleg.

Based on the difficulties and disadvantages of agricultural and chemical methods for reducing infestations and infections, considerable effort is put into genetically engineering and optimizing the crop plants themselves in order to make them more tolerant towards environmental conditions and pests.

In case of maize and other crop plants, the lipoxygenase (Lox) pathway is known to play a role regarding resistance to pathogens. However, previous studies show that the actual function of the Lox pathway with respect to resistance towards certain pathogens is highly unpredictable due to an extremely high degree of host- and pathogen specificity to the extent that within the same host species, Lox-derived metabolism can even have completely opposite effects on pathogen resistance in a pathogen species-specific manner.

In the Lox pathway, various highly specialized forms of lipoxygenases catalyse the synthesis of hydroperoxy polyunsaturated fatty acids, which are substrates to at least seven different enzyme families. For example, plant oxylipins produced via the Lox pathway have been demonstrated to function as environmentally and developmentally regulated defence- and development signals. It has also been demonstrated that these molecules function as powerful regulators of sporogenesis and mycotoxin biosynthesis in fungi. Specifically, it could be demonstrated that fatty acid hydroperoxides derived from 9-Lox induce condition and mycotoxin production.

In 2007, Gao et al. (MPMI, vol. 20, No. 8, 2007, pp. 922-933) generated maize mutants lacking functional 9-Lox by disruption of ZmLox3 (gene coding for 9-Lox) via transposon mutagenesis. Accordingly, decreased levels of 9-Lox-derived hydroperoxides were observed. Consequently, in kernels of the lox3 mutants reduced condition and reduced production of mycotoxin fumonisin B1 by *Fusarium verticillioides* were observed as compared to the wild type. Additionally, lox3 mutants demonstrated reduced disease severity of various fungi-derived diseases, such as anthracnose leaf blight (*Colletotrichum graminicola*), southern leaf blight (*Cochliobolus heterostrophus*), and stalk rots (*Fusarium verticillioides* and *Colletotrichum graminicola*). They conclude from these findings that 9-LOX-based metabolism apparently is required for fungal pathogenesis, including disease development and production of spores and mycotoxins.

However, in 2008, Gao et al. (MPMI, vol. 21, No. 1, 2008, pp. 98-109) demonstrated that lox3-4 knockout mutants of maize displayed increased attractiveness to root-knot nematodes (*Meloidogyne incognita*). They observed that in these lox3-4 knockout mutants a phenylalanine ammonia lyase (PAL) gene was not inducible in a root-knot nematode-dependent manner. This suggests a PAL-mediated metabolism to be of importance for root-knot nematode resistance. Moreover, in lox3-4 knockout mutants a root-specific increase in jasmonic acid, ethylene, and salicylic acid and overexpression of the respective biosynthetic genes was observed. Therefore, the ZmLox3-mediated metabolic pathway apparently is required for the three major defence signalling pathways for the resistance against nematodes.

Therefore, there is a great need in defining new molecular mechanisms to increase tolerance or resistance of major crop plants towards their cognate and specific pathogens, by specifically studying and controlling endogenous signalling pathways to optimize plant defence against pathogens and thus yields. By defining new ways to influence and control Lox3-pathways in different crop plants in response to some specific insect and fungal pathogens triggering a specific response in the respective target plant, these objects could be achieved by the methods as presented and disclosed below.

SUMMARY OF THE INVENTION

In a first aspect, the present invention relates to a method for conferring or increasing resistance or tolerance to an insect and, optionally a fungal pathogen to/in a plant comprising the steps of:

(i) providing at least one plant cell;
(ii) introducing into the at least one plant cell at least one gene silencing construct, at least one genome editing system or a genome modification, which leads to a targeted knock-down or a knock-out of a Lox3 gene endogenous to the plant;
(iii) obtaining at least one modified plant cell having reduced or abolished expression of the Lox3 gene; and
(iv) obtaining at least one plant cell, tissue, organ, plant, or seed having reduced or abolished expression of the Lox3 gene, optionally after an additional step of regenerating the plant tissue, organ, plant or seed from the at least one modified cell.

In one embodiment of the method described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum, Diplodia* species, *Cercospora zeina* and *Cercospora zeae-maydis* to/in maize (*Zea mays*).

In another embodiment of the method described above, the method is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*).

In one embodiment of the method described above, the Lox3 gene is represented by a nucleic acid sequence of SEQ ID NO: 6, 7, 9, 10, 12, 13, 15, 16, 87 or 88 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 6, 7, 9, 10, 12, 13, 15, 16, 87 or 88.

In another embodiment of the method described above, the Lox3 gene encodes an amino acid sequence of SEQ ID NO: 8, 11, 14, 17 or 89 or an amino acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 8, 11, 14, 17 or 89.

In a further embodiment of the method described above, the Lox3 gene is represented by a nucleic acid sequence of SEQ ID NO: 75, 76, 77, 78, 83, 84, 85 or 86 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 75, 76, 77, 78, 83, 84, 85 or 86.

In yet another embodiment of the method described above, the Lox3 gene encodes an amino acid sequence of SEQ ID NO: 79, 80, 81 or 82 or an amino acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 79, 80, 81 or 82.

In an embodiment of the method described above, in step (ii) a construct is introduced into the at least one plant cell, which targets the Lox3 gene for gene silencing.

In one embodiment of the method described above, the construct is or the construct encodes an RNAi construct comprising a sense and an antisense sequence targeting the Lox3 gene, the RNAi construct forming an RNA hairpin upon transcription.

In one embodiment of the method described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

In another embodiment of the method described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

In yet another embodiment of the method described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98% or at least 99% to the sequence of SEQ ID NO: 3.

In a further embodiment of the method described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

In yet a further embodiment of the method described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and a vector is introduced into the plant cell, which vector comprises or consists of a nucleic acid sequence of SEQ ID NO: 5, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5.

In one embodiment of the method described above, the construct is introduced into the at least one plant cell by transformation or transfection mediated by biolistic bombardment, *Agrobacterium*-mediated transformation, micro- or nanoparticle delivery, chemical transfection, or a combination thereof.

In a further embodiment of the method described above, in step (ii) at least one genome editing system is introduced into the at least one cell, which targets the Lox3 gene, wherein the at least one genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same.

In one embodiment of the method described above, the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or the at least one genome editing system, is selected from a zinc finger nuclease system, or a transcription activator-like nuclease system, or a meganuclease system, or any combination, variant, or an active fragment thereof.

In another embodiment of the method described above, the at least one genome editing system is introduced into the at least one cell by transformation or transfection mediated by biolistic bombardment, *Agrobacterium*-mediated transformation, micro- or nanoparticle delivery, chemical transfection, or a combination thereof.

In yet another embodiment of the method described above, the method is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*), and the at least one genome editing system comprises a crRNA encoded by a nucleic acid sequence of any of SEQ ID NOS: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NOs: 46 to 49.

In one embodiment of the method described above, the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

In another embodiment of the method described above, in step (ii) a mutagenesis is performed on a single or on a plurality of cell(s) by applying chemicals or radiation.

In one embodiment of the method described above, an alkylating agent, in particular ethyl methanesulfonate is applied to the single or the plurality of cell(s) to induce mutagenesis.

In another embodiment of the method described above, one or more mutations in the Lox3 gene are inserted and identified by TILLING in step (ii).

In a further embodiment of the method described above, one or more cell(s) with knock-down or knock-out mutations in the Lox3 gene are selected in step (ii).

In another aspect, the present invention relates to a maize cell, maize tissue, maize organ, maize plant or maize seed obtained or obtainable by a method according to any of the embodiments described above.

In a further aspect the present invention relates to an oilseed rape cell, oilseed rape tissue, oilseed rape organ, oilseed rape plant or oilseed rape seed obtained or obtainable by a method according to any of the embodiments described above.

In yet a further aspect, the present invention relates to an expression construct, which targets the Lox3 gene in maize for gene silencing, wherein the construct encodes an RNAi construct comprising a sense and an antisense sequence targeting the Lox3 gene endogenous to a maize plant, which RNAi construct forms an RNA hairpin upon transcription.

In a further aspect, the present invention relates to an expression construct, which targets the Lox3 gene in oilseed rape for gene silencing, wherein the construct encodes an RNAi construct comprising a sense and an antisense sequence targeting the Lox3 gene endogenous to an oilseed rape plant, which RNAi construct forms an RNA hairpin upon transcription.

In one embodiment of the expression construct described above, the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

In another embodiment of the expression construct described above, the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

In yet another embodiment of the expression construct described above, the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98% or at least 99% to the sequence of SEQ ID NO: 3.

In one embodiment of the expression construct described above, the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

In another aspect, the present invention relates to a vector comprising or consisting of a nucleic acid sequence of SEQ ID NO: 5 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5.

In yet another aspect, the present invention relates to an RNAi hairpin construct conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*), wherein the RNAi hairpin construct comprises a nucleic acid sequence of SEQ ID NO: 4, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

In a further aspect, the present invention relates to an expression construct encoding a genome editing system, which targets the Lox3 gene in maize, wherein the genome editing system comprises
   (a) at least one site-specific nuclease or site-specific nickase, and optionally, in case a CRISPR system is used, at least one guide molecule or a sequence encoding the same, and (b) optionally, at least one repair template, or a sequence encoding the same.

In another aspect the present invention relates to an expression construct encoding a genome editing system, which targets the Lox3 gene in oilseed rape, wherein the genome editing system comprises (a) at least one site-specific nuclease or site-specific nickase, and optionally, in case a CRISPR system is used, at least one guide molecule or a sequence encoding the same, and
(b) optionally, at least one repair template, or a sequence encoding the same.

In one embodiment of the expression construct described above, the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or the at least one genome editing system is selected from a zinc finger nuclease system, or a transcription activator-like nuclease system, or a meganuclease system, or any combination, variant, or an active fragment thereof.

In another embodiment of the expression construct described above, the expression construct comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NO: 46 to 49.

In a further embodiment of the expression construct described above, the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

In another aspect, the present invention relates to a vector encoding an expression construct according to any of the embodiments described above.

In further aspect, the present invention relates to a maize cell, maize tissue, maize organ, maize plant or maize seed comprising an expression construct or a vector according to any of the embodiments described above.

In yet a further aspect, the present invention relates to an oilseed rape cell, oilseed rape tissue, oilseed rape organ, oilseed rape plant or oilseed rape seed comprising an expression construct or a vector according to any of the embodiments described above.

In one aspect the present invention relates to the use of at least one gene silencing construct, at least one genome editing system or a genome modification, which leads to a targeted knock-down or a knock-out of the endogenous a Lox3 gene, for conferring or increasing resistance or tolerance to one or more insect(s) and, optionally one or more fungal pathogen(s) to a plant.

In one aspect the present invention relates to the use of at least one gene silencing construct, at least one genome editing system or a genome modification, which leads to a targeted knock-down or a knock-out of the endogenous a Lox3 gene, for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In another aspect the present invention relates to the use of at least one gene silencing construct, at least one genome editing system or a genome modification, which leads to a targeted knock-down or a knock-out of the endogenous a Lox3 gene, for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and *Plasmodiophora brassicae* to/in oilseed rape (*Brassica napus*).

In a further aspect, the present invention relates to the use of a construct, the construct being or encoding an RNAi construct comprising a sense and an antisense sequence targeting the endogenous Lox3 gene of a maize plant, wherein the RNAi construct forms an RNA hairpin upon transcription, for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In yet another aspect, the present invention relates to the use of a construct, the construct being or encoding an RNAi construct comprising a sense and an antisense sequence targeting the endogenous Lox3 gene of an oilseed rape plant, wherein the RNAi construct forms an RNA hairpin upon transcription, for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and *Plasmodiophora brassicae* to/in oilseed rape (*Brassica napus*).

In one embodiment of the use described above the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

In another embodiment of the use described above, the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

In a further embodiment of the use described above, the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98%, or at least 99% to the sequence of SEQ ID NO: 3.

In one embodiment of the use described above, the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

In another aspect, the present invention relates to the use of a vector, which vector comprises or consists of a nucleic acid sequence of SEQ ID NO: 5, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5 for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In yet another aspect, the present invention relates to a use of a genome editing system, which targets the endogenous Lox3 gene in a maize plant, wherein the genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same
for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In a further aspect, the present invention relates to a use of a genome editing system, which targets the endogenous Lox3 gene in an oilseed rape plant, wherein the genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same
for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and *Plasmodiophora brassicae* to/in oilseed rape (*Brassica napus*).

In one aspect, the present invention relates to a use of an expression construct encoding a genome editing system, which targets the endogenous Lox3 gene in a maize plant, wherein the genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same,
wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or the at least one genome editing system is selected from a zinc finger nuclease system, or a transcription activator-like nuclease system, or a meganuclease system, or any combination, variant, or an active fragment thereof for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In another aspect, the present invention relates to a use of an expression construct encoding a genome editing system, which targets the endogenous Lox3 gene in an oilseed rape plant, wherein the genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same,
wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or the at least one genome editing system is selected from a zinc finger nuclease system, or a transcription activator-like nuclease system, or a meganuclease system, or any combination, variant, or an active fragment thereof for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma lingam* and *Plasmodiophora brassicae* to/in oilseed rape (*Brassica napus*).

In one embodiment of the use described above, the expression construct comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NO: 46 to 49.

In another embodiment of the use described above, the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

In a another aspect, the present invention relates to a use of a vector encoding an genome editing system as defined above for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In a further aspect, the present invention relates to a use of a vector encoding an genome editing system as defined above for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma lingam* and Plasmodiophora brassicae to/in oilseed rape (*Brassica napus*).

Brief Description of Sequences

| SEQ ID NO. | Description |
|---|---|
| 1 | RNAi target region sense strand before RGA2intronII |
| 2 | RNAi target region antisense strand after the RGA2intronII |
| 3 | RGA2intronII sequence from *Triticum aestivum*—second intron of RGA2 (resistance gene analog; gene involved in leaf rust resistance in wheat) according to Loutre et al., 2009, The Plant Journal 60, 1043-1054 |
| 4 | Sequence of RNAi cassette (RNAi target region sense strand before RGA2intronII + RGA2intronII + RNAi target region antisense strand after the RGA2intronII) |
| 5 | Sequence of a complete exemplary RNAi vector, here starting with ColE1 ori |
| 6 | Zm00001eb054040_B73AGP05_T001_genomic (ZmLox3)—Genomic sequence of Lox3 from *Zea mays* |
| 7 | Zm00001eb054040_B73AGP05_T001_CDS (ZmLox3)—Coding sequence of Lox3 from *Zea mays* |
| 8 | Zm00001eb054040_B73AGP05_T001_pro (ZmLox3)—Amino acid sequence of Lox3 from *Zea mays* |
| 9 | ZmLox3_gDNA_A188—genomic sequence of Lox3 from *Zea mays* line A188 |
| 10 | ZmLox3_CDS_A188—coding sequence of Lox3 from *Zea mays* line A188 |
| 11 | ZmLox3_protein_A188—amino acid sequence of Lox3 from *Zea mays* line A188 |
| 12 | SL57_Zm00001d033623(LOX3)_gDNA—tropical corn line SL57—genomic sequence of Lox3 from tropical corn line SL57 (*Zea mays*) |
| 13 | SL57_Zm00001d033623(LOX3)_CDS—tropical corn line SL57—coding sequence of Lox3 from tropical corn line SL57 (*Zea mays*) |
| 14 | SL57_Zm00001d033623(LOX3)_protein—tropical corn line SL57—amino acid sequence of Lox3 from tropical corn line SL57 (*Zea mays*) |
| 15 | ZmLox3_PH207_genomic—genomic sequence of Lox3 from *Zea mays* line PH207 |
| 16 | ZmLox3_PH207_CDS—coding sequence of Lox3 from *Zea mays* line PH207 |
| 17 | ZmLox3_PH207_protein—amino acid sequence of Lox3 from *Zea mays* line PH207 |
| 18 | Primer for Lox3 qRT-PCR:S3460—Corn—Primer for expression anlysis of Lox3 in *Zea mays* |
| 19 | Primer for Lox3 qRT-PCR: S3461—Corn—Primer for expression anlysis of Lox3 in *Zea mays* |
| 20 | Primer for Ef-Tu qRT-PCR: S3428—Primer for expression analysis of the housekeeping gene Elongation factor 1-alpha |
| 21 | Primer for Ef-Tu qRT-PCR: S3429—Primer for expression analysis of the housekeeping gene Elongation factor 1-alpha |
| 22 | Elongation factor 1-alpha (EF1) gene from A188—coding sequence of Elongation factor 1-alpha (EF1) gene from *Zea mays* line A188 |
| 23 | Elongation factor 1-alpha (EF1) protein from A188—amino acid sequence of Elongation factor 1-alpha (EF1) gene from *Zea mays* line A188 |

-continued

| SEQ ID NO. | Description |
|---|---|
| 24 | ZmPLT5 PRT—amino acid sequence of PLETHORA transcription factor (PLT) from *Zea mays* |
| 25 | ZmPLT5 CDS—coding sequence of PLETHORA transcription factor (PLT) from *Zea mays* |
| 26 | RBP8 PRT—amino acid sequence of regeneration booster protein |
| 27 | RBP8 CDS—coding sequence of regeneration booster protein |
| 28 | LbCpf1-RR PRT—amino acid sequence of Cpf1 from *Lachnospiraceae bacterium* RR |
| 29 | LbCpf1-RR CDS—coding sequence of Cpf1 from *Lachnospiraceae bacterium* RR |
| 30 | tdTomato PRT—amino acid sequence of fluorescent protein tdTomato |
| 31 | tdTomato CDS—coding sequence of fluorescent protein tdTomato |
| 32 | Protospacer m7GEP336 DNA—DNA sequence of protospacer m7GEP336 |
| 33 | Protospacer m7GEP337 DNA—DNA sequence of protospacer m7GEP337 |
| 34 | Protospacer m7GEP338 DNA—DNA sequence of protospacer m7GEP338 |
| 35 | Protospacer m7GEP339 DNA—DNA sequence of protospacer m7GEP339 |
| 36 | Zm00008a004913_pro.pro—amino acid sequence of Lox3 from *Zea mays* mutant Zm00008a004913 |
| 37 | WVP18-09358-016_pro—amino acid sequence of Lox3 from *Zea mays* mutant WVP18-09358-016 |
| 38 | WVP18-09344-014_pro.pro—amino acid sequence of Lox3 from *Zea mays* mutant WVP18-09344-014 |
| 39 | WVP18-09309-014_339-009_pro.pro—amino acid sequence of Lox3 from *Zea mays* mutant WVP18-09309-014 |
| 40 | WVP18-09307-014_pro.pro—amino acid sequence of Lox3 from *Zea mays* mutant WVP18-09307-014 |
| 41 | Zm00008a004913_CDS—coding sequence of Lox3 from *Zea mays* mutant Zm00008a004913 |
| 42 | WVP18-09358-016_CDS.seq—coding sequence of Lox3 from *Zea mays* mutant WVP18-09358-016 |
| 43 | WVP18-09344-014_CDS.seq—coding sequence of Lox3 from *Zea mays* mutant WVP18-09344-014 |
| 44 | WVP18-09309-014_339-009_CDS.seq—coding sequence of Lox3 from *Zea mays* mutant WVP18-09309-014 |
| 45 | WVP18-09307-014_CDS.seq—coding sequence of Lox3 from *Zea mays* mutant WVP18-09307-014 |
| 46 | crRNA1—DNA sequencing coding for crRNA1 for targeting the OSR lox3 gene |
| 47 | crRNA2.1—DNA sequencing coding for crRNA2.1 for targeting the OSR lox3 gene |
| 48 | crRNA2.2—DNA sequencing coding for crRNA2.2 for targeting the OSR lox3 gene |
| 49 | crRNA3—DNA sequencing coding for crRNA3 for targeting the OSR lox3 gene |
| 50 | pZFNnptII-LbCpf1-tDT-lox3_TTTV—plasmid sequence of pZFNnptII-LbCpf1-tDT-lox3_TTTV |
| 51 | cruaxxxxxxf02x—forward primer cruaxxxxxxf02x for analyzing the presence of the transgene |
| 52 | cruaxxxxxxr01x—reverse primer cruaxxxxxxr01x for analyzing the presence of the transgene |
| 53 | nptIIxxxf01—forward primer nptIIxxxf01 for analyzing the presence of the transgene |
| 54 | nptIIxxxr01—reverse primer nptIIxxxr01 for analyzing the presence of the transgene |
| 55 | tDTxxxf04—forward primer tDTxxxf04 for analyzing the presence of the transgene |
| 56 | tDTxxxr01—reverse primer tDTxxxr01 for analyzing the presence of the transgene |
| 57 | CruaxxxMGB—probe CruaxxxMGB for analyzing the presence of the transgene |
| 58 | nptIIxxxMGB—probe nptIIxxxMGB for analyzing the presence of the transgene |
| 59 | tDTxxxMGB—probe tDTxxxMGB for analyzing the presence of the transgene |
| 60 | Fwmfor nuclease—fowrad primer LbCpf1 for nuclease test |
| 61 | LbCpf1-Rv—reverse primer LbCpf1 for nuclease test DNA-LbCpf1 |
| 62 | Probe—probe for nuclease test |
| 63 | IR106_lox3_F1—primer IR106_lox3_F1 for editing profile analysis |
| 64 | IR106_lox3_F2—primer IR106_lox3_F2 for editing profile analysis |
| 65 | IR106_lox3_F3—primer IR106_lox3_F3 for editing profile analysis |
| 66 | IR106_lox3_F4—primer IR106_lox3_F4 for editing profile analysis |
| 67 | IR106_lox3_R1—primer IR106_lox3_R1 for editing profile analysis |
| 68 | IR106_lox3_R2—primer IR106_lox3_R2 for editing profile analysis |

| SEQ ID NO. | Description |
| --- | --- |
| 69 | IR106_lox3_R3—primer IR106_lox3_R3 for editing profile analysis |
| 70 | IR106_lox3_R4—primer IR106_lox3_R4 for editing profile analysis |
| 71 | 946R—primer 946R for amplicon sequencing |
| 72 | 1145F—primer 1145F for amplicon sequencing |
| 73 | 346F—primer 346F for amplicon sequencing |
| 74 | 1948R—primer 1948R for amplicon sequencing |
| 75 | OSR Lox3 genomic DNA BnaC08g37760D_At_ortholog:AT1G17420—genomic DNA sequence of Lox3 from oil seed rape (*Brassica napus*) |
| 76 | OSR Lox3 genomic DNA BnaA08g23120D_At_ortholog: AT1G17420—genomic DNA sequence of Lox3 from oil seed rape (*Brassica napus*) |
| 77 | OSR Lox3 genomic DNA BnaA09g45010D_At_ortholog:AT1G17420—genomic DNA sequence of Lox3 from oil seed rape (*Brassica napus*) |
| 78 | OSR Lox3 genomic DNA BnaC08g48320D_At_ortholog:AT1G17420—genomic DNA sequence of Lox3 from oil seed rape (*Brassica napus*) |
| 79 | OSR Lox3 PRT BnaC08g37760D_At_ortholog:AT1G17420—amino acid sequence of Lox3 from oil seed rape (*Brassica napus*) |
| 80 | OSR Lox3 PRT BnaA08g23120D_At_ortholog:AT1G17420—amino acid sequence of Lox3 from oil seed rape (*Brassica napus*) |
| 81 | OSR Lox3 PRT BnaA09g45010D_At_ortholog:AT1G17420—amino acid sequence of Lox3 from oil seed rape (*Brassica napus*) |
| 82 | OSR Lox3 PRT BnaC08g48320D_At_ortholog:AT1G17420—amino acid sequence of Lox3 from oil seed rape (*Brassica napus*) |
| 83 | OSR Lox3 CDS BnaC08g37760D_At_ortholog: AT1G17420—coding sequence of Lox3 from oil seed rape (*Brassica napus*) |
| 84 | OSR Lox3 CDS BnaA09g45010D_At_ortholog:AT1G17420—coding sequence of Lox3 from oil seed rape (*Brassica napus*) |
| 85 | OSR Lox3 CDS BnaA09g45010D_At_ortholog:AT1G17420—coding sequence of Lox3 from oil seed rape (*Brassica napus*) |
| 86 | OSR Lox3 CDS BnaC08g48320D_At_ortholog:AT1G17420—coding sequence of Lox3 from oil seed rape (*Brassica napus*) |
| 87 | Zm00001eb054040_B73AGP05_T002_CDS—coding sequence of an alternative transcript of Lox3 from *Zea mays* |
| 88 | Zm00001eb054040_B73AGP05_T002_genomic—genomic sequence coding for an alternative transcript of Lox3 from *Zea mays* |
| 89 | Zm00001eb054040_B73AGP05_T002_pro—amino acid sequence of an alternative splice variant of Lox3 from *Zea mays* |

Definitions

A plant exhibits "resistance" or "tolerance" to an insect or fungal pathogen, when symptoms of infestation are reduced or not observed at all when the plant is exposed to the pathogen under conditions allowing infestation. Indirectly, resistance and tolerance can also be observed by looking at the performance of the pathogen on resistant or tolerant plants compared to plants with no resistance or tolerance. For example, the amount, size, or weight of pathogen can be observed and compared. Larval weight of insects may for example and not limitation be reduced in resistant or tolerant plants compared to a control. Typically, a resistant or tolerant plant shows reduced yield loss compared to a non-resistant plant infested with the same pathogen under the same conditions. Ideally, in a resistant plant, the yield loss caused by infestation is completely compensated, meaning that the plant produces as much yield as a plant, which was not exposed to the pathogen at all but grown under the same conditions.

"Insect pathogens" or "fungal pathogens" are any insects or fungi, which invade and infest crop plants and cause damage and ultimately yield loss in crop plants. For each crop plant, a number of insect or fungal pathogens are known to the skilled person. In some cases, fungal diseases are favoured by the mechanical damage caused by invading insects so that damage can be exaggerated. Therefore, resistance or tolerance to insect pests can also provide a degree of fungal resistance.

The terms "RNA interference" or "RNAi" or "RNA silencing" or "gene silencing" as used herein interchangeably refer to a gene down-regulation (or knock-down) mechanism meanwhile demonstrated to exist in all eukaryotes. The mechanism was first recognized in plants where it was called "post-transcriptional gene silencing" or "PTGS". In RNAi, small RNAs function to guide specific effector proteins to a target nucleotide sequence by complementary base pairing resulting in degradation of the target. A "gene silencing construct" or "RNAi construct" usually comprises so called "sense" and "antisense" sequences. The sense and antisense sequences are complementary sequences, which are present in reverse orientation in a nucleic acid sequence. If a nucleic acid construct comprises a sense and a corresponding antisense sequence, the two complementary sequences form an RNA double strand upon transcription, which results in an "RNA hairpin". In an RNA hairpin, sense sequences and corresponding antisense sequences, together form a double strand and are separated by an "intervening intron loop sequence" forming the loop of the hairpin structure. An "RNAi construct" may also comprise more than one sense and antisense pair and form several loops.

A "genome editing system" refers to a combination of a site-specific nuclease or site-specific nickase or a functional active fragment or variant thereof together with the cognate guide RNA (or pegRNA or crRNA) guiding the relevant CRISPR nuclease to its target site to be cleaved. A "site-specific nuclease" refers to a nuclease or an active fragment thereof, which is capable to specifically recognize and cleave DNA at a certain target site. Such nucleases typically produce a double strand break (DSB), which is then repaired by nonhomologous end-joining (NHEJ) or homologous recombi-nation (HR). The nucleases include zinc-finger nucleases, transcription activator-like effector nucleases, engineered homing endonucleases, recombinases, transposases and meganucleases and CRISPR nucleases and/or any combination, variant or active fragment thereof. The genome editing system may be a CRISPR/Cas system including CRISPR/Cas9 systems, CRISPR/Cas13 systems, CRISPR/Cpf1 (CRISPR/Cas12a) systems, CRISPR/C2C2 systems, CRISPR/CasX systems, CRISPR/CasY systems, CRISPR/Cmr systems, CRISPR/Csm systems, CRISPR/MAD2 systems, CRISPR/MAD7 systems, CRISPR/CasZ systems, or catalytically active fragment thereof. The "guide molecule", in particular the "guide RNA" (gRNA) may be a trans-activating CRISPR RNA (tracrRNA) plus a synthetic CRISPR RNA (crRNA) or a single guide RNA (sgRNA), which comprises the sequence information targeting the genomic sequence for cleavage by the nuclease.

A "CRISPR nuclease", as used herein, is any nuclease which has been identified in a naturally occurring CRISPR system, which has subsequently been isolated from its natural context, and which preferably has been modified or combined into a recombinant construct of interest to be suitable as tool for targeted genome engineering. Any CRISPR nuclease can be used and optionally reprogrammed or additionally mutated to be suitable for the various embodiments according to the present invention as long as the original wild-type CRISPR nuclease provides for DNA recognition, i.e., binding properties. Said DNA recognition can be PAM (protospacer adjacent motif) dependent. CRISPR nucleases having optimized and engineered PAM recognition patterns can be used and created for a specific application. The expansion of the PAM recognition code can be suitable to target site-specific effector complexes to a target site of interest, independent of the original PAM specificity of the wild-type CRISPR-based nuclease. Cpf1 variants can comprise at least one of a S542R, K548V, N552R, or K607R mutation, preferably mutation S542R/K607R or S542R/K548V/N552R in AsCpf1 from Acidaminococcus. Furthermore, modified Cas or Cpf1 variants or any other modified CRISPR effector variants, e.g., Cas9 variants, can be used according to the methods of the present invention as part of a base editing complex, e.g., BE3, VQR-BE3, EQR-BE3, VRER-BE3, SaBE3, SaKKH-BE3 (see Kim et al., Nat. Biotech., 2017, doi: 10.1038/nbt.3803). Therefore, according to the present invention, artificially modified CRISPR nucleases are envisaged, which might indeed not be any "nucleases" in the sense of double-strand cleaving enzymes, but which are nickases or nuclease-dead variants, which still have inherent DNA recognition and thus binding ability. Suitable Cpf1-based effectors for use in the methods of the present invention are derived from Lachnospiraceae bacterium (LbCpf1, e.g., NCBI Reference Sequence: WP_051666128.1), or from *Francisella tularensis* (FnCpf1, e.g., UniProtKB/Swiss-Prot: A0Q7Q2.1). Variants of Cpf1 are known (cf. Gao et al., BioRxiv, dx.doi.org/10.1101/091611). Variants of AsCpf1 with the mutations S542R/K607R and S542R/K548V/N552R that can cleave target sites with TYCV/CCCC and TATV PAMs, respectively, with enhanced activities in vitro and in vivo are thus envisaged as site-specific effectors according to the present invention. Genome-wide assessment of off-target activity indicated that these variants retain a high level of DNA targeting specificity, which can be further improved by introducing mutations in non-PAM-interacting domains. Together, these variants increase the targeting range of AsCpf1 to one cleavage site for every ~8.7 base pairs (bp) in non-repetitive regions of the human genome, providing a useful addition to the CRISPR/Cas genome engineering toolbox (see Gao et al., supra).

The terms "SDN-1", "SDN-2", and "SDN-3" as used herein are abbreviations for the platform technique "site-directed nuclease" 1, 2, or 3, respectively, as caused by any site directed nuclease of interest, including, for example, Meganucleases, Zinc-Finger Nucleases (ZFNs), Transcription Activator Like Effector Nucleases (TALENs), and CRISPR nucleases. SDN-1 produces a double-stranded or single-stranded break in the genome of a plant without the addition of foreign DNA. For SDN-2 and SDN-3, an exogenous nucleotide template is provided to the cell during the gene editing. For SDN-2, however, no recombinant foreign DNA is inserted into the genome of a target cell, but the endogenous repair process copies, for example, a mutation as present in the template to induce a (point) mutation. In contrast, SDN-3 mechanism uses the introduced template during repair of the DNA break so that genetic material is introduced into the genomic material.

A "genome modification" in the context of the present invention refers to any change of a (nucleic acid) sequence that results in at least one difference in the (nucleic acid) sequence distinguishing it from the original sequence. In particular, a modification can be achieved by insertion or addition of one or more nucleotide(s), or substitution or deletion of one or more nucleotide(s) of the original sequence or any combination of these.

A "knock-down" of a gene refers to an experimental technique by which the expression of the gen is reduced. A reduced expression can e.g., be achieved by gene silencing. A "knock-out", on the other hand, leads to an abolished expression, i.e., the gene is not expressed at all. This can for example and not limitation be achieved by replacing or interrupting the sequence of the target gene by genome editing.

A nucleic acid molecule or gene that is "endogenous" to a cell or organism refers to a nucleic acid molecule that naturally occurs in the genome of this cell or organism. On the other hand, a nucleic acid molecule that is "exogenous" to a cell or organism refers to a nucleic acid molecule that does not naturally occur in this cell or organism but has been introduced by a transgenic event.

"Regenerating" a plant, tissue, organ or seed is done by culturing a modified or edited cell in a way that may include steps of de-differentiation and differentiation to obtain specialized tissue or a whole plant, which carries the modification or edit, preferably in every cell. Techniques for regeneration of a plant are well known to the skilled person.

A "nucleic acid construct", "construct" or "expression construct" refers to a nucleic acid molecule encoding or comprising one or more genetic elements, which upon introduction into a target cell can be transcribed and/or translated into a functional form, e.g., RNA(s) or polypeptide(s) or protein(s). A nucleic acid construct may also comprise regulatory sequences such as promoter and terminator sequences facilitating expression of the genetic element(s) as well as spacers and introns. The genetic elements of the present invention can also be encoded on a set of constructs, which constructs can be introduced into a cell simultaneously or consecutively.

A (nucleic acid) construct of the present invention "targets" a genomic sequence or a gene when it contains sequence information, which allows recognition of the genomic sequence or gene and can thus interfere with the sequence, e.g., by site-specific cleavage or silencing. The targeting can be affected either by direct interaction with the genomic sequence itself or by interaction with the transcript of the genomic sequence. For example, if the nucleic acid construct of the present invention comprises or encodes a sense and a corresponding antisense sequence targeting a genomic sequence, an RNA silencing or RNA interference (RNAi) mechanism is activated upon transcription of the construct, which leads to the destruction of the transcript of the genomic target sequence and thus suppresses expression of the target. In another case, the nucleic acid construct may encode a site-specific nuclease and a guide RNA, which results in cleavage of the target sequence.

"Transformation" or "Transfection" of a plant cell with a construct or set of constructs refers to any established technique to introduce nucleic acid molecules into a cell, such as biolistic approaches (e.g., particle bombardment), microinjection, permeabilising the cell membrane with various treatments such as electroporation or PEG treatment or *Agrobacterium tumefaciens* mediated transformation. Generally, incorporating (a) nucleic acid construct(s), for example by way of transformation, may be accomplished with techniques that are basically known to the person skilled in the art. For example, the nucleic acid construct can be incorporated into the plant cells by infecting a plant tissue or a plant cell with *Agrobacterium tumefaciens* containing the nucleic acid sequence to be transferred in its plasmid that can be integrated into the plant genome. Incorporating by means of a biolistic transfer is another option, wherein the nucleic acid construct to be incorporated into the plant cell is applied to gold particles or tungsten particles, which are then shot into the cells at a high speed. Another option known to the person skilled in the art for incorporating a nucleic acid construct into a plant cell, is the protoplast transformation, wherein either polyethylene glycol is added to the protoplasts in the presence of the nucleic acid molecules to be incorporated, or the protoplasts are exposed to a short current impulse, so that the protoplast membrane transiently becomes permeable for the nucleic acid construct(s).

The term "vector" refers to an element used for introducing a nucleic acid construct or set of nucleic acid constructs into a cellular system. The vector may be a plasmid or plasmid vector, cosmid, artificial yeast artificial chromosomes (YAC), bacterial artificial chromosome (BAC) or P1 artificial chromosomes (PACs), phagemid, bacterial phage-based vector, an isolated single-stranded or double-stranded nucleic acid sequence, comprising DNA and RNA sequences in linear or circular form, or a mixture thereof, for introduction or transformation into a plant, plant cell, tissue, organ or material according to the present disclosure.

The terms "plant" or "plant cell" or "part of a plant" as used herein refer to a plant organism, a plant organ, differentiated and undifferentiated plant tissues, plant cells, seeds, and derivatives and progeny thereof. Plant cells include without limitation, for example, cells from seeds, from mature and immature cells or organs, including embryos, meristematic tissues, seedlings, callus tissues in different differentiation states, leaves, flowers, roots, shoots, male or female gametophytes, sporophytes, pollen, pollen tubes and microspores and protoplasts.

"Mutagenesis" refers to a technique, by which modifications or mutations are introduced into a nucleic acid sequence in a random or non-site-specific way. For example, mutations can be induced by certain chemicals such as EMS (ethyl methanesulfonate) or ENU (N-ethyl-N-nitrosourea) or physically, e.g., by irradiation with UV or gamma rays. "Site-specific modifications", on the other hand, rely on the action of site-specific effectors such as nucleases, nickases, recombinases, transposases, base editors. These tools recognize a certain target sequence and allow to introduce a modification at a specific location within the target sequence.

"TILLING" (Targeting Induced Local Lesions in Genomes) is a process, which allows to identify mutations in a specific gene after an (unspecific) mutagenesis has been performed. Mutagenesis may for example and not limitation be performed using a chemical mutagen such as EMS. Then, a sensitive DNA screening technique is used to identify single base mutations. Methods for performing TILLING are known to the skilled person.

Whenever the present disclosure relates to the percentage of identity of nucleic acid or amino acid sequences to each other these values define those values as obtained by using the EMBOSS Water Pairwise Sequence Alignments (nucleotide) programme (www.ebi.ac.uk/Tools/psa/emboss_water/nucleotide.html) nucleic acids or the EM-BOSS Water Pairwise Sequence Alignments (protein) programme (www.ebi.ac.uk/Tools/psa/emboss_water/) for amino acid sequences. Alignments or sequence comparisons as used herein refer to an alignment over the whole length of two sequences compared to each other. Those tools provided by the European Molecular Biology Laboratory (EMBL) European Bioinformatics Institute (EBI) for local sequence alignments use a modified Smith-Waterman algorithm (see www.ebi.ac.uk/Tools/psa/and Smith, T. F. & Waterman, M. S. "Identification of common molecular subsequences" Journal of Molecular Biology, 1981 147 (1): 195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5. The skilled person is well aware of the fact that, for example, a sequence encoding a protein can be "codon-optimized" if the respective sequence is to be used in another organism in comparison to the original organism a molecule originates from.

BRIEF DESCRIPTION OF DRAWINGS

FIG. 7 shows infection rates of *F. graminearum* (FG) and *F. verticilloides* (FV) in homozygous mutant class for PH207m034b and PH207m034h.

DETAILED DESCRIPTION

Figure 1:
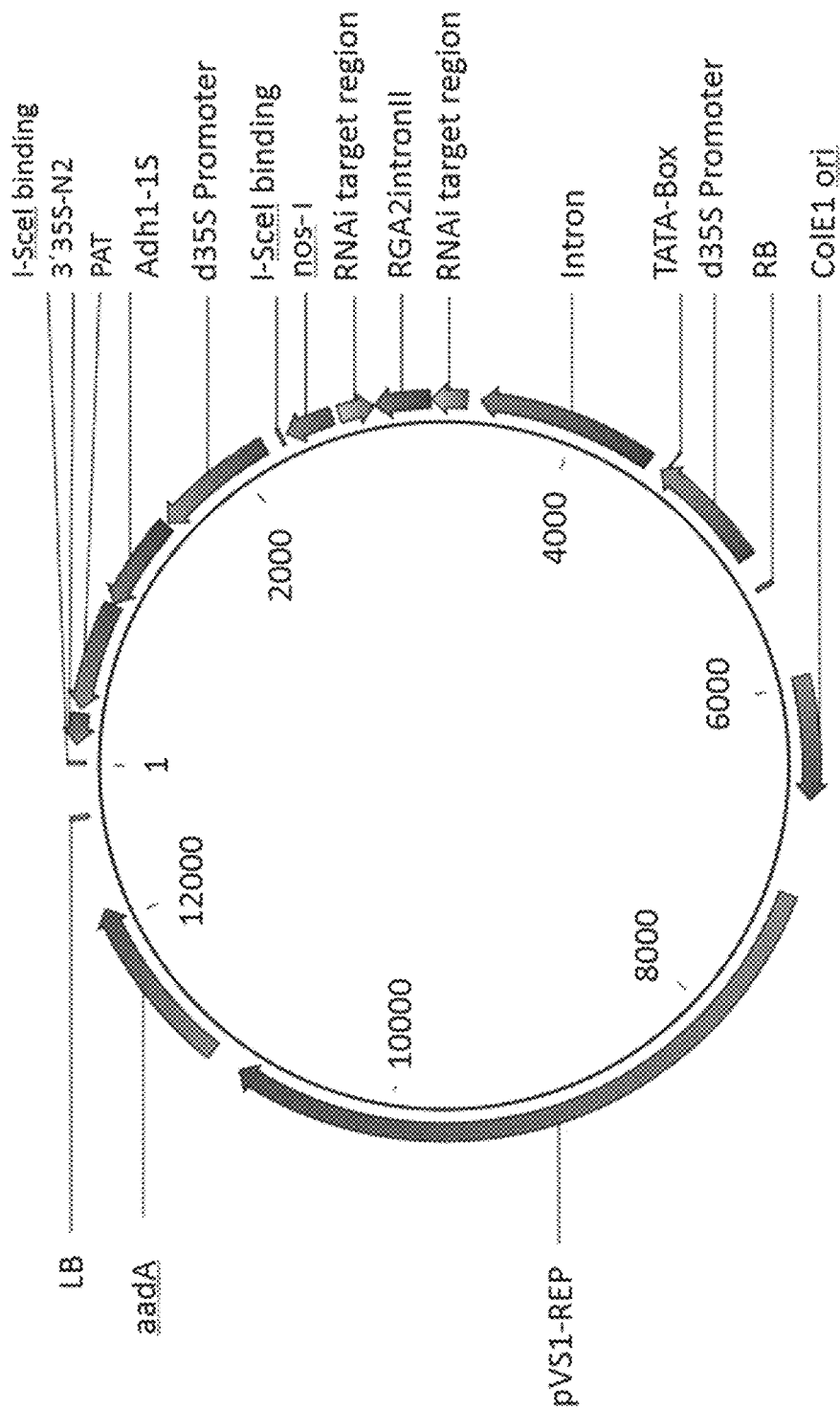
FIG. 1 shows the binary vector used for RNAi mediated downregulation of ZmLox3. An RNAi hairpin construct directed against the ZmLox3 gene was inserted into a binary vector for corn transformation. The T-DNA of the binary vector was transformed into the corn genotype A188. The intron between the d35S promoter and the RNAi target region is the first intron of the maize polyubiquitin gene (ZmUbi; Christensen, A. H., Quail, P. H. Ubiquitin promoter-based vectors for high-level expression of selectable and/or screenable marker genes in monocotyledonous plants. Transgenic Research 5, 213-218 (1996). https://doi.org/10.1007/BF01969712).

The present invention provides means and methods to confer resistance or tolerance to several relevant insect pathogens and, optionally—in addition—fungal pathogens, in plants. In particular, highly damaging diseases in corn (Zm) and oil seed rape (OSR) are addressed in the following disclosure. In some cases, fungal diseases are favoured by the mechanical damage caused by invading insects so that damage can be exaggerated. It was thus shown that resistance or tolerance to insect pests can also provide a degree of fungal resistance or tolerance. Insect infestation in crop plants is often managed using insecticide treatments and Bt traits, i.e., genetically modified (GM) plants, which produce insecticidal toxins. The present invention provides a novel approach to manage insect pests using a non-GM trait. Through a product development by TILLING, a non-GM trait increasing insect tolerance could be achieved. This can be used in addition to pesticides to reduce their use and/or to protect the crop against insects when pesticides cannot be applied (e.g., when it rains). Additionally, a knock-down using gene silencing and a knock-out using genome editing techniques could be achieved.

In a first aspect, the present invention relates to a method for conferring or increasing resistance or tolerance to an insect and, optionally a fungal pathogen to/in a plant comprising the steps of:
(i) providing at least one plant cell;
(ii) introducing into the at least one plant cell at least one gene silencing construct, at least one genome editing system or a genome modification, which leads to a targeted knock-down or a knock-out of a Lox3 gene endogenous to the plant;
(iii) obtaining at least one modified plant cell having reduced or abolished expression of the Lox3 gene; and
(iv) obtaining at least one plant cell, tissue, organ, plant or seed having reduced or abolished expression of the Lox3 gene, optionally after an additional step of regenerating the plant tissue, organ, plant or seed from the at least one modified cell.

It was established in the context of the present invention that reduced or abolished expression of the endogenous Lox3 gene in plants confers or increases resistance to insect pests and can at the same time also provide a degree of resistance to fungal pathogens. To reduce or abolish expression of the endogenous Lox3 gene, three different approaches may be taken: Lox3 expression may be reduced by gene silencing using an RNAi hairpin construct, which contains as sense and antisense sequences sections of the endogenous Lox3 gene. Alternatively, a genome editing system can be used, which introduces a double strand break (DSB) at or in the endogenous Lox3 sequence resulting in a disruption or (partial) replacement of the Lox3 locus. Finally, it is also possible to introduce mutations into the endogenous Lox3 by random mutagenesis and identify such mutations, which provide the desired knock-down or knock-out effect.

In a preferred embodiment, the method described above is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

The above-mentioned pathogens cause a lot of damage to corn and reduce yields significantly. Using the approaches described herein, resistance or tolerance to these pathogens can be conferred or increased. Another important crop plant, oil seed rape, may also suffer from certain insect or fungal pests.

In another preferred embodiment, the method described above therefore is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and *Plasmodiophora brassicae* to/in oilseed rape (*Brassica napus*).

The Lox3 gene in corn (*Zea mays*) is represented by the genomic DNA sequence of SEQ ID NO: 6, while the coding sequence is represented by the sequence of SEQ ID NO: 7. For the corn lines A188, a tropical corn line, the line PH207 and an alternative transcript, the genomic sequences and coding sequences are respectively represented by the sequences of SEQ ID NOS: 9 (A188, genomic DNA), 10 (A188, coding sequence), 12 (tropical corn line, genomic DNA), 13 (tropical corn line, coding sequence), 15 (PH207, genomic DNA), 16 (PH207, coding sequence), 87 (alternative transcript, coding sequence) and 88 (alternative transcript, genomic sequence).

In one embodiment of the method described above, the Lox3 gene is therefore represented by a nucleic acid sequence of SEQ ID NO: 6, 7, 9, 10, 12, 13, 15, 16, 87 or 88 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 6, 7, 9, 10, 12, 13, 15, 16, 87 or 88.

The protein (amino acid) sequences of Lox3 in corn (*Zea mays*) translated from the above nucleic acid sequences are represented by the sequences of SEQ ID NOS: 8 (ZmLox3 protein), 11 (A188, ZmLox3 protein), 14 (tropical corn line, ZmLox3 protein), 17 (PH207, ZmLox3 protein) and 89 (alternative transcript, ZmLox3 protein).

In one embodiment of the method described above, the Lox3 gene therefore encodes an amino acid sequence of SEQ ID NO: 8, 11, 14, 17 or 89 an amino acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 8, 11, 14, 17 or 89.

The Lox3 gene in oil seed rape (*Brassica napus*) is represented by the genomic DNA sequences of SEQ ID NOs: 75, 76, 77 and 78 while the coding sequences are represented by the sequences of SEQ ID NOS: 83, 84, 85 and 86.

In one embodiment of the method described above, the Lox3 gene is therefore represented by a nucleic acid sequence of SEQ ID NO: 75, 76, 77, 78, 83, 84, 85 or 86 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 75, 76, 77, 78, 83, 84, 85 or 86.

The protein (amino acid) sequences of Lox3 in oil seed rape (*Brassica napus*) translated from the above nucleic acid sequences are represented by the sequences of SEQ ID NOs: 79, 80, 81 and 82.

In one embodiment, the Lox3 gene therefore encodes an amino acid sequence of SEQ ID NO: 79, 80, 81 or 82 or an amino acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 79, 80, 81 or 82.

In a further embodiment of the method according to any of the embodiments described above, in step (ii) a construct is introduced into the at least one plant cell, which targets the Lox3 gene for gene silencing.

RNAi techniques for targeted gene silencing are well known in the art. To this end, an RNAi construct is introduced into a plant cell, which contains sequence information of the genomic target to be silenced in the cell. The construct is preferably introduced in form of a DNA sequence, which is then transcribed into functional RNA in the cell. In particular, the RNAi construct encodes sense and antisense sequences, which represents (a fragment of) the genomic target. The complementary sense and antisense sequences, which are present in reverse orientation in the construct form an RNA double strand upon transcription, which results in an RNA hairpin with an intervening intron loop sequence. The presence of the RNAi construct ultimately results in a reduced expression of the target, i.e., a knock-down.

In one embodiment of the method described above, the construct encodes an RNAi construct comprising a sense and an antisense sequence targeting the Lox3 gene, the RNAi construct forming an RNA hairpin upon transcription.

Preferably, the sense and antisense sequences have a length of 40 to 500 nucleotides, more preferably 100 to 300 nucleotides.

In one embodiment of the method described in any of the embodiment described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

In another embodiment of the method described in any of the embodiment described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

In yet another embodiment of the method described in any of the embodiment described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98% or at least 99% to the sequence of SEQ ID NO: 3.

In one embodiment of the method described in any of the embodiment described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

The RNAi construct may preferably be introduced on a vector encoding the RNAi hairpin, which is formed upon transcription.

In one embodiment of the method according to any of the embodiments described above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and a vector is introduced into the plant cell, which vector comprises or consists of a nucleic acid sequence of SEQ ID NO: 5, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5.

The introduction of the construct into the plant cell may for example and not limitation be achieved by means of transformation or transfection. Besides transformation methods based on biological approaches, like *Agrobacterium* transformation or viral vector mediated plant transformation, methods based on physical delivery methods, like particle bombardment or microinjection, have evolved as prominent techniques for importing genetic material into a plant cell or tissue of interest. Helenius et al. ("Gene delivery into intact plants using the Helios™ Gene Gun", Plant Molecular Biology Reporter, 2000, 18 (3): 287-288) discloses a particle bombardment as physical method for transferring material into a plant cell. Currently, there are a variety of plant transformation methods to introduce genetic material in the form of a genetic construct into a plant cell of interest, comprising biological and physical means known to the skilled person on the field of plant biotechnology, which can be applied. A common biological means is transformation with *Agrobacterium* spp. which has been used for decades for a variety of different plant materials. Viral vector mediated plant transformation represents a further strategy for introducing genetic material into a cell of interest. Physical means finding application in plant biology are particle bombardment, also named biolistic transfection or microparticle-mediated gene transfer, which refers to a physical delivery method for transferring a coated microparticle or nanoparticle comprising a nucleic acid or a genetic construct of interest into a target cell or tissue. Physical introduction means are suitable to introduce nucleic acids, i.e., RNA and/or DNA, and proteins. Likewise, transformation or transfection methods exist for specifically introducing a nucleic acid or an amino acid construct of interest into a plant cell, including electroporation, microinjection, nanoparticles, and cell-penetrating peptides (CPPs). Furthermore, chemical-based transfection methods exist to introduce genetic constructs and/or nucleic acids and/or proteins, comprising inter alia transfection with calcium phosphate, transfection using liposomes, e.g., cationic liposomes, or transfection with cationic polymers, including DEAD-dextran or polyethylenimine, or combinations thereof. Every delivery method has to be specifically fine-tuned and optimized so that a construct of interest can be introduced into a specific compartment of a target cell of interest in a fully functional and active way.

In one embodiment of the method described above, the construct is introduced into the at least one plant cell by transformation or transfection mediated by biolistic bombardment, *Agrobacterium*-mediated transformation, micro- or nanoparticle delivery, chemical transfection, or a combination thereof.

As already mentioned above, as an alternative to gene silencing, the knock-down or knock-out of the endogenous Lox3 gene to confer or enhance resistance or tolerance can also be effected by genome editing.

In one embodiment of the method described above, in step (ii) at least one genome editing system is introduced into the at least one cell, which targets the Lox3 gene, wherein the at least one genome editing system comprises (a) at least one site-specific nuclease or site-specific nickase, and optionally, in case a CRISPR system is used, at least one guide molecule or a sequence encoding the same, and (b) optionally, at least one repair template, or a sequence encoding the same.

Genome editing techniques allow to introduce a double strand break at one or more predetermined target site(s), i.e., by or within the endogenous Lox3 thereby disrupting the Lox3 locus and optionally inserting an exogenous sequence or replacing an endogenous sequence. The double strand break is introduced by a site-specific nuclease such as meganucleases, zinc finger nucleases (ZFNs), transcription activator-like effector nucle-ases (TALENs), or the clustered regularly interspaced short palindromic repeat (CRISPR) nucleases. The nucleases cause double strand breaks (DSBs) at specific cleaving sites, which are repaired by nonhomologous end-joining (NHEJ) or homologous recombination (HR). The use of a repair template guides the cellular repair process so that the results of the repair are error-free and predictable. A repair template preferably comprises symmetric or asymmetric homology arms, which are complementary to the sequences flanking a double strand break and therefore allow to insert a sequence or close the break in a controlled manner.

In one embodiment of the method described above, the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or the at least one genome editing system is selected from a zinc finger nuclease system, or a transcription activator-like nuclease system, or a meganuclease system, or any combination, variant, or an active fragment thereof.

A preferred Cpf1 (Cas12a) nuclease to be used in the method of the present invention is encoded by the nucleic acid sequence of SEQ ID NO: 29, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 29.

The preferred Cpf1 (Cas12a) nuclease is further represented by the amino acid sequence of SEQ ID NO: 28 or an amino acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 28.

The genome editing system can be introduced by transformation or transfection mediated by biolistic bombardment, *Agrobacterium*-mediated transformation, micro- or nanoparticle delivery, chemical transfection, or a combination thereof as explained in more detail above in the context of the RNAi construct.

A CRISPR system includes the use of a guide RNA (gRNA) or CRISPR (crRNA), which guides the CRISPR nuclease to the target site by sequence recognition.

In one embodiment of the method described in any of the embodiments above, the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*), in particular a tropical maize line, and the at least one genome editing system comprises a protospacer having a nucleic acid sequence of SEQ ID NO: 32, 33, 34 or 35, or a nucleic acid sequence having 85%, 86%, 87%, 88%, 89%, 90%, 91%, 92%, 93%, 94%, 95%, 96%, 97%, 98% or at least 99% to the sequence of any of SEQ ID NOs: 32, 33, 34 or 35.

In one embodiment of the method described in any of the embodiments above, the method is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*), and the at least one genome editing system comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NOs: 46 to 49.

In one embodiment of this method, the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

A further alternative to introduce a modification, which results in reduced or abolished expression of endogenous Lox3, is by mutagenesis. From a range of mutants, the ones with the desired knock-down or knock-out can then be identified, e.g., by TILLING.

In one embodiment of the method described above, in step (ii) a mutagenesis is performed on a single or on a plurality of cell(s) by applying chemicals or radiation.

Preferably, an alkylating agent, in particular ethyl methanesulfonate is applied to the single or the plurality of cell(s) to induce mutagenesis.

In one embodiment of the method described above, one or more mutations in the Lox3 gene are inserted and identified by TILLING in step (ii).

In another embodiment of the method described above, one or more cell(s) with knock-down or knock-out mutations in the Lox3 gene are selected in step (ii).

In one embodiment of the method described above, the maize mutant selected in step (ii) comprises a Lox3 with an amino acid sequence selected from the sequences of SEQ ID NOs: 36 to 40 or an amino acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NOs: 36 to 40.

In another embodiment of the method described above, the maize mutant selected in step (ii) comprises a Lox3 encoded by a nucleic acid sequence selected from the sequences of SEQ ID NOs: 41 to 45 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NOs: 41 to 45.

In another aspect, the present invention relates to a maize cell, maize tissue, maize organ, maize plant or maize seed obtained or obtainable by a method according to any of the embodiments described above.

In a further aspect, the present invention relates to an oilseed rape cell, oilseed rape tissue, oilseed rape organ, oilseed rape plant or oilseed rape seed obtained or obtainable by a method according to any of the embodiments described above.

The present invention also provides expression constructs for specifically targeting the Lox3 gene in maize and in oil seed rape for gene silencing. To obtain such a construct, sequences from the respective endogenous Lox3 gene are used as sense and antisense sequences, which form an RNA hairpin upon transcription in the cell.

In one aspect, the present invention relates to an expression construct, which targets the Lox3 gene in maize for gene silencing, wherein the construct encodes an RNAi construct comprising a sense and an antisense sequence targeting the Lox3 gene endogenous to a maize plant, which RNAi construct forms an RNA hairpin upon transcription.

In another aspect, the present invention relates to an expression construct, which targets the Lox3 gene in oilseed rape for gene silencing, wherein the construct encodes an RNAi construct comprising a sense and an antisense sequence targeting the Lox3 gene endogenous to an oilseed rape plant, which RNAi construct forms an RNA hairpin upon transcription.

Preferably, the sense and antisense sequences have a length of 40 to 500 nucleotides, more preferably 100 to 300 nucleotides.

In one embodiment of the expression construct described above, the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

In another embodiment of the expression construct described above, the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

In yet another embodiment of the expression construct described above, the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98% or at least 99% to the sequence of SEQ ID NO: 3.

In a further embodiment of the expression construct described above, the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

In another aspect, the present invention relates to a vector comprising or consisting of a nucleic acid sequence of SEQ ID NO: 5 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5.

In yet another aspect, the present invention relates to an RNAi hairpin construct conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum, Diplodia* species, *Cercospora zeina* and *Cercospora zeae-maydis* to/in maize (*Zea mays*), wherein the RNAi hairpin construct comprises a nucleic acid sequence of SEQ ID NO: 4, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

The present invention also provides constructs, which target the endogenous Lox3 gene in maize and oilseed rape for genome editing. Such genome editing systems comprise a site-specific nuclease, in case of a CRISPR based system, a guide RNA and, optionally a repair template.

In one aspect the present invention relates to an expression construct encoding a genome editing system, which targets the Lox3 gene in maize, wherein the genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same.

In another aspect, the present invention relates to an expression construct encoding a genome editing system, which targets the Lox3 gene in oilseed rape, wherein the genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same.

In one embodiment of the expression construct described above, the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or the at least one genome editing system is selected from a zinc finger nuclease system, or a transcription activator-like nuclease system, or a meganuclease system, or any combination, variant, or an active fragment thereof.

In one embodiment of the expression construct described above, the expression construct comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NO: 46 to 49.

In another embodiment of the expression construct described above, the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

In one embodiment of the expression construct described above, the expression construct comprises a protospacer having a nucleic acid sequence of SEQ ID NO: 32, 33, 34 or 35, or a nucleic acid sequence having 85%, 86%, 87%, 88%, 89%, 90%, 91%, 92%, 93%, 94%, 95%, 96%, 97%, 98% or at least 99% to the sequence of any of SEQ ID NOS: 32, 33, 34 or 35.

In yet another aspect, the present invention relates to a vector encoding an expression construct according to any of the embodiments described above.

The present invention also provides a maize cell, maize tissue, maize organ, maize plant or maize seed or an oilseed rape cell, oilseed rape tissue, oilseed rape organ, oilseed rape plant or oilseed rape seed comprising an expression construct or a vector according to any of the embodiments described above.

Furthermore, the present invention provides a use of an expression construct according to any of the embodiments described above for conferring or increasing resistance or tolerance to an insect and, optionally a fungal pathogen to/in a plant, in particular for use in a method according to any of the embodiments described above.

In one aspect, the present invention relates to a use of at least one gene silencing construct, at least one genome editing system or a genome modification, which leads to a targeted knock-down or a knock-out of the endogenous a Lox3 gene, for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum, Diplodia* species, *Cercospora zeina* and *Cercospora zeae-maydis* to/in maize (*Zea mays*).

In another aspect, the present invention relates to a use of at least one gene silencing construct, at least one genome editing system or a genome modification, which leads to a targeted knock-down or a knock-out of the endogenous a Lox3 gene, for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and *Plasmodiophora brassicae* to/in oilseed rape (*Brassica napus*).

According to one approach described in detail above, an RNAi or gene silencing construct may be used for conferring or increasing resistance or tolerance to an insect and, optionally a fungal pathogen to/in a plant.

In one aspect, the present invention therefore relates to the use of a construct, the construct being or encoding an RNAi construct comprising a sense and an antisense sequence targeting the endogenous Lox3 gene of a maize plant, wherein the RNAi construct forms an RNA hairpin upon transcription, for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In another aspect, the present invention relates to the use of a construct, the construct being or encoding an RNAi construct comprising a sense and an antisense sequence targeting the endogenous Lox3 gene of an oilseed rape plant, wherein the RNAi construct forms an RNA hairpin upon transcription, for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and *Plasmodiophora brassicae* to/in oilseed rape (*Brassica napus*).

In one embodiment of the use described above, the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

In another embodiment of the use according to any of the embodiments described above, the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

In yet another embodiment of the use according to any of the embodiments described above, the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98%, or at least 99% to the sequence of SEQ ID NO: 3.

In one embodiment of the use described above, the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

The present invention also relates to the use of a vector, which vector comprises or consists of a nucleic acid sequence of SEQ ID NO: 5, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5 for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In another aspect, the present invention also relates to the use of a genome editing system according to any of the embodiments described above.

In one embodiment of the use described above, the genome editing system targets the endogenous Lox3 gene in a maize plant, wherein the genome editing system comprises
  (a) at least one site-specific nuclease or site-specific nickase, and optionally, in case a CRISPR system is used, at least one guide molecule or a sequence encoding the same, and
  (b) optionally, at least one repair template, or a sequence encoding the same for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

In one embodiment of the use described above, the genome editing system comprises a protospacer having a nucleic acid sequence of SEQ ID NO: 32, 33, 34 or 35, or a nucleic acid sequence having 85%, 86%, 87%, 88%, 89%, 90%, 91%, 92%, 93%, 94%, 95%, 96%, 97%, 98% or at least 99% to the sequence of any of SEQ ID NOs: 32, 33, 34 or 35.

In another embodiment of the use described above, the genome editing system targets the endogenous Lox3 gene in an oilseed rape plant, wherein the genome editing system comprises (a) at least one site-specific nuclease or site-specific nickase, and optionally, in case a CRISPR system is used, at least one guide molecule or a sequence encoding the same, and (b) optionally, at least one repair template, or a sequence encoding the same for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora brassicae to/in oilseed rape (*Brassica napus*).

The present invention also relates to the use of an expression construct encoding a genome editing system, which targets the endogenous Lox3 gene in a maize plant, wherein the genome editing system comprises (a) at least one site-specific nuclease or site-specific nickase, and optionally, in case a CRISPR system is used, at least one guide molecule or a sequence encoding the same, and (b) optionally, at least one repair template, or a sequence encoding the same, wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or wherein the at least one genome editing system is selected from a zinc finger nuclease system, or a transcription activator-like nuclease system, or a meganuclease system, or any combination, variant, or an active fragment thereof for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum, Diplodia* species, *Cercospora zeina* and *Cercospora zeae-maydis* to/in maize (*Zea mays*).

Furthermore, the present invention also relates to a use of an expression construct encoding a genome editing system, which targets the endogenous Lox3 gene in an oilseed rape plant, wherein the genome editing system comprises (a) at least one site-specific nuclease or site-specific nickase, and optionally, in case a CRISPR system is used, at least one guide molecule or a sequence encoding the same, and (b) optionally, at least one repair template, or a sequence encoding the same, wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or wherein the at least one genome editing system is selected from a zinc finger nuclease system, or a transcription activator-like nuclease system, or a meganuclease system, or any combination, variant, or an active fragment thereof for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora brassicae to/in oilseed rape (*Brassica napus*).

In one embodiment of the use described above, the expression construct comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NO: 46 to 49.

In another embodiment of the use described above, the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

The present invention also relates to the use a vector encoding an genome editing system as defined above for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum, Diplodia* species, *Cercospora zeina* and *Cercospora zeae-maydis* to/in maize (*Zea mays*).

Finally, the present invention also relates to the use of a vector encoding an genome editing system as defined above for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora brassicae to/in oilseed rape (*Brassica napus*).

Example 1: Generation of RNAi Corn Lines with Lox3 Knock-Down

An RNAi hairpin construct directed against the ZmLox3 gene was constructed (FIG. 1, SEQ ID NOs: 1 to 5) and transformed into corn genotype A188 by *Agrobacterium tumefaciens* mediated transformation. Transgenic T0 plants were identified by PCR and transferred into the greenhouse for T1 seed production by selfing. A segregation analysis was performed with T1 plants. Homozygous ZmLox3_RNAi plants and non-transgenic, azygous plants were selected and T2 seeds were produced. The T2 seeds were used for the insect resistance assays.

Figure 2:
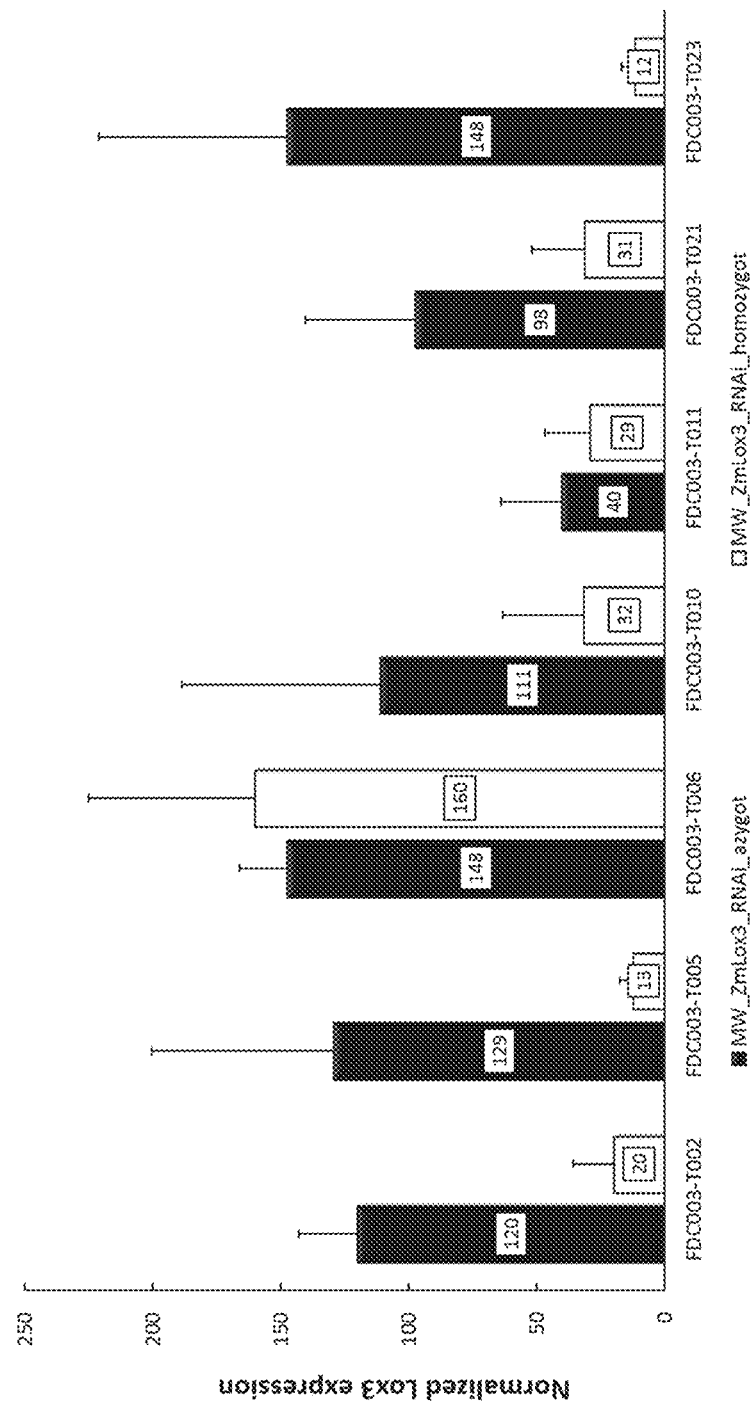
FIG. 2 shows the reduction of ZmLox3 expression in transgenic ZmLox3_RNAi lines. Leaf samples of homozygous GM (genetically modified) plants were analyzed by qRT-PCR for expression of ZmLox3 gene and compared with the gene expression of non-transgenic, azygous plants. The lines FDC003-T002, FDC003-T005, FDC003-T010, FDC003-T021 and FDC003-T023 show a strong reduction of Lox3 expression. The Lox3 expression was normalized against the expression of the house-keeping gene EF1. Mean of 3 and 5 plants are shown. Azygous lines n=3 plants. GM lines n=5 plants.

Downregulation of ZmLox3 gene (SEQ ID NO: 6-16, 87-89) in the ZmLox3_RNAi lines was shown by qRT-PCR after isolation of RNA from leaves of homozygous GM and non-transgenic, azygous plants (FIG. 2). The expression of ZmLox3 was measured using the primer S3460 (SEQ ID NO: 18) and primer S3461 (SEQ ID NO: 19). Lox3 expression was normalized against the expression of the housekeeping gene Elongation factor 1-alpha (EF1, SEQ ID NO: 22 and 23) using the primer S3428 (SEQ ID NO: 20) and the primer S3429 (SEQ ID NO: 21).

The expression analysis of corn leaves revealed that the lines FDC003-T002, FDC003-T005, FDC003-T010, FDC003-T021 and FDC003-T023 show a strong reduction of Lox3 expression (FIG. 2).

Example 2: Determine Insect Resistance by Measuring Larval Weight of Fall Army Worm Feeding on Lox3 RNAi Lines The purpose of this experiment was to evaluate if Lox3 gene down-regulation is linked to fall armyworm tolerance in corn. To test this, fall armyworm (*Spodoptera frugiperda*) larval performance was chosen as a measure of antibiosis-based resistance.

Three ZmLox3_RNAi corn lines (FDC003-T002, FDC003-T011 and FDC003-T023) were evaluated using unmodified A188 corn as control. Three independent insect resistance experiments were performed. For each experiment, five biological replicates were used for A188 and for each ZmLox3_RNAi lines. Three newly hatched fall armyworm larva were added into individual Falcon tubes containing corn leaves. Fresh leaves were provided daily and after ten days the larva weight was scored.

Figure 3:
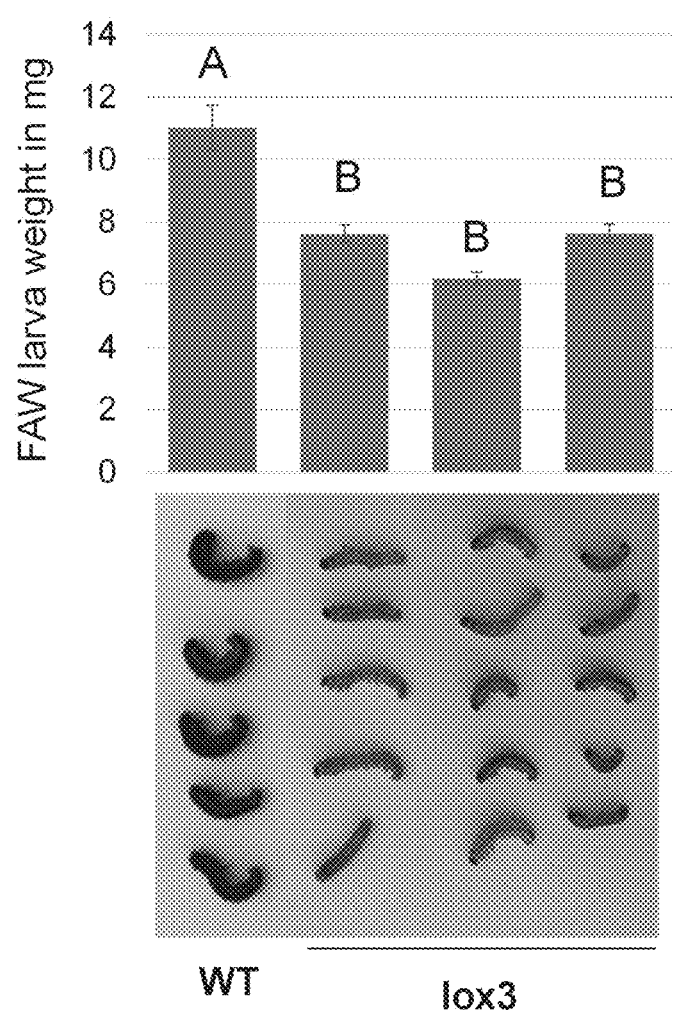
FIG. 3 shows enhanced insect resistance of ZmLox3_RNAi lines. Fall armyworm larva weight (in mg) 10 days after fed on A188 corn leaves (WT (A)) and fed on three different ZmLox3_RNAi lines (B1: FDC003-T002, B2: FDC003-T011 and B3: FDC003-T023). Data are from 3 independent experiments pulled together (mean+/−SE). Different letters represent groups that are significantly different (ANOVA and Tukey's honest significant difference post hoc, n=75; P<0.05).

All tested lines conferred a significant increase of resistance against fall armyworm (FIG. 3). These data showed that the ZmLox3 gene is a susceptibility gene for fall armyworm and that down-regulation of ZmLox3 expression can improve resistance.

Example 3: Determine Fungal Resistance of Lox3 RNAi Lines

Since stalk and ear rot caused by *Fusarium* spp. are favored by the mechanical damage caused by invading insects, the Lox3 mediated insect resistance may have an effect on fungal resistance.

Figure 4:
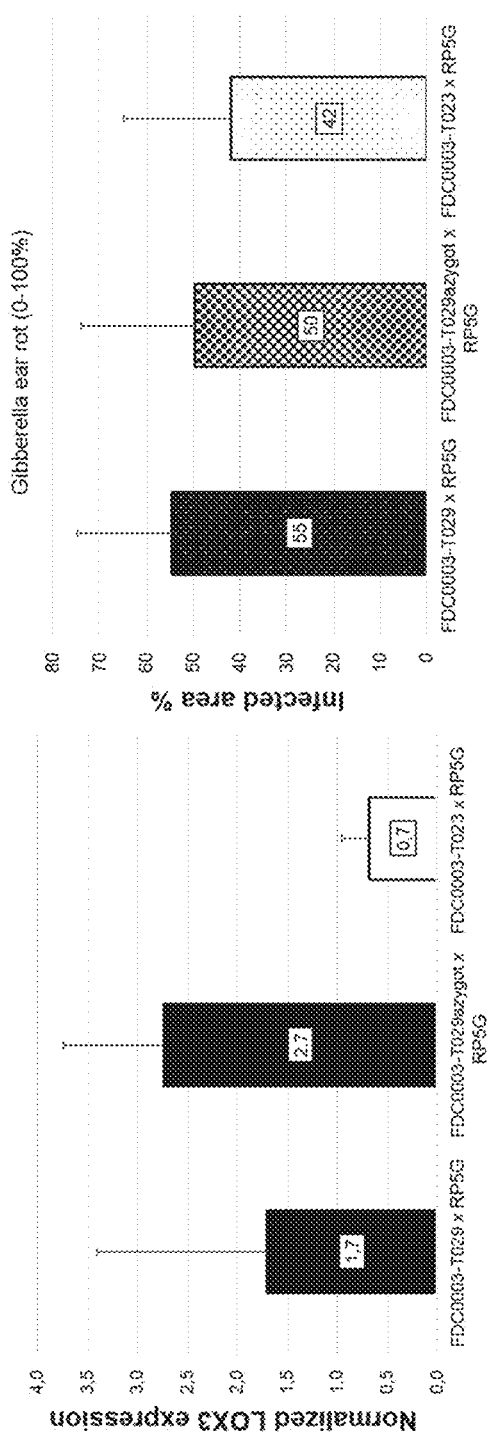
FIG. 4 shows enhanced fungal resistance of ZmLox3_RNAi line FDC0003-T023 Left: Disease scores of *Gibberella* ear rot infected corn cobs of hybrids from FDC0003-T029, FDC0003-T029 azygous and FDC0003-T023 tester line RP5G. Infected area of 40-50 heads of each hybrid was measured 40 days after infection of corn plants with *Fusarium graminearum* in the greenhouse. Right: Lox3 expression of leaves from the hybrids FDC003-T029, FDC0003-T029 azygous and FDC0003-T023 with tester line RP5G at the end of the fungal assay. The Lox3 expression was determined with qRT-PCR and is reduced in the hybrid FDC0003-T023, which shows enhanced fungal resistance and insect resistance.
Figure 5:
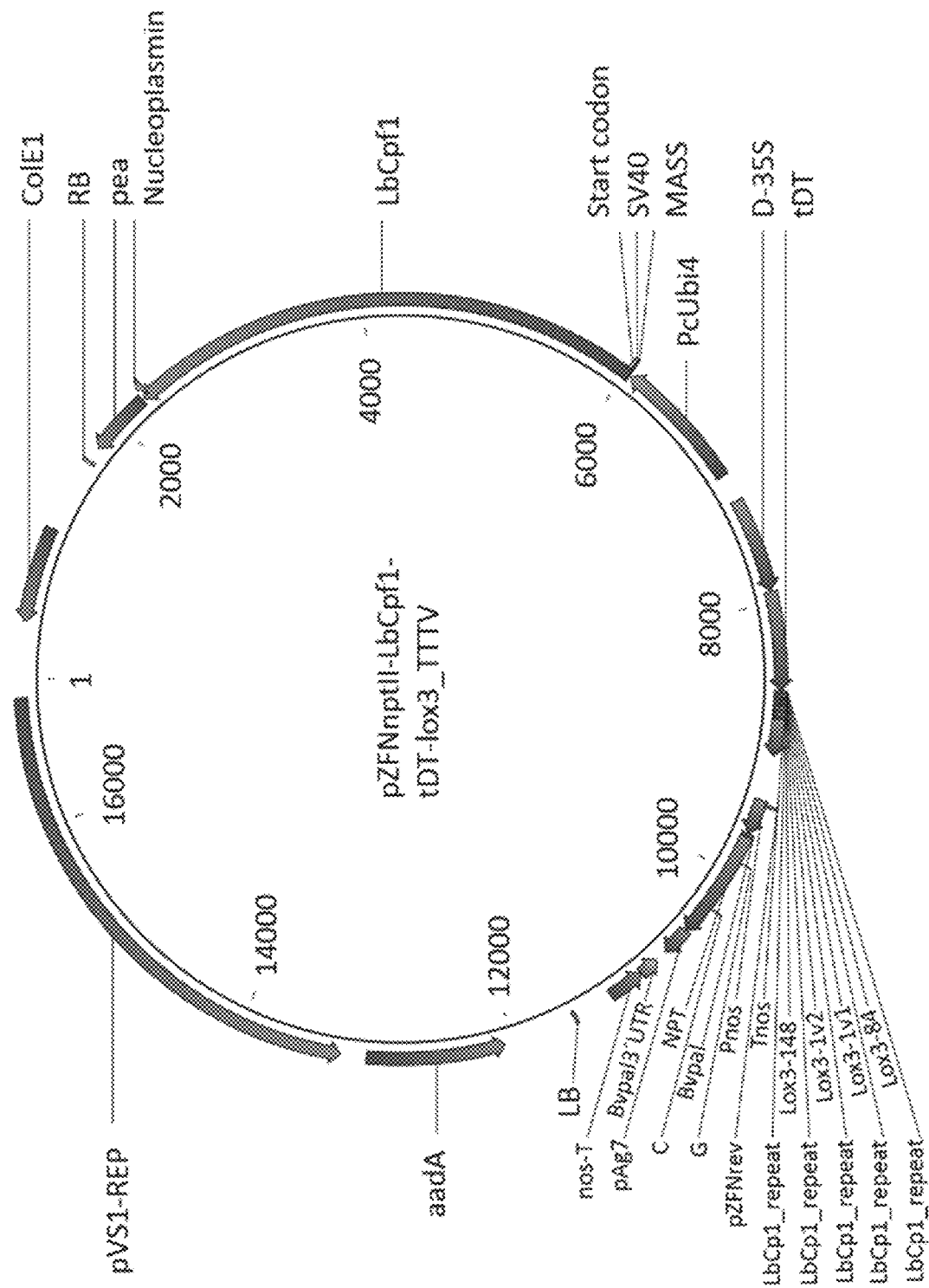
FIG. 5 shows the binary vector used for generation of Lox3 SDN-1 knock-down in tropical corn by genome editing.

The insect resistant line FDC003-T023 was crossed with the tester line RP5G and compared with test crosses of FDC0003-T029 and FDC0003-T029 azygous with the tester line RP5G, which did not show LOX3 reduction as determined by qRT-PCR (FIG. 4, left). The FDC003-T023 hybrid showed 13 and 8% less *Fusarium* infection compared to the FDC0003-T029 and FDC0003-T029 azygous hybrids (FIG. 4, right), which revealed that an insect resistant RNAi line also has higher fungal resistance.

Example 4: Generation of Lox3 SDN1 Knock-Down in Tropical Corn by Genome Editing Lox3 was knocked out in tropical corn genotypes by means of a site-directed nuclease.
1. Tropical corn lines were grown in soil from seed for five weeks and immature tassels were harvested as previously described (WO2021170785).
2. Tassel material was bombarded using the following vectors:
   a. TGCD035 (ZmPLT5, SEQ ID Nos: 24 and 25)
   b. GEZM145 (RBP8, SEQ ID Nos: 26 and 27)
   c. GEZM152 (gRNA, protospacer m7GEP336: GCACGTTCTTGCGCATGAGCA, SEQ ID NO: 32)
   d. GEZM153 (gRNA, protospacer m7GEP337: GCGCCACCGTCGTTGACAGCA, SEQ ID NO: 33)
   e. GEZM154 (gRNA, protospacer m7GEP338: CTGTGCAGACAACGGCAACCG, SEQ ID NO: 34)
   f. GEZM155 (gRNA, protospacer m7GEP339: AGCTTCTCCACCTCCCAGTCG, SEQ ID NO: 35)
   g. GEMT121 (LbCpf1-RR and tdTomato, SEQ ID Nos: 28-31)
3. Using the standard regeneration protocol for tropical corn lines, 12 plants were sampled and analyzed by amplicon sequencing using the following primers:

TABLE 1

| Primer | Sequence | SEQ ID NO |
| --- | --- | --- |
| 946R | GCTCTCTCGGCCCCCACTTTTT | 71 |
| 1145F | TGTTCTGCGCCCAGGCTACA | 72 |
| 346F | TCGCGAACACACCGGTCGTA | 73 |
| 1948R | ACTCACATGCCTCGCCCTCA | 74 |

Three plants were identified with edits in the Lox3 gene. All three plants were edited in multiple locations (Table 2).

TABLE 2

|  | Target 1 | Target 2 | Target 3 |
| --- | --- | --- | --- |
| GEZM152T012 | 100%: 3&12 bp deletions | 100%: 3&12 bp deletions | 50%: 15 bp deletion |
| GEZM152T013 | 50%: 5 bp deletion | 50%: 5 bp deletion | 50%: 23 bp deletion |
| GEZM152T014 | 100%: 3 & 11 bp deletions | 100%: 3 & 11 bp deletions | 50%: 15 bp deletion |

4. Plants were transferred from media to soil and kept in short day conditions (in a lean-in Conviron) for as long as possible to trigger tassel and ear development before ultimately moving them to standard greenhouse conditions.

Example 5: Determine Tropical Corn Insect Resistance by Measuring Larval Weight of Fall Armyworm Feeding on Lox3 SDN1 Tropical Corn Edited Lines The purpose of this experiment was to evaluate if Lox3 gene knock-out is linked to fall armyworm tolerance in tropical corn (SL57). To test this, fall armyworm (*Spodoptera frugiperda*) larval performance was chosen as a measure of antibiosis-based resistance.

Three ZmLox3_SDN-1 tropical corn lines (GEZM152T012, GEZM152T013, GEZM152T014) were evaluated using unmodified SL57 tropical corn as control. Three independent insect resistance experiments were performed. For each experiment, five biological replicates were used for the unmodified SL57 tropical corn and for each ZmLox3_SDN-1 lines. Three newly hatched fall armyworm larva were added into individual Falcon tubes containing corn leaves. Fresh leaves were provided daily and after ten days the larva weight was scored.

Example 6: Generation of Lox3 TILLING Mutants

EMS mutagenesis: A mutagenized population (EMS treatment) from PH207 was developed. The exonic region 7 of Zm00008a004913 was screened and 5 positive mutants harboring amino acid changes and stop codons were detected (SEQ ID NOS: 36-40, Table 3). In Zm00008a004913 cDNA of Mutant WVP18-09344-014 C at position 1876 replaced by T (see also SEQ ID NO: 43), leading to an amino acid exchange from P to S at position 569 (see also SEQ ID NO: 37); in Zm00008a004913 cDNA of Mutant WVP18-09309-014 and WVP18-09339-009 G at position 2004 replaced by A (see also SEQ ID NO: 44), leading to an amino acid exchange from W to STOP at position 668 (see also SEQ ID NO: 39); in Zm00008a004913 cDNA of Mutant WVP18-09358-016 G at position 2079 replaced by A (see also SEQ ID NO: 42), leading to an amino acid exchange from Wto STOP at position 693 (see also SEQ ID NO: 37); in Zm00008a004913 cDNA of Mutant WVP18-09307-014 G at position 2287 replaced by A (see also SEQ ID NO: 45), leading to an amino acid exchange from G to S at position 763 (see also SEQ ID NO: 40). After selfing of these mutants to produce two homozygote classes (homozygote wildtype and mutant), they have been evaluated in the field for resistance to two *Fusarium* species (*F. graminearum, F. verticillioides*, see Example 7).

TABLE 3

| Name | Gen-Name | Code | Pos CDS | Base WT | Base Mut | Position in AS sequence | AS WT | AS Mut |
|---|---|---|---|---|---|---|---|---|
| WP18-09344-014 | LOX3 | PH207m034b | 1876 | C | T | 569 | P | S |
| WP18-09309-014 | LOX3 | PH207m034d | 2004 | G | A | 668 | W | STOP |
| WVP18-09339-009 | LOX3 | PH207m034d | 2004 | G | A | 668 | W | STOP |
| WVP18-09358-016 | LOX3 | PH207m034f | 2079 | G | A | 693 | W | STOP |
| WVP18-09307-014 | LOX3 | PH207m034h | 2287 | G | A | 763 | G | S |

Example 7: Determine Fungal Resistance of Lox3 TILLING Mutants

After selfing of these mutants to produce two homozygote classes (homozygote wildtype and mutant), they have been evaluated in the field for resistance to two *Fusarium* species (*F. graminearum* (FG), *F. verticilloides* (FV)).

In 2020 plants were grown in rows with 20 plants per row in the location GON and in 2021 in MUR. Ten plants of each experimental unit were inoculated four to six days after the experimental unit was flowering, excluding the first plant of the row to avoid possible border effect. Rows were declared as flowering when at least 50% of the plants in the row presented extruded silks. Female flowering (FF) dates were collected for each row daily.

1 ml of an inoculum suspension with a concentration of 15.000 conidia ml-1 (*F. graminearum* (FG)) and 1,000,000 conidia ml-1 (*F. verticilloides* (FV)) was inoculated into the maize silk channel with a self-refilling syringe. The experiments for the two different species were kept separate.

Approximately 50 days after inoculation, cobs were dehusked and all plants were visually assessed for *Fusarium* symptoms by estimating the percentage of the ear covered by mycelium. The remnant not-inoculated plants of each experimental unit were used as a control of the proportion of naturally infected cobs. The arithmetic mean of the 10 assessed inoculated were employed for further analyses.

The homozygous mutant class for PH207m034b and PH207m034h showed lower infection of *F. graminearum* (FG) and *F. verticilloides* (FV) (FIG. 7).

Example 8: Determine Insect Resistance of Lox3 TILLING Mutants

The purpose of this experiment was to evaluate if Lox3 Tilling stop-mutations is linked to fall armyworm tolerance in temperate corn (line PH207). To test this, fall armyworm (*Spodoptera frugiperda*) larval performance was chosen as a measure of antibiosis-based resistance.

Two different Stop-Mutants for Lox3, the according wild-types derived from a heterozygote mutant plant and the line PH207 which is the parent of the mutant population were evaluated. Three independent insect resistance experiments were performed and for each experiment, five biological replicates were used. Three newly hatched fall armyworm larva were added into individual Falcon tubes containing corn leaves. Fresh leaves were provided daily and after ten days the larva weight was scored.

Example 9: Generation of Lox3 SDN1 Knock-Down in OSR by Genome Editing

1. Agro-based transformation, the nuclease was provided in the same construct together with the gRNAs (FIG. 5: construct map, plasmid sequence: pZFNnptII-LbCpf1-tDT-lox3_TTTV, SEQ ID NO: 50); four crRNAs were used in total to target the OSR lox3 gene (SEQ ID Nos: 46-49); BnLox3 sequences SEQ ID Nos: 75-86.

a. Agro-based transformation was adopted to generate GE plants using various different starting materials of seedlings between 1 to 10 days old.

The oil seed rape transformation protocol includes the following steps:

1. Seed sterilization with 70% ethanol and bleach
2. Seed germination on germination medium
3. *Agrobacterium* culture of a strain containing the construct of interest
4. Preparation of *Agrobacterium* for inoculation
5. Preparation of plant material and co-culture
6. Recovery of callus
7. Selection
8. Shoot growth
9. Rooting 2. Molecular analyses: Next Generation Sequencing (NGS), digital droplet PCR (ddPCR) and Decomposition Regression to Identify Variations for Editing Events (DRIVE)
   a. The SDN-1 gene edited plants were first analyzed for the presence of the transgene by qPCR using the settings shown in tables 5 and 6:

TABLE 5

|  | primer | work stock concentration (uM) | SEQ ID NO |
|---|---|---|---|
| Primers | cruaxxxxxxf02x | 20 | 51 |
|  | cruaxxxxxxr01x | 20 | 52 |
|  | nptIIxxxf01 | 20 | 53 |
|  | nptIIxxxr01 | 20 | 54 |
|  | tDTxxxf04 | 20 | 55 |
|  | tDTxxxr01 | 20 | 56 |
| probes | CruaxxxMGB | 10 | 57 |
|  | nptIIxxxMGB | 10 | 58 |
|  | tDTxxxMGB | 10 | 59 | qPCR parameters:

TABLE 6

| 50° C. | 2 min | |
| 95° C. | 5 min | |
| 95° C. | 15 s | 40 cycles |
| 60° C. | 30 s | | b. The transgenic plants were then analyzed by qPCR using the primers sets SEQ ID 60, 61 and 62 (probe) for nuclease test.
c. The editing profile was then obtained by amplifying and sequencing the PCR product using the primers sets as shown in table 7 and then run Drive analysis on OMICS to get editing information.

TABLE 7

| Primer | | SEQ ID NO: |
|---|---|---|
| IR106_lox3_F1 | CCTCTGACCTCCAAAAGACCCTTA | 63 |
| IR106_lox3_F2 | CCATTACTTGTTTGGTCGGCGT | 64 |
| IR106_lox3_F3 | GCCATCACTTGTTTTCTCGGC | 65 |
| IR106_lox3_F4 | CCGTCACTTGTTTTCTCGGC | 66 |
| IR106 lox3_R1 | TCAAAGGCTAATATAACTGACACGT | 67 |
| IR106_lox3_R2 | GGCAAACGCGTTTCCTTAATTCA | 68 |
| IR106_lox3_R3 | ATAACGCTGATGTGCTAAGC | 69 |
| IR106_lox3_R4 | GTTAATAACGCTGATGTACTAAGC | 70 |

Example 10: Determine OSR Insect Resistance by Measuring Leaf Damage from Diamondback Moth and by Measuring Aphid Reproduction from Insect Feeding on Lox3 SDN1 Edited Line The purpose of this experiment was to evaluate if Lox3 gene knock-out is linked to diamondback moth and green peach aphid tolerance in OSR (Palma). To test this, diamondback moth (*Plutella xylostella*) feeding damage and green peach aphid (*Myzus persicae*) reproduction were chosen as a measure of plant resistance.

One Lox3_SDN-1 OSR line was evaluated using unmodified Palma OSR as control. Three independent insect resistance experiments were performed and for each experiment, fourteen biological replicates were used.

For the test using diamondback moth, four newly hatched larva were placed on each one-week-old OSR seedlings. Four days later, the percentage of plant damage (=percentage of leaf eaten by the larva) was visually scored using a 0 to 100% scale.

For the test using green peach aphid, one adult aphid was placed on each one-week-old OSR seedlings. Seven days later, the number of aphids on each seedling was recorded (adult aphid+progeny).

Example 11: Determine Fungal Resistance of Lox3 Edited Lines

Clubroot Test

Infected oil seed rape roots were collected in the field. 100 g of infected roots were crushed with 400 ml water. The solution was then roughly filtered. Two different isolates were used in the screening, isolate A (Mendel-based varieties show still resistance) and C (Mendel-based varieties are highly susceptible).

OSR plants to be tested were sown in sand and were picked after 10 to 14 days. Roots were washed and incubated in the spore solution for 15 to 20 minutes. Plants were then removed and planted into a soil/sand substrate. Afterwards the spore solution was additionally pipetted directly on to the plants. Afterwards they were grown under greenhouse conditions for approximately 6 weeks.

Figure 6:
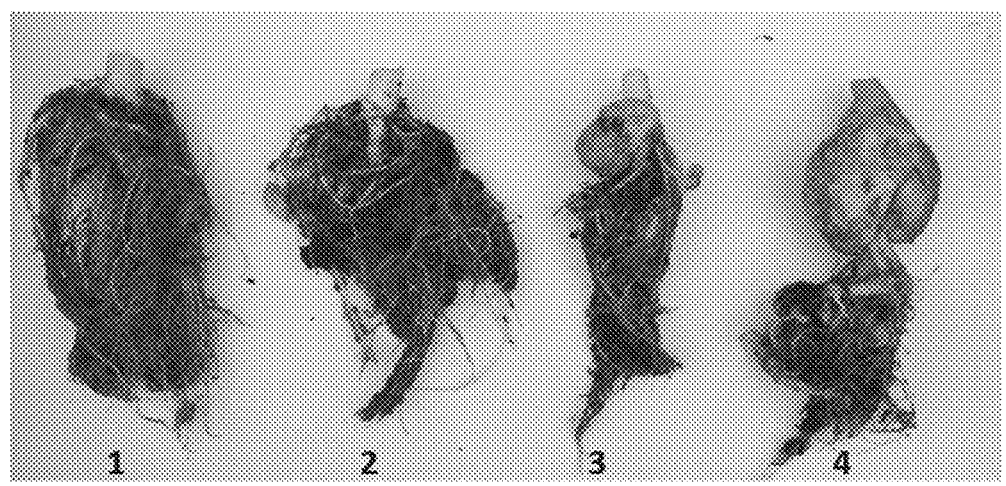
FIG. 6 shows the scoring scheme of the clubroot test performed in Example 11.

After washing of the roots, the gall formation was scored from 1, meaning no gall formation to 4 strong gall formation (FIG. 6). A disease index (DI) was calculated (E. Diederichsen and M. D. Sacristan, Plant Breeding 115, 5-10 (1996), Disease response of resynthesized *Brassica napus* L. lines carrying different combinations of resistance to Plasmodiophora brassicae Wor.) by using the following formula:

$$DI = \frac{\sum (0n_0 + 1n_1 + 2n_2 + 3n_3)}{3N} \times 100$$

The values n0 to n3 correspond to the number of plants per class and N being the total number of tested plants. Genotypes with a DI<10 were assessed to be highly resistant. A DI between 10-25 leads to an assessment as resistant and genotypes with a DI>25 are rated as susceptible.

Blackleg Test

OSR seedlings were germinated in soil in a controlled environment chamber at 20-24° C. for seven days. Each fully expanded cotyledon was wounded twice by puncturing it with a needle. The wounded sites were inoculated with a 107 pycnidiospore solution obtained from a German field isolate (pycnidia harvested from media grown fungus, suspended in sterile water and quantified). In order to delay cotyledon senescence, true leaves were cut at the petiole insertion. After about 10 days the symptoms were scored on a scale of 1-6 (1-3=resistant, 4-6=susceptible) based on the increasing injury of the cotyledon and the sporulation of the fungus.

LIST OF EMBODIMENTS

The following is a non-exhaustive list of embodiments.

Item 1. A method for conferring or increasing resistance or tolerance to an insect and, optionally a fungal pathogen to/in a plant comprising the steps of:
(i) providing at least one plant cell;
(ii) introducing into the at least one plant cell at least one gene silencing construct, at least one genome editing system or a genome modification, which leads to a targeted knock-down or a knock-out of a Lox3 gene endogenous to the plant;
(iii) obtaining at least one modified plant cell having reduced or abolished expression of the Lox3 gene; and
(iv) obtaining at least one plant cell, tissue, organ, plant or seed having reduced or abolished expression of the Lox3 gene, optionally after an additional step of regenerating the plant tissue, organ, plant or seed from the at least one modified cell.

Item 2. The method of item 1, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

Item 3. The method of item 1, wherein the method is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma lingam* and *Plasmodiophora brassicae* to/in oilseed rape (*Brassica napus*).

Item 4. The method according to item 2, wherein the Lox3 gene is represented by a nucleic acid sequence of SEQ ID NO: 6, 7, 9, 10, 12, 13, 15, 16, 87 or 88 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 6, 7, 9, 10, 12, 13, 15, 16, 87 or 88.

Item 5. The method according to item 2 or 4, wherein the Lox3 gene encodes an amino acid sequence of SEQ ID NO: 8, 11, 14, 17 or 89 an amino acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 8, 11, 14, 17 or 89.

Item 6. The method according to item 3, wherein the Lox3 gene is represented by a nucleic acid sequence of SEQ ID NO: 75, 76, 77, 78, 83, 84, 85 or 86 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 75, 76, 77, 78, 83, 84, 85 or 86.

Item 7. The method according to item 3 or 6, wherein the Lox3 gene encodes an amino acid sequence of SEQ ID NO: 79, 80, 81 or 82 or an amino acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 79, 80, 81 or 82.

Item 8. The method according to any of the preceding items, wherein in step (ii) a construct is introduced into the at least one plant cell, which targets the Lox3 gene for gene silencing.

Item 9. The method according to item 8, wherein the construct is or wherein the construct encodes an RNAi construct comprising a sense and an antisense sequence targeting the Lox3 gene, the RNAi construct forming an RNA hairpin upon transcription.

Item 10. The method according to item 9, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and wherein the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

Item 11. The method according to item 9 or 10, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and wherein the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

Item 12. The method according to any of items 9 to 11, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and wherein the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98% or at least 99% to the sequence of SEQ ID NO: 3.

Item 13. The method according to item 8, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and wherein the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

Item 14. The method according to item 8, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*) and wherein a vector is introduced into the plant cell, which vector comprises or consists of a nucleic acid sequence of SEQ ID NO: 5, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5.

Item 15. The method according to any of items 8 to 14, wherein the construct is introduced into the at least one plant cell by transformation or transfection mediated by biolistic bombardment, *Agrobacterium*-mediated transformation, micro- or nanoparticle delivery, chemical transfection, or a combination thereof.

Item 16. The method according to any of items 1 to 7, wherein in step (ii) at least one genome editing system is introduced into the at least one cell, which targets the Lox3 gene, wherein the at least one genome editing system comprises
(a) at least one site-specific nuclease or site-specific nickase, and optionally, in case a CRISPR system is used, at least one guide molecule or a sequence encoding the same, and
(b) optionally, at least one repair template, or a sequence encoding the same.

Item 17. The method according to item 16, wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or wherein the at least one genome editing system is selected from a zinc finger nuclease system, or a transcription activator-like nuclease system, or a meganuclease system, or any combination, variant, or an active fragment thereof.

Item 18. The method of item 16 or 17 wherein the at least one genome editing system is introduced into the at least one maize cell by transformation or transfection mediated by biolistic bombardment, *Agrobacterium*-mediated transformation, micro- or nanoparticle delivery, chemical transfection, or a combination thereof.

Item 19. The method of any of items 16 to 18, wherein the method is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*), wherein the at least one genome editing system comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NOs: 46 to 49.

Item 20. The method of item 19, wherein the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

Item 21. The method according to any of items 1 to 7, wherein in step (ii) a mutagenesis is performed on a single or on a plurality of cell(s) by applying chemicals or radiation.

Item 22. The method according to item 21, wherein an alkylating agent, in particular ethyl methanesulfonate is applied to the single or the plurality of cell(s) to induce mutagenesis.

Item 23. The method according to item 21 or 22, wherein one or more mutations in the Lox3 gene are inserted and identified by TILLING in step (ii).

Item 24. The method according to any of items 21 to 23, wherein one or more cell(s) with knock-down or knock-out mutations in the Lox3 gene are selected in step (ii).

Item 25. A maize cell, maize tissue, maize organ, maize plant or maize seed obtained or obtainable by a method according to any of items 1, 2, 4, 5, 8 to 18 or 21 to 24.

Item 26. An oilseed rape cell, oilseed rape tissue, oilseed rape organ, oilseed rape plant or oilseed rape seed obtained or obtainable by a method according to any of items 1, 3, 6 to 9 or 15 to 24.

Item 27. An expression construct, which targets the Lox3 gene in maize for gene silencing, wherein the construct encodes an RNAi construct comprising a sense and an antisense sequence targeting the Lox3 gene endogenous to a maize plant, which RNAi construct forms an RNA hairpin upon transcription.

Item 28. An expression construct, which targets the Lox3 gene in oilseed rape for gene silencing, wherein the construct encodes an RNAi construct comprising a sense and an antisense sequence targeting the Lox3 gene endogenous to an oilseed rape plant, which RNAi construct forms an RNA hairpin upon transcription.

Item 29. The expression construct according to item 27, wherein the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

Item 30. The expression construct according to item 27 or 29, wherein the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

Item 31. The expression construct according to any of items 27, 29 or 30, wherein the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98% or at least 99% to the sequence of SEQ ID NO: 3.

Item 32. The expression construct according to item 27, wherein the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

Item 33. A vector comprising or consisting of a nucleic acid sequence of SEQ ID NO: 5 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5.

Item 34. An RNAi hairpin construct conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*), wherein the RNAi hairpin construct comprises a nucleic acid sequence of SEQ ID NO: 4, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

Item 35. An expression construct encoding a genome editing system, which targets the Lox3 gene in maize, wherein the genome editing system comprises
 (a) at least one site-specific nuclease or site-specific nickase, and optionally, in case a CRISPR system is used, at least one guide molecule or a sequence encoding the same, and
 (b) optionally, at least one repair template, or a sequence encoding the same.

Item 36. An expression construct encoding a genome editing system, which targets the Lox3 gene in oilseed rape, wherein the genome editing system comprises
 (a) at least one site-specific nuclease or site-specific nickase, and optionally, in case a CRISPR system is used, at least one guide molecule or a sequence encoding the same, and
 (b) optionally, at least one repair template, or a sequence encoding the same.

Item 37. The expression construct according to item 35 or 36, wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or wherein the at least one genome editing system is selected from a zinc finger nuclease system, or a transcription activator-like nuclease system, or a meganuclease system, or any combination, variant, or an active fragment thereof.

Item 38. The expression construct according to item 36 or 37, wherein the expression construct comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NO: 46 to 49.

Item 39. The expression construct according to item 36 or 37, wherein the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

Item 40. A vector encoding an expression construct according to any of items 35 to 39.

Item 41. A maize cell, maize tissue, maize organ, maize plant, or maize seed comprising an expression construct or a vector according to any of items 35, 37 or 40.

Item 42. An oilseed rape cell, oilseed rape tissue, oilseed rape organ, oilseed rape plant or oilseed rape seed comprising an expression construct or a vector according to any of items 36 to 39 or 40.

Item 43. A use of at least one gene silencing construct, at least one genome editing system or a genome modification, which leads to a targeted knock-down or a knock-out of the endogenous a Lox3 gene, for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

Item 44. A use of at least one gene silencing construct, at least one genome editing system or a genome modification, which leads to a targeted knock-down or a knock-out of the endogenous a Lox3 gene, for conferring or increasing resistance or tolerance to one or more insect(s)

selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*).

Item 45. A use of a construct, the construct being or encoding an RNAi construct comprising a sense and an antisense sequence targeting the endogenous Lox3 gene of a maize plant, wherein the RNAi construct forms an RNA hairpin upon transcription, for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

Item 46. A use of a construct, the construct being or encoding an RNAi construct comprising a sense and an antisense sequence targeting the endogenous Lox3 gene of an oilseed rape plant, wherein the RNAi construct forms an RNA hairpin upon transcription, for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*).

Item 47. The use according to item 45, wherein the sense sequence is encoded by a nucleic acid sequence of SEQ ID NO: 1, or a nucleic acid sequence having a sequence identity of at least 90%, 91%, 92%, 93%, 94%, 95%, 96%, 97%, 98% or at least 99% to the sequence of SEQ ID NO: 1.

Item 48. The use according to item 45 or 47, wherein the antisense sequence is encoded by a nucleic acid sequence of SEQ ID NO: 2, or a nucleic acid sequence having a sequence identity of at least 90%, 91%, 92%, 93%, 94%, 95%, 96%, 97%, 98% or at least 99% to the sequence of SEQ ID NO: 2.

Item 49. The use according to any of items 45, 47 or 48, wherein the RNA hairpin has an intervening intron loop sequence comprising a nucleic acid sequence of SEQ ID NO: 3, or a nucleic acid sequence having a sequence identity of at least 85%, 86%, 87%, 88%, 89%, 90%, 91%, 92%, 93%, 94%, 95%, 96%, 97%, 98%, or at least 99% to the sequence of SEQ ID NO: 3.

Item 50. The use according to item 45 wherein the construct comprises a nucleic acid sequence of SEQ ID NO: 4, or a nucleic acid sequence having a sequence identity of at least 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 4.

Item 51. A use of a vector, which vector comprises or consists of a nucleic acid sequence of SEQ ID NO: 5, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 5 for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

Item 52. A use of a genome editing system, which targets the endogenous Lox3 gene in a maize plant, wherein the genome editing system comprises
(a) at least one site-specific nuclease or site-specific nickase, and optionally, in case a CRISPR system is used, at least one guide molecule or a sequence encoding the same, and
(b) optionally, at least one repair template, or a sequence encoding the same
for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

Item 53. A use of a genome editing system, which targets the endogenous Lox3 gene in an oilseed rape plant, wherein the genome editing system comprises
(a) at least one site-specific nuclease or site-specific nickase, and optionally, in case a CRISPR system is used, at least one guide molecule or a sequence encoding the same, and
(b) optionally, at least one repair template, or a sequence encoding the same
for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen selected from the group consisting of *Phoma* lingam and Plasmodiophora *brassicae* to/in oilseed rape (*Brassica napus*).

Item 54. A use of an expression construct encoding a genome editing system, which targets the endogenous Lox3 gene in a maize plant, wherein the genome editing system comprises
(a) at least one site-specific nuclease or site-specific nickase, and optionally, in case a CRISPR system is used, at least one guide molecule or a sequence encoding the same, and
(b) optionally, at least one repair template, or a sequence encoding the same,
wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or wherein the at least one genome editing system is selected from a zinc finger nuclease system, or a transcription activator-like nuclease system, or a meganuclease system, or any combination, variant, or an active fragment thereof for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

Item 55. A use of an expression construct encoding a genome editing system, which targets the endogenous Lox3 gene in an oilseed rape plant, wherein the genome editing system comprises
(a) at least one site-specific nuclease or site-specific nickase, and optionally, in case a CRISPR system is used, at least one guide molecule or a sequence encoding the same, and
(b) optionally, at least one repair template, or a sequence encoding the same,
wherein the at least one genome editing system is selected from a CRISPR/Cas system, preferably from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, or a CRISPR/Csm system, or wherein the at least one genome editing system is selected from a zinc finger nuclease system, or a transcription activator-like nuclease system, or a meganuclease system, or any combination, variant, or an active fragment thereof for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*).

Item 56. Use according to item 55 wherein the expression construct comprises a crRNA encoded by a nucleic acid sequence of any of SEQ ID NOs: 46 to 49, or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of any of SEQ ID NO: 46 to 49.

Item 57. Use according to item 55 or 56, wherein the genome editing system is encoded by a plasmid of the nucleic acid sequence of SEQ ID NO: 50 or a nucleic acid sequence having a sequence identity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% to the sequence of SEQ ID NO: 50.

Item 58. A use of a vector encoding an genome editing system as defined in item 54 for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*) and, optionally conferring or increasing resistance or tolerance to one or more fungal pathogen(s) selected from the group consisting of *Fusarium* species, *Colletotrichum* species, in particular *Colletotrichum graminicola* and *Colletotrichum sublineolum*, *Diplodia* species, *Cercospora zeina* and *Cercospora zeae-maydis* to/in maize (*Zea mays*).

Item 59. A use of a vector encoding an genome editing system as defined in any of items 55 to 57 for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*) and, optionally conferring or increasing resistance or tolerance to one or more fungal pathogen(s) selected from the group consisting of *Phoma* lingam and Plasmodiophora *brassicae* to/in oilseed rape (*Brassica napus*).

The invention claimed is:

1. A method for conferring or increasing resistance or tolerance to an insect and comprising the steps of:

(i) providing at least one *Zea mays* plant cell;

(ii) introducing into the at least one *Zea mays* plant cell at least one gene silencing construct, at least one genome editing system or a genome modification, which leads to a targeted knock-down of a Lox3 gene endogenous to the *Zea mays* plant;

(iii) obtaining at least one modified *Zea mays* plant cell having reduced expression of the Lox3 gene;

(iv) obtaining at least one *Zea mays* plant cell, tissue, organ, plant, or seed having reduced expression of the Lox3 gene after an additional step of regenerating the *Zea mays* plant tissue, organ, plant, or seed from the at least one modified *Zea mays* plant cell; and (v) testing the at least one *Zea mays* plant cell, tissue, organ, plant, or seed having reduced expression of the Lox3 gene for increased resistance or tolerance to the insect, wherein the Lox3 gene is represented by the nucleic acid sequence of SEQ ID NO: 6, 7, 9, 10, 12, 13, 15, 16, 87, or 88 or a nucleic acid sequence having a sequence identity of at least 95% to the sequence of SEQ ID NO: 6, 7, 9, 10, 12, 13, 15, 16, 87, or 88, and wherein the Lox3 gene encodes the amino acid sequence of SEQ ID NO: 8, 11, 14, 17 or 89 or an amino acid sequence having a sequence identity of at least 95% to the sequence of SEQ ID NO: 8, 11, 14, 17 or 89.

2. The method according to claim 1, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*).

3. The method according to claim 1, wherein the method is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*).

4. The method according to claim 1, wherein in step (ii) a construct is introduced into the at least one *Zea mays* plant cell, which targets the Lox3 gene for gene silencing.

5. The method according to claim 4, wherein the construct is or wherein the construct encodes an RNAi construct comprising a sense and an antisense sequence targeting the Lox3 gene, the RNAi construct forming an RNA hairpin upon transcription.

6. The method according to claim 5, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*), and wherein the sense sequence is encoded by the nucleic acid sequence of SEQ ID NO: 1, or a nucleic acid sequence having a sequence identity of at least 95% to the sequence of SEQ ID NO: 1.

7. The method according to claim 6, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*), and wherein the antisense sequence is encoded by the nucleic acid sequence of SEQ ID NO: 2, or a nucleic acid sequence having a sequence identity of at least 95% to the sequence of SEQ ID NO: 2, or wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*), and wherein the RNA hairpin has an intervening intron loop sequence comprising the nucleic acid sequence of SEQ ID NO: 3, or a nucleic acid sequence having a sequence identity of at least 95% to the sequence of SEQ ID NO: 3.

8. The method according to claim 4, wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*), and wherein the construct comprises the nucleic acid sequence of SEQ ID NO: 4, or a nucleic acid sequence having a sequence identity of at least 95% to the sequence of SEQ ID NO: 4, or wherein the method is for conferring or increasing resistance or tolerance to one or more insect(s) selected from the group consisting of fall army worm (*Spodoptera frugiperda*), corn leafhopper (*Dalbulus maidis*) and green belly stink bug (*Dichelops melacanthus*), and wherein a vector is introduced into the plant cell, which vector comprises or consists of the nucleic acid sequence of SEQ ID NO: 5, or a nucleic acid sequence having a sequence identity of at least 95% to the sequence of SEQ ID NO: 5.

9. The method according to claim 4, wherein the construct is introduced into the at least one *Zea mays* plant cell by transformation or transfection mediated by biolistic bombardment, *Agrobacterium*-mediated transformation, micro- or nanoparticle delivery, chemical transfection, or a combination thereof.

10. The method according to claim 1, wherein in step (ii) at least one genome editing system is introduced into the at least one *Zea mays* plant cell, which targets the Lox3 gene, wherein the at least one genome editing system comprises
   (a) at least one site-specific nuclease or site-specific nickase, and, in case a CRISPR system is used, at least one guide molecule or a sequence encoding the same, and/or
   (b) at least one repair template, or a sequence encoding the same.

11. The method according to claim 10, wherein the at least one genome editing system is selected from a CRISPR/MAD7 system, a CRISPR/Cpf1 (CRISPR/Cas12a) system, a CRISPR/MAD2 system, a CRISPR/Cas9 system, a CRISPR/CasX system, a CRISPR/CasY system, a CRISPR/Cas13 system, and a CRISPR/Csm system, or wherein the at least one genome editing system is selected from a zinc finger nuclease system, or a transcription activator-like nuclease system, or a meganuclease system, or any combination, variant, or an active fragment thereof.

12. The method of claim 10, wherein the at least one genome editing system is introduced into the at least one *Zea mays* cell by transformation or transfection mediated by biolistic bombardment, *Agrobacterium*-mediated transformation, micro- or nanoparticle delivery, chemical transfection, or a combination thereof.

13. The method of claim 10, wherein the method is for conferring or increasing resistance or tolerance to one or more insect(s) selected from the group consisting of green peach aphid (*Myzus persicae*), diamondback moth (*Plutella xylostella*), cabbage stem flea beetle (*Psylliodes chrysocephala*), crucifer flea beetle (*Phyllotreta cruciferae*), striped flea beetle (*Phyllotreta striolata*), hop flea beetle (*Psylliodes punctulata*), rape stem weevil (*Ceutorhynchus picitarsis*) and cabbage stem weevil (*Ceutorhynchus quadridens*), wherein the at least one genome editing system comprises a crRNA encoded by the nucleic acid sequence of any of SEQ ID NOs: 46 to 49, or a nucleic acid sequence having a sequence identity of at least 95% to the sequence of any of SEQ ID NOs: 46 to 49.

14. The method of claim 13, wherein the genome editing system is encoded by a plasmid of the nucleic acid sequence of SEQ ID NO: 50 or a nucleic acid sequence having a sequence identity of at least 95% to the sequence of SEQ ID NO: 50.

15. The method according to claim 1, wherein in step (ii) a mutagenesis is performed on a single *Zea mays* plant cell or on a plurality of *Zea mays* plant cells by applying chemicals or radiation, and/or
   wherein an alkylating agent is applied to the single *Zea mays* plant cell or the plurality of *Zea mays* plant cells to induce mutagenesis and/or
   wherein one or more mutations in the Lox3 gene are inserted and identified by TILLING in step (ii).

16. The method according to claim 15, wherein one or more *Zea mays* cell(s) with knock-down mutations in the Lox3 gene are selected in step (ii).

* * * * *